(12) United States Patent
Kaleko et al.

(10) Patent No.: US 10,548,955 B2
(45) Date of Patent: Feb. 4, 2020

(54) CARBAPENEMASES FOR USE WITH ANTIBIOTICS FOR THE PROTECTION OF THE INTESTINAL MICROBIOME

(71) Applicant: SYNTHETIC BIOLOGICS, INC., Rockville, MD (US)

(72) Inventors: Michael Kaleko, Rockville, MD (US); Sheila Connelly, Rockville, MD (US)

(73) Assignee: Synthetic Biologics, Inc., Rockville, MD (US)

( * ) Notice: Subject to any disclaimer, the term of this patent is extended or adjusted under 35 U.S.C. 154(b) by 55 days.

(21) Appl. No.: 15/866,044

(22) Filed: Jan. 9, 2018

(65) Prior Publication Data

US 2018/0221461 A1    Aug. 9, 2018

Related U.S. Application Data

(62) Division of application No. 15/051,187, filed on Feb. 23, 2016, now abandoned.

(60) Provisional application No. 62/190,806, filed on Jul. 10, 2015, provisional application No. 62/155,621, filed on May 1, 2015, provisional application No. 62/119,602, filed on Feb. 23, 2015.

(51) Int. Cl.
| | | |
|---|---|---|
| *C12N 9/86* | (2006.01) | |
| *A61K 38/50* | (2006.01) | |
| *A61K 38/14* | (2006.01) | |
| *A61K 31/00* | (2006.01) | |
| *A61K 35/741* | (2015.01) | |
| *A61K 9/00* | (2006.01) | |
| *A61K 9/50* | (2006.01) | |

(52) U.S. Cl.
CPC ............ *A61K 38/50* (2013.01); *A61K 9/0053* (2013.01); *A61K 31/00* (2013.01); *A61K 35/741* (2013.01); *A61K 38/14* (2013.01); *C12N 9/86* (2013.01); *A61K 9/5026* (2013.01); *A61K 9/5078* (2013.01); *C12Y 305/02006* (2013.01)

(58) Field of Classification Search
CPC .......... C12N 9/86; C12N 15/09; C12N 15/17; C12Y 305/02006; C01N 2333/986
See application file for complete search history.

(56) References Cited

U.S. PATENT DOCUMENTS

| | | |
|---|---|---|
| 2,890,986 A | 6/1959 | Kraut et al. |
| 2,941,995 A | 6/1960 | Doyle et al. |
| 2,982,696 A | 5/1961 | Puetzer et al. |
| 3,070,511 A | 12/1962 | Weitnauer |
| 3,150,059 A | 9/1964 | Kleinschmidt et al. |
| 3,239,394 A | 3/1966 | Walton |
| 3,488,729 A | 1/1970 | Chauvette et al. |
| 3,499,909 A | 3/1970 | Weissenburger et al. |
| 5,607,671 A | 3/1997 | Heino |
| 7,319,030 B2 | 1/2008 | Koski et al. |
| 7,745,193 B2 | 6/2010 | Giannotta et al. |
| 7,989,192 B2 | 8/2011 | Kaariainen et al. |
| 8,894,994 B2 | 11/2014 | Koski et al. |
| 2004/0248279 A1 | 12/2004 | Sawada et al. |
| 2005/0158843 A1 | 7/2005 | Koski et al. |
| 2005/0249716 A1 | 11/2005 | Bourgeois et al. |
| 2009/0181004 A1 | 7/2009 | Kaariainen et al. |
| 2009/0311234 A1 | 12/2009 | Koski et al. |
| 2013/0216622 A1 | 8/2013 | Koski et al. |

FOREIGN PATENT DOCUMENTS

| | | |
|---|---|---|
| EP | 0384559 A1 | 8/1990 |
| EP | 0420600 A2 | 4/1991 |
| EP | 0420600 A3 | 11/1992 |
| EP | 1564286 A1 | 8/2005 |
| FI | 59265 B | 3/1981 |
| FI | 880017 A | 7/1988 |
| GB | 1241844 A | 8/1971 |
| GB | 1463513 A | 2/1977 |
| GB | 2199582 A | 7/1988 |
| WO | 1988/07865 A1 | 10/1988 |
| WO | 1993/13795 A1 | 7/1993 |
| WO | 1997/03185 A1 | 1/1997 |
| WO | 2003/040352 A1 | 5/2003 |
| WO | 2004/016248 A2 | 2/2004 |
| WO | 2005/078075 A2 | 8/2005 |
| WO | 2006/122835 A1 | 11/2006 |
| WO | 2007/147945 A1 | 12/2007 |
| WO | 2008/065247 A1 | 6/2008 |
| WO | 2011/148041 A1 | 12/2011 |
| WO | 2013011072 A1 | 1/2013 |
| WO | 2016/057744 A1 | 4/2016 |

OTHER PUBLICATIONS

Li et al. 2013; Biochemical characteristics of New Delhi metallo-beta-lactamase-1 show unexpected difference to other MBLs. PLoS ONE 8(4): e61914. doi: 10.1371/journal.pone.0061914.*

Yong et al. 2009; Characterization of a new metallo-beta-lactamse gene blaNDM-1, and a novel erythromycin esterase gene carried on a unique genetic structure in Klebsiella pneumonia sequence Type 14 from India. Antimicrobial Agents and Chemotherapy. 53(12): 5046-5054.*

Altschul et al., "Gapped BLAST and PSI-BLAST: A New Generation of Protein Database Search Programs," Nucleic Acids Research, 1997, vol. 25, No. 17, pp. 3389-3402.

Ambler et al., "A Standard Numbering Scheme for the Class A Beta-Lactamases," Biochem. J., 1991, 276, pp. 269-270.

(Continued)

*Primary Examiner* — Karen Cochrane Carlson

(74) *Attorney, Agent, or Firm* — Morgan, Lewis & Bockius LLP

(57) ABSTRACT

This invention relates, in part, to various compositions and methods for protecting the gastrointestinal microbiome from antibiotic disruption.

14 Claims, 48 Drawing Sheets

Specification includes a Sequence Listing.

(56) References Cited

OTHER PUBLICATIONS

Ambler, "the structure of β-lactamases," Phil. Trans. R. Soc. Lond. B 289: 321-331 (1980).
Bonnet, "Growing Group of Extended-Spectrum β-Lactamases: the CTX-M Enzymes," Antimicrob. Agents Chemother. 48(1):1-14 (2004).
Bonomo et al., "β-Lactamase mutations far from the active site influence inhibitor binding," Biochim. Biophys. Acta 1247:121-125 (1995).
Brogard et al., "Biliary Elimination of Ticarcillin Plus Clavulanic Acid (Ciaventin®)," Experimental and Clinical Study, International Journal of Clinical Pharmacology, Therapy and Toxicology, 1989, vol. 27, No. 3, pp. 135-144.
Broun et al., "Catalytic plasticity of fatty acid modification enzymes underlying chemical diversity of plant lipids," Science 1998, vol. 282: 1315-1317.
Bush et al., "A Functional Classification Scheme for β-Lactamases and Its Correlation with Molecular Structure," Antimicrobial Agents and Chemotherapy, Jun. 1995, vol. 39, No. 6, pp. 1211-1233.
Bush, "Metallo-β-Lactamases: A Class Apart," Clinical Infectious Diseases, 1998; 27(Suppl 1):S48-53.
Canica et al., "Phenotypic Study of Resistance of β-Lactamase-Inhibito-Resistant TEM Enzymes Which Differ by Naturally Occurring Variations and by Site-Directed Substitution at Asp276," Antimicrob. Agents Chemother. 42 (6):1323-1328 (1998).
Carfi et al., "1.85 Å Resolution Structure of the Zinc II β-Lactamase from Bacillus cereus," Acta Cryst. (1998) D54: 313-323.
Carfi et al., "The 3-D structure of a zinc metallo-β-lactamase from Bacillus cereus reveals a new type of protein fold," The EMBO Journal, 1995, vol. 14 No. 20: 4914-4921.
Carfi et al., "X-ray Structure of the Zn11 β-Lactamase from Bacteroides fragilis in an Orthorhombic Crystal Form," Acta. Cryst. (1998) D54: 47-57.
Chambliss, "The forgotten dosage form: enteric coated tablets," (1983) Pharm Technol 7, 124-140.
Chen et al.,"β-Lactamase Genes of the Penicillin-Susceptible Bacillus anthracis Sterne Strain," J. Bacteriol. 185 (3):823-830 (2003).
Chica et al., "Semi-rational approaches to engineering enzyme activity: combining the benefits of directed evolution and rational design," Curr. Opin. Biotechnol., 2005, vol. 16: 378-384.
Cole, "Hydrolysis of Penicillins and Related Compounds by the Cell-Bound Penicillin Acylase of *Escherichia coli*," (1969) Biochem. J. 115, 733-739.
Colombo et al., "The ybxl Gene of Bacillus Subtilis 168 Encodes a Class D β-Lactamase of Low Activity," Antimicrobial Agents and Chemotherapy, Feb. 2004, vol. 48, No. 2, pp. 484-490.
Concha et al., "Crystal Structure of the IMP-1 Metallo β-Lactamase from Pseudomonas aeruginosa and Its Complex with a Mercaptocarboxylate Inhibitor: Binding Determinants of a Potent, Broad-Spectrum Inhibitor," Biochemistry (2000) 39(15): 4288-4298.
Crawford, et al., "Over-expression, purification, and characterization of metallo-β-lactamase ImiS from Aeromonas veronii bv. sobria," Protein Expression and Purification 36 (2004) 272-279.
Davies and Abraham, "Separation, Purification and Properties of β-Lactamase I and β-Lactamase II from Bacillus cereus 569/H/9," (1974) Biochem. J. 143:115-127.
Delmas et al., "Structural Insights into Substrate Recognition and Product Expulsion in CTX-M Enzymes," J. Mol. Biol. 400:108-120 (2010).
Devos et al., "Practical limits of function prediction," Proteins: Structure, Function, and Genetics. 2000, vol. 41: 98-107.
Donskey, "Antibiotic Regimens and Intestinal Colonization with Antibiotic-Resistant Gram-Negative Bacilli," Clinical Infectious Diseases, 2006, 43 Suppl 2, pp. S62-69.
Drawz et al., "The Role of a Second-Shell Residue in Modifying Substrate and Inhibitor Interactions in the SHV β-Lactamase: A Study of Ambler Position Asn276," Biochem. 48(21):4557-4566 (2009).

Drawz, et al., "Three Decades of β-Lactamase Inhibitors," Clin Microbiol Rev., 2010, vol. 23, No. 1, pp. 160-201.
Fey et al., Cetriaxone-Resistant *Salmonella* Infection Acquired by a Child from Cattle, New England J. Med., 2000, 342,1242-1249.
Fonze et al., "Crystal Structures of the Bacillus Licheniformis BS3 Class A β-Lactamase and of the Acyl-Enzyme Adduct Formed with Cefoxitin," Biochemistry, 2002, 41, 1877-1885.
Galleni et al., "Standard Numbering Scheme for Class B β-Lactamases," Antimicrobial Agents and Chemotherapy, Mar. 2001, vol. 45, No. 3, pp. 660-663.
Garau et al., "Update of the Standard Numbering Scheme for Class B β-Lactamases," Guest Commentary, Antimicrobial Agents and Chemotherapy, Jul. 2004, pp. 2347-2349, vol. 48, No. 7.
Garau et al., "A Metallo-β-lactamase Enzyme in Action: Crystal Structures of the Monozinc Carbapenemase CphA and its Complex with Biapenem," J. Mol. Biol. (2005) 345, 785-795.
Gazouli et al., "Effect of substitution of Asn for Arg-276 in the cefotaxime-hydrolyzing class A β-lactamase CTX-M-4," FEMS Microbiol. Lett. 168:289-293 (1998).
Gebhard et al., "Mapping the Distribution of Conformational Information Throughout a Protein Sequence," J. Mol. Biol., 2006, 358, pp. 280-288.
Giakkoupi et al., "Aspartic acid for asparagine substitution at position 276 reduces susceptibility to mechanism-based inhibitors in SHV-1 and SHV-5 β-lactamases," J. Antimicrobial. Chemother. 43:23-29 (1999).
Harmoinen et al., "Enzymic Degradation of a β-Lactam Antibiotic, Ampicillin, in the Gut: A Novel Treatment Modality," Journal of Antimicrobial Chemotherapy, 2003,51, pp. 361-365.
Harmoinen et al., "Orally Administered Targeted Recombinant Beta-Lactamase Prevents Ampicillin-Induced Selective Pressure on the Gut Microbiota: A Novel Approach to Reducing Antimicrobial Resistance," Antimicrobial Agents and Chemotherapy, Jan. 2004, vol. 48, No. 1, pp. 75-79.
Hata et al., "Substrate Deacylation Mechanisms of Serine-β-lactamases," Biol. Pharm. Bull. 29:2151-2159 (2006).
Herzberg, "Refined Crystal Structure of β-Lactamase from *Staphylococcus aureus* PC1 at 2.0 Å Resolution," J. Mol. Biol. 217:701-719 (1991).
Higgins et al., "In Vitro Activities of the β-Lactamase Inhibitors Clavulanic Acid, Sulbactam, and Tazobactam Alone or in Combination with β-Lactams against Epidemiologically Characterized Multidrug-Resistant Acinetobacter baumannii Strains," Antimicrobial Agents and Chemotherapy, May 2004, vol. 48, No. 5, pp. 1586-1592.
Hirschi A et al. (Abstract) "Campylobacter pylori, Gastritis and Ulcus pepticum," Wien. Klin. Wsch. 14:493-497 (1987).
Horton et al., "Engineering hybrid genes without the use of restriction enzymes: gene splicing by overlap extension," 1989, Gene 77:61-68 (1989).
Huber et al. "Chapter 2. Preparative Methods for 7-Aminocephalosporanic Acid and 6-Aminopenicillanic Acid," (1972) In: Flynn E, ed. Cephalosporins and Penicillins. New York: Academic Press, 27-73.
Hyman, "Anaphylactic Shock After Therapy With Penicillinase," (1959) JAMA 169, 593-594.
Illing et al., "Use of integrational plasmid excision to identify cellular localization of gene expression during sporulation in Bacillus subtilis," J. Bacteriol. 172(12):6937-6941 (1990).
Iserhard et al., "Epidemiology and Treatment of Gastric Campylobacter pylori Infection: more Questions than Answers," (1990) Hepato-Gastroenterol 37, 38-44.
International Search Report PCT/US2015/000228, dated Apr. 19, 2016, 6 pages.
Izui et al., "Large Exopenicillinase, Initial Extracellular Form Detected in Cultures of Bacillus licheniformis," Biochemistry, 1980, 19, pp. 1882-1886.
Jones et al., Cefoperazone: A Review of its Antimicrobial Spectrum, β-Lactamase Stability, Enzyme Inhibition, and Other in Vitro Characteristics, 1983, Rev. Infectious Disease 5 S108-S126.
Kaleko, et al., "SYN-004, a Class A β-Lactamase Therapy for the Prevention of Antibiotic-Induced Disruption of Intestinal Microflora", Open Forum Infect Dis, Oct. 9, 2014, I (suppl 1): SI15-SI16.

(56) References Cited

OTHER PUBLICATIONS

Kato et al., "Nucleotide Sequence of the β-Lactamase Gene of *Alkalophilic bacillus* sp. Strain 170," J. Gen. Microbiol. 131:3317-3324 (1985).
Katz, "Probiotics for the Prevention of Antibiotic-associated Diarrhea and Clostridium difficile Diarrhea," J. Clin. Gastroenterol., Mar. 2006, vol. 40, No. 3, pp. 249-255.
Kim and Buyn, "Purification and properties of ampicillin acylase from Pseudomonas melanogenum," (1990) Biochim Biophys Acta 1040, 12-18.
Kim et al., "Construction of spore mutants of Bacillus subtilis for the development as a host for foreign protein production," Biotechnology Letters 23:999-1004 (2001).
Kisselev L., "Polypeptide release factors in prokaryotes and eukaryotes: same function, different structure," Structure, 2002, vol. 10: 8-9.
Knox and Moews, "β-Lactamase of Bacillus licheniformis 749/C: Refinement at 2 Å Resolution and Analysis of Hydration," J. Mol. Bioi., 1991, 220, pp. 435-455.
Knox, "Extended-spectrum and inhibitor-resistant TEM-Type β-lactamases: Mutations, Specificity, and Three-Dimensional Structure," Antimicrob. Agents Chemother., 1995, 39, 2593-2601.
Korhonen et al., "Milk Immunoglobulins and Complement Factors," British Journal of Nutrition, 2000, 84 Suppl 1, pp. S75-80.
Kropp et al., "Metabolism of Thienamycin and Related Carbapenem Antibiotics by the Renal Dipeptidase, Dehydropeptidase-I," (1982) Antimicrob Agents Chemother 22, 62-70.
Kumakura et al., "Metabolic Fate of Clavulanic Acid and BRL 28500 in the Rat and Dog," Chemotherapy (Tokyo), 1986, 34 Suppl 4, pp. 187-201.
Lambert et al., "Susceptibility of Campylobacter pyloridis to 20 antimicrobial agents," (1986) Antimicrob Agents Chemother 30, (210): 510-511.
Li et al., "Bottlenecks in the expression and secretion of heterologous proteins in Bacillus subtilis," Res. Microbiol. 155:605-610 (2004).
Lim et al., "Cloning, Nucleotide Sequence, and Expression of the Bacillus cereus 5/B/6 β-Lactamase II Structural Gene," J. Bacteriol. 170:2873-2878 (1988).
Madan, "Methods of preparing microcapsules: interfacial polymerization," (1978) Pharm Technol 2, 68-75.
Madgwick and Waley, "β-Lactamase I from Bacillus cereus," Biochem. J. 248(3):657-662 (1987).
Madonna et al., "Nucleotide sequence of the β-lactamase I gene of Bacillus cereus strains 569/H and 5/B," Nucl. Acids Res. 15(4):1877 (1987).
Mandell and Sande, "Chapter 46. Antimicrobial Agents," (1990) In: Goodman and Gilman's, The Pharmacological Basis of Therapeutics, 8th Edition. New York: Pergamon Press, 1065-1097.
Marciano et al., "Analysis of the plasticity of location of the Arg244 positive charge within the active site of the TEM-1 β-lactamase," Prot. Sci. 18:2080-2089 (2009).
Marmur, "A Procedure for the Isolation of Deoxyribonucleic Acid from Micro-organisms," J. Mol. Biol. (1961) 3: 208-218.
Matagne et al., "Catalytic properties of class A β-lactamases: efficiency and diversity," Biochem. J. 330:581-598 (1998).
Matagne et al., "Ragged N-termini and other Variants of Class A β-Lactamases Analysed by Chromatofocusing," Biochem. J., 1991, 273, pp. 503-510.
Mentula et al., "Inhibition of ampicillin-induced emergence of resistance in intestinal coliforms by targeted recombinant β-lactamase," International Journal of Antimicrobial Agents, (2004)24:555-561.
Mezes, et al., "Construction of penP delta 1, Bacillus licheniformis 749/C β-Lactamase Lacking Site for Lipoprotein Modification," The Journal of Biological Chemistry, 1993, vol. 258, No. 18, pp. 11211-11218.
O'Callaghan et al., "Novel Method for Detection of β-Lactamases by Using a Chromogenic Cephalosporin Substrate," Antimicrobial Agents and Chemotherapy, Apr. 1972, vol. 1, No. 4, pp. 283-288.
Pedraza-Reyes et al., "Temporal Regulation and Forespore-Specific Expression of the Spore Photoproduct Lyase Gene by Sigma-G RNA Polymerase during Bacillus subtilis Sporulation," J. Bacteriol. 176(13): 3983-3991. 1994.
Perez-Llarena et al., "Structure-function studies of arginine at position 276 in CTX-M β-lactamases," J. Antimicrob. Chemother. 61(4):792-797 (2008).
Pitout, (Abstract) "IPSAT P1A, a class A beta-lactamase therapy for the prevention of penicillin-induced disruption to the intestinal microflora," Current Opinion in investigational drugs (London, England: 2000) 10.8 (2009): 838-844.
Pluckthun and Knowles, "The consequence of of stepwise deletions from the signal-processing site of β-lactamase," J. Biol.Chem., 1987, vol. 262 (9): 3951-3957.
Rauws and Tytgat, "Cure of duodenal ulcer associated with eradication of Helicobacter pylori," (1990) Lancet 335, 1233-1235.
Rauws et al., "Campylobacter pyloridis-Associated Chronic Active Antral Gastritis," (1988) Gastroenterol 94, 33-40.
Rice et al., "β-Lactam Antibiotics and Gastrointestinal Colonization with Vancomycin-Resistant Enterococci," J. Infect. Dis., 2004, 189, pp. 1113-1118.
Sambrook and Russell. Molecular Cloning: A Laboratory Manual. "In vitro Amplification of DNA by the Polymerase Chain Reaction," vol. 2, Ch. 8, pp. 8.1-8.126. 2001.
Sande et al., "Chapter 44. Antimicrobial Agents," (1990) In: Goodman and Gilman's, The Pharmacological Basis of Therapeutics, 8th Edition. New York: Pergamon Press, 1018-1046.
Santillana et al., "Crystal structure of the carbapenemase OXA-24 reveals insights into the mechanism of carbapenem hydrolysis," Proc. Natl. Acad. Sci. USA, 104:5354-5359 (2007).
Santos et al., "Folding of an Abridged β-Lactamase," Biochemistry, 2004, 43, pp. 1715-1723.
Saunders et al., "Use of Chromosomal Integration in the Establishment and Expression of blaZ, a *Staphylococcus aureus* 62 -lactamase Gene, in Bacillus subtilis," J. Bacteriol. 157(3): 718-726. 1984.
Saves et al., "The Asparagine to Aspartic Acid Substitution at Position 276 of TEM-35 and TEM-36 Is Involved in the β-Lactamase Resistance to Clavulanic Acid," J. Biol. Chem. 270:18240-18245 (1995).
Sawa et al., (Abstract) "The Effect of Cefixime on Bacterial Flora in the Intestinal Tracts of Healthy Male Volunteers," (1985) Chemotherapy (Tokyo) 33, Suppl. 6, 169-180.
Sen et al., "Developments in directed evolution for improving enzyme functions," Appl. Biochem. Biotechnol., Aug. 18, 2007, vol. 143: 212-223.
Shimooka et al, (Abstract) "Absorption, Distribution, and Excretion of Sulbactam and Ampicillin after Intravenous Administration in Rats and Dogs," Chemotherapy (Tokyo), 1988, 36 Suppl 8, pp. 66-80.
Simm et al., "Characterization of Monomeric L1 Metallo-β-lactamase and the Role of the N-terminal Extension in Negative Cooperativity and Antibiotic Hydrolysis," The Journal of Biological Chemistry (Jul. 2002) vol. 277 No. 27: 24744-24752.
Sjolund et al., "Long-Term Persistence of Resistant *Enterococcus* Species after Antibiotics To Eradicate Helicobacter pylori," Ann. Intern. Med. 139:483-487 (2003).
Stiefel et al., "Oral Administration of β-Lactamase Preserves Colonization Resistance of Piperacillin-Treated Mice," J. Infect. Dis., 2003, 188, pp. 1605-1609.
Stiefel et al., "Orally Administered Recombinant Metallo-β-Lactamase Preserves Colonization Resistance of Piperacillin-Tazobactam-Treated Mice," Antimicrobial Agents and Chemotherapy, Dec. 2005, vol. 49, No. 12, pp. 5190-5191.
Stiefel, et al. "Gastrointestinal Colonization with a Cephalosporinase-Producing Bacteroides Species Preserves Colonization Resistance against Vancomycin-Resistant Enterococcus and Clostridium difficile in Cephalosporin-Treated Mice." Antimicrobial Agents and Chemotherapy, 2014, vol. 58, No. 8, pp. 4535-4542.
Sullivan et al., "Effect of Antimicrobial Agents on the Ecological Balance of Human Microflora," Lancet Infect. Dis., 2001, vol. 1, pp. 101-114.
Tarkkanen et al., "P1A Recombinant β-Lactamase Prevents Emergence of Antimicrobial Resistance in Gut Microflora of Healthy

(56) References Cited

OTHER PUBLICATIONS

Subjects during Intravenous Administration of Ampicillin," Antimicrob. Agents Chemother. 53:2455-2462 (2009).

Therapeutic Drugs (1991), Dollery C, ed. Edinburgh: Churchill Livingstone, "Ceftriaxone (sodium)," c 127-c133.

Tranier et al., "The High Resolution Crystal Structure for Class A β-Lactamase PER-1 Reveals the Bases for Its Increase in Breadth of Activity," J. Biol. Chem. 275:28075-28082 (2000).

Walsh et al., "Metallo-β-Lactamases: the Quiet before the Storm?" Clinical Microbiology Reviews (Apr. 2005) vol. 18 No. 2: 306-325.

Walther-Rasmussen et al., "Terminal truncations in AmpC β-lactamase from a clinical isolate of Pseudomonas aeruginosa," Eur. J. Biochem. (1999) 263: 478-485.

Westphal et al., "Assessment of Biliary Excretion of Piperacilin-Tazobactam in Humans," Antimicrobial Agents and Chemotherapy, Aug. 1997, vol. 41, No. 8, pp. 1636-1640.

Whisstock et al., "Prediction of protein function from protein sequence," Q. Rev. Biophysics., 2003, vol. 36 (3): 307-340.

Wildfeuer et al., "Pharmacokinetics of Sulbactam and Ampicillin Intravenously Applied in Combination to Healthy Volunteers and Patients", Arzneimittei-Forschung, 1988, vol. 38, No. 11, pp. 1640-1643.

Wishart et al., "A single mutation converts a novel phosphotyrosine binding domain into a dual-specificity phosphatase," J. Biol. Chem., 1995, vol. 270(45): 26782-26785.

Witkowski et al., "Conversion of β-ketoacyl synthase to a Malonyl Decarboxylase by replacement of the active cysteine with glutamine," Biochemistry, 1999, vol. 38: 11643-11650.

Database UniProtKB/Swiss-Prot: P00808 (BLAC_BACLI), 1986.

Girlich et al., "Value of the Modified Hodge Test for Detection o Emerging Carbapenemases in Enterobacteriaceae", Journal of Clinical Microbiology, 2012, vol. 50, No. 2, pp. 477-479.

Gerrits et al., Helicobacter Ppylori and Antimicrobial Resistance: Molecular Mechanism and Clinical Implications. The Lancet Infectious Disease, 2006, vol. 6, pp. 699-709.

International Search Report PCT/US2016/019129, dated Jun. 30, 2016, 4 pages.

International Search Report PCT/US2016/021152, dated Jun. 30, 2016, 4 pages.

Patel et al., "Status Report on Carbapenemases: Challenges and Prospects", Expert review of Anti-Infective Therapy, 2011, vol. 9, No. 5, pp. 555-570.

Garau et al. 2004; Update of the standard numbering scheme for class B b-lactamases. Antimicrobial Agents and Chemotherapy. 48(7): 2347-2349.

Yigit et al. 2001: Novel carbapenem-hydroyzing Beta-lactamase, KPC-1, from carbapenem-resistant strain of Klebsiella pneumoniae. Antimicrobial Agents and Chemotherapy. 45(4): 1151-1161.

\* cited by examiner

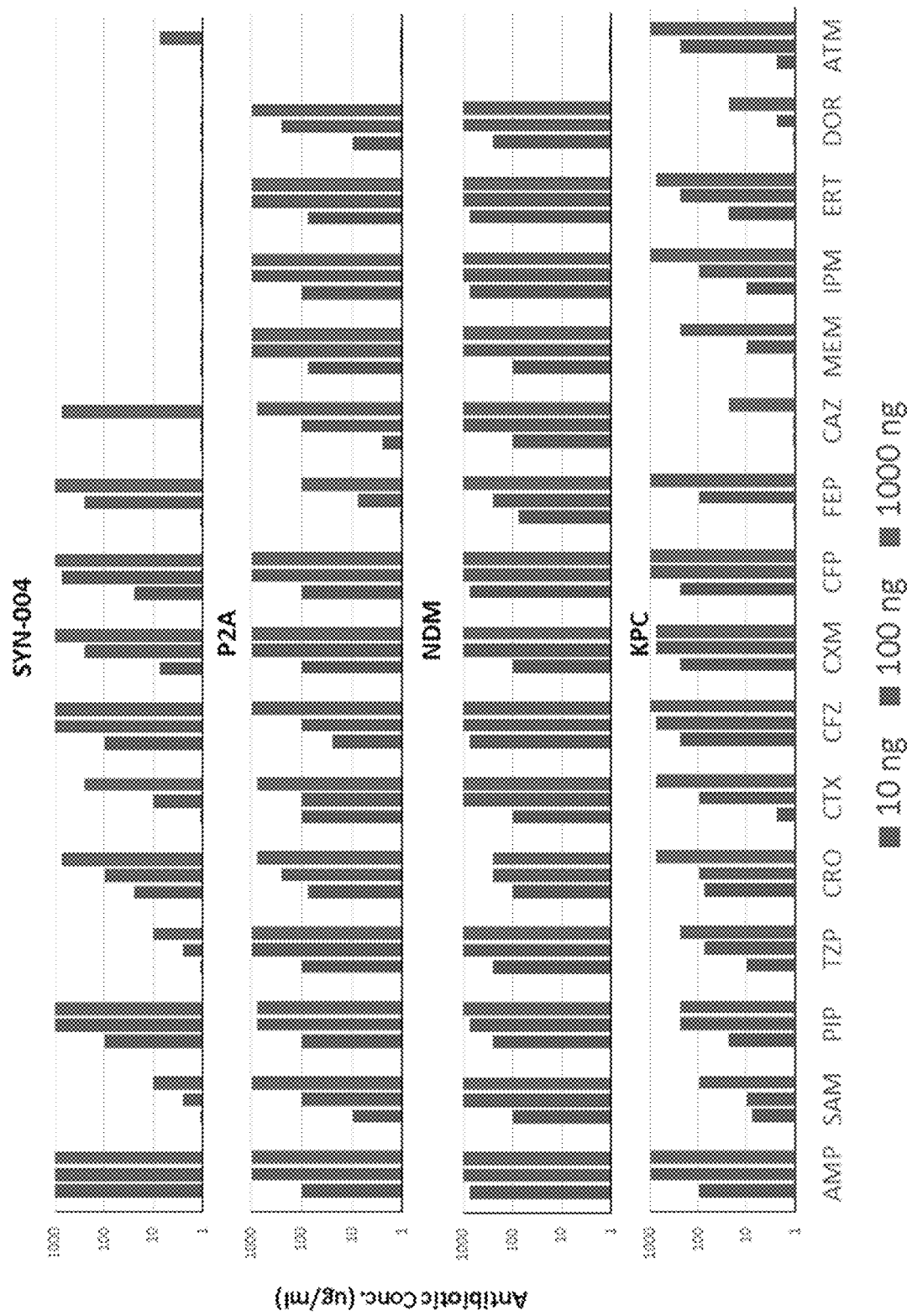

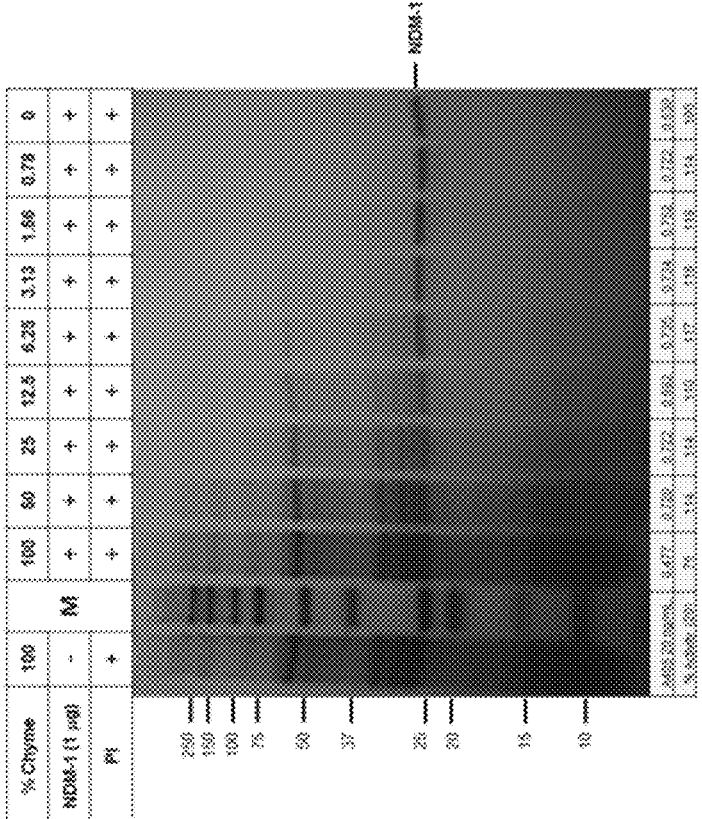
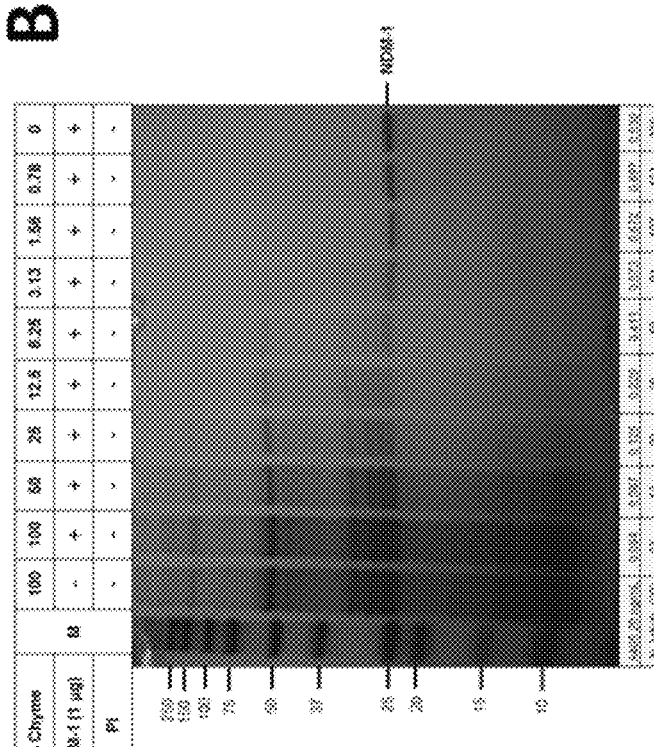
FIG. 25

FIG. 28

Full-Length NDM (24.8 kDa) with chyme cleavage sites indicated
GQQMETGDQRFGDLVFRQLAPNVWQHTSYLDMPGFGAVASNGLIVRDGGRVLVVDTAWTDDQTAQILNWIKQEINLP
VALAVVTHAHQDKMGGMDALHAAGIATYANALSNQLAPQEGMVAAQHSLTFAANGWVEPATAPNFGPLKVFYPGPGH
TSDNITVGIDGTDIAFGGCLIKDSKAKSLGNLGDADTEHYAASARAFGAAFPKASMIVMSHSAPDSRAAITHTARMA
DKLR (SEQ ID No:71)

SLTFA: Elastase cleavage site (SEQ ID No:77)
NLGDA: Chyme cleavage site (SEQ ID No:78)
Underline: additional chyme cleavage region corresponding to Fragment 2

FIG. 29

Fragment 1: 19.5 kDa
GQQMETGDQRFGDLVFRQLAPNVWQHTSYLDMPGFGAVASNGLIVRDGGRVLVVDTAWTDDQTAQILNWIKQEINLP
VALAVVTHAHQDKMGGMDALHAAGIATYANALSNQLAPQEGMVAAQHSLTFAANGWVEPATAPNFGPLKVFYPGPGH
TSDNITVGIDGTDIAFGGCLIKDSKAKSLG (SEQ ID No:72)

Fragment 3 and Fragment 6: 13.4 kDa
GQQMETGDQRFGDLVFRQLAPNVWQHTSYLDMPGFGAVASNGLIVRDGGRVLVVDTAWTDDQTAQILNWIKQEINLP
VALAVVTHAHQDKMGGMDALHAAGIATYANALSNQLAPQEGMVAAQH (SEQ ID No:73)

Fragment 4 and Fragment 7: 11.5 kDa
SLTFAANGWVEPATAPNFGPLKVFYPGPGHTSDNITVGIDGTDIAFGGCLIKDSKAKSLGNLGDADTEHYAASARAF
GAAFPKASMIVMSHSAPDSRAAITHTARMADKLR (SEQ ID No:74)

Fragment 5: 6.1 kDa
SLTFAANGWVEPATAPNFGPLKVFYPGPGHTSDNITVGIDGTDIAFGGCLIKDSKAKSLG (SEQ ID No:75)

Fragment 5: 5.4 kDa
NLGDADTEHYAASARAFGAAFPKASMIVMSHSAPDSRAAITHTARMADKLR (SEQ ID No:76)

FIG. 30

```
P2A         2   GTISISQLNKNVWRTELGYFNG--EAVPSNGLVLNTSKGLVLVDSSWDNKLTKELIEMVE    61
(SEQ ID No:37)  G +   QL  NVW HT       G  AV SNGL++      +++VD++W  +  T +++   ++
NDM        12   GDLVFRQLAPNVWQHTSYLDMPGFGAVASNGLIVRDGGRVLVVDTAWTDDQTAQILNWIK    71
(SEQ ID No:71)
P2A        62   KKFQKRVTDVIITHAHADRIGGITALKERGIKAHSTALTAELAKNSGY---KKPL-----   113
                ++   V   ++THAH D++GG+ AL   GI  ++ AL+ +LA   G    +  L
NDM        72   QEINLPVALAVVTHAHQDKMGGMDALHAAGIATYANALSNQLAPQEGMVAAQHSLTKAAN   131

P2A       114   GDLQTITSLKFGNTKVETFYPGKGHTEDNIVVWLPQYQILAGGCLVKSAEAKDLGNVADA   173
                G ++   T+  FG  KV  FYPG GHT DNI V +     I  GGCL+K  ++AK LGN+ DA
NDM       132   GWVEPATAPNFGPLKV--FYPGPGHTSDNITVGIDGTDIAFGGCLIKDSKAKSLGNLGDA   189

P2A       174   YVNEWSTSIENVLKRYGNINSVVPGHGEVGDKGLLLHT   211
                ++ S         +   + +V H      +  + HT
NDM       190   DTEHYAASARAFGAAFPKASMIVMSHSAPDSRAAITHT   227
```

CARBAPENEMASES FOR USE WITH ANTIBIOTICS FOR THE PROTECTION OF THE INTESTINAL MICROBIOME

PRIORITY

This application is a division of U.S. patent application Ser. No. 15/051,187, filed Feb. 23, 2016, which claims the benefit of and priority to U.S. Provisional Patent Application Nos. 62/119,602, filed Feb. 23, 2015, 62/155,621, filed May 1, 2015, and 62/190,806, filed Jul. 10, 2015, the entire contents of all of which are incorporated by reference herein.

FIELD OF THE INVENTION

This invention relates, in part, to various compositions and methods for protecting the gastrointestinal microbiome from antibiotic disruption.

DESCRIPTION OF THE TEXT FILE SUBMITTED ELECTRONICALLY

The contents of the text file submitted electronically herewith are incorporated herein by reference in their entirety. A computer readable format copy of the Sequence Listing (filename: SYN-010D1_SequenceListing.txt; date recorded: Jan. 9, 2018; file size: 145 KB).

BACKGROUND

The gastrointestinal (GI) tract, which houses over one thousand distinct bacterial species and an estimated excess of $1\times10^{14}$ microorganisms, appears to be central in defining human host health status and a key part of the microbiome. Disruption of this microbiome is believed to be causative of a number of disorders.

Indeed, antibiotics, often a frontline therapy to prevent deleterious effects of microbes on human health can induce disruption in the microbiome, including in the GI tract, and lead to further disease. For instance, beta-lactam antibiotics are excreted in the bile, which can damage the colonic microflora and lead to serious illnesses such as *Clostridium difficile* infection.

Current approaches to avoid this scenario include oral agents that degrade beta-lactam antibiotics in the small intestine to protect the microbiome. However, current therapies target only specific antibiotics and thus there is a need to expand the spectrum of these microbiome-sparing agents.

There remains a need for agents that prevent microbiome disruption by antibiotics while not reducing or eradicating the beneficial anti-infective effects of these antibiotics in a subject.

SUMMARY OF THE INVENTION

Accordingly, the present invention provides compositions and methods for protecting the gastrointestinal microbiome of a subject. In one aspect, methods for protecting the microbiome of the GI tract are provided in which an effective amount of a pharmaceutical composition comprising an antibiotic-degrading agent is administered to a subject who is undergoing treatment or has recently undergone treatment with an antibiotic, wherein the antibiotic-degrading agent is capable of inactivating or degrading or hydrolyzing the antibiotic. In some embodiments, the antibiotic-degrading agent is a broad spectrum carbapenemase, including, without limitation, P2A, NDM-1, and KPC-1/2.

In various embodiments, the antibiotic is a beta-lactam antibiotic, which may be administered orally or parenterally. In an embodiment, the antibiotic is administered intravenously.

In some aspects, the present invention is based, in part, on the discovery that one or more antibiotic-degrading agents (e.g. a broad spectrum carbapenemase such as P2A, NDM-1, and KPC-1/2) can be formulated to release in one or more locations within the GI tract at which the antibiotic-degrading agent inactivates (e.g. hydrolyzes) an orally or parenterally delivered antibiotic (e.g. a beta lactam antibiotic) and, in doing so, protects the microbiome. However, in some embodiments, the antibiotic-degrading agent does not interfere with intestinal absorption of the antibiotic and, accordingly, does not interfere with systemic blood or plasma levels of the antibiotic. For example, the antibiotic-degrading agent may hydrolyze excess or residual antibiotic that is not absorbed from the GI tract, e.g. after an oral dose, or is returned in active form to the intestinal tract from the systemic circulation, e.g. after an oral or parenteral dose. The invention further identifies the location of such antibiotic-degrading agent release or activation. By way of illustration, in some embodiments, the following two approaches may be employed separately or in combination: utilization of formulations designed to release antibiotic-degrading agent at the desired location in the GI tract and combining the antibiotic with an antibiotic-degrading agent inhibitor. In the latter, in some embodiments, the inhibitor tracks with the antibiotic and serves to protect the antibiotic from the antibiotic-degrading agent. As the concentration of inhibitor decreases, the antibiotic-degrading agent becomes active. Any residual or excess antibiotic that remains in the intestine or reenters with the bile is inactivated prior to encountering the colonic microbiome.

DESCRIPTION OF THE FIGURES

FIGS. 21A, 21B, and 21C show enzymatic activity. FIG. 21A shows a comparison of P3A (i.e. SYN-004), P2A, NDM, and KPC antibiotic inactivation activities via assessment of bacterial growth. The top graph displays the bacterial growth in the presence of 10 ng/ml of the beta-lactamase enzymes, the middle graph displays the bacterial growth in the presence of 100 ng/ml of the enzymes, and the bottom graph displays the bacterial growth in the presence of 1000 ng/ml of the enzymes. The abbreviations for the antibiotics are as follows: AMP: ampicillin, SAM: ampicillin/sulbactam, PIP: pipercillin, TZP: pipercillin/taxobactam, CRO: ceftriaxone, CTX: cefotaxime, CFZ: cefozolin, CXM: cefuroxime, CFP: cefoperazone, FEP: cefepime, CAZ: ceftazidime, MEM: meropenem, IPM: imipenem, ERT: ertapenem, DOR: doripenem, and ATM: aztreonam. The bar graphs are, left to right: SYN-004, P2A, NDM, and KPC, in series for each antibiotic. FIG. 21B displays same data as FIG. 21A, but with the addition of CDR: cefdinir; LEX:

cephalexin; and CAZ/AVI: cefoperazone/avibactam. FIG. 21C displays the same data as FIG. 21A grouped by beta-lactamase enzyme directly comparing the different enzyme concentrations. The bars are, left to right, 10 ng, 100 ng, and 100 ng, repeated for each antibiotic.

FIG. 25 shows biological activity of NDM incubated in dilutions of mixed human chyme with and without protease inhibitors. NDM at a concentration of 100 μg/mL was incubated in chyme dilutions, 100%, 50%, 25%, 12.5%, 6.25%, 3.13%, 1.56%, 0.78% and 0% without (Panel A) or with (Panel B) SigmaFAST protease inhibitors (PI) cocktail without EDTA according to the following table for 30 minutes at 37° C. Twenty microliters of each sample (2 μg) was removed and transferred to 20 μL of 2× denaturing sample buffer for a final concentration of 50 ng/μl. The samples were boiled and 10 μL (1 μg of NDM) subjected to analysis by SDS-PAGE. The remaining sample was evaluated for biological activity using the CENTA reagent. Biological activity of each sample is displayed under each gel.

FIG. 28 shows NDM amino acid sequence with chyme cleavage sites indicated. The chyme cleavage sites are indicated by boxes. The SLTFA site corresponds to the elastase cleavage site (Fragments 4, 5 and 7, Table 21 and FIG. 29). The NLGDA site corresponds to a chyme cleavage site (Fragment 5; Table 21 and FIG. 29). Fragment 2 (Table 21) has an N-terminus of the native NDM protein (GQQME; SEQ ID NO:70), however, the cleavage fragment (predicted to be between the elastase and the chyme cleavage sites, indicated by the underline) was not detected.

FIG. 29 shows the sequence of the NDM cleavage fragments. The NDM fragment numbers correspond to FIG. 27. Fragments 3 (chyme digestion) and Fragment 6 (elastase digestion) are the same fragments, as are Fragments 4 (chyme digestion) and Fragment 7 (elastase digestion). Fragment 5 contains at least two fragments of 6.1 and 5.4 kDa.

FIG. 30 shows a sequence alignment of P2A and NDM. The two mapped NDM cleavage sites are displayed in bold text, and the predicted cleavage area is displayed by underlining.

DETAILED DESCRIPTION

Figure 1:
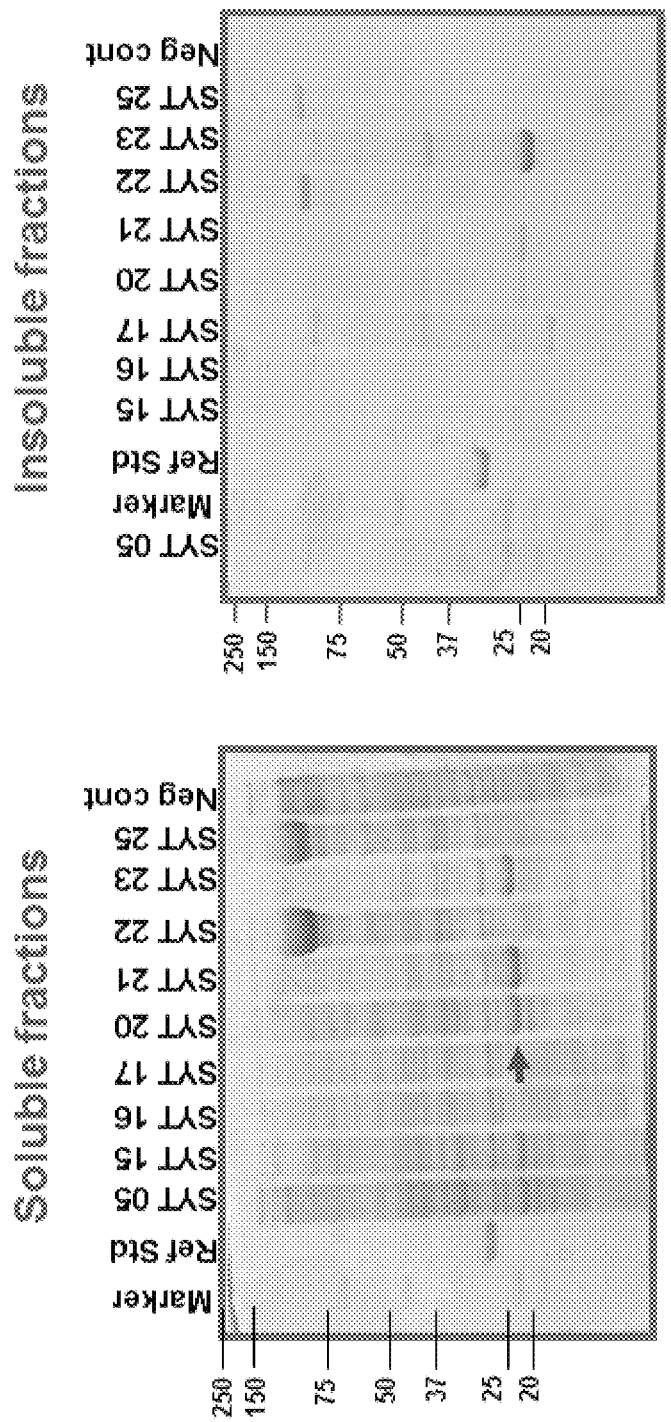
FIG. 1 shows P2A protein expression. Bacterial strains were grown in media supplemented with 100 μM $ZnSO_4$. Equal volumes of cell lysates from the soluble (left panel) or insoluble (right panel) fractions were analyzed by SDS-PAGE. The protein size marker was Precision Plus Protein Prestained Standards (Marker) (Bio-Rad), and the reference standard (Ref Std) was the beta-lactamase protein, P3A. Negative control was lysate from untransformed cells. The P2A product is indicated with an arrow.

The present invention is based, in part, on the discovery that antibiotic-degrading agents (for example, beta-lactamases such as carbapenemases) can protect the gastrointestinal microbiome of a subject who is undergoing treatment or has undergone treatment with an antibiotic. Administration of antibiotics often disrupts the ecological balance of normal intestinal microbiota due to residual unabsorbed antibiotics being excreted into the intestines (e.g., the distal small intestine and/or the large intestine). Antibiotic-degrading agents inactivate the unabsorbed antibiotics in the GI tract thereby restoring and/or maintaining the normal intestinal microbiota of a subject (e.g. a healthy balance (e.g. a healthy ratio and/or distribution)) and preventing any overgrowth of potentially pathogenic microorganisms.

Antibiotic-Degrading Agents and Pharmaceutical Compositions

The present invention is directed, in part, to pharmaceutical compositions, formulations, and uses of one or more antibiotic-degrading agents. As used herein, an antibiotic-degrading agent refers to a protein or an enzyme which degrades or inactivates antibiotics and renders the antibiotic biologically inactive. In various embodiments, the antibiotic-degrading agent is a beta-lactamase which degrades a broad spectrum of carbapenems and cephems. In an embodiment, the antibiotic-degrading agent is a broad spectrum carbapenemase.

Carbapenemases are a diverse group of beta-lactamases that are active not only against the oxyimino-cephalosporins and cephamycins but also against the carbapenems. The present invention contemplates the use of class A, B, C, and/or D carbapenemases. In illustrative embodiments, the carbapenemase may be a metallo-beta-lactamase or a serine-beta-lactamase. In various embodiments, the broad spectrum carbapenemase is selected from, for example, an IMP-type carbapenemases (metallo-beta-lactamases), VIMs (Verona integron-encoded metallo-beta-lactamases), OM (oxacillinase) group of beta-lactamases, KPCs (*Klebsiella pneumonia* carbapenemases), CMY (Class C), SME, IMI, NMC, GES (Guiana extended spectrum), CcrA, SFC-1, SHV-38, and NDM (New Delhi metallo-beta-lactamases, e.g. NDM-1) beta-lactamases.

In some embodiments, the broad spectrum carbapenemase is P2A or a derivative thereof, as described, for example, in WO 2007/147945, the entire contents of which are incorporated herein by reference. The P2A enzyme belongs to class B and is a metallo-enzyme that requires one or two zinc ions as a cofactor for enzyme activity. In an embodiment, the broad spectrum carbapenemase is P2A. The P2A enzyme may have at least about 60%, at least about 70%, at least about 80%, at least about 90%, at least about 95%, at least about 97%, at least about 98%, at least about 99%, or 100% identity to the following amino acid sequence:

P2A
(SEQ ID NO: 37)
ETGTISISQLNKNVWVHTELGYFNGEAVPSNGLVLNTSKGLVLVDSSWDN

KLTKELIEMVEKKFQKRVTDVIITHAHADRIGGITALKERGIKAHSTALT

AELAKNSGYEEPLGDLQTITSLKFGNTKVETFYPGKGHTEDNIVVWLPQY

QILAGGCLVKSAEAKDLGNVADAYVNEWSTSIENVLKRYGNINSVVPGHG

EVGDKGLLLHTLDLLK.

In some embodiments, the P2A is stable in human chyme, including, for example, the chyme of a patient in need of the present methods. In some embodiments, the P2A, optionally orally administered, degrades one or more of ampicillin, ceftriaxone, meropenem, and cefotaxime in the GI tract. In some embodiments, the P2A preserves the microbiome from susceptibility to antibiotics, e.g. by preventing alterations in the GI microflora as compared to subjects not receiving antibiotics. In some embodiments, the P2A finds use in preventing *C. difficile* infection (CDI) and/or a *C. difficile*-associated disease.

In some embodiments, the broad spectrum carbapenemase is a *Klebsiella pneumoniae* carbapenemase (KPC). Illustrative KPCs include, but are not limited to, KPC-1/2, KPC-3, KPC-4, KPC-5, KPC-6, KPC-7, KPC-8, KPC-9, KPC-10, KPC-11, KPC-12, KPC-13, KPC-14, KPC-15, and KPC-17. KPC-1 and KPC-2 enzymes have identical amino acid sequence and can be referred to as KPC-1, KPC-2, or KPC-1/2. In an embodiment, the broad spectrum carbapenemase is KPC-1/2. In an embodiment, the broad spectrum carbapenemase is KPC-3. The KPC enzymes may have at least about 60%, at least about 70%, at least about 80%, at least about 90%, at least about 95%, at least about 97%, at least about 98%, at least about 99%, or 100% identity to the following amino acid sequences:

KPC-1/2
(SEQ ID NO: 38)
MSLYRRLVLLSCLSWPLAGFSATALTNLVAEPFAKLEQDFGGSIGVYAMDTGSGATVSYRAEER

FPLCSSFKGFLAAAVLARSQQQAGLLDTPIRYGKNALVPWSPISEKYLTTGMTVAELSAAAVQYS

DNAAANLLLKELGGPAGLTAFMRSIGDTTFRLDRWELELNSAIPSDARDTSSPRAVTESLQKLTL

GSALAAPQRQQFVDWLKGNTIGNHRIRAAVPADWAVGDKTGTCGVYGTANDYAVVWPTGRA

PIVLAVYTRAPNKDDKHSEAVIAAAARLALEGLGVNGQ.

KPC-3
(SEQ ID NO: 39)
MSLYRRLVLLSCLSWPLAGFSATALTNLVAEPFAKLEQDFGGSIGVYAMDTGSGATVSYRAEER

FPLCSSFKGFLAAAVLARSQQQAGLLDTPIRYGKNALVPWSPISEKYLTTGMTVAELSAAAVQYS

DNAAANLLLKELGGPAGLTAFMRSIGDTTFRLDRWELELNSAIPGDARDTSSPRAVTESLQKLTL

GSALAAPQRQQFVDWLKGNTIGNHRIRAAVPADWAVGDKTGTCGVYGTANDYAVVWPTGRA

PIVLAVYTRAPNKDDKYSEAVIAAAARLALEGLGVNGQ

KPC-4
(SEQ ID NO: 40)
MSLYRRLVLLSCLSWPLAGFSATALTNLVAEPFAKLEQDFGGSIGVYAMDTGSGATVSYRAEER

FPLCSSFKGFLAAAVLARSQQQAGLLDTPIRYGKNALVRWSPISEKYLTTGMTVAELSAAAVQY

SDNAAANLLLKELGGPAGLTAFMRSIGDTTFRLDRWELELNSAIPGDARDTSSPRAVTESLQKLT

LGSALAAPQRQQFVDWLKGNTTGNHRIRAAVPADWAVGDKTGICGGYGTANDYAVVWPTGR

APIVLAVYTRAPNKDDKHSEAVIAAAARLALEGLGVNGQ

KPC-5
(SEQ ID NO: 41)
MSLYRRLVLLSCLSWPLAGFSATALTNLVAEPFAKLEQDFGGSIGVYAMDTGSGATVSYRAEER

FPLCSSFKGFLAAAVLARSQQQAGLLDTPIRYGKNALVRWSPISEKYLTTGMTVAELSAAAVQY

SDNAAANLLLKELGGPAGLTAFMRSIGDTTFRLDRWELELNSAIPGDARDTSSPRAVTESLQKLT

LGSALAAPQRQQFVDWLKGNTTGNHRIRAAVPADWAVGDKTGTCGVYGTANDYAVVWPTGR

APIVLAVYTRAPNKDDKHSEAVIAAAARLALEGLGVNGQ

KPC-6
(SEQ ID NO: 42)
MSLYRRLVLLSCLSWPLAGFSATALTNLVAEPFAKLEQDFGGSIGVYAMDTGSGATVSYRAEER

FPLCSSFKGFLAAAVLARSQQQAGLLDTPIRYGKNALVPWSPISEKYLTTGMTVAELSAAAVQYS

DNAAANLLLKELGGPAGLTAFMRSIGDTTFRLDRWELELNSAIPGDARDTSSPRAVTESLQKLTL

GSALAAPQRQQFVDWLKGNTTGNHRIRAAVPADWAVGDKTGICGGYGTANDYAVVWPTGRA

PIVLAVYTRAPNKDDKHSEAVIAAAARLALEGLGVNGQ

KPC-7
(SEQ ID NO: 43)
MSLYRRLVLLSCLSWPLAGFSATALTNLVAEPFAKLEQDFGGSIGVYAIDTGSGATVSYRAEERF

PLCSSFKGFLAAAVLARSQQQAGLLDTPIRYGKNALVPWSPISEKYLTTGMTVAELSAAAVQYS

DNAAANLLLKELGGPAGLTAFMRSIGDTTFRLDRWELELNSAIPGDARDTSSPRAVTESLQKLTL

GSALAAPQRQQFVDWLKGNTIGNHRIRAAVPADWAVGDKTGTCGVYGTANDYAVVWPTGRA

PIVLAVYTRAPNKDDKYSEAVIAAAARLALEGLGVNGQ

KPC-8
(SEQ ID NO: 44)
MSLYRRLVLLSCLSWPLAGFSATALTNLVAEPFAKLEQDFGGSIGVYAMDTGSGATVSYRAEER

FPLCSSFKGFLAAAVLARSQQQAGLLDTPIRYGKNALVPWSPISEKYLTTGMTVAELSAAAVQYS

DNAAANLLLKELGGPAGLTAFMRSIGDTTFRLDRWELELNSAIPGDARDTSSPRAVTESLQKLTL

-continued

GSALAAPQRQQFVDWLKGNTTGNHRIRAAVPADWAVGDKTGICGGYGTANDYAVVWPTGRA

PIVLAVYTRAPNKDDKYSEAVIAAAARLALEGLGVNGQ

KPC-9
(SEQ ID NO: 45)
MSKYRRLVLLSCLSWPLAGFSATALTNLVAEPFAKLEQDFGGSIGVYAMDTGSGATVSYRAEER

FPLCSSFKGFLAAAVLARSQQQAGLLDTPIRYGKNALVPWSPISEKYLTTGMTVAELSAAAVQYS

DNAAANLLLKELGGPAGLTAFMRSIGDTTFRLDRWELELNSAIPGDARDTSSPRAVTESLQKLTL

GSALAAPQRQQFVDWLKGNTIGNHRIRAAVPADWAVGDKTGICGAYGTANDYAVVWPTGRA

PIVLAVYTRAPNKDDKYSEAVIAAAARLALEGLGVNGQ

KPC-10 (*Acinetobacter baumannii*)
(SEQ ID NO: 46)
MSLYRRLVLLSCLSWPLAGFSATALTNLVAEPFAKLEQDFGGSIGVYAMDTGSGATVSYRAEER

FPLCSSFKGFLAAAVLARSQQQAGLLDTPIRYGKNALVRWSPISEKYLTTGMTVAELSAAAVQY

SDNAAANLLLKELGGPAGLTAFMRSIGDTTFRLDRWELELNSAIPGDARDTSSPRAVTESLQKLT

LGSALAAPQRQQFVDWLKGNTTGNHRIRAAVPADWAVGDKTGTCGVYGTANDYAVVWPTGR

APIVLAVYTRAPNKDDKYSEAVIAAAARLALEGLGVNGQ

KPC-11
(SEQ ID NO: 47)
MSLYRRLVLLSCLSWPLAGFSATALTNLVAEPFAKLEQDFGGSIGVYAMDTGSGATVSYRAEER

FPLCSSFKGFLAAAVLARSQQQAGLLDTPIRYGKNALVLWSPISEKYLTTGMTVAELSAAAVQYS

DNAAANLLLKELGGPAGLTAFMRSIGDTTFRLDRWELELNSAIPGDARDTSSPRAVTESLQKLTL

GSALAAPQRQQFVDWLKGNTIGNHRIRAAVPADWAVGDKTGICGVYGTANDYAVVWPTGRA

PIVLAVYTRAPNKDDKHSEAVIAAAARLALEGLGVNGQ

KPC-12 (*Klebsiella pneumonia*)
(SEQ ID NO: 48)
MSLYRRLVLLSCLSWPLAGFSATALTNLVAEPFAKLEQDFGGSIGVYAMDTGSGATVSYRAEER

FPLCSSFKGFLAAAVLARSQQQAGLLDTPIRYGKNALVPWSPISEKYLTTGMTVAELSAAAVQYS

DNAAANLLLKELGGPAGLTAFMRSIGDTTFRLDRWELEMNSAIPGDARDTSSPRAVTESLQKLT

LGSALAAPQRQQFVDWLKGNTTGNHRIRAAVPADWAVGDKTGTCGVYGTANDYAVVWPTGR

APIVLAVYTRAPNKDDKHSEAVIAAAARLALEGLGVNGQ

KPC-13 (*Enterobacter cloacae*)
(SEQ ID NO: 49)
MSLYRRLVLLSCLSWPLAGFSATALTNLVAEPFAKLEQDFGGSIGVYAMDTGSGATVSYRAEER

FPLCSSFKGFLAAAVLARSQQQAGLLGTPIRYGKNALVPWSPISEKYLTTGMTVAELSAAAVQY

SDNAAANLLLKELGGPAGLTAFMRSIGDTTFRLDRWELELNSAIPGDARDTSSPRAVTESLQKLT

LGSALAAPQRQQFVDWLKGNTTGNHRIRAAVPADWAVGDKTGTCGVYGTANDYAVVWPTGR

APIVLAVYTRAPNKDDKYSEAVIAAAARLALEGLGVNGQ

KPC-14 (*Klebsiella pneumoniae*)
(SEQ ID NO: 50)
MSLYRRLVLLSCLSWPLAGFSATALTNLVAEPFAKLEQDFGGSIGVYAMDTGSGATVSYRAEER

FPLCSSFKGFLAAAVLARSQQQAGLLDTPIRYGKNALVPWSPISEKYLTTGMTVAELSAAAVQYS

DNAAANLLLKELGGPAGLTAFMRSIGDTTFRLDRWELELNSAIPGDARDTSSPRAVTESLQKLTL

GSALAAPQRQQFVDWLKGNTTGNHRIRAAVPADWAVGDKTGTCGVYANDYAVVWPTGRAPIV

LAVYTRAPNKDDKHSEAVIAAAARLALEGLGVNGQ

```
KPC-15 (Klebsiella pneumoniae)
                                                       (SEQ ID NO: 51)
MSLYRRLVLLSCLSWPLAGFSATALTNLVAEPFAKLEQDFGGSIGVYAMDTGSGATVSYRAEER

FPLCSSFKGFLAAAVLARSQQQAGLLDTPIRYGKNALVRWSPISEKYLTTGMTVLELSAAAVQYS

DNAAANLLLKELGGPAKLTAFMRSIGDTTFRLDRWELELNSAIPGDARDTSSPRAVTESLQKLTL

GSALAAPQRQQFVDWLKGNTTGNHRIRAAVPADWAVGDKTGICGGYGTANDYAVVWPTGRA

PIVLAVYTRAPNKDDKYSEAVIAAAARLALEGLGVNGQ

KPC-17 (Klebsiella pneumoniae)
                                                       (SEQ ID NO: 52)
MSLYRRLVLLSCLSWPLAGFSATALTNLVAEPFAKLEQDFGGSIGVYAMDTGSGATVSYRAEER

FPLCSSFKGFLAAAVLARSQQQAGLLDTPIRYGKNALVPWSPISEKYLTTGMTVAELSAAAVQYS

DNAAANLLLKELGGPAGLTAFMRSIGDTTFRLDRWELELNSAIPGDARDTSSPRAVTESLQKLTL

GSALAAPQRQQLVDWLKGNTIGNHRIRAAVPADWAVGDKTGICGVYGTANDYAVVWPTGRA

PIVLAVYTRAPNKDDKHSEAVIAAAARLALEGLGVNGQ
```

In some embodiments, the broad spectrum carbapenemase is a New Delhi metallo-β-lactamase (NDM). Illustrative NDMs include, but are not limited to, NDM-1, NDM-2, NDM-3, NDM-4, NDM-5, NDM-6, NDM-7, NDM-8, NDM-9, NDM-10, NDM-11, NDM-12, and NDM-13. In an embodiment, the broad spectrum carbapenemase is NDM-1. In an embodiment, the broad spectrum carbapenemase is NDM-4. The NDM enzymes may have at least about 60%, at least about 70%, at least about 80%, at least about 90%, at least about 95%, at least about 97%, at least about 98%, at least about 99%, or 100% identity to the following amino acid sequences:

```
NDM-1
                                                       (SEQ ID NO: 53)
MELPNIMHPVAKLSTALAAALMLSGCMPGEIRPTIGQQMETGDQRFGDLVFRQLAPNVWQHTS

YLDMPGFGAVASNGLIVRDGGRVLVVDTAWTDDQTAQILNWIKQEINLPVALAVVTHAHQDKMG

GMDALHAAGIATYANALSNQLAPQEGMVAAQHSLTFAANGWVEPATAPNFGPLKVFYPGPGHT

SDNITVGIDGTDIAFGGCLIKDSKAKSLGNLGDADTEHYAASARAFGAAFPKASMIVMSHSAPDS

RAAITHTARMADKLR

NDM-2 (Acinetobacter baumannii)
                                                       (SEQ ID NO: 54)
MELPNIMHPVAKLSTALAAALMLSGCMAGEIRPTIGQQMETGDQRFGDLVFRQLAPNVWQHTS

YLDMPGFGAVASNGLIVRDGGRVLVVDTAWTDDQTAQILNWIKQEINLPVALAVVTHAHQDKMG

GMDALHAAGIATYANALSNQLAPQEGMVAAQHSLTFAANGWVEPATAPNFGPLKVFYPGPGHT

SDNITVGIDGTDIAFGGCLIKDSKAKSLGNLGDADTEHYAASARAFGAAFPKASMIVMSHSAPDS

RAAITHTARMADKLR

NDM-3 (E coli)
                                                       (SEQ ID NO: 55)
MELPNIMHPVAKLSTALAAALMLSGCMPGEIRPTIGQQMETGDQRFGDLVFRQLAPNVWQHTS

YLDMPGFGAVASNGLIVRDGGRVLVVDTAWINDQTAQILNWIKQEINLPVALAVVTHAHQDKMG

GMDALHAAGIATYANALSNQLAPQEGMVAAQHSLTFAANGWVEPATAPNFGPLKVFYPGPGHT

SDNITVGIDGTDIAFGGCLIKDSKAKSLGNLGDADTEHYAASARAFGAAFPKASMIVMSHSAPDS

RAAITHTARMADKLR

NDM-4 (E coli)
                                                       (SEQ ID NO: 56)
MELPNIMHPVAKLSTALAAALMLSGCMPGEIRPTIGQQMETGDQRFGDLVFRQLAPNVWQHTS

YLDMPGFGAVASNGLIVRDGGRVLVVDTAWTDDQTAQILNWIKQEINLPVALAVVTHAHQDKMG

GMDALHAAGIATYANALSNQLAPQEGLVAAQHSLTFAANGWVEPATAPNFGPLKVFYPGPGHT
```

-continued

SDNITVGIDGTDIAFGGCLIKDSKAKSLGNLGDADTEHYAASARAFGAAFPKASMIVMSHSAPDS

RAAITHTARMADKLR

NDM-5 (*E coli*)
(SEQ ID NO: 57)
MELPNIMHPVAKLSTALAAALMLSGCMPGEIRPTIGQQMETGDQRFGDLVFRQLAPNVWQHTS

YLDMPGFGAVASNGLIVRDGGRVLLVDTAWTDDQTAQILNWIKQEINLPVALAVVTHAHQDKMG

GMDALHAAGIATYANALSNQLAPQEGLVAAQHSLTFAANGWVEPATAPNFGPLKVFYPGPGHT

SDNITVGIDGTDIAFGGCLIKDSKAKSLGNLGDADTEHYAASARAFGAAFPKASMIVMSHSAPDS

RAAITHTARMADKLR

NDM-6 (*E coli*)
(SEQ ID NO: 58)
MELPNIMHPVAKLSTALAAALMLSGCMPGEIRPTIGQQMETGDQRFGDLVFRQLAPNVWQHTS

YLDMPGFGAVASNGLIVRDGGRVLVVDTAWTDDQTAQILNWIKQEINLPVALAVVTHAHQDKMG

GMDALHAAGIATYANALSNQLAPQEGMVAAQHSLTFAANGWVEPATAPNFGPLKVFYPGPGHT

SDNITVGIDGTDIAFGGCLIKDSKAKSLGNLGDADTEHYAASVRAFGAAFPKASMIVMSHSAPDS

RAAITHTARMADKLR

NDM-7 (*E coli*)
(SEQ ID NO: 59)
MELPNIMHPVAKLSTALAAALMLSGCMPGEIRPTIGQQMETGDQRFGDLVFRQLAPNVWQHTS

YLDMPGFGAVASNGLIVRDGGRVLVVDTAWTDDQTAQILNWIKQEINLPVALAVVTHAHQDKMG

GMNALHAAGIATYANALSNQLAPQEGLVAAQHSLTFAANGWVEPATAPNFGPLKVFYPGPGHT

SDNITVGIDGTDIAFGGCLIKDSKAKSLGNLGDADTEHYAASARAFGAAFPKASMIVMSHSAPDS

RAAITHTARMADKLR

NDM-8 (*E coli*)
(SEQ ID NO: 60)
MELPNIMHPVAKLSTALAAALMLSGCMPGEIRPTIGQQMETGDQRFGDLVFRQLAPNVWQHTS

YLDMPGFGAVASNGLIVRDGGRVLVVDTAWTDDQTAQILNWIKQEINLPVALAVVTHAHQDKMG

GMGALHAAGIATYANALSNQLAPQEGLVAAQHSLTFAANGWVEPATAPNFGPLKVFYPGPGHT

SDNITVGIDGTDIAFGGCLIKDSKAKSLGNLGDADTEHYAASARAFGAAFPKASMIVMSHSAPDS

RAAITHTARMADKLR

NDM-9 (*Klebsiella pneumoniae*)
(SEQ ID NO: 61)
MELPNIMHPVAKLSTALAAALMLSGCMPGEIRPTIGQQMETGDQRFGDLVFRQLAPNVWQHTS

YLDMPGFGAVASNGLIVRDGGRVLVVDTAWTDDQTAQILNWIKQEINLPVALAVVTHAHQDKMG

GMDALHAAGIATYANALSNQLAPQKGMVAAQHSLTFAANGWVEPATAPNFGPLKVFYPGPGHT

SDNITVGIDGTDIAFGGCLIKDSKAKSLGNLGDADTEHYAASARAFGAAFPKASMIVMSHSAPDS

RAAITHTARMADKLR

NDM-10 (*Klebsiella pneumoniae* subsp. *Pneumoniae*)
(SEQ ID NO: 62)
MELPNIMHPVAKLSTALAAALMLSGCMPGEISPTIDQQMETGDQRFGDLVFRQLAPNVWQHTS

YLDMPSFGAVTSNGLIVRDGGRVLVVDTAWTDDQTAQILNWIKQEINLPVALAVVTHAHQDKMG

GMDALHAAGIATYANALSNQLAPQEGMVAAQHSLTFAANGWVEPATAPNFGPLKVFYPGPGHT

SDNITVGIDRTDIAFGGCLIKDSKAKSLGNLGDADTEHYAASARAFGAAFPKASMIVMSHSAPDS

RAAITHTARMADKLR

NDM-11
(SEQ ID NO: 63)
MELPNIMHPVAKLSTALAAALMLSGCMPGEIRPTIGQQMETGDQRFGDLVFRQLAPNVWQHTS

YLDMPGFGAVASNGLIVRDGGRVLVVDTAWTDDQTAQILNWIKQEINLPVALAVVTHAHQDKMG

GMDALHAAGIATYANALSNQLAPQEGLVAAQHSLTFAANGWVEPATAPNFGPLKVFYPGPGHT

SDNITVGIDGTDIAFGGCLIKDSKAKSLGNLDDADTEHYAASARAFGAAFPKASMIVMSHSAPDS

RAAITHTARMADKLR

NDM-12
(SEQ ID NO: 64)
MELPNIMHPVAKLSTALAAALMLSGCMPGEIRPTIGQQMETGDQRFGDLVFRQLAPNVWQHTS

YLDMPGFGAVASNGLIVRDGGRVLVVDTAWTDDQTAQILNWIKQEINLPVALAVVTHAHQDKMG

GMDALHAAGIATYANALSNQLAPQEGLVAAQHSLTFAANGWVEPATAPNFGPLKVFYPGPGHT

SDNITVGIDGTDIAFGGCLIKDSKAKSLGNLDDADTEHYAASARAFGAAFPKASMIVMSH

SAPDSRAAITHTARMADKLR

NDM-13
(SEQ ID NO: 65)
MELPNIMHPVAKLSTALAAALMLSGCMPGEIRPTIGQQMETGDQRFGDLVFRQLAPNVWQHTS

YLDMPGFGAVASNGLIVRDGGRVLVVDTAWINDQTAQILNWIKQEINLPVALAVVTHAHQDKMG

GMDALHAAGIATYANALSNQLAPQEGLVAAQHSLTFAANGWVEPATAPNFGPLKVFYPGPGHT

SDNITVGIDGTDIAFGGCLIKDSKAKSLGNLGDADTEHYAASARAFGAAFPKASMIVMSH

SAPDSRAAITHTARMADKLR

In some embodiments, the broad spectrum carbapenemase is an IMP-type carbapenemase. Illustrative IMP-type enzymes include, but are not limited to, IMP-1, IMP-4, IMP-8, IMP-11, IMP-43 and IMP-44. Additional IMP-type enzymes are described in, for example, Queenan et al. (2007) Clin. Microbiol. Rev. 20(3):440-458, the entire disclosure of which is incorporated herein by reference in its entirety.

In some embodiments, the broad spectrum carbapenemase is a VIM (Verona integron-encoded metallo-beta-lactamase). Illustrative VIM enzymes include, but are not limited to, VIM-1, VIM-2, VIM-3, VIM-4, and VIM-19. Additional VIM enzymes are described in, for example, Queenan et al. (2007) Clin. Microbiol. Rev. 20(3):440-458, the entire disclosure of which is incorporated herein by reference in its entirety.

In some embodiments, the broad spectrum carbapenemase is an OXA (oxacillinase) group of beta-lactamase. Illustrative OXA beta-lactamases include, but are not limited to, OXA-23, OXA-24, OXA-27, OXA-40, OXA-48, OXA-49, OXA-50, OXA-51, OXA-58, OXA-64, OXA-71, and OXA-181. Additional OXA type carbapenemases are described in, for example, Walther-Rasmussen et al., Journal of Antimicrobial Chemotherapy (2006), 57:373-383 and Queenan et al. (2007) Clin. Microbiol. Rev. 20(3):440-458, the entire disclosures of which are incorporated herein by reference in their entireties.

In some embodiments, the broad spectrum carbapenemase is a CMY (class C carbapenemase) enzyme. An illustrative CMY enzyme with carbapenemase activity is CMY-10, as described in, for example, Lee et al., (2006) Research Journal of Microbiology (1):1-22, the entire disclosure of which is incorporated herein by reference in its entirety.

In some embodiments, the broad spectrum carbapenemase is a SME enzyme (for Serratia marcescens). Illustrative SME enzymes include, but are not limited to, SME-1, SME-2, or SME-3, as described in, for example, Queenan et al. (2007) Clin. Microbiol. Rev. 20(3):440-458, the entire disclosure of which is incorporated herein by reference in its entirety.

In some embodiments, the broad spectrum carbapenemase is an IMI enzyme (imipenem hydrolyzing beta-lactamase). Illustrative IMI enzymes include, but are not limited to, IMI-1 or IMI-2, as described in, for example, Queenan et al. (2007) Clin. Microbiol. Rev. 20(3):440-458, the entire disclosure of which is incorporated herein by reference in its entirety.

In some embodiments, the broad spectrum carbapenemase is a NMC enzyme (not metalloenzyme carbapenemase). An illustrative NMC enzyme is NMC-A, as described in, for example, Queenan et al. (2007) Olin. Microbiol. Rev. 20(3):440-458, the entire disclosure of which is incorporated herein by reference in its entirety.

In some embodiments, the broad spectrum carbapenemase is a GES enzyme (Guiana extended spectrum). Illustrative GES enzymes include, but are not limited to, GE-2, GES-4, GES-5, GES-6, GES-7, GES-8, GES-9, GES-11, GES-14, and GES-18 as described in, for example, Queenan et al. (2007) Clin. Microbiol. Rev. 20(3):440-458 and Johnson of al., (2014) Crystal Structures of Class A, B, and D β-Lactamases http://www.carbapenemase.ca/crystal_structures.html, the entire disclosures of which are incorporated herein by reference in their entireties.

In some embodiments, the broad spectrum carbapenemase is the CcrA (CfiA) metallo-beta-lactamase.

In some embodiments, the broad spectrum carbapenemase is the SFC-1 enzyme from Serratia fonticola or SHV-38 enzyme from K. pneumoniae, as described in, for example, Walther-Rasmussen of al., (2007) Journal of Antimicrobial Chemotherapy, 60:470-482.

In some embodiments, mutagenesis or modification of an antibiotic-degrading agent is performed to derive advantageous enzymes to be utilized by methods of the present invention. For example, mutagenesis or modification may be carried out to derive antibiotic-degrading agents with improved enzymatic activity or expand the spectrum of antibiotics that are degraded by the enzyme. In some embodiments, derivatives of the antibiotic-degrading agent are obtained by site-directed mutagenesis, random mutagenesis, structure-activity analysis, and/or directed evolution approaches. For example, in some embodiments, mutational design is based on structural data (e.g. crystal structure data, homolog models, etc.) which are available to one skilled in the art at known databases, for example, Swiss-Prot Protein Sequence Data Bank, NCBI, and PDB.

In some embodiments, the antibiotic-degrading agent includes one or more (e.g. about 1, or about 2, or about 3, or about 4, or about 5, or about 6, or about 7, or about 8, or about 9, or about 10, or about 15, or about 20, or about 30, or about 40, or about 50, or about 60, or about 70, or about 80, or about 90, or about 100, or about 110, or about 120, or about 130, or about 140, or about 150) mutations relative to the wild-type sequence of the agent. In some embodiments, the antibiotic-degrading agent may include a sequence with at least 30%, 35%, 40%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.8%, or 99.9% identity relative to the wild-type sequence of the agent (or about 60%, about 65%, about 70%, about 75%, about 80%, about 85%, about 90%, about 95%, about 96%, about 97%, about 98%, or about 99% identity to the wild-type sequence of the agent). Percent identity may be assessed with conventional bioinformatic methods.

In some embodiments, the antibiotic-degrading agent includes one or more (e.g. about 1, or about 2, or about 3, or about 4, or about 5, or about 6, or about 7, or about 8, or about 9, or about 10, or about 15, or about 20, or about 30, or about 40, or about 50, or about 60, or about 70, or about 80, or about 90, or about 100, or about 110, or about 120, or about 130, or about 140, or about 150) mutations relative to SEQ ID NOS: 19-39, 37-65, 66, or 68 as disclosed herein. In some embodiments, the antibiotic-degrading agent may include a sequence with at least 30%, 35%, 40%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.8%, or 99.9% identity relative to the wild-type sequence of the agent (or about 60%, about 65%, about 70%, about 75%, about 80%, about 85%, about 90%, about 95%, about 96%, about 97%, about 98%, or about 99% identity to SEQ ID NOS: 19-39, 37-65, 66, or 68.

In various embodiments, the antibiotic-degrading agent may include one or more amino acid substitutions. In an embodiment, the amino acid substitution may include a naturally occurring amino acid, such as a hydrophilic amino acid (e.g. a polar and positively charged hydrophilic amino acid, such as arginine (R) or lysine (K); a polar and neutral of charge hydrophilic amino acid, such as asparagine (N), glutamine (Q), serine (S), threonine (T), proline (P), and cysteine (C), a polar and negatively charged hydrophilic amino acid, such as aspartate (D) or glutamate (E), or an aromatic, polar and positively charged hydrophilic amino acid, such as histidine (H)) or a hydrophobic amino acid (e.g. a hydrophobic, aliphatic amino acid such as glycine (G), alanine (A), leucine (L), isoleucine (I), methionine (M), or valine (V), a hydrophobic, aromatic amino acid, such as phenylalanine (F), tryptophan (W), or tyrosine (Y) or a non-classical amino acid (e.g. selenocysteine, pyrolysine, N-formylmethionine β-alanine, GABA and δ-Aminolevulinic acid. 4-Aminobenzoic acid (PABA), D-isomers of the common amino acids, 2,4-diaminobutyric acid, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosme, citrulline, homocitrulline, cysteic acid, t-butylglycine, t-butylalanine, phenylglycine, cyclohexylalanine, β-alanine, fluoro-amino acids, designer amino acids such as β methyl amino acids, C α-methyl amino acids, N α-methyl amino acids, and amino acid analogs in general). Mutations may be made to the gene sequence of the antibiotic-degrading agent by reference to the genetic code, including taking into account codon degeneracy.

In various embodiments, the antibiotic-degrading agents possess desirable characteristics, including, for example, having an ability to efficiently target a broad spectra of antibiotics. In various embodiments, the antibiotic-degrading agents possess desirable enzyme kinetic characteristics. For example, in some embodiments, the antibiotic-degrading agents possess a low $K_M$ for at least one antibiotic, including, for example, a $K_M$ of less than about 500 µM, or about 100 µM, or about 10 µM, or about 1 µM, or about 0.1 µM (100 nM), or about 0.01 µM (10 nM), or about 1 nM. In various embodiments, the antibiotic-degrading agents possess a high $V_{max}$ for at least one antibiotic, including, for example, $V_{max}$ which is greater than about $100\ s^{-1}$, or about $1000\ s^{-1}$, or about $10000\ s^{-1}$, or about $100000\ s^{-1}$, or about $1000000\ s^{-1}$. In various embodiments, the antibiotic-degrading agents possess catalytic efficiency that is greater than about $10^6\ M^{-1}\ s^{-1}$ for at least one antibiotic.

In various embodiments, the antibiotic-degrading agents are stable and/or active in the GI tract, e.g. in one or more of the mouth, esophagus, stomach, small intestine (e.g. duodenum, jejunum, ileum), and large intestine, (e.g. cecum, colon ascendens, colon transversum, colon descendens, colon sigmoidenum, and rectum). In a specific embodiment, the antibiotic-degrading agent is stable and/or active in the large intestine, optionally selected from one or more of colon transversum, colon descendens, colon ascendens, colon sigmoidenum and cecum. In a specific embodiment, the antibiotic-degrading agent is stable and/or active in the small intestine, optionally selected from one or more of duodenum, jejunum, and ileum. In a specific embodiment, the antibiotic-degrading agent is stable and/or active in the ileum, and/or the terminal ileum, and/or the cecum, and/or the ileocecal junction.

In some embodiments, the antibiotic-degrading agent is resistant to proteases in the GI tract, including for example, the small intestine. In some embodiments, the antibiotic-degrading agent is substantially active at a pH of about 6.0 to about 7.5, e.g. about 6.0, or about 6.1, or about 6.2, or about 6.3, or about 6.4, or about 6.5, or about 6.6, or about 6.7, or about 6.8, or about 6.9, or about 7.0, or about 7.1, or about 7.2, or about 7.3, or about 7.4, or about 7.5 (including, for example, via formulation, as described herein). In various embodiments, the antibiotic-degrading agent is resistant to one or more antibiotic-degrading agent inhibitors, optionally selected from, for example, avibactam, tazobactam, sulbactam, EDTA, and clavulanic acid. In a specific embodiment, the antibiotic-degrading agent is NDM and it is not substantially inhibited by sulbactam or tazobactam. In other embodiments as described herein, the antibiotic-degrading agents of the present invention are susceptible to one or more inhibitors, and this property is exploited to ensure antibiotic hydrolysis does not interfere with the therapeutic benefit of the antibiotic. In some embodiments, stable refers to an enzyme that has a long enough half-life and maintains sufficient activity for therapeutic effectiveness.

In some embodiments, the antibiotic-degrading agents described herein, include derivatives that are modified, i.e., by the covalent attachment of any type of molecule to the antibiotic-degrading agent such that covalent attachment does not prevent the activity of the enzyme. For example, but not by way of limitation, derivatives include antibiotic-degrading agents that have been modified by, inter alia, glycosylation, lipidation, acetylation, pegylation, phosphorylation, amidation, derivatization by known protecting/blocking groups, proteolytic cleavage, linkage to a cellular ligand or other protein, etc. Any of numerous chemical modifications can be carried out, including, but not limited to specific chemical cleavage, acetylation, or formylation, etc. Additionally, the derivative can contain one or more non-classical amino acids.

In still other embodiments, the antibiotic-degrading agents described herein may be modified to add effector moieties such as chemical linkers, detectable moieties such as for example fluorescent dyes, enzymes, substrates, bioluminescent materials, radioactive materials, and chemiluminescent moieties, or functional moieties such as for example streptavidin, avidin, biotin, a cytotoxin, a cytotoxic agent, and radioactive materials.

The antibiotic-degrading agents described herein can possess a sufficiently basic functional group, which can react with an inorganic or organic acid, or a carboxyl group, which can react with an inorganic or organic base, to form a pharmaceutically acceptable salt. A pharmaceutically acceptable acid addition salt is formed from a pharmaceutically acceptable acid, as is well known in the art. Such salts include the pharmaceutically acceptable salts listed in, for example, *Journal of Pharmaceutical Science*, 66, 2-19 (1977) and *The Handbook of Pharmaceutical Salts; Properties, Selection, and Use*. P. H. Stahl and C. G. Wermuth (eds.), Verlag, Zurich (Switzerland) 2002, which are hereby incorporated by reference in their entirety.

Pharmaceutically acceptable salts include, by way of non-limiting example, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, camphorsulfonate, pamoate, phenylacetate, trifluoroacetate, acrylate, chlorobenzoate, dinitrobenzoate, hydroxybenzoate, methoxybenzoate, methylbenzoate, o-acetoxybenzoate, naphthalene-2-benzoate, isobutyrate, phenylbutyrate, α-hydroxybutyrate, butyne-1,4-dicarboxylate, hexyne-1,4-dicarboxylate, caprate, caprylate, cinnamate, glycollate, heptanoate, hippurate, malate, hydroxymaleate, malonate, mandelate, mesylate, nicotinate, phthalate, teraphthalate, propiolate, propionate, phenylpropionate, sebacate, suberate, p-bromobenzenesulfonate, chlorobenzenesulfonate, ethylsulfonate, 2-hydroxyethylsulfonate, methylsulfonate, naphthalene-1-sulfonate, naphthalene-2-sulfonate, naphthalene-1,5-sulfonate, xylenesulfonate, and tartarate salts.

The term "pharmaceutically acceptable salt" also refers to a salt of the antibiotic-degrading agents having an acidic functional group, such as a carboxylic acid functional group, and a base. Suitable bases include, but are not limited to, hydroxides of alkali metals such as sodium, potassium, and lithium; hydroxides of alkaline earth metal such as calcium and magnesium; nickel, cobalt, manganese, hydroxides of other metals, such as aluminum and zinc; ammonia, and organic amines, such as unsubstituted or hydroxy-substituted mono-, di-, or tri-alkylamines, dicyclohexylamine; tributyl amine; pyridine; N-methyl, N-ethylamine; diethylamine; triethylamine; mono-, bis-, or tris-(2-OH-lower alkylamines), such as mono-; bis-, or tris-(2-hydroxyethyl) amine, 2-hydroxy-tert-butylamine, or tris-(hydroxymethyl) methylamine, N,N-di-lower alkyl-N-(hydroxyl-lower alkyl)-amines, such as N,N-dimethyl-N-(2-hydroxyethyl) amine or tri-(2-hydroxyethyl)amine; N-methyl-D-glucamine; and amino acids such as arginine, lysine, and the like.

In some embodiments, the compositions described herein are in the form of a pharmaceutically acceptable salt.

Further, any antibiotic-degrading agents described herein can be administered to a subject as a component of a composition that comprises a pharmaceutically acceptable carrier or vehicle. Such compositions can optionally comprise a suitable amount of a pharmaceutically acceptable excipient so as to provide the form for proper administration.

Pharmaceutical excipients can be liquids, such as water and oils, including those of petroleum, animal, vegetable, or synthetic origin, such as peanut oil, soybean oil, mineral oil, sesame oil and the like. The pharmaceutical excipients can be, for example, saline, gum acacia, gelatin, starch paste, talc, keratin, colloidal silica, urea and the like. In addition, auxiliary, stabilizing, thickening, lubricating, and coloring agents can be used. In one embodiment, the pharmaceutically acceptable excipients are sterile when administered to a subject. Water is a useful excipient when any agent described herein is administered intravenously. Saline solutions and aqueous dextrose and glycerol solutions can also be employed as liquid excipients, specifically for injectable solutions. Suitable pharmaceutical excipients also include starch, glucose, cellulose, hypromellose, lactose, sucrose, gelatin, malt, rice, flour, chalk, silica gel, sodium stearate, glycerol monostearate, talc, sodium chloride, dried skim milk, glycerol, propylene, glycol, povidone, crospovidone, water, ethanol and the like. Any agent described herein, if desired, can also comprise minor amounts of wetting or emulsifying agents, or pH buffering agents. Other examples of suitable pharmaceutical excipients are described in *Remington's Pharmaceutical Sciences* 1447-1676 (Alfonso R. Gennaro eds., 19th ed. 1995), incorporated herein by reference.

Where necessary, the antibiotic-degrading agents and/or pharmaceutical compositions (and/or additional therapeutic agents) can include a solubilizing agent. Also, the agents can be delivered with a suitable vehicle or delivery device. Compositions for administration can optionally include a local anesthetic such as, for example, lignocaine to lessen pain at the site of the injection. Combination therapies outlined herein can be co-delivered in a single delivery vehicle or delivery device.

Antibiotics

In various embodiments, the antibiotic-degrading agents degrade or inactivate one or more antibiotics. In various embodiments, the subject is undergoing treatment or has recently undergone treatment with one or more antibiotics. In various embodiments, the described antibiotic-degrading agents and/or pharmaceutical compositions (and/or additional therapeutic agents) are formulated in a manner that preserves the therapeutic (e.g. systemic) action of one or more antibiotics while preventing the action of excess amounts of these antibiotics lower in the GI tract, where they may disrupt the GI microbiota. For instance, such antibiotics may be administered orally or parenterally (e.g. intravenously) and residual or excess antibiotic may remain in the GI tract (e.g. from lack of absorption into the blood stream and/or via secretion into the intestinal lumen either directly or via the bile). Such excess or residual antibiotic may disrupt the GI microbiota (e.g. disrupt a healthy balance (e.g. a healthy ratio and/or healthy distribution) of intestinal microbiota in a subject). In certain embodiments, the orally administered antibiotics are selected from penicillins, cephalosporins, monobactams, and carbapenems.

Penicillins include, for example, Amdinocillin, Amoxicillin (e.g. NOVAMOX, AMOXIL); Ampicillin (e.g. PRINCIPEN); Azlocillin; Carbenicillin (e.g. GEOCILLIN); Cloxacillin (e.g. TEGOPEN); Cyclacillin, Dicloxacillin (e.g. DYNAPEN); Flucloxacillin (e.g. FLOXAPEN); Mezlocillin (e.g. MEZLIN); Methicillin (e.g. STAPHCILLIN); Nafcillin (e.g. UNIPEN); Oxacillin (e.g. PROSTAPHLIN); Penicillanic Acid, Penicillin G (e.g. PENTIDS or PFIZERPEN); Penicillin V (e.g. VEETIDS (PEN-VEE-K)); Piperacillin (e.g. PIPRACIL); Sulbactam, Temocillin (e.g. NEGABAN); and Ticarcillin (e.g. TICAR).

Illustrative penicillins include:

| Generic | Brand Name |
| --- | --- |
| Amoxicillin | AMOXIL, POLYMOX, TRIMOX, WYMOX |
| Ampicillin | OMNIPEN, POLYCILLIN, POLYCILLIN-N, PRINCIPEN, TOTACILLIN |
| Bacampicillin | SPECTROBID |
| Carbenicillin | GEOCILLIN, GEOPEN |
| Cloxacillin | CLOXAPEN |
| Dicloxacillin | DYNAPEN, DYCILL, PATHOCIL |
| Flucloxacillin | FLOPEN, FLOXAPEN, STAPHCILLIN |
| Mezlocillin | MEZLIN |
| Nafcillin | NAFCIL, NALLPEN, UNIPEN |
| Oxacillin | BACTOCILL, PROSTAPHLIN |
| Penicillin G | BICILLIN L-A, CRYSTICILLIN 300 A.S., PENTIDS, PERMAPEN, PFIZERPEN, PFIZERPEN-AS, WYCILLIN |
| Penicillin V | BEEPEN-VK, BETAPEN-VK, LEDERCILLIN VK, V-CILLIN K |
| Piperacillin | PIPRACIL |
| Pivampicillin | |
| Pivmecillinam | |
| Ticarcillin | TICAR |

Cephalosporins include, for example, a first generation cephalosporin (e.g. Cefadroxil (e.g. DURICEF); Cefazolin (e.g. ANCEF); Ceftolozane, Cefalotin/Cefalothin (e.g. KEFLIN); Cefalexin (e.g. KEFLEX); a second generation cephalosporin (e.g. Cefaclor (e.g. DISTACLOR); Cefamandole (e.g. MANDOL); Cefoxitin (e.g. MEFOXIN); Cefprozil (e.g. CEFZIL); Cefuroxime (e.g. CEFTIN, ZINNAT)); a third generation cephalosporin (e.g. Cefixime (e.g. SUPRAX); Cefdinir (e.g. OMNICEF, CEFDIEL); Cefditoren (e.g. SPECTRACEF); Cefoperazone (e.g. CEFOBID); Cefotaxime (e.g. CLAFORAN); Cefpodoxime (e.g. VANTIN); Ceftazidime (e.g. FORTAZ); Ceftibuten (e.g. CEDAX) Ceftizoxime (e.g. CEFIZOX); and Ceftriaxone (e.g. ROCEPHIN)); a fourth generation cephalosporin (e.g. Cefepime (e.g. MAXIPIME)); or a fifth generation cephalosporin (e.g. Ceftaroline fosamil (e.g. TEFLARO); Ceftobiprole (e.g. ZEFTERA)). Also included is Latamoxef (or moxalactam). In a specific embodiment, cephalosporins include, for example, cefoperazone, ceftriaxone or cefazolin.

Illustrative cephalosporins include

| Generic | Brand Name |
| --- | --- |
| First Generation | |
| Cefacetrile (cephacetrile) | CELOSPOR, CELTOL, CRISTACEF |
| Cefadroxil (cefadroxyl) | DURICEF, ULTRACEF |
| Cefalexin (cephalexin) | KEFLEX, KEFTAB |
| Cefaloglycin (cephaloglycin) | KEFGLYCIN |
| Cefalonium (cephalonium) | |
| Cefaloridine (cephaloradine) | |
| Cefalotin (cephalothin) | KEFLIN |
| Cefapirin (cephapirin) | CEFADYL |
| Cefatrizine | |
| Cefazaflur | |
| Cefazedone | |
| Cefazolin (cephazolin) | ANCEF, KEFZOL |
| Cefradine (cephradine) | VELOSEF |
| Cefroxadine | |
| Ceftezole | |
| Second Generation | |
| Cefaclor | CECLOR, CECLOR CD, DISTACLOR, KEFLOR, RANICOR |
| Cefamandole | MANDOL |
| Cefmetazole | |
| Cefonicid | MONOCID |
| Cefotetan | CEFOTAN |
| Cefoxitin | MEFOXIN |
| Cefprozil (cefproxil) | CEFZIL |
| Cefuroxime | CEFTIN, KEFUROX, ZINACEF, ZINNAT |
| Cefuzonam | |
| Third Generation | |
| Cefcapene | |
| Cefdaloxime | |
| Cefdinir | OMNICEF, CEFDIEL |
| Cefditoren | SPECTRACEF |
| Cefetamet | |
| Cefixime | SUPRAX |
| Cefmenoxime | CEFMAX |
| Cefodizime | |
| Cefotaxime | CLAFORAN |
| Cefpimizole | |
| Cefpodoxime | VANTIN |
| Cefteram | |
| Ceftibuten | CEDAX |
| Ceftiofur | EXCEDE |
| Ceftiolene | |
| Ceftizoxime | CEFIZOX |
| Ceftriaxone | ROCEPHIN |
| Cefoperazone | CEFOBID |
| Ceftazidime | CEPTAZ, FORTUM, FORTAZ, TAZICEF, TAZIDIME |
| Fourth Generation | |
| Cefclidine | |
| Cefepime | MAXIPIME |
| Cefluprenam | |
| Cefoselis | |
| Cefozopran | |
| Cefpirome | CEFROM |
| Cefquinome | |
| Fifth Generation | |
| Ceftobiprole | ZEFTERA |
| Ceftaroline | TEFLARO |
| Not Classified | |
| Cefaclomezine | |
| Cefaloram | |
| Cefaparole | |

| Generic | Brand Name |
| --- | --- |
| Cefcanel | |
| Cefedrolor | |
| Cefempidone | |
| Cefetrizole | |
| Cefivitril | |
| Cefmatilen | |
| Cefmepidium | |
| Cefovecin | |
| Cefoxazole | |
| Cefrotil | |
| Cefsumide | |
| Cefuracetime | |
| Ceftioxide | |

Monobactams include, for example, aztreonam (e.g. AZACTAM, CAYSTON), tigemonam, nocardicin A, and tabtoxin.

Carbapenems include, for example, meropenem, imipenem (by way of non-limiting example, imipenem/cilastatin), ertapenem, doripenem, panipenem/betamipron, biapenem, razupenem (PZ-601), tebipenem, lenapenem, and tomopenem. Carbapenems also include thienamycins.

Illustrative carbapenems include

| Generic | Brand Name |
| --- | --- |
| Imipenem, Imipenem/cilastatin | PRIMAXIN |
| Doripenem | DORIBAX |
| Meropenem | MERREM |
| Ertapenem | INVANZ |

In various embodiments, the antibiotic may be administered orally or parenterally. For example, the antibiotic may be administered via oral, intradermal, intramuscular, intraperitoneal, intravenous, subcutaneous, intranasal, epidural, sublingual, intranasal, intracerebral, intravaginal, transdermal, rectal, inhalation, or topical routes. In an embodiment, the antibiotic is orally administered. In another embodiment, the antibiotic is administered parenterally. In an embodiment, the antibiotic is administered intravenously.

Inhibitors of Antibiotic-Degrading Agents

In various embodiments, the described antibiotic-degrading agents and/or pharmaceutical compositions (and/or additional therapeutic agents) are formulated in a manner that preserves the therapeutic (e.g. systemic) action of one or more antibiotics while preventing the action of residual or excess amounts these antibiotics lower in the GI tract, where they may disrupt the GI microbiota. This dual purpose may be effected, in part, by the use of one or more inhibitors of the antibiotic-degrading agents (another approach, with may supplement or supplant the inhibitor approach, is by formulation for selective release in specific areas of the GI tract, as described elsewhere herein). For example, the described antibiotic-degrading agent may be administered in a patient that receives one or more inhibitors of the antibiotic-degrading agent (e.g. sequential or simultaneous co-administration, or co-formulation) such that the one or more inhibitors act to protect the antibiotics higher in the GI tract (e.g. ileum and above) by reducing or eliminating activity of the antibiotic-degrading agent. However, the one or more inhibitors do not have such inhibitory effects on activity of the antibiotic-degrading agent lower in the GI tract (e.g. distal small intestine and/or the colon) and therefore allow the described antibiotic-degrading agent to degrade or inactivate residual or excess antibiotic lower in the GI tract and thus prevent or mitigate damage to the GI microbiota.

In some embodiments, the antibiotic-degrading agent inhibitor tracks with the antibiotic such that both are available for absorption in the proximal small intestine. The antibiotic-degrading agent inhibitor serves to protect the antibiotic from the antibiotic-degrading agent in the proximal small intestine. The antibiotic and the inhibitor are then both absorbed into the bloodstream and thereby removed from the proximal small intestine. As the concentration of inhibitor decreases in the small intestine, the antibiotic-degrading agent becomes active. Any residual or excess antibiotic that remains in the intestine or re-enters with the bile is inactivated prior to encountering the colonic microbiome.

In some embodiments, the antibiotic-degrading agent inhibitor includes, for example, tazobactam, sulbactam, EDTA, clavulanic acid, avibactam, trans-7-oxo-6-(sulphooxy)-1,6-diazabicyclo-[3.2.1]-octane-2-carboxamide, monobactam derivatives, ATMO derivatives, penems (e.g., BRL42715 and derivatives thereof, Syn1012, oxapenems, trinems, 1-β-methylcarbapenems), penicillin and cephalosporin sulfone derivatives (e.g., C-2/C-3-substituted penicillin and cephalosporin sulfones, C-6-substituted penicillin sulfones), non-β-lactam inhibitors (e.g., boronic acid transition state analogs, phosphonates, NXL104, hydroxamates) and metallo-β-lactamase inhibitors such as thiol derivatives, pyridine dicarboxylates, trifluoromethyl ketones and alcohols, carbapenem analogs, tricyclic natural products, succinate derivatives, and C-6-mercaptomethyl penicillinates. Co-formulations of an antibiotic with one or more antibiotic-degrading agent inhibitors are also provided in some embodiments (e.g. Augmentin is a mixture of amoxicillin and clavulanic acid; Sultamicillin is a mixture of ampicillin and sulbactam).

Further, any of the antibiotic-degrading agent inhibitors described in Drawz, Clin Microbiol Rev. January 2010; 23(1): 160-201 and WO 2009/091856A, the contents of which are hereby incorporated by reference in their entirety, are encompassed by the present invention.

In some embodiments, the antibiotic-degrading agent inhibitor is one or more β-lactamase inhibitors as described in U.S. Pat. No. 8,912,169, the contents of which are hereby incorporated by reference in their entirety.

In some embodiments, the antibiotic-degrading agent inhibitor is one or more metallo-β-lactamase inhibitor as described in U.S. Pat. Nos. 7,022,691 and 8,093,294 and US Patent Publication No. 2012/0329770, the contents of which are hereby incorporated by reference in their entirety.

In some embodiments, the antibiotic-degrading agent inhibitor is one or more NDM inhibitors as described in US Patent Publication No. 2014/0221330, the contents of which are hereby incorporated by reference in their entirety.

Formulations and Administration

In various embodiments, the described antibiotic-degrading agents and/or pharmaceutical compositions (and/or additional therapeutic agents) are formulated in a manner that preserves the therapeutic (e.g. systemic) action of one or more antibiotics while preventing the action of residual or excess amounts these antibiotics lower in the GI tract, where they may disrupt the GI microbiota. This dual purpose may be effected, in part, by formulating one or more of an antibiotic-degrading agent, an antibiotic, and an inhibitor to for selective release in specific areas of the GI tract.

Various methods may be used to formulate and/or deliver the agents described herein to a location of interest. For example, the antibiotic-degrading agents and/or pharmaceutical compositions (and/or additional therapeutic agents) described herein may be formulated as a composition adapted for delivery to the gastrointestinal tract. The gastrointestinal tract includes organs of the digestive system such as mouth, esophagus, stomach, duodenum, small intestine, large intestine and rectum and includes all subsections thereof (e.g. the small intestine may include the duodenum, jejunum and ileum; the large intestine may include the colon transversum, colon descendens, colon ascendens, colon sigmoidenum and cecum). For example, the antibiotic-degrading agents and/or pharmaceutical compositions (and/or additional therapeutic agents) described herein may be formulated for delivery to one or more of the stomach, small intestine, large intestine and rectum and includes all subsections thereof (e.g. duodenum, jejunum and ileum, colon transversum, colon descendens, colon ascendens, colon sigmoidenum and cecum). In some embodiments, the compositions described herein may be formulated to deliver to the upper or lower GI tract. In an embodiment, the antibiotic-degrading agents and/or pharmaceutical compositions (and/or additional therapeutic agents) may be administered to a subject, by, for example, directly or indirectly contacting the mucosal tissues of the gastrointestinal tract.

For example, in various embodiments, the present invention provides modified release formulations comprising at least one antibiotic-degrading agent (and/or additional therapeutic agents), wherein the formulation releases a substantial amount of the antibiotic-degrading agent (and/or additional therapeutic agents) into one or more regions of the GI tract. For example, the formulation may release at least about 60% of the antibiotic-degrading agent after the stomach and into one or more regions of the GI tract. In various embodiments, the modified release formulations comprising at least one antibiotic-degrading agent (and/or additional therapeutic agents) are released in a manner that allows for the therapeutic (e.g. systemic) activity of one or more antibiotic (or an antibiotic-degrading agent inhibitor) but prevents or mitigates the deleterious effects of excess antibiotics on the microbiota of the GI tract. In various embodiments, the modified release formulations comprising at least one antibiotic-degrading agent (and/or additional therapeutic agents) are released distal to the release and/or absorption of one or more antibiotic (or an antibiotic-degrading agent inhibitor). For example, in various embodiments, the modified release formulations comprising at least one antibiotic-degrading agent (and/or additional therapeutic agents) are released distal to the ileum and below. For example, in various embodiments, the modified release formulations comprising at least one antibiotic-degrading agent (and/or additional therapeutic agents) are released in the distal small intestine and/or the colon.

In various embodiments, the modified-release formulation of the present invention releases at least 60% of the antibiotic-degrading agent (or additional therapeutic agents) after the stomach into one or more regions of the intestine. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the antibiotic-degrading agent (or additional therapeutic agents) in the intestine.

In various embodiments, the modified-release formulation of the present invention releases at least 60% of the antibiotic-degrading agent (or additional therapeutic agents) in the small intestine. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the antibiotic-degrading agent (or additional therapeutic agents) in the small intestine.

In one embodiment, the modified-release formulation of the present invention releases at least 60% of the antibiotic-degrading agent (or additional therapeutic agents) in the duodenum. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the antibiotic-degrading agent (or additional therapeutic agents) in the duodenum.

In one embodiment, the modified-release formulation of the present invention releases at least 60% of the antibiotic-degrading agent (or additional therapeutic agents) in the jejunum. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the antibiotic-degrading agent (or additional therapeutic agents) in the jejunum.

In one embodiment, the modified-release formulation of the present invention releases at least 60% of the antibiotic-degrading agent (or additional therapeutic agents) in the ileum and/or the ileocecal junction. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the antibiotic-degrading agent (or additional therapeutic agents) in the ileum and/or the ileocecal junction.

In various embodiments, the modified-release formulation of the present invention releases at least 60% of the antibiotic-degrading agent (or additional therapeutic agents) in the large intestine. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the antibiotic-degrading agent (or additional therapeutic agents) in the large intestine.

In one embodiment, the modified-release formulation of the present invention releases at least 60% of the antibiotic-degrading agent (or additional therapeutic agents) in the cecum. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the antibiotic-degrading agent (or additional therapeutic agents) in the cecum.

In one embodiment, the modified-release formulation of the present invention releases at least 60% of the antibiotic-degrading agent (or additional therapeutic agents) in the ascending colon. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the antibiotic-degrading agent (or additional therapeutic agents) in the ascending colon.

In one embodiment, the modified-release formulation of the present invention releases at least 60% of the antibiotic-degrading agent (or additional therapeutic agents) in the transverse colon. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the antibiotic-degrading agent (or additional therapeutic agents) in the transverse colon.

In one embodiment, the modified-release formulation of the present invention releases at least 60% of the antibiotic-degrading agent (or additional therapeutic agents) in the descending colon. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the antibiotic-degrading agent (or additional therapeutic agents) in the descending colon.

In one embodiment, the modified-release formulation of the present invention releases at least 60% of the antibiotic-degrading agent (or additional therapeutic agents) in the sigmoid colon. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the antibiotic-degrading agent (or additional therapeutic agents) in the sigmoid colon.

In one embodiment, the modified-release formulation of the present invention releases at least 60% of the antibiotic-degrading agent (or additional therapeutic agents) in the ileum, and/or the terminal ileum, and/or the cecum, and/or the ileocecal junction. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the antibiotic-degrading agent (or additional therapeutic agents) in the ileum, and/or the terminal ileum, and/or the cecum, and/or the ileocecal junction.

In various embodiments, the modified-release formulation does not substantially release the antibiotic-degrading agent (or additional therapeutic agents) in the stomach.

In certain embodiments, the modified-release formulation releases the antibiotic-degrading agent (or additional therapeutic agents) at a specific pH. For example, in some embodiments, the modified-release formulation is substantially stable in an acidic environment and substantially unstable (e.g., dissolves rapidly or is physically unstable) in a near neutral to alkaline environment. In some embodiments, stability is indicative of not substantially releasing while instability is indicative of substantially releasing. For example, in some embodiments, the modified-release formulation is substantially stable at a pH of about 7.0 or less, or about 6.5 or less, or about 6.0 or less, or about 5.5 or less, or about 5.0 or less, or about 4.5 or less, or about 4.0 or less, or about 3.5 or less, or about 3.0 or less, or about 2.5 or less, or about 2.0 or less, or about 1.5 or less, or about 1.0 or less. In some embodiments, the present formulations are stable in lower pH areas and therefore do not substantially release in, for example, the stomach. In some embodiments, modified-release formulation is substantially stable at a pH of about 1 to about 4 or lower and substantially unstable at pH values that are greater. In these embodiments, the modified-release formulation does not substantially release in the stomach. In these embodiments, the modified-release formulation substantially releases in the small intestine (e.g. one or more of the duodenum, jejunum, and ileum) and/or large intestine (e.g. one or more of the cecum, ascending colon, transverse colon, descending colon, and sigmoid colon). In some embodiments, modified-release formulation is substantially stable at a pH of about 4 to about 5 or lower and consequentially is substantially unstable at pH values that are greater and therefore is not substantially released in the stomach and/or small intestine (e.g. one or more of the duodenum, jejunum, and ileum). In these embodiments, the modified-release formulation is substantially released in the large intestine (e.g. one or more of the cecum, ascending colon, transverse colon, descending colon, and sigmoid colon). In various embodiments, the pH values recited herein may be adjusted as known in the art to account for the state of the subject, e.g. whether in a fasting or postprandial state.

In some embodiments, the modified-release formulation is substantially stable in gastric fluid and substantially unstable in intestinal fluid and, accordingly, is substantially released in the small intestine (e.g. one or more of the duodenum, jejunum, and ileum) and/or large intestine (e.g. one or more of the cecum, ascending colon, transverse colon, descending colon, and sigmoid colon).

In some embodiments, the modified-release formulation is substantially unstable in the ileum, and/or the terminal ileum, and/or the cecum, and/or the ileocecal junction. Without wishing to be bound by theory, this particular region of the GI tract is advantageous as it is distal to antibiotic absorption and is proximal to the GI microbiome, while also being high enough in the GI tract to allow mixing.

In some embodiments, the modified-release formulation is stable in gastric fluid or stable in acidic environments. These modified-release formulations release about 30% or less by weight of the antibiotic-degrading agent and/or additional therapeutic agent in the modified-release formulation in gastric fluid with a pH of about 4 to about 5 or less, or simulated gastric fluid with a pH of about 4 to about 5 or less, in about 15, or about 30, or about 45, or about 60, or about 90 minutes. Modified-release formulations of the of the invention may release from about 0% to about 30%, from about 0% to about 25%, from about 0% to about 20%, from about 0% to about 15%, from about 0% to about 10%, about 5% to about 30%, from about 5% to about 25%, from about 5% to about 20%, from about 5% to about 15%, from about 5% to about 10% by weight of the antibiotic-degrading agent and/or additional therapeutic agent in the modified-release formulation in gastric fluid with a pH of 4-5 or less or simulated gastric fluid with a pH of 4-5 or less, in about 15, or about 30, or about 45, or about 60, or about 90 minutes. Modified-release formulations of the invention may release about 1%, about 2%, about 3%, about 4%, about 5%, about 6%, about 7%, about 8%, about 9%, or about 10% by weight of the total antibiotic-degrading agent and/or additional therapeutic agent in the modified-release formulation in gastric fluid with a pH of 5 or less, or simulated gastric fluid with a pH of 5 or less, in about 15, or about 30, or about 45, or about 60, or about 90 minutes.

In some embodiments, the modified-release formulation is unstable in intestinal fluid. These modified-release formulations release about 70% or more by weight of the antibiotic-degrading agent and/or additional therapeutic agent in the modified-release formulation in intestinal fluid or simulated intestinal fluid in about 15, or about 30, or about 45, or about 60, or about 90 minutes. In some embodiments, the modified-release formulation is unstable in near neutral to alkaline environments. These modified-release formulations release about 70% or more by weight of the antibiotic-degrading agent and/or additional therapeutic agent in the modified-release formulation in intestinal fluid with a pH of about 4-5 or greater, or simulated intestinal fluid with a pH of about 4-5 or greater, in about 15, or about 30, or about 45, or about 60, or about 90 minutes. A modified-release formulation that is unstable in near neutral or alkaline environments may release 70% or more by weight of antibiotic-degrading agent and/or additional therapeutic agent in the modified-release formulation in a fluid having a pH greater than about 5 (e.g., a fluid having a pH of from about 5 to about 14, from about 6 to about 14, from about 7 to about 14, from about 8 to about 14, from about 9 to about 14, from about 10 to about 14, or from about 11 to about 14) in from about 5 minutes to about 90 minutes, or from about 10 minutes to about 90 minutes, or from about 15 minutes to about 90 minutes, or from about 20 minutes to about 90 minutes, or from about 25 minutes to about 90 minutes, or from about 30 minutes to about 90 minutes, or from about 5 minutes to about 60 minutes, or from about 10 minutes to about 60 minutes, or from about 15 minutes to about 60 minutes, or from about 20 minutes to about 60 minutes, or from about 25 minutes to about 90 minutes, or from about 30 minutes to about 60 minutes.

Examples of simulated gastric fluid and simulated intestinal fluid include, but are not limited to, those disclosed in the 2005 Pharmacopeia 23NF/28USP in Test Solutions at page 2858 and/or other simulated gastric fluids and simulated intestinal fluids known to those of skill in the art, for example, simulated gastric fluid and/or intestinal fluid prepared without enzymes.

In various embodiments, the modified-release formulations comprising an antibiotic-degrading agent are substantially stable in chyme. For example, there is, in some embodiments, a loss of less than about 50% or about 40%, or about 30%, or about 20%, or about 10% of antibiotic-degrading agent activity in about 10, or 9, or 8, or 7, or 6, or 5, or 4, or 3, or 2, or 1 hour from administration.

In various embodiments, the modified-release formulation of the present invention may utilize one or more modified-release coatings such as delayed-release coatings to provide for effective, delayed yet substantial delivery of the antibiotic-degrading agent to the GI tract together with, optionally, additional therapeutic agents. In one embodiment, the delayed-release coating includes an enteric agent that is substantially stable in acidic environments and substantially unstable in near neutral to alkaline environments. In an embodiment, the delayed-release coating contains an enteric agent that is substantially stable in gastric fluid. The enteric agent can be selected from, for example, solutions or dispersions of methacrylic acid copolymers, cellulose acetate phthalate, hydroxypropylmethyl cellulose phthalate, polyvinyl acetate phthalate, carboxymethylethylcellulose, and EUDRAGIT-type polymer (poly(methacrylic acid, methylmethacrylate), hydroxypropyl methylcellulose acetate succinate, cellulose acetate trimellitate, shellac or other suitable enteric coating polymers. The EUDRAGIT-type polymer include, for example, EUDRAGIT FS 30D, L 30 D-55, L 100-55, L 100, L 12, 5, L 12, 5 P, RL 30 D, RL PO, RL 100, RL 12, 5, RS 30 D, RS PO, RS 100, RS 12, 5, NE 30 D, NE 40 D, NM 30 D, S 100, S 12, 5, and S 12, 5 P. In some embodiments, one or more of EUDRAGIT FS 30D, L 30 D-55, L 100-55, L 100, L 12, 5, L 12, 5 P RL 30 D, RL PO, RL 100, RL 12, 5, RS 30 D, RS PO, RS 100, RS 12, 5, NE 30 D, NE 40 D, NM 30 D, S 100, S 12, 5 and S 12, 5 P is used. The enteric agent may be a combination of the foregoing solutions or dispersions. In various embodiments, different types of EUDRAGIT can be combined or multiple different types of EUDRAGIT coatings may be combined to achieve targeted delivery. For example, the modified-release formulation may include two coatings of enteric polymers (e.g., EUDRAGIT), an outer layer, and an inner layer of partially neutralized enteric polymer and a buffer agent. Such formulation allows more rapid release of the agents initiated at the targeted pH compared to a single coating of the enteric polymer and can be used for targeted delivery to, for example, the ileum and/or ileocecal junction.

In one embodiment, the modified-release formulation may include one or more delayed-release coating(s) which remain essentially intact, or may be essentially insoluble, in gastric fluid. The stability of the delayed-release coating can be pH dependent. Delayed-release coatings that are pH dependent will be substantially stable in acidic environments (pH of about 5 or less), and substantially unstable in near neutral to alkaline environments (pH greater than about 5). For example, the delayed-release coating may essentially disintegrate or dissolve in near neutral to alkaline environments such as are found in the small intestine (e.g. one or more of the duodenum, jejunum, and ileum) and/or large intestine (e.g. one or more of the cecum, ascending colon, transverse colon, descending colon, and sigmoid colon).

By way of non-limiting example, there are various EUDRAGIT formulations that dissolve at rising pH, with formulations that dissolve at pH >5.5 (EUDRAGIT L30 D-550), pH >6.0 (EUDRAGIT L12, 5), and pH >7.0 (EUDRAGIT FS 30D). Since the ileum has the highest pH in the small intestine, ranging from 7.3 to 7.8, the use of EUDRAGIT FS 30D to coat a formulation containing the antibiotic-degrading enzyme, may delay the dissolution of the formulation until it reaches the ileum thereby localizing the release of the antibiotic-degrading enzyme to the ileum. However, the jejunum has a pH ranging from 6.6 to 7.4, therefore, the release may initiate in some patients in the jejunum, if the pH is at 7.0 or above. In such embodiments, the antibiotic-degrading enzyme may be delivered with an antibiotic/inhibitor combination as described. The different types of EUDRAGIT can be combined with each other, or multiple different types of EUDRAGIT coatings can be combined to fine tune the dissolution profile to achieve targeted delivery to achieve optimal function. For example, DUOCOAT (KUECEPT) that uses two coatings of enteric polymers (like EUDRAGIT), an outer layer, and an inner layer of partially neutralized enteric polymer and a buffer agent. The DUOCOAT technology allows more rapid release of the therapeutic agent initiated at the targeted pH compared to a single coating of the enteric polymer (Liu et al., 2009; European J. Pharm. Biopharma. 74:311), the entire contents of all of which are incorporated herein by reference). Release was demonstrated to be targeted to the ileum and/or ileocecal junction in ten healthy volunteers (Varum et al., 2013; European J. Pharm. Biopharma. 84:573), the entire contents of all of which are incorporated herein by reference).

In another embodiment, the delayed-release coating may degrade as a function of time when in aqueous solution without regard to the pH and/or presence of enzymes in the solution. Such a coating may comprise a water insoluble polymer. Its solubility in aqueous solution is therefore independent of the pH. The term "pH independent" as used herein means that the water permeability of the polymer and its ability to release pharmaceutical ingredients is not a function of pH and/or is only very slightly dependent on pH. Such coatings may be used to prepare, for example, sustained release formulations. Suitable water insoluble polymers include pharmaceutically acceptable non-toxic polymers that are substantially insoluble in aqueous media, e.g., water, independent of the pH of the solution. Suitable polymers include, but are not limited to, cellulose ethers, cellulose esters, or cellulose ether-esters, i.e., a cellulose derivative in which some of the hydroxy groups on the cellulose skeleton are substituted with alkyl groups and some are modified with alkanoyl groups. Examples include ethyl cellulose, acetyl cellulose, nitrocellulose, and the like. Other examples of insoluble polymers include, but are not limited to, lacquer, and acrylic and/or methacrylic ester polymers, polymers or copolymers of acrylate or methacrylate having a low quaternary ammonium content, or mixture thereof and the like. Other examples of insoluble polymers include EUDRAGIT RS, EUDRAGIT RL, and EUDRAGIT NE. Insoluble polymers useful in the present invention include polyvinyl esters, polyvinyl acetals, polyacrylic acid esters, butadiene styrene copolymers, and the like. In one embodiment, colonic delivery is achieved by use of a slowly-eroding wax plug (e.g., various PEGS, including for example, PEG6000) or pectin.

Alternatively, the stability of the modified-release formulation can be enzyme-dependent. Delayed-release coatings that are enzyme dependent will be substantially stable in fluid that does not contain a particular enzyme and substantially unstable in fluid containing the enzyme. The delayed-release coating will essentially disintegrate or dissolve in fluid containing the appropriate enzyme. Enzyme-dependent control can be brought about, for example, by using materials which release the active ingredient only on exposure to enzymes in the intestine, such as galactomannans. Also, the stability of the modified-release formulation can be dependent on enzyme stability in the presence of a microbial enzyme present in the gut flora. For example, in various embodiments, the delayed-release coating may be degraded by a microbial enzyme present in the gut flora. In an embodiment, the delayed-release coating may be degraded by a bacteria present in the small intestine. In another embodiment, the delayed-release coating may be degraded by a bacteria present in the large intestine.

In various embodiments, the modified-release formulations of the present invention are designed for immediate release (e.g. upon ingestion). In various embodiments, the modified-release formulations may have sustained-release profiles, i.e. slow release of the active ingredient(s) in the body (e.g., GI tract) over an extended period of time. In various embodiments, the modified-release formulations may have a delayed-release profile, i.e. not immediately release the active ingredient(s) upon ingestion; rather, postponement of the release of the active ingredient(s) until the composition is lower in the gastrointestinal tract; for example, for release in the small intestine (e.g., one or more of duodenum, jejunum, ileum) or the large intestine (e.g., one or more of cecum, ascending, transverse, descending or sigmoid portions of the colon, and rectum). For example, a composition can be enteric coated to delay release of the active ingredient(s) until it reaches the small intestine or large intestine. In some embodiments, there is not a substantial amount of the active ingredient(s) of the present formulations in the stool.

In various embodiments, the modified release formulation is designed for release in the colon. Various colon-specific delivery approaches may be utilized. For example, the modified release formulation may be formulated using a colon-specific drug delivery system (CODES) as described for example, in Li et al., AAPS PharmSciTech (2002), 3(4): 1-9, the entire contents of which are incorporated herein by reference. Drug release in such a system is triggered by colonic microflora coupled with pH-sensitive polymer coatings. For example, the formulation may be designed as a core tablet with three layers of polymer. The first coating is an acid-soluble polymer (e.g., EUDRAGIT E), the outer coating is enteric, along with an hydroxypropyl methylcellulose barrier layer interposed in between. In another embodiment, colon delivery may be achieved by formulating the antibiotic-degrading agent (and/or additional therapeutic agent) with specific polymers that degrade in the colon such as, for example, pectin. The pectin may be further gelled or crosslinked with a cation such as a zinc cation. In an embodiment, the formulation is in the form of ionically crosslinked pectin beads which are further coated with a polymer (e.g., EUDRAGIT polymer). Additional colon specific formulations include, but are not limited to, pressure-controlled drug delivery systems (prepared with, for example, ethylcellulose) and osmotic controlled drug delivery systems (i.e., ORDS-CT).

Formulations for colon specific delivery of antibiotic-degrading agents (and/or additional therapeutic agents), as described herein, may be evaluated using, for example, in vitro dissolution tests. For example, parallel dissolution studies in different buffers may be undertaken to characterize the behavior of the formulations at different pH levels. Alternatively, in vitro enzymatic tests may be carried out. For example, the formulations may be incubated in fermenters containing suitable medium for bacteria, and the amount of drug released at different time intervals is determined. Drug release studies can also be done in buffer medium containing enzymes or rat or guinea pig or rabbit cecal contents and the amount of drug released in a particular time is determined. In a further embodiment, in vivo evaluations may be carried out using animal models such as dogs, guinea pigs, rats, and pigs. Further, clinical evaluation of colon specific drug delivery formulations may be evaluated by calculating drug delivery index (DDI) which considers the relative ratio of RCE (relative colonic tissue exposure to the drug) to RSC (relative amount of drug in blood i.e. that is relative systemic exposure to the drug). Higher drug DDI indicates better colon drug delivery. Absorption of drugs from the colon may be monitored by colonoscopy and intubation.

In various embodiments, the present formulation provide for substantial uniform dissolution of the antibiotic-degrading agent (and/or additional therapeutic agent) in the area of release in the GI tract. In an embodiment, the present formulation minimizes patchy or heterogeneous release of the antibiotic-degrading agent. For example, when releasing in the distal small intestine or, especially the colon, the distribution of antibiotic-degrading agent (and/or additional therapeutic agent) may be heterogeneous and therefore require formulation to minimize local effects.

In some embodiments, a dual pulse formulation is provided. In various embodiments, the present invention provides for modified-release formulations that release multiple doses of the antibiotic-degrading agent, at different locations along the intestines, at different times, and/or at different pH. In an illustrative embodiment, the modified-release formulation comprises a first dose of the antibiotic-degrading agent and a second dose of the antibiotic-degrading agent, wherein the first dose and the second dose are released at different locations along the intestines, at different times, and/or at different pH. For example, the first dose is released at the duodenum, and the second dose is released at the ileum. In another example, the first dose is released at the jejunum, and the second dose is released at the ileum. In other embodiments, the first dose is released at a location along the small intestine (e.g., the duodenum), while the second dose is released along the large intestine (e.g., the ascending colon). In various embodiments, the modified-release formulation may release at least one dose, at least two doses, at least three doses, at least four doses, at least five doses, at least six doses, at least seven doses, or at least eight doses of the antibiotic-degrading agent at different locations along the intestines, at different times, and/or at different pH. Further the dual pulse description herein applies to modified-release formulations that release an antibiotic-degrading agent and an additional therapeutic agent.

In some embodiments, a dual pulse formulation is provided in which a dose of the antibiotic-degrading agent and a dose of an antibiotic (or an inhibitor of antibiotic-degrading agent) are released at different locations along the intestines, at different times, and/or at different pH. For example, the dose of an antibiotic (or an inhibitor of antibiotic-degrading agent) is released distal to the dose of the antibiotic-degrading agent. In another example, the dose of an antibiotic (or an inhibitor of antibiotic-degrading agent) is released proximal to the dose of the antibiotic-degrading agent. For example, the dose of antibiotic (or an inhibitor of antibiotic-degrading agent) is released in the ileum and upstream and the dose of the antibiotic-degrading agent is released in the distal small intestine and/or the colon.

In various embodiments, the invention provides a formulation comprising: a core particle having a base coat comprising one or more antibiotic-degrading agents, and a delayed-release coating disposed over the coated core particle. The delayed-release coating may be substantially stable in acidic environments and/or gastric fluid, and/or substantially unstable in near neutral to alkaline environments or intestinal fluid thereby exposing the coated core particle to intestinal fluid. The base coat comprising one or more antibiotic-degrading agents may further comprise one or more additional therapeutic agents. Optionally a plurality of base coats may be applied to the core particle each of which may contain an antibiotic-degrading agent and/or an additional therapeutic agent. In an embodiment, the core particle includes sucrose. In an embodiment, an antibiotic-degrading agent can be sprayed onto an inert core (e.g., a sucrose core) and spray-dried with an enteric layer (e.g., EUDRAGIT L30 D-55) to form antibiotic-degrading agent containing pellets or beads.

Optionally, the core particle may comprise one or more antibiotic-degrading agents and/or one or more additional therapeutic agents. In one embodiment, one or more doses of the antibiotic-degrading agent may be encapsulated in a core particle, for example, in the form of a microsphere or a mini-sphere. For example, the antibiotic-degrading agent may be combined with a polymer (e.g., latex), and then formed into a particulate, micro-encapsulated enzyme preparation, without using a sucrose core. The microspheres or mini-spheres thus formed may be optionally covered with a delayed-release coating.

A variety of approaches for generating particulates (such as microspheres, mini-spheres, aggregates, other) may be utilized for the inclusion of enzymatic proteins. They typically involve at least two phases, one containing the protein, and one containing a polymer that forms the backbone of the particulate. Most common are coacervation, where the polymer is made to separate from its solvent phase by addition of a third component, or multiple phase emulsions, such as water in oil in water (w/o/w) emulsion where the inner water phase contains the protein, the intermediate organic phase contains the polymer, and the external water phase stabilizers that support the w/o/w double emulsion until the solvents can be removed to form, for example, microspheres or mini-spheres. Alternatively, the antibiotic-degrading agent and stabilizing excipients (for example, trehalose, mannitol, Tween 80, polyvinyl alcohol) are combined and sprayed from aqueous solution and collected. The particles are then suspended in a dry, water immiscible organic solvent containing polymer and release modifying compounds, and the suspension sonicated to disperse the particles. An additional approach uses aqueous phases but no organic solvent. Specifically, the enzymatic protein, buffer components, a polymer latex, and stabilizing and release-modifying excipients are dissolved/dispersed in water. The aqueous dispersion is spray-dried, leading to coalescence of the latex, and incorporation of the protein and excipients in particles of the coalesced latex. When the release modifiers are insoluble at acidic conditions but soluble at higher pHs (such as carboxylic acid) then release from the matrix is inhibited in the gastric environment. In an embodiment, the antibiotic-degrading agent may be initially solubilized as an emulsion, microemulsion, or suspension and then formulated into solid mini-spheres or microspheres. The formulation may then be coated with, for example, a delayed-release, sustained-release, or controlled-release coating to achieve delivery at a specific location such as, for example, the intestines.

In various embodiments, the formulation may comprise a plurality of modified-release particles or beads or pellets or microspheres. In an embodiment, the formulation is in the form of capsules comprising multiple beads. In another embodiment, the formulation is in the form of capsules comprising multiple pellets. In another embodiment, the formulation is in the form of capsules comprising multiple microspheres or mini-spheres.

In some embodiments, before applying the delayed-release coating to a coated core particle, the particle can optionally be covered with one or more separating layers comprising pharmaceutical excipients including alkaline compounds such as for instance pH-buffering compounds. The separating layer essentially separates the coated core particle from the delayed-release coating.

The separating layer can be applied to the coated core particle by coating or layering procedures typically used with coating equipment such as a coating pan, coating granulator or in a fluidized bed apparatus using water and/or organic solvents for the coating process. As an alternative the separating layer can be applied to the core material by using a powder coating technique. The materials for separating layers are pharmaceutically acceptable compounds such as, for instance, sugar, polyethylene glycol, polyvinylpyrrolidone, polyvinyl alcohol, polyvinyl acetate, hydroxypropyl cellulose, methyl-cellulose, ethylcellulose, hydroxypropyl methylcellulose, carboxymethylcellulose sodium and others, used alone or in mixtures. Additives such as plasticizers, colorants, pigments, fillers, anti-tacking and anti-static agents, such as for instance magnesium stearate, sodium stearyl fumarate, titanium dioxide, talc and other additives can also be included in the separating layer.

In some embodiments, the coated particles with the delayed-release coating may be further covered with an overcoat layer. The overcoat layer can be applied as described for the other coating compositions. The overcoat materials are pharmaceutically acceptable compounds such as sugar, polyethylene glycol, polyvinylpyrrolidone, polyvinyl alcohol, polyvinyl acetate, hydroxypropyl cellulose, methylcellulose, ethylcellulose, hydroxypropyl methylcellulose, carboxymethylcellulose sodium and others, used alone or in mixtures. The overcoat materials can prevent potential agglomeration of particles coated with the delayed-release coating, protect the delayed-release coating from cracking during the compaction process or enhance the tableting process.

In various embodiments, the antibiotic-degrading agent described herein is lyophilized, e.g. using methods known in the art. In some embodiments, lyophilized antibiotic-degrading agent is placed in an enterically coated soft gel or capsule.

In various embodiments, the antibiotic-degrading agent described herein is formulated as a composition adapted for microorganism-based release. In some embodiments, the antibiotic-degrading agent is formulated for release by a genetically-modified microorganism, optionally selected from a fungi, a bacteria, and an algae. In some embodiments, the genetically-modified microorganism is resistant to one or more antibiotic. For example, the invention may pertain to a composition comprising a genetically-modified microorganism comprising one or more antibiotic-degrading agents that is formulated for GI tract delivery as described herein and that releases the antibiotic-degrading agents, e.g. by secretion. For example, a genetically-modified microorganism comprising one or more antibiotic-degrading agents may be formulated for release in the distal small intestine and/or colon and, when released, in turn, secretes or otherwise releases (e.g. via genetically-modified microorganism death or digestion) the antibiotic-degrading agent so it may eliminate residual or excess antibiotic and prevent GI tract microbiota disruption.

In various embodiments, the genetically-modified microorganism comprising one or more antibiotic-degrading agents is formulated so as to deliver viable microorganisms to the intestines where active antibiotic-degrading agents are secreted by the genetically-modified microorganisms. In one embodiment, the genetically-modified microorganism comprising one or more antibiotic-degrading agents is formulated as an enteric-coated capsule which directly releases the recombinant genetically-modified microorganism in the intestines. In other embodiments, the genetically-modified microorganism comprising one or more antibiotic-degrading agents can be formulated as a gelatin capsule, or the genetically-modified microorganism comprising one or more antibiotic-degrading agents can be dissolved in a liquid and ingested. In such embodiments, the genetically-modified microorganism comprising one or more antibiotic-degrading agents is delivered anywhere along the GI tract. As described herein, the genetically-modified microorganism comprising one or more antibiotic-degrading agents can be released in the distal small intestine and/or the colon; however, delivery anywhere in the GI tract is also imagined, for example, where the genetically-modified microorganism comprising one or more antibiotic-degrading agents is able to transit to the area of interest without loss of activity or disruption of the systemic activity of the antibiotics. By way of illustration, in some embodiments, a recombinant yeast cell, for example, *Saccharomyces boulardii*, is resistant to stomach acid and remains viable during transit to the intestine, where it secretes active antibiotic-degrading agents for neutralizing residual or excess antibiotic in the lower GI tract.

In some embodiments, genetically-modified microorganism comprising one or more antibiotic-degrading agents quickly transits through the small intestine but transits slowly in the colon and therefore remains in the colon longer and any antibiotic-degrading agents it secretes or releases concentrates in the colon.

In some embodiments, the genetically-modified microorganism is a yeast cell. In various embodiments, the yeast cell is selected from *Saccharomyces* spp., *Hansenula* spp., *Kluyveromyces* spp. *Schizzosaccharomyces* spp. *Zygosaccharoinyces* spp., *Pichia* spp., *Monascus* spp., *Geotrichum* spp. and *Yarrowia* spp. In various embodiments, the present invention contemplates expression of an antibiotic-degrading agent in a recombinant yeast cell. The recombinant yeast cell may be generated by stable integration into yeast chromosomal DNA of expression cassette(s) that encode and can express the one or more antibiotic-degrading agents. Alternatively, recombinant yeast cell may be generated using a process in which the yeast maintains an expression cassette(s) that encode and can express the one or more antibiotic-degrading agents on a stable episome. The recombinant yeast cell may be any yeast cell that is capable of surviving in the mammalian intestine. In various embodiments, the yeast cell has a known probiotic capacity, such as yeast strains selected from kefir, kombucha or dairy products.

In one embodiment, the recombinant yeast cell is *Saccharomyces cerevisiae*. In another embodiment, the recombinant yeast cell is the *Saccharomyces cerevisiae* subspecies *Saccharomyces boulardii* (by way of non-limiting example, ATCC 74352 and/or any cells in U.S. Pat. Nos. 6,010,695 and 7,799,328 the contents of which are hereby incorporated by reference in their entirety). *S. cerevasiae* has been marketed for over 40 years as a probiotic. It has been used for the prevention and the treatment of diarrheal diseases, including antibiotic-associated diarrhea and *C. difficile* infection (Kelesidis and Pothoulakis, Ther. Advan. Gastroent. (2012), 5:111-125 and Hatoum et al. Frontiers in Microbiology (2012), 3:1-12). *S. boulardii* differs from other *S. cerevasiae* strains as the optimal growth temperature of *S. boulardii* is 37° C. while other strains prefer lower temperatures (between 30° C. and 33° C.), *S. boulardii* is resistant to low pH and is highly tolerant to bile acids (Edwards-Ingram et al. Appl. Environ. Microbiol, (2007), 73:2458-2467, Graff et al. J. Gen. Appl. Microbiol. (2008), 54:221-227). *S. boulardii* was demonstrated to survive the intestinal tract in humans (Klein et al., Pharm. Res. (1993), 10:1615-1619) where 0.1% viable yeast was recovered in feces after a single administration of $10^{10}$ cells. Concurrent antibiotic treatment increased recovery two-fold (Klein et al., Pharm. Res. (1993), 10:1615-1619).

In one embodiment, the recombinant yeast cell is *Pichia pastoris*.

In some embodiments, the genetically-modified microorganism is a bacterial cell. In some embodiments, the bacterial cell is a *Bacillus* spp. In some embodiments, the genetically-modified microorganism is an algal cell (e.g. *Chlamydomonas* spp., e.g. *Chlamydomonas reinhardtii*) or the chloroplasts thereof.

In some embodiments, the genetically-modified microorganism is one or more of *Saccharomyces boulardii; Pichia pastoris; Lactobacillus rhamnosus* GG; *Lactobacillus plantarum* 299v; *Clostridium butyricum* M588; *Clostridium difficile* VP20621 (non-toxigenic *C. difficile* strain); combination of *Lactobacillus casei, Lactobacillus acidophilus* (Bio-K+CL1285); combination of *Lactobacillus casei, Lactobacillus bulgaricus, Streptococcus thermophilus* (Actimel); combination of *Lactobacillus acidophilus, Bifidobacterium bifidum* (Florajen3); combination of *Lactobacillus acidophilus, Lactobacillus bulgaricus delbrueckii* subsp. *bulgaricus, Lactobacillus bulgaricus casei, Lactobacillus bulgaricus plantarum, Bifidobacterium longum, Bifidobacterium infantis, Bifidobacterium breve*, and *Streptococcus salivarius* subsp. *thermophilus* (VSL #3)).

Such genetically-modified microorganisms may be administered as described herein, including by way of example, enterally, such as orally.

In various embodiments, such genetically-modified microorganisms comprising one or more antibiotic-degrading agents described herein are formulated using any of the formulation parameters as described herein. In some embodiments, the genetically-modified microorganisms comprising one or more antibiotic-degrading agents described herein are lyophilized. By way of non-limiting example, lyophilization can be via methods known in the art, including those described in U.S. Pat. No. 7,799,328, the contents of which are hereby incorporated by reference in their entirety. In some embodiments, lyophilized genetically-modified microorganisms comprising one or more antibiotic-degrading agents described herein are placed in an enterically coated soft gel or capsule.

In various embodiments, the formulations of the present invention take the form of those as described in U.S. Provisional Patent Application No. 62/061,507, the entire contents of all of which are incorporated herein by reference.

In various embodiments, the formulations of the present invention take the form of those as described in one or more of U.S. Pat. Nos. 8,535,713 and 8,9117,77 and US Patent Publication Nos. 20120141585, 20120141531, 2006/001896, 2007/0292523, 2008/0020018, 2008/0113031, 2010/0203120, 2010/0255087, 2010/0297221, 2011/0052645, 2013/0243873, 2013/0330411, 2014/0017313, and 2014/0234418, the contents of which are hereby incorporated by reference in their entirety.

In various embodiments, the formulations of the present invention take the form of those as described in International Patent Publication No. WO 2008/135090, the contents of which are hereby incorporated by reference in their entirety.

In various embodiments, the formulations of the present invention take the form of those described in one or more of U.S. Pat. Nos. 4,196,564; 4,196,565; 4,247,006; 4,250,997; 4,268,265; 5,317,849; 6,572,892; 7,712,634; 8,074,835; 8,398,912; 8,440,224; 8,557,294; 8,646,591; 8,739,812; 8,810,259; 8,852,631; and 8,911,788 and US Patent Publication Nos. 2014/0302132; 2014/0227357; 20140088202; 20130287842; 2013/0295188; 2013/0307962; and 20130184290 the contents of which are hereby incorporated by reference in their entirety.

Any antibiotic-degrading agent and/or pharmaceutical composition (and/or additional therapeutic agents) described herein can take the form of solutions, suspensions, emulsion, drops, tablets, pills, pellets, capsules, capsules containing liquids, capsules containing multiparticulates, powders, suppositories, emulsions, aerosols, sprays, suspensions, delayed-release formulations, sustained-release formulations, controlled-release formulations, or any other form suitable for use. In one embodiment, the composition is in the form of a capsule or a tablet (see, e.g., U.S. Pat. No. 5,698,155).

The formulations comprising the antibiotic-degrading agents and/or pharmaceutical compositions (and/or additional therapeutic agents) may conveniently be presented in unit dosage forms. For example, the dosage forms may be prepared by methods which include the step of bringing the therapeutic agents into association with a carrier, which constitutes one or more accessory ingredients. Typically, the formulations are prepared by uniformly and intimately bringing the therapeutic agent into association with a liquid carrier, a finely divided solid carrier, or both, and then, if necessary, shaping the product into dosage forms of the desired formulation (e.g., wet or dry granulation, powder blends, etc., followed by press tableting)

In some embodiments, the administration the antibiotic-degrading agents and/or pharmaceutical compositions (and/ or additional therapeutic agents) is any one of oral, intravenous, and parenteral. In some embodiments, the administration of the antibiotic-degrading agents and/or pharmaceutical compositions (and/or additional therapeutic agents) is not intravenous in order to, for example, prevent interference with an antibiotic administered systemically. In other embodiments, routes of administration include, for example: oral, intradermal, intramuscular, intraperitoneal, intravenous, subcutaneous, intranasal, epidural, sublingual, intranasal, intracerebral, intravaginal, transdermal, rectally, by inhalation, or topically, particularly to the ears, nose, eyes, or skin. In some embodiments, the administering is effected orally or by parenteral injection.

In various embodiments, the administration the antibiotic-degrading agents and/or pharmaceutical compositions (and/or additional therapeutic agents) is into the GI tract via, for example, oral delivery, nasogastral tube, intestinal intubation (e.g. an enteral tube or feeding tube such as, for example, a jejunal tube or gastro-jejunal tube, etc.), endoscopy, colonoscopy, or enema.

In an embodiment, the antibiotic-degrading agents and/or pharmaceutical compositions (and/or additional therapeutic agents) described herein can be administered orally. In other embodiments, the antibiotic-degrading agents and/or pharmaceutical compositions (and/or additional therapeutic agents) can also be administered by any other convenient route, for example, by intravenous infusion or bolus injection, by absorption through epithelial or mucocutaneous linings (e.g., oral mucosa, rectal and intestinal mucosa, etc.) and can be administered together with an additional therapeutic agent. Administration can be systemic or local. In some embodiments, administration is not at the site of infection to avoid, for example, hydrolysis of an antibiotic at the site of infection. Various delivery systems are known, e.g., encapsulation in liposomes, microparticles, microcapsules, capsules, etc., and can be used for administration.

In one embodiment, the antibiotic-degrading agents and/or pharmaceutical compositions (and/or additional therapeutic agents) described herein is formulated as a composition adapted for oral administration to humans. Compositions for oral delivery can be in the form of tablets, lozenges, aqueous or oily suspensions, granules, powders, sprinkles, emulsions, capsules, syrups, or elixirs, for example. Orally administered compositions can comprise one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration to provide a sustained action over an extended period of time. Selectively permeable membranes surrounding an osmotically active agent driving any antibiotic-degrading agents (and/or additional therapeutic agents) described herein are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be useful. Oral compositions can include standard excipients such as mannitol, lactose, starch, magnesium stearate, sodium saccharin, cellulose, ethacrylic acid and derivative polymers thereof, and magnesium carbonate. In one embodiment, the excipients are of pharmaceutical grade. Suspensions, in addition to the active compounds, may contain suspending agents such as, for example, ethoxylated isostearyl alcohols, polyoxyethylene sorbitol and sorbitan esters, microcrystalline cellulose, aluminum metahydroxide, bentonite, agar-agar, tragacanth, etc., and mixtures thereof.

In various embodiments, the antibiotic-degrading agents and/or pharmaceutical compositions (and/or additional therapeutic agent) are formulated as solid dosage forms such as tablets, pellets, dispersible powders, granules, and capsules. In one embodiment, the antibiotic-degrading agents and/or pharmaceutical compositions (and/or additional therapeutic agent) are formulated as a capsule. In another embodiment, the antibiotic-degrading agents and/or pharmaceutical compositions (and/or additional therapeutic agent) are formulated as a tablet. In yet another embodiment, the antibiotic-degrading agents and/or pharmaceutical compositions (and/or additional therapeutic agent) are formulated as a soft-gel capsule. In a further embodiment, the antibiotic-degrading agents and/or pharmaceutical compositions (and/or additional therapeutic agent) are formulated as a gelatin capsule.

Dosage forms suitable for parenteral administration (e.g. intravenous, intramuscular, intraperitoneal, subcutaneous and intra-articular injection and infusion) include, for example, solutions, suspensions, dispersions, emulsions, and the like. They may also be manufactured in the form of sterile solid compositions (e.g. lyophilized composition), which can be dissolved or suspended in sterile injectable medium immediately before use. They may contain, for example, suspending or dispersing agents.

Administration and Dosage

It will be appreciated that the actual dose of the antibiotic-degrading agent (and/or additional therapeutic agents) to be administered according to the present invention will vary according to, for example, the particular dosage form and the mode of administration. Many factors that may modify the action of the antibiotic-degrading agent (e.g., body weight, gender, diet, time of administration, route of administration, rate of excretion, condition of the subject, drug combinations, genetic disposition and reaction sensitivities) can be taken into account by those skilled in the art. Administration can be carried out continuously or in one or more discrete doses within the maximum tolerated dose.

Optimal administration rates for a given set of conditions can be ascertained by those skilled in the art using conventional dosage administration tests.

Individual doses of the antibiotic-degrading agent (and/or additional therapeutic agents) can be administered in unit dosage forms (e.g., tablets or capsules) containing, for example, from about 0.01 mg to about 5,000 mg, from about 0.01 mg to about 4,000 mg, from about 0.01 mg to about 3,000 mg, from about 0.01 mg to about 2,000 mg, from about 0.01 mg to about 1,000 mg, from about 0.01 mg to about 950 mg, from about 0.01 mg to about 900 mg, from about 0.01 mg to about 850 mg, from about 0.01 mg to about 800 mg, from about 0.01 mg to about 750 mg, from about 0.01 mg to about 700 mg, from about 0.01 mg to about 650 mg, from about 0.01 mg to about 600 mg, from about 0.01 mg to about 550 mg, from about 0.01 mg to about 500 mg, from about 0.01 mg to about 450 mg, from about 0.01 mg to about 400 mg, from about 0.01 mg to about 350 mg, from about 0.01 mg to about 300 mg, from about 0.01 mg to about 250 mg, from about 0.01 mg to about 200 mg, from about 0.01 mg to about 150 mg, from about 0.01 mg to about 100 mg, from about 0.1 mg to about 90 mg, from about 0.1 mg to about 80 mg, from about 0.1 mg to about 70 mg, from about 0.1 mg to about 60 mg, from about 0.1 mg to about 50 mg, from about 0.1 mg to about 40 mg, from about 0.1 mg to about 30 mg, from about 0.1 mg to about 20 mg, from about 0.1 mg to about 10 mg, from about 0.1 mg to about 5 mg, from about 0.1 mg to about 3 mg, from about 0.1 mg to about 1 mg of the active ingredient per unit dosage form, or from about 5 mg to about 80 mg per unit dosage form. For example, a unit dosage form can include about 0.01 mg, about 0.02 mg, about 0.03 mg, about 0.04 mg, about 0.05 mg, about 0.06 mg, about 0.07 mg, about 0.08 mg, about 0.09 mg, about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 2 mg, about 3 mg, about 4 mg, about 5 mg, about 6 mg, about 7 mg, about 8 mg, about 9 mg about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1,000 mg, about 2,000 mg, about 3,000 mg, about 4,000 mg, or about 5,000 mg of the active ingredient, inclusive of all values and ranges therebetween.

In one embodiment, the antibiotic-degrading agent (and/or additional therapeutic agents) is administered at an amount of from about 0.01 mg to about 100 mg daily, an amount of from about 0.01 mg to about 5,000 mg daily, about 0.01 mg to about 4,000 mg daily, about 0.01 mg to about 3,000 mg daily, about 0.01 mg to about 2,000 mg daily, about 0.01 mg to about 1,000 mg daily, from about 0.01 mg to about 950 mg daily, from about 0.01 mg to about 900 mg daily, from about 0.01 mg to about 850 mg daily, from about 0.01 mg to about 800 mg daily, from about 0.01 mg to about 750 mg daily, from about 0.01 mg to about 700 mg daily, from about 0.01 mg to about 650 mg daily, from about 0.01 mg to about 600 mg daily, from about 0.01 mg to about 550 mg daily, from about 0.01 mg to about 500 mg daily, from about 0.01 mg to about 450 mg daily, from about 0.01 mg to about 400 mg daily, from about 0.01 mg to about 350 mg daily, from about 0.01 mg to about 300 mg daily, from about 0.01 mg to about 250 mg daily, from about 0.01 mg to about 200 mg daily, from about 0.01 mg to about 150 mg daily, from about 0.1 mg to about 100 mg daily, from about 0.1 mg to about 95 mg daily, from about 0.1 mg to about 90 mg daily, from about 0.1 mg to about 85 mg daily, from about 0.1 mg to about 80 mg daily, from about 0.1 mg to about 75 mg daily, from about 0.1 mg to about 70 mg daily, from about 0.1 mg to about 65 mg daily, from about 0.1 mg to about 60 mg daily, from about 0.1 mg to about 55 mg daily, from about 0.1 mg to about 50 mg daily, from about 0.1 mg to about 45 mg daily, from about 0.1 mg to about 40 mg daily, from about 0.1 mg to about 35 mg daily, from about 0.1 mg to about 30 mg daily, from about 0.1 mg to about 25 mg daily, from about 0.1 mg to about 20 mg daily, from about 0.1 mg to about 15 mg daily, from about 0.1 mg to about 10 mg daily, from about 0.1 mg to about 5 mg daily, from about 0.1 mg to about 3 mg daily, from about 0.1 mg to about 1 mg daily, or from about 5 mg to about 80 mg daily. In various embodiments, the antibiotic-degrading agent (and/or additional therapeutic agents) is administered at a daily dose of about 0.01 mg, about 0.02 mg, about 0.03 mg, about 0.04 mg, about 0.05 mg, about 0.06 mg, about 0.07 mg, about 0.08 mg, about 0.09 mg, about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 2 mg, about 3 mg, about 4 mg, about 5 mg, about 6 mg, about 7 mg, about 8 mg, about 9 mg about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1,000 mg, about 2,000 mg, about 3,000 mg, about 4,000 mg, or about 5,000 mg inclusive of all values and ranges therebetween.

In some embodiments, a suitable dosage of the antibiotic-degrading agent (and/or additional therapeutic agents) is in a range of about 0.01 mg/kg to about 100 mg/kg of body weight of the subject, for example, about 0.01 mg/kg, about 0.02 mg/kg, about 0.03 mg/kg, about 0.04 mg/kg, about 0.05 mg/kg, about 0.06 mg/kg, about 0.07 mg/kg, about 0.08 mg/kg, about 0.09 mg/kg, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, 1.9 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg body weight, about 20 mg/kg body weight, about 30 mg/kg body weight, about 40 mg/kg body weight, about 50 mg/kg body weight, about 60 mg/kg body weight, about 70 mg/kg body weight, about 80 mg/kg body weight, about 90 mg/kg body weight, or about 100 mg/kg body weight, inclusive of all values and ranges therebetween. In other embodiments, a suitable dosage of the antibiotic-degrading agents (and/or additional therapeutic agents) in a range of about 0.01 mg/kg to about 100 mg/kg of body weight, in a range of about 0.01 mg/kg to about 90 mg/kg of body weight, in a range of about 0.01 mg/kg to about 80 mg/kg of body weight, in a range of about 0.01 mg/kg to about 70 mg/kg of body weight, in a range of about 0.01 mg/kg to about 60 mg/kg of body weight, in a range of about 0.01 mg/kg to about 50 mg/kg of body weight, in a range of about 0.01 mg/kg to about 40 mg/kg of body weight, in a range of about 0.01 mg/kg to about 30 mg/kg of body weight, in a range of about 0.01 mg/kg to about 20 mg/kg of body weight, in a range of about 0.01 mg/kg to about 10 mg/kg of body weight, in a range of about 0.01 mg/kg to about 9 mg/kg of body weight, in a range of about 0.01 mg/kg to about 8 mg/kg of body weight, in a range of about 0.01 mg/kg to about 7 mg/kg of body weight, in a range of 0.01 mg/kg to about 6 mg/kg of body weight, in a range of about 0.05 mg/kg to about 5 mg/kg of body weight, in a range of about 0.05 mg/kg to about 4 mg/kg of body weight, in a range of about 0.05 mg/kg to about 3 mg/kg of body weight, in a range of about 0.05 mg/kg to about 2 mg/kg of body weight, in a range of about 0.05 mg/kg to about 1.5 mg/kg of body weight, or in a range of about 0.05 mg/kg to about 1 mg/kg of body weight.

In accordance with certain embodiments of the invention, the antibiotic-degrading agent may be administered, for example, more than once daily (e.g., about two times, three times, four times, five times, six times, seven times, eight times, nine times, or ten times daily), about once per day, about every other day, about every third day, about once a week, about once every two weeks, about once every month, about once every two months, about once every three months, about once every six months, or about once every year.

Additional Therapeutic Agents and Combination Therapy or Co-Formulation

Administration of the present formulations may be combined with additional therapeutic agents. Co-administration of the additional therapeutic agent and the present formulations may be simultaneous or sequential. Further, the present formulations may comprise an additional therapeutic agent (e.g. via co-formulation). For example, the additional therapeutic agent and the antibiotic-degrading agent may be combined into a single formulation. Alternatively, the additional therapeutic agent and the antibiotic-degrading agent may be formulated separately.

In one embodiment, the additional therapeutic agent and the antibiotic-degrading agent are administered to a subject simultaneously. The term "simultaneously" as used herein, means that the additional therapeutic agent and the antibiotic-degrading agent are administered with a time separation of no more than about 60 minutes, such as no more than about 30 minutes, no more than about 20 minutes, no more than about 10 minutes, no more than about 5 minutes, or no more than about 1 minute. Administration of the additional therapeutic agent and the antibiotic-degrading agent can be by simultaneous administration of a single formulation (e.g., a formulation comprising the additional therapeutic agent and the antibiotic-degrading agent) or of separate formulations (e.g., a first formulation including the additional therapeutic agent and a second formulation including the antibiotic-degrading agent).

In a further embodiment, the additional therapeutic agent and the antibiotic-degrading agent are administered to a subject simultaneously but the release of additional therapeutic agent and the antibiotic-degrading agent from their respective dosage forms (or single unit dosage form if co-formulated) in the GI tract occurs sequentially.

Co-administration does not require the additional therapeutic agents to be administered simultaneously, if the timing of their administration is such that the pharmacological activities of the additional therapeutic agent and the antibiotic-degrading agent overlap in time. For example, the additional therapeutic agent and the antibiotic-degrading agent can be administered sequentially. The term "sequentially" as used herein means that the additional therapeutic agent and the antibiotic-degrading agent are administered with a time separation of more than about 60 minutes. For example, the time between the sequential administration of the additional therapeutic agent and the antibiotic-degrading agent can be more than about 60 minutes, more than about 2 hours, more than about 5 hours, more than about 10 hours, more than about 1 day, more than about 2 days, more than about 3 days, or more than about 1 week apart. The optimal administration times will depend on the rates of metabolism, excretion, and/or the pharmacodynamic activity of the additional therapeutic agent and the antibiotic-degrading agent being administered. Either the additional therapeutic agent or the antibiotic-degrading agent may be administered first.

Co-administration also does not require the additional therapeutic agents to be administered to the subject by the same route of administration. Rather, each additional therapeutic agent can be administered by any appropriate route, for example, parenterally or non-parenterally.

In some embodiments, the additional therapeutic agent is an anti-bacterial agent, which includes, but is not limited to, cephalosporin antibiotics (cephalexin, cefuroxime, cefadroxil, cefazolin, cephalothin, cefaclor, cefamandole, cefoxitin, cefprozil, and ceftobiprole); fluoroquinolone antibiotics (cipro, Levaquin, floxin, tequin, avelox, and norflox); tetracycline antibiotics (tetracycline, minocycline, oxytetracycline, and doxycycline); penicillin antibiotics (amoxicillin, ampicillin, penicillin V, dicloxacillin, carbenicillin, vancomycin, and methicillin); monobactam antibiotics (aztreonam); and carbapenem antibiotics (ertapenem, doripenem, imipenem/cilastatin, and meropenem). In some embodiments, any of the penicillin, cephalosporin, monobactam, and carbapenem antibiotics described herein may be the additional therapeutic agent. In some embodiments, the additional therapeutic agent is an anti-bacterial agent, which includes, but is not limited to, the antibiotics described elsewhere herein.

In some embodiments, the additional therapeutic agent is an antibiotic-degrading agent inhibitor. Illustrative inhibitors include, any of the agents described herein. Illustrative inhibitors include tazobactam, sulbactam, EDTA, clavulanic acid, avibactam, monobactam derivatives, ATMO derivatives, penems (e.g., BRL42715 and derivatives thereof, Syn1012, oxapenems, trinems, 1β-methylcarbapenems), penicillin and cephalosporin sulfone derivatives (e.g., C-2/C-3-substituted penicillin and cephalosporin sulfones, C-6-substituted penicillin sulfones), non-β-lactam inhibitors (e.g., boronic acid transition state analogs, phosphonates, NXL104, hydroxamates) and metallo-β-lactamase inhibitors such as thiol derivatives, pyridine dicarboxylates, trifluoromethyl ketones and alcohols, carbapenem analogs, tricyclic natural products, succinate derivatives, and C-6-mercaptomethyl penicillinates.

In some embodiments, the additional therapeutic agent is an adjunctive therapy that is used in, for example, the treatment of CDI as described herein. In some embodiments, the additional therapeutic agent is metronidazole (e.g. FLAGYL), fidaxomicin (e.g. DIFICID), or vancomycin (e.g. VANCOCIN), rifaximin, charcoal-based binders/adsorbents (e.g. DAV132), fecal bacteriotherapy, probiotic therapy (see, e.g., *Intnat'l J Inf Dis*, 16 (11): e786, the contents of which are hereby incorporated by reference, illustrative probiotics include *Saccharomyces boulardii; Lactobacillus rhamnosus* GG; *Lactobacillus plantarum* 299v; *Clostridium butyricum* M588; *Clostridium difficile* VP20621 (non-toxigenic *C. difficile* strain); combination of *Lactobacillus casei, Lactobacillus acidophilus* (Bio-K+ CL1285); combination of *Lactobacillus casei, Lactobacillus bulgaricus, Streptococcus thermophilus* (Actimel); combination of *Lactobacillus acidophilus, Bifidobacterium bifidum* (Florajen3); combination of *Lactobacillus acidophilus, Lactobacillus bulgaricus delbrueckii* subsp. *bulgaricus, Lactobacillus bulgaricus casei, Lactobacillus bulgaricus plantarum, Bifidobacterium longum, Bifidobacterium infantis, Bifidobacterium breve, Streptococcus salivarius* subsp. *thermophilus* (VSL #3)) and antibody or other biologic therapy (e.g. monoclonal antibodies against *C. difficile* toxins A and B as described in *N Engl J Med*. 2010; 362(3):197, the content of which are hereby incorporated by reference in their entirety; neutralizing binding proteins, for example, arranged as multimers, which are directed to one or more of SEQ ID NOs, recited in United States Patent Publication No. 2013/0058962 (e.g. one or more of SEQ ID Nos.: 59, 60, 95, 67, 68, and 87), the contents of which are hereby incorporated by reference); or any neutralizing binding protein directed against *C. difficile* binary toxin.

In some embodiments, the additional therapeutic agent is an antidiarrheal agent. Antidiarrheal agents suitable for use in the present invention include, but are not limited to, DPP-IV inhibitors, natural opioids, such as tincture of opium, paregoric, and codeine, synthetic opioids, such as diphenoxylate, difenoxin and loperamide, bismuth subsalicylate, lanreotide, vapreotide and octreotide, motiln antagonists, COX2 inhibitors like celecoxib, glutamine, thalidomide and traditional antidiarrheal remedies, such as kaolin, pectin, berberine and muscarinic agents.

In some embodiments, the additional therapeutic agent is an anti-inflammatory agent such as steroidal anti-inflammatory agents or non-steroidal anti-inflammatory agents (NSAIDS), Steroids, particularly the adrenal corticosteroids and their synthetic analogues, are well known in the art. Examples of corticosteroids useful in the present invention include, without limitation, hydroxyltriamcinolone, alpha-methyl dexamethasone, beta-methyl betamethasone, beclomethasone dipropionate, betamethasone benzoate, betamethasone dipropionate, betamethasone valerate, clobetasol valerate, desonide, desoxymethasone, dexamethasone, diflorasone diacetate, diflucortolone valerate, fluadrenolone, fluclorolone acetonide, flumethasone pivalate, fluosinolone acetonide, fluocinonide, flucortine butylester, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone acetonide, medrysone, amcinafel, amcinafide, betamethasone and the balance of its esters, chloroprednisone, clocortelone, clescinolone, dichlorisone, difluprednate, flucloronide, flunisolide, fluoromethalone, fluperolone, fluprednisolone, hydrocortisone, meprednisone, paramethasone, prednisolone, prednisone, beclomethasone dipropionate. (NSAIDS) that may be used in the present invention, include but are not limited to, salicylic acid, acetyl salicylic acid, methyl salicylate, glycol salicylate, salicylmides, benzyl-2,5-diacetoxybenzoic acid, ibuprofen, fulindac, naproxen, ketoprofen, etofenamate, phenylbutazone, and indomethacin. Additional anti-inflammatory agents are described, for example, in U.S. Pat. No. 4,537,776, the entire contents of which are incorporated by reference herein.

In some embodiments, the additional therapeutic agent may be an analgesic. Analgesics useful in the compositions and methods of the present invention include, without limitation, morphine, codeine, heroine, methadone and related compounds, thebaine, orpiavine, and their derivatives, buprenorphine, the piperidines, morphinans, benzomorphans, tetrahydroisoquinolines, thiambutanes, benzylamines, tilidine, viminol, nefopam, capsaicin(8-methyl-N-vanillyl-6E-nonenamide), "synthetic" capsaicin(N-vanillylnonamide), and related compounds.

In some embodiments, the additional therapeutic agent may be an anti-viral agent that includes, but is not limited to, Abacavir, Acyclovir, Adefovir, Amprenavir, Atazanavir, Cidofovir, Darunavir, Delavirdine, Didanosine, Docosanol, Efavirenz, Elvitegravir, Emtricitabine, Enfuvirtide, Etravirine, Famciclovir, and Foscarnet.

In some embodiments, the present invention provides for the co-administration (e.g. via co-formulation or separate formulations) of one or more of the antibiotic-degrading agents described herein. In some embodiments, the present invention provides for the co-administration of one or more of the antibiotic-degrading agents described herein with other antibiotic-degrading agents known in the art. For example, the antibiotic-degrading agents described herein may be co-administered with one or more beta-lactamase enzyme of class EC 3.5.2.6. In some embodiments, the antibiotic-degrading agents described herein may be co-administered with one or more of a group 1, 2, 3, or 4 beta-lactamase, in accordance with the functional classification scheme proposed by Bush et al. (1995, Antimicrob. Agents Chemother. 39: 1211-1233; the entire contents of which are incorporated herein by reference) or a class A, B, C, or D beta-lactamase, in accordance with the Ambler classification which divides beta-lactamases based on their amino acid sequences (Ambler 1980, Philos Trans R Soc Lond B Biol Sci. 289: 321-331; the entire contents of which are incorporated herein by reference).

In various embodiments, the antibiotic-degrading agents described herein may be co-administered with one or more beta-lactamase enzymes that inactive or hydrolyze penicillins and/or cephalosporins. In an embodiment, the antibiotic-degrading agents described herein may be co-administered with one or more beta-lactamases selected from P1A, P3A or SYN-004 (synonyms for the same enzyme), or P4A. In an embodiment, the beta-lactamase is P1A or a derivative thereof. The P1A enzyme is a recombinant form of *Bacillus licheniformis* 749/C small exo beta-lactamase (see WO 2008/065247) which belongs to class A and is grouped to subgroup 2a in functional classification. *B. licheniformis* beta-lactamase and its P1A derivative are considered as penicillinases which have high hydrolytic capacity to degrade e.g. penicillin, ampicillin, amoxicillin or piperacillin and they are generally inhibited by active site-directed beta-lactamase inhibitors such as clavulanic acid, sulbactam or tazobactam. In another embodiment, the beta-lactamase is P3A or a derivative thereof as described, for example, in WO 2011/148041 and WO 2015/161243, the entire contents of all of which are incorporated herein by reference. In a further embodiment, the beta-lactamase is P4A or a derivative thereof as described, for example, in WO 2015/161243, the entire contents of which are incorporated herein by reference.

For all additional therapeutic agent compositions and methods, targeting to various parts of the GI tract may be employed as described herein.

In some embodiments, the present formulations are administered to a subject to avoid treatment with an additional therapeutic agent. For example, in the context of preventing *C. difficile* infection (CDI) and/or a *C. difficile*-associated disease, the present formulations may be provided to a subject to avoid the necessity of receiving, for example, vancomycin.

Methods of Treatment

In various aspects, the present invention provides methods for protecting a subject's gastrointestinal microbiome, comprising administering an effective amount of a pharmaceutical composition comprising an antibiotic-degrading agent, for example, any of the formulations described herein. In various embodiments, the subject is undergoing treatment or has recently undergone treatment with an antibiotic. The antibiotic-degrading agent is capable of degrading or inactivating the antibiotic and may be any one of the antibiotic-degrading agent described herein. In various embodiments, the antibiotic is one or more of a penicillin, cephalosporin, monobactam, and carbapenem as described herein. In an embodiment, the antibiotic-degrading agent is P2A and the antibiotic is ertapenem. In an embodiment, the antibiotic-degrading agent is NDM-1 and the antibiotic is cefepime and/or cefoperazone. In another embodiment, the antibiotic-degrading agent is KPC-1/2 and the antibiotic is aztreonam.

In various embodiments, the subjects include, but are not limited to, subjects that are at a particular risk for a microbiome-mediated disorder, such as, by way of non-limiting example, those undergoing treatment or having recently undergone treatment with an antibiotic. For example, the subject may have taken an antibiotic during the past about 30 or so days and/or have an immune system that is weak (e.g. from a chronic illness) and/or is a women and/or is elderly (e.g. over about 65 years old) and/or is an elderly woman and/or is undergoing (or has undergone) treatment with for heartburn or stomach acid disorders (e.g. with agents such as PREVACID, TAGAMET, PRILOSEC, or NEXIUM and related drugs) and/or has recently been in the hospital, including in an intensive care unit, or lives in a nursing home. Accordingly, in some embodiments, the methods and uses of the present invention treat or prevent a nosocomial infection and/or a secondary emergent infection and/or a hospital acquired infection (HAI).

In some embodiments, the methods and uses of the present invention include those in which an initial and/or adjunctive therapy is administered to a subject. Initial and/or adjunctive therapy indicates therapy that is used to treat for example, a microbiome-mediated disorder or disease upon detection of such disorder or disease. In some embodiments, the initial and/or adjunctive therapy is one or more of metronidazole, vancomycin, fidaxomicin, rifaximin, charcoal-based binder/adsorbent, fecal bacteriotherapy, probiotic therapy, and antibody therapy, as described herein. In various embodiments, the methods and uses of the present invention include use of the pharmaceutical compositions and formulations including antibiotic-degrading agent (and/or additional therapeutic agent) as an adjuvant to any of these initial and/or adjunctive therapies (including co-administration or sequential administration). In various embodiments, the methods and uses of the present invention include use of the pharmaceutical compositions and formulations including antibiotic-degrading agent (and/or additional therapeutic agent) in a subject undergoing initial and/or adjunctive therapies.

In some embodiments, the methods and uses of the present invention include those in which an antibiotic and an inhibitor of antibiotic-degrading agent are administered to a subject. In various embodiments, the subject may be receiving a co-formulation of an antibiotic with one or more antibiotic-degrading agent inhibitors (e.g. Augmentin is a mixture of amoxicillin and clavulanic acid). Such co-formulations include, but are not limited to, amoxicillin-clavulanic acid (Augmentin, ticarcillin-clavulanic acid (Timentin), ampicillin-sulbactam (Sultamicillin, e.g. Unasyn), piperacillin-tazobactam (Zosyn), and cefoperazone-sulbactam. In various embodiments, methods of the present invention comprise further administering an antibiotic-degrading agent inhibitor that releases in the GI tract proximal to the antibiotic-degrading agent. In an embodiment, the antibiotic-degrading agent inhibitor may be released at various parts of the GI tract where the antibiotic may be active. For example, the antibiotic-degrading agent inhibitor may be released at the stomach, duodenum, jejunum and ileum. Illustrative antibiotic-degrading agent inhibitors include, for example, tazobactam, sulbactam, EDTA, clavulanic acid, avibactam, monobactam derivatives, ATMO derivatives, penems (e.g., BRL42715 and derivatives thereof, Syn1012, oxapenems, trinems, 1-β-methylcarbapenems), penicillin and cephalosporin sulfone derivatives (e.g., C-2/C-3-substituted penicillin and cephalosporin sulfones, C-6-substituted penicillin sulfones), non-β-lactam inhibitors (e.g., boronic acid transition state analogs, phosphonates, NXL104, hydroxamates) and metallo-β-lactamase inhibitors such as thiol derivatives, pyridine dicarboxylates, trifluoromethyl ketones and alcohols, carbapenem analogs, tricyclic natural products, succinate derivatives, and C-6-mercaptomethyl penicillinates.

In various embodiments, the methods of the invention comprise treating or preventing a microbiome-mediated disorder. Illustrative microbiome-mediated disorder includes, but are not limited to, for example, those found in Table 3 of WO 2014/121298, the entire contents of which are incorporated herein by reference. For example, the microbiome-mediated disorder may be selected from an antibiotic-induced adverse effect, a *C. difficile* infection (CDI), a *C. difficile*-associated disease, ulcerative colitis, Crohn's disease, and irritable bowel syndrome. In various embodiments, the microbiome-mediated disorder is an antibiotic-induced adverse effect, a *C. difficile* infection (CDI), or a *C. difficile*-associated disease. In an embodiment, the present invention provides methods for treating an antibiotic-induced adverse effect in the GI tract, comprising administering an effective amount of a pharmaceutical composition or formulation including antibiotic-degrading agent (and/or additional therapeutic agent) described herein to a subject who is undergoing treatment or has recently undergone treatment with an antibiotic. In another embodiment, the present invention provides methods for preventing an antibiotic-induced adverse effect in the GI tract, comprising administering an effective amount of a pharmaceutical composition or formulation including antibiotic-degrading agent (and/or additional therapeutic agent) described herein to a subject who is undergoing treatment or has recently undergone treatment with an antibiotic.

In some embodiments, the subject is a human child. For example, microbiome disruption is linked to multiple metabolic, immune, neurological, etc. disorders. Early exposure to antibiotics (e.g. within about the first 2 years of life) can disrupt the microbiome and lead to eventual disease. Bailey, et al. JAMA Pediatr. 168(11), November 2014, the entire contents of which are hereby incorporated by reference, describes how early exposure to antibiotics is linked to obesity. Accordingly, in some embodiments, the present methods protect the microbiome of a child and prevent diseases such as obesity.

In an embodiment, the present invention provides methods for treating *C. difficile* infection (CDI) and/or a *C. difficile*-associated disease, comprising administering an effective amount of a pharmaceutical composition or formulation including antibiotic-degrading agent (and/or additional therapeutic agent) described herein to a subject who is undergoing treatment or has recently undergone treatment with an antibiotic. In another embodiment, the present invention provides methods for preventing *C. difficile* infection (CDI) and/or a *C. difficile*-associated disease, comprising administering an effective amount of a pharmaceutical composition or formulation including antibiotic-degrading agent (and/or additional therapeutic agent) described herein to a subject who is undergoing treatment or has recently undergone treatment with an antibiotic.

In various embodiments, the antibiotic-induced adverse effect and/or CDI or *C. difficile*-associated disease is one or more of: antibiotic-associated diarrhea, *C. difficile* diarrhea (CDD), *C. difficile* intestinal inflammatory disease, colitis, pseudomembranous colitis, fever, abdominal pain, dehydration and disturbances in electrolytes, megacolon, peritonitis, and perforation and/or rupture of the colon. Additional diseases, disorders and conditions which are suitable for treatment with the compositions and methods of the invention include those listed in Table 3 of WO 2014/121298, the entire contents of which are incorporated herein by reference.

In various embodiments, the present uses and methods pertain to co-treatment (simultaneously or sequentially) with the pharmaceutical composition or formulation including antibiotic-degrading agent (and/or additional therapeutic agent) described herein and/or any initial and/or adjunctive therapy, or treatment with a co-formulation of the pharmaceutical composition or formulation including antibiotic-degrading agent (and/or any additional therapeutic agent) described herein and/or any initial and/or adjunctive therapy for treatment of the various diseases described herein.

In various embodiments, the microbiome-mediated disorder is treated or prevented in the context of initial onset or relapse/recurrence (e.g. due to continued or restarted antibiotic therapy). For example, in a subject that has previously suffered from a microbiome-mediated disorder (e.g., CDI), the present pharmaceutical composition or formulation including antibiotic-degrading agent (and/or additional therapeutic agent) may be administered upon the first symptoms of recurrence in the subject. By way of non-limiting example, symptoms of recurrence include, in a mild case, about 5 to about 10 watery bowel movements per day, no significant fever, and only mild abdominal cramps while blood tests may show a mild rise in the white blood cell count up to about 15,000 (normal levels are up to about 10,000), and, in a severe case, more than about 10 watery stools per day, nausea, vomiting, high fever (e.g. about 102-104° F.), rectal bleeding, severe abdominal pain (e.g. with tenderness), abdominal distention, and a high white blood count (e.g. of about 15,000 to about 40,000).

Regardless of initial onset or relapse/recurrence, the microbiome-mediated disorder may be diagnosed via any of the symptoms described herein (e.g. watery diarrhea about 3 or more times a day for about 2 days or more, mild to bad cramping and pain in the belly, fever, blood or pus in the stool, nausea, dehydration, loss of appetite, loss of weight, etc.). Regardless of initial onset or relapse/recurrence, the microbiome-mediated disorder may also be diagnosed via enzyme immunoassays (e.g. to detect the *C. difficile* toxin A or B antigen and/or glutamine dehydrogenase (GDH), which is produced by *C. difficile* organisms), polymerase chain reactions (e.g., to detect the *C. difficile* toxin A or B gene or a portion thereof (e.g. tcdA or tcdB), including the ILLU-MIGENE LAMP assay), a cell cytotoxicity assay. For example, any of the following tests may be used: Meridian ImmunoCard Toxins A/B; Wampole Toxin A/B Quik Chek; Wampole C. diff Quik Chek Complete; Remel Xpect *Clostridium difficile* Toxin A/B; Meridian Premier Toxins A/B; Wampole *C. difficile* Tox A/B II; Remel Prospect Toxin A/B EIA; Biomerieux Vidas *C. difficile* Toxin A&B; BD Geneohm C. diff; Prodesse Progastro CD; and Cepheid Xpert C. diff. In various embodiments, the clinical sample is a subject's stool sample.

Also a flexible sigmoidoscopy "scope" test and/or an abdominal X-ray and/or a computerized tomography (CT) scan, which provides images of the colon, may be used in assessing a subject (e.g. looking for characteristic creamy white or yellow plaques adherent to the wall of the colon). Further, biopsies (e.g. of any region of the GI tract) may be used to assess a potential microbiome-mediated disorder (e.g., CDI and/or *C. difficile* associated disease) in subject.

In various embodiments, the methods and uses of the present invention relate to pharmaceutical compositions and formulations including antibiotic-degrading agent (and/or additional therapeutic agent) which release the antibiotic-degrading agent (and/or additional therapeutic agent) in a location in the GI tract in which it degrades or inactivates excess antibiotic residue. In an embodiment, the methods and uses of the present invention relate to pharmaceutical compositions and formulations including antibiotic-degrading agent (and/or additional therapeutic agent) which degrade or inactivate residual or excess antibiotic before it enters the GI tract, including the small and/or large intestine. In an embodiment, the methods and uses of the present invention relate to pharmaceutical compositions and formulations including antibiotic-degrading agent (and/or additional therapeutic agent) which degrade or inactivate residual or excess antibiotic before it enters the large intestine. In an embodiment, the methods and uses of the present invention relate to pharmaceutical compositions and formulations including antibiotic-degrading agent (and/or additional therapeutic agent) which degrade or inactivate residual or excess antibiotic in the GI tract. In various embodiments, the pharmaceutical compositions and formulations including antibiotic-degrading agent (and/or additional therapeutic agent) as described herein releases the antibiotic-degrading agent (and/or additional therapeutic agent) in a location in the GI tract that is distal to the release of the antibiotic. In various embodiments, the antibiotic-degrading agent (and/or additional therapeutic agent) is released in a location in the GI tract where it prevents a microbicidal activity of the residual or excess antibiotic on GI tract microbiota.

In some embodiments, methods and uses of the present invention relate to pharmaceutical compositions and formulation including antibiotic-degrading agent (and/or additional therapeutic agent) which maintain a normal intestinal microbiota and/or prevent the overgrowth of one or more pathogenic microorganisms in the GI tract of a subject. In various embodiments, the present invention provides for pharmaceutical compositions and methods that mitigate or prevent the overgrowth of various coliforms in a subject's gut (including coliforms that are virulent and/or antibiotic resistant). In various aspects, the methods, pharmaceutical compositions and formulations described herein prevent or diminish secondary infections with resistant organisms and may, in some embodiments, diminish antibiotic resistance development. Further, the methods, pharmaceutical compositions and formulations described herein may allow for use of antibiotics which are currently avoided due to resistance concerns and/or reduce the need for co-administration or co-formulation with one or more inhibitor of antibiotic-degrading agents.

In various embodiments, the antibiotic-degrading agents and/or pharmaceutical compositions (and/or additional therapeutic agents) do not substantially interfere with blood or plasma levels of an antibiotic. For example, the antibiotic-degrading agents and/or pharmaceutical compositions (and/or additional therapeutic agents) of the present invention allow for a subject to receive an antibiotic that might be required for an infection and do not interfere with the systemic activity of the antibiotic. In an embodiment, the antibiotic-degrading agents and/or pharmaceutical compositions (and/or additional therapeutic agents) does not substantially interfere with blood or plasma levels of the antibiotic. Rather, the antibiotic-degrading agents and/or pharmaceutical compositions (and/or additional therapeutic agents) inactivate excess antibiotic that may populate parts of the GI tract and in doing so, prevent the disruption of the microbiota that is linked to the various disease states described herein.

In various embodiments, the pharmaceutical compositions and formulations including antibiotic-degrading agent and/or additional therapeutic agent are not systemically absorbed. In various embodiments, the pharmaceutical compositions and formulations including antibiotic-degrading agent (and/or additional therapeutic agent) function to eliminate antibiotics from interfering with the microbiota of a microbiome (e.g. the gut, including the large intestine). In some embodiments, the pharmaceutical compositions and formulations including antibiotic-degrading agent (and/or additional therapeutic agent) do not interfere with the antibiotic absorption from the gut and/or enterohepatically sufficiently to alter the half-lives of antibiotic circulation. In some embodiments, the compositions and formulations including antibiotic-degrading agent (and/or additional therapeutic agent) do not interfere with the antibiotic absorption from the gut and/or enterohepatically enough to be clinically important.

In some embodiments, the terms "patient" and "subject" are used interchangeably. In some embodiments, the subject and/or animal is a mammal, e.g., a human, mouse, rat, guinea pig, dog, cat, horse, cow, pig, rabbit, sheep, or non-human primate, such as a monkey, chimpanzee, or baboon. In other embodiments, the subject and/or animal is a non-mammal, such as, for example, a zebrafish. In some embodiments, the subject and/or animal may comprise fluorescently-tagged cells (with e.g. GFP). In some embodiments, the subject and/or animal is a transgenic animal comprising a fluorescent cell.

In various embodiments, methods of the invention are useful in treatment a human subject. In some embodiments, the human is a pediatric human. In other embodiments, the human is an adult human. In other embodiments, the human is a geriatric human. In other embodiments, the human may be referred to as a subject. In some embodiments, the human is a female. In some embodiments, the human is a male.

In certain embodiments, the human has an age in a range of from about 1 to about 18 months old, from about 18 to about 36 months old, from about 1 to about 5 years old, from about 5 to about 10 years old, from about 10 to about 15 years old, from about 15 to about 20 years old, from about 20 to about 25 years old, from about 25 to about 30 years old, from about 30 to about 35 years old, from about 35 to about 40 years old, from about 40 to about 45 years old, from about 45 to about 50 years old, from about 50 to about 55 years old, from about 55 to about 60 years old, from about 60 to about 65 years old, from about 65 to about 70 years old, from about 70 to about 75 years old, from about 75 to about 80 years old, from about 80 to about 85 years old, from about 85 to about 90 years old, from about 90 to about 95 years old or from about 95 to about 100 years old. In one embodiment, the human is a child. In one embodiment, the human is a female.

In other embodiments, the subject is a non-human animal, and therefore the invention pertains to veterinary use. In a specific embodiment, the non-human animal is a household pet. In another specific embodiment, the non-human animal is a livestock animal.

Kits

The invention provides kits that can simplify the administration of any agent described herein. An illustrative kit of the invention comprises any composition described herein in unit dosage form. In one embodiment, the unit dosage form is a container, such as a pre-filled syringe or a pill bottle or a blister pack, which can be sterile, containing any agent described herein and a pharmaceutically acceptable carrier, diluent, excipient, or vehicle. The kit can further comprise a label or printed instructions instructing the use of any agent described herein. The kit can also further comprise one or more additional therapeutic agents described herein. In one embodiment, the kit comprises a container containing an effective amount of a composition of the invention and an effective amount of another composition, such those described herein.

In one embodiment, the kit contains an antibiotic-degrading agent as described herein (by way of non-limiting illustration, P2A, KPC-1/2, or NDM-1, which is optionally formulated as described herein) and/or an antibiotic as described herein, optionally along with any of the additional therapeutic agents described herein. For example, in some embodiments, the kit contains an antibiotic-degrading agent and an antibiotic provided in a blister pack that signals to the subject to ingest both agents.

In some embodiments, the additional therapeutic agent is an adjunctive therapy that is used in, for example, the treatment of CDI as described herein. In some embodiments, the additional therapeutic agent is metronidazole (e.g. FLAGYL), fidaxomicin (e.g. DIFICID), or vancomycin (e.g. Vancocin), rifaximin, fecal bacteriotherapy, charcoal-based binders/adsorbents (e.g. DAV132), probiotic therapy (see, e.g., Intnat'l J Inf Dis, 16 (11): e786, the contents of which are hereby incorporated by reference, illustrative probiotics include Saccharomyces boulardii; Lactobacillus rhamnosus GG; Lactobacillus plantarum 299v; Clostridium butyricum M588; Clostridium difficile VP20621 (non-toxigenic C. difficile strain); combination of Lactobacillus casei, Lactobacillus acidophilus (Bio-K+CL1285); combination of Lactobacillus casei, Lactobacillus bulgaricus, Streptococcus thermophilus (Actimel); combination of Lactobacillus acidophilus, Bifidobacterium bifidum (Florajen3); combination of Lactobacillus acidophilus, Lactobacillus bulgaricus delbrueckii subsp. bulgaricus, Lactobacillus bulgaricus casei, Lactobacillus bulgaricus plantarum, Bifidobacterium longum, Bifidobacterium infantis, Bifidobacterium breve, Streptococcus salivarius subsp. thermophilus (VSL #3)) and antibody or other biologic therapy (e.g. monoclonal antibodies against C. difficile toxins A and B as described in N Engl J Med. 2010; 362(3):197, the content of which are hereby incorporated by reference in their entirety; neutralizing binding proteins, for example, arranged as multimers, which are directed to one or more of SEQ ID NOs. recited in United States Patent Publication No. 2013/0058962 (e.g. one or more of SEQ ID Nos.: 59, 60, 95, 67, 68, and 87), the contents of which are hereby incorporated by reference); or any neutralizing binding protein directed against C. difficile binary toxin. In some embodiments, any of the antibiotics including penicillins and cephalosporins described herein may be the additional therapeutic agent.

Methods of Production

The invention also provides for methods of producing any of the antibiotic-degrading agents in host cells. In an embodiment, the host cell is Escherichia coli (E. coli). Illustrative host cells are further described, for example, in Example 1 and Examples 6-9. In other embodiments, the host cells may be, for example, yeast cells, Chinese hamster ovary (CHO) cells, human embryonic kidney 293 (HEK 293) cells, HeLa cells, baby hamster kidney (BHK) cells, monkey kidney cells (COS), or human hepatocellular carcinoma cells (e.g., Hep G2). In one embodiment, the host cell is a Bacillus spp. especially in B. licheniformis or B. subtilis.

In various embodiments, the methods of the invention include providing a host cell (e.g., E. coli cell) transformed with a vector comprising a sequence encoding the antibiotic-degrading agent, culturing the host cell (e.g., E. coli cell) to induce expression of the antibiotic-degrading agent, and recovering the antibiotic-degrading agent from a cellular fraction prepared from the host cell (e.g., E. coli cell). In an embodiment, the antibiotic-degrading agent is recovered from a soluble fraction prepared from the host cell. In various embodiments, the antibiotic-degrading agent may be any of the antibiotic-degrading agents as described herein. For example, the antibiotic-degrading agent may be a broad spectrum carbapenemase, selected from P2A, New Delhi metallo-β-lactamases (e.g. NDM-1 and/or NDM-2), and *K. pneumonia* carbapenemases (e.g. one or more of KPC-1/2, KPC°-3, KPC-4, KPC-5, KPC-6, KPC-7, KPC-8, KPC-9, KPC-10, and KPC-11). In an embodiment, the antibiotic-degrading agent is P2A. In another embodiment, the antibiotic-degrading agent is KPC-1/2. In a further embodiment, the antibiotic-degrading agent is NDM-1. In various embodiments, the antibiotic-degrading agent comprises an amino acid sequence having at least about 60%, at least about 70%, at least about 80%, at least about 90%, at least about 95%, at least about 97%, at least about 98%, at least about 99%, or 100% identity with one or more of SEQ ID NOs: 19-39, 37-65, 66, or 68.

In some embodiments, an inducible system is utilized to induce expression of the antibiotic-degrading agent in the host cell. In such embodiments, expression of the antibiotic-degrading agent may be induced in *E. coli* cell such as BL21 (DE3) or BLR (DE3). In an embodiment, induction is effected by addition of isopropyl β-D-1-thiogalactopyranoside (IPTG). In various embodiments, about 0.01 mM, about 0.02 mM, about 0.03 mM, about 0.04 mM, about 0.05 mM, about 0.06 mM, about 0.07 mM, about 0.08 mM, about 0.09 mM, about 0.1 mM, about 0.2 mM, about 0.3 mM, about 0.4 mM, about 0.5 mM, about 0.6 mM, about 0.7 mM, about 0.8 mM, about 0.9 mM, about 1 mM, about 2 mM, about 3 mM, about 4 mM, about 5 mM, about 6 mM, about 7 mM, about 8 mM, about 9 mM, or about 10 mM of IPTG is used for induction. In an embodiment, about 0.1 mM of IPTG is used for induction. In various embodiments, induction is carried about for about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, or about 24 hours. In an embodiment, induction is carried out for 4 hours. In another embodiment, induction is carried out for 20 hours. In various embodiments, induction is carried out at about 15° C., about 16° C., about 17° C., about 18° C., about 19° C., about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., about 35° C., about 35° C., or about 37° C. In an embodiment, induction is carried out at about 18° C. In another embodiment, induction is carried out at about 25° C. In a further embodiment, induction is carried out at about 37° C.

In various embodiments, the methods of the invention yield a homogeneous antibiotic-degrading agent preparation. In various embodiments, the methods involve (a) preparing an expression construct that expresses an antibiotic-degrading agent protein which comprises an amino acid sequence having at least about 60%, at least about 70%, at least about 80%, at least about 90%, at least about 95%, at least about 97%, at least about 98%, at least about 99%, or 100% identity with one or more of SEQ ID NOs: 19-39, 37-65, 66, or 68; (b) transforming a host cell with the expression construct; and (c) isolating the an antibiotic-degrading agent protein preparation produced by the bacterial host cell in culture, wherein the antibiotic-degrading agent protein preparation produced by the host cell in culture is substantially homogeneous.

The invention also provides for polynucleotides encoding any of the antibiotic-degrading agents as described herein, including, for example, replicable expression vectors comprising such polynucleotides. Such polynucleotides may further comprise, in addition to sequences encoding the antibiotic-degrading agents, one or more expression control elements. For example, the polynucleotide, may comprise one or more promoters or transcriptional enhancers, ribosomal binding sites, transcription termination signals, and polyadenylation signals, as expression control elements. In addition, the polynucleotides may include, for example, leader sequences to facilitate secretion of the antibiotic-degrading agents from host cells. Leader sequences for facilitating secretion in eukaryotic, yeast, and/or prokaryotic cells may be utilized. Illustrative secretion signal sequences, include, but are not limited to, alpha-factor full, alpha-factor, alpha-amylase, glucoamylase, inulinase, invertase, killer protein, lysozyme, and serum albumin sequences. Additional leader sequences are described in Examples 1 and 6. Polynucleotides encoding any of the antibiotic-degrading agents as described herein can be incorporated into expression vectors, which can be introduced into host cells through conventional transfection or transformation techniques. In various embodiments, the expression vector comprises a sequence that is at least 60%, at least about 70%, at least about 80%, at least about 90%, at least about 95%, at least about 97%, at least about 98%, at least about 99%, or 100% identity with one or more of SEQ ID NOS: 1-18, 67, or 69.

In various embodiments, the host cell (e.g., *E. coli* cell) is cultured in the presence of zinc. In an embodiment, the zinc is added to the culture media as $ZnSO_4$. In certain embodiments, the host cell (e.g., *E. coli* cell) is cultured in the presence of about 5 μM, or about 10 μM, or about 20 μM, or about 30 μM, or about 40 μM, or about 50 μM, or about 60 μM, or about 70 μM, or about 80 μM, or about 90 μM, or about 100 μM, or about 150 μM, or about 200 μM zinc. In certain embodiments, the host cell (e.g., *E. coli* cell) is cultured in the presence of about 5 μM, or about 10 μM, or about 20 μM, or about 30 μM, or about 40 μM, or about 50 μM, or about 60 μM, or about 70 μM, or about 80 μM, or about 90 μM, or about 100 μM, or about 150 μM, or about 200 μM $ZnSO_4$. In certain embodiments, the zinc increases the amount of antibiotic-degrading agent protein in a soluble fraction prepared from the host cell and reduces the amount of antibiotic-degrading agent protein in inclusion bodies relative to culturing in the absence of zinc. In various embodiments, the antibiotic-degrading agent recovered from the host cell is substantially soluble. In an embodiment, the antibiotic-degrading agent is substantially soluble in the cytoplasm or periplasmic space of the host cell (e.g., *E. coli* cell). In certain embodiments, the additional of zinc increases the yield of the antibiotic-degrading agent protein relative to a method that does not include zinc. In various embodiments, the methods involve (a) preparing an expression construct that expresses an antibiotic-degrading agent protein which comprises an amino acid sequence having at least about 60%, at least about 70%, at least about 80%, at least about 90%, at least about 95%, at least about 97%, at least about 98%, at least about 99%, or 100% identity with one or more of SEQ ID NOs: 19-39, 37-65, 66, or 68; (b) transforming a host cell with the expression construct; and (c) isolating the antibiotic-degrading agent protein preparation produced by the bacterial host cell in culture, the culture comprising zinc, wherein the antibiotic-degrading agent protein preparation produced by the host cell in culture has substantially greater yield than an antibiotic-degrading agent protein preparation produced by the bacterial host cell in culture not comprising zinc.

In various embodiments, the methods of the present invention yield substantially active antibiotic-degrading agents. For example, the methods of the present invention may yield at least about 1 gram, about 2 grams, about 3 grams, about 4 grams, about 5 grams, about 6 grams, about 7 grams, about 8 grams, about 9 grams, about 10 grams, about 11 grams, about 12 grams, about 13 grams, about 14 grams, about 15 grams, about 16 grams, about 17 grams, about 18 grams, about 19 grams, about 20 grams, about 21 grams, about 22 grams, about 23 grams, about 24 grams, about 25 grams, about 26 grams, about 27 grams, about 28 grams, about 29 grams, about 30 grams, about 31 grams, about 32 grams, about 33 grams, about 34 grams, about 35 grams, about 36 grams, about 37 grams, about 38 grams, about 39 grams, about 40 grams, about 41 grams, about 42 grams, about 43 grams, about 44 grams, about 45 grams, about 46 grams, about 47 grams, about 48 grams, about 49 grams, or about 50 grams of substantially active antibiotic-degrading agent per liter of culture. In an embodiment, the methods of the present invention yield at least about 10 grams of substantially active antibiotic-degrading agents per liter of culture. In another embodiment, the methods of the present invention yield at least about 15 grams of substantially active antibiotic-degrading agents per liter of culture.

In various embodiments, culturing of the host cells may be carried out in a shake flask or a bioreactor. In an embodiment, the antibiotic-degrading agent is KPC-1/2 and the culturing is carried out in a shake flask. In another embodiment, the antibiotic-degrading agent is P2A or NDM-1 and the culturing is carried out in a bioreactor.

EXAMPLES

Example 1. Design of P2A, NDM-1, and KPC-1/2 E. coli Expression Plasmids and Generation of Transformed Bacterial Strains The purpose of this study is, among others, to generate a panel of transformed bacterial strains to screen for carbapenemase expression.

For E. coli-mediated expression of the carbapenemases, P2A, NDM-1 (Yong et al., Antimicrob. Agents Chemother. (2009), 53:5046-5054) and KPC1/2 [Yigit et al., Antimicrob. Agents Chemother. (2001) 45:1151-1161, Yigit et al., Antimicrob. Agents Chemother. (2003), 47:3881-3889)], a total of 39 expression plasmids and 104 bacterial strains were generated. For P2A, 3 gene variants (SEQ ID NOS: 1-3), 9 plasmids and 25 bacterial strains, for NMD-1, 8 gene variants (SEQ ID NOS: 4-11), 17 plasmids and 44 bacterial strains, and for KPC1/2, 7 gene variants (SEQ ID NOS: 12-18), 13 plasmids and 35 bacterial strains were generated and tested. The gene expression constructs differed by plasmid backbone (e.g., pBR322 or pUC, for medium and high copy number, respectively), promoter (e.g., T7 or phoA, inducible by IPTG, or by reduction of phosphate in the media, respectively), leader sequence (e.g., STII, pelB, tat) to direct periplasmic protein accumulation, or no leader for cytoplasmic expression, the N-termini of the carbapenemase enzyme, and the bacterial host (e.g., BL21, BL21 degP, BL21 T7 LysY, BL21 T7 LysY degP, MG1655 T7+, W3110 degP, NEB Shuffle, or NEB Shuffle T7+). The expression cassettes were synthesized and cloned into the plasmids, pCYT10, pCYT11, pCYT12, pCYT13 (CYTOVANCE), as indicated. The sequences of all plasmids were verified by DNA sequencing. Tables 1-3 show the characteristics of various bacterial strains.

Specifically, gene variants, 3 for P2A (SEQ ID NOs: 1-3), 8 for NDM-1 (SEQ ID NOs: 4-11), and 7 for KPC (SEQ ID NOs: 12-18), differing in the N-terminal sequence and/or signal sequence (Tables 1.3), were synthesized and cloned into the expression plasmids, pCYT10, pCYT11, pCYT12, or pCYT13 (Table 4, CYTOVANCE) as indicated for a total of 9 P2A plasmids, 17 NDM plasmids, and 13 KPC plasmids (Tables 1-3). The 39 plasmids were transformed into the indicated bacteria, for a total of 104 transformed bacterial strains (Tables 1-3). Bacteria utilized for transformations included BL21, BL21 degP, BL21 T7 LysY, BL21 T7 LysY degP, MG1655 T7+, W3110 degP, NEB Shuffle, or NEB Shuffle T7+ (Tables 1-3). Colonies were picked, grown overnight, and diluted 1:50 into 24 well dishes (3 ml volume per well) and grown overnight. A total of 2×1.0 ml sample was saved per strain.

Sequences for the carbapenemase gene variants are included below:

```
P2A (SEQ ID NOS: 1-3): 3 gene variants, native, STII leader, or tat leader
P2A_1_10 (used in plasmids pP2A-1, pP2A-3, pP2A-5, pP2A-7)-Native no leader
Nucleic Acid Sequence:
                                                                    (SEQ ID NO: 1)
ATGGAAACGGGCACCATTAGCATTAGCCAACTCAACAAAAACGTTTGGGTCCACACCGAGTTAGG

CTATTTCAACGGTGAAGCCGTGCCGAGCAATGGTTTGGTTCTGAATACGTCCAAGGGTCTGGTGT

TGGTAGACTCCAGCTGGGACAATAAGCTGACCAAAGAACTGATCGAAATGGTTGAGAAAAAGTTC

CAGAAGCGTGTGACTGATGTCATTATCACCCATGCGCACGCGGACCGCATCGGTGGCATTACCGC

GCTGAAAGAGCGTGGCATTAAAGCACATAGCACGGCACTGACGGCTGAGCTGGCGAAGAACAGCG

GCTACGAAGAACCGCTGGGTGATCTGCAGACCATCACGTCGCTGAAGTTTGGCAACACCAAAGTC

GAGACTTTTTACCCAGGTAAGGGTCATACCGAAGATAACATCGTGGTTTGGCTGCCGCAGTACCA

AATCCTGGCCGGTGGCTGCCTGGTTAAGAGCGCAGAGGCGAAAGATCTGGGTAATGTCGCGGACG

CTTATGTGAACGAGTGGAGCACCTCTATTGAAAATGTTTTGAAACGTTATGGTAATATCAATAGC

GTTGTGCCGGGTCACGGTGAGGTCGGCGACAAAGGTCTGCTGTTGCACACGCTGGATCTGCTGAA

GTGATAA
```

Amino Acid Sequence:
(SEQ ID NO: 19)
METGTISISQ LNKNVWVHTE LGYFNGEAVP SNGLVLNTSK GLVLVDSSWD NKLTKELIEM

VEKKFQKRVT DVIITHAHAD RIGGITALKE RGIKAHSTAL TAELAKNSGY EEPLGDLQTI

TSLKFGNTKV ETFYPGKGHT EDNIVVWLPQ YQILAGGCLV KSAEAKDLGN VADAYVNEWS

TSIENVLKRY GNINSVVPGH GEVGDKGLLL HTLDLLK

P2A_2_10 (plasmids pP2A-2, pP2A-4, pP2A-6, pP2A-8)-STII leader
Nucleic Acid Sequence:
(SEQ ID NO: 2)
ATGAAAAAAAACATTGCATTTCTGCTGGCGAGCATGTTTGTTTTTAGCATTGCAACCAATGCATA

TGCCGAAACGGGCACCATTAGCATTAGCCAACTCAACAAAAACGTTTGGGTCCACACCGAGTTAG

GCTATTTCAACGGTGAAGCCGTGCCGAGCAATGGTTTGGTTCTGAATACGTCCAAGGGTCTGGTG

TTGGTAGACTCCAGCTGGGACAATAAGCTGACCAAAGAACTGATCGAAATGGTTGAGAAAAAGTT

CCAGAAGCGTGTGACTGATGTCATTATCACCCATGCGCACGCGGACCGCATCGGTGGCATTACCG

CGCTGAAAGAGCGTGGCATTAAAGCACATAGCACGGCACTGACGGCTGAGCTGGCGAAGAACAGC

GGCTACGAAGAACCGCTGGGTGATCTGCAGACCATCACGTCGCTGAAGTTTGGCAACACCAAAGT

CGAGACTTTTTACCCAGGTAAGGGTCATACCGAAGATAACATCGTGGTTTGGCTGCCGCAGTACC

AAATCCTGGCCGGTGGCTGCCTGGTTAAGAGCGCAGAGGCGAAAGATCTGGGTAATGTCGCGGAC

GCTTATGTGAACGAGTGGAGCACCTCTATTGAAAATGTTTTGAAACGTTATGGTAATATCAATAG

CGTTGTGCCGGGTCACGGTGAGGTCGGCGACAAAGGTCTGCTGTTGCACACGCTGGATCTGCTGA

AGTGATAA

Amino Acid Sequence: (STII leader amino acid sequence is shown in bold)
(SEQ ID NO: 20)
MKKNIAFLLA SMFVFSIATN AYAETGTISI SQLNKNVWVH TELGYFNGEA VPSNGLVLNT

SKGLVLVDSS WDNKLTKELI EMVEKKFQKR VTDVIITHAH ADRIGGITAL KERGIKAHST

ALTAELAKNS GYEEPLGDLQ TITSLKFGNT KVETFYPGKG HTEDNIVVWL PQYQILAGGC

LVKSAEAKDL GNVADAYVNE WSTSIENVLK RYGNINSVVP GHGEVGDKGL LLHTLDLLK

P2A_3_13 (plasmid pP2A-9)-Tat leader
Nucleic Acid Sequence:
(SEQ ID NO: 3)
ATGAAGCAGGCATTACGAGTAGCATTTGGTTTTCTCATACTGTGGGCATCAGTTCTGCATGCTGA

AACGGGCACCATTAGCATTAGCCAACTCAACAAAAACGTTTGGGTCCACACCGAGTTAGGCTATT

TCAACGGTGAAGCCGTGCCGAGCAATGGTTTGGTTCTGAATACGTCCAAGGGTCTGGTGTTGGTA

GACTCCAGCTGGGACAATAAGCTGACCAAAGAACTGATCGAAATGGTTGAGAAAAAGTTCCAGAA

GCGTGTGACTGATGTCATTATCACCCATGCGCACGCGGACCGCATCGGTGGCATTACCGCGCTGA

AAGAGCGTGGCATTAAAGCACATAGCACGGCACTGACGGCTGAGCTGGCGAAGAACAGCGGCTAC

GAAGAACCGCTGGGTGATCTGCAGACCATCACGTCGCTGAAGTTTGGCAACACCAAAGTCGAGAC

TTTTTACCCAGGTAAGGGTCATACCGAAGATAACATCGTGGTTTGGCTGCCGCAGTACCAAATCC

TGGCCGGTGGCTGCCTGGTTAAGAGCGCAGAGGCGAAAGATCTGGGTAATGTCGCGGACGCTTAT

GTGAACGAGTGGAGCACCTCTATTGAAAATGTTTTGAAACGTTATGGTAATATCAATAGCGTTGT

GCCGGGTCACGGTGAGGTCGGCGACAAAGGTCTGCTGTTGCACACGCTGGATCTGCTGAAGTGAT

AA

Amino Acid Sequence: (Tat leader amino acid sequence is shown in bold)
(SEQ ID NO: 21)
MKQALRVAFG FLILWASVLH AETGTISISQ LNKNVWVHTE LGYFNGEAVP SNGLVLNTSK

GLVLVDSSWD NKLTKELIEM VEKKFQKRVT DVIITHAHAD RIGGITALKE RGIKAHSTAL

TAELAKNSGY EEPLGDLQTI TSLKFGNTKV ETFYPGKGHT EDNIVVWLPQ YQILAGGCLV

KSAEAKDLGN VADAYVNEWS TSIENVLKRY GNINSVVPGH GEVGDKGLLL HTLDLLK

NDM (SEQ ID NOS: 4-11): 8 gene variants, native (delta 38), native (delta 37),
native (delta 35), STII delta 38, STII delta 37, STII delta 35,
PelB delta 38, or Tat delta 38 NDM_1_10 (plasmid pNDM-1, pMDM-4,
pNDM-7, pNDM-10)-Native delta-38
Nucleic Acid Sequence:
(SEQ ID NO: 4)
ATGGAAACCGGTGATCAGCGTTTTGGTGATTTAGTCTTTCGTCAATTGGCCCCAAACGTCTGGCA

GCATACCAGCTATCTGGATATGCCGGGTTTCGGTGCTGTTGCCAGCAACGGCCTGATCGTGCGTG

ACGGTGGCCGCGTGCTGGTTGTTGATACCGCCTGGACCGATGATCAGACGGCGCAGATTCTGAAT

TGGATCAAACAAGAAATCAATCTGCCGGTTGCGCTGGCAGTGGTCACCCACGCGCACCAAGACAA

AATGGGTGGCATGGACGCACTGCACGCGGCTGGTATTGCGACGTACGCAAATGCACTGAGCAACC

AGCTGGCACCGCAGGAGGGCATGGTTGCGGCGCAGCATAGCCTGACCTTTGCGGCGAATGGTTGG

GTGGAGCCGGCGACGGCTCCGAACTTCGGCCCGTTGAAAGTGTTCTATCCGGGTCCGGGTCACAC

CTCGGACAACATCACCGTCGGTATTGATGGCACCGACATTGCCTTCGGCGGCTGCCTGATCAAAG

ACAGCAAGGCAAAGTCCCTGGGCAATCTGGGTGATGCGGACACTGAGCACTACGCCGCGAGCGCA

CGCGCATTCGGTGCGGCATTTCCTAAGGCCTCCATGATTGTTATGAGCCATTCTGCGCCGGACAG

CCGTGCCGCGATCACGCACACGGCGCGTATGGCTGACAAGCTGCGCTAATGA

Amino Acid Sequence:
(SEQ ID NO: 22)
METGDQRFGD LVFRQLAPNV WQHTSYLDMP GFGAVASNGL IVRDGGRVLV VDTAWTDDQT

AQILNWIKQE INLPVALAVV THAHQDKMGG MDALHAAGIA TYANALSNQL APQEGMVAAQ

HSLTFAANGW VEPATAPNFG PLKVFYPGPG HTSDNITVGI DGTDIAFGGC LIKDSKAKSL

GNLGDADTEH YAASARAFGA AFPKASMIVM SHSAPDSRAA ITHTARMADK LR

NDM_2_10 (plasmid pNDM-2, pMDM-5, pNDM-8, pNDM-11)-STII leader + delta-38
Nucleic Acid Sequence:
(SEQ ID NO: 5)
ATGAAAAAGAACATTGCATTTCTGCTGGCGAGCATGTTTGTTTTTAGCATTGCAACCAATGCATA

TGCCATGGAAACCGGTGATCAGCGTTTTGGTGATTTAGTCTTTCGTCAATTGGCCCCAAACGTCT

GGCAGCATACCAGCTATCTGGATATGCCGGGTTTCGGTGCTGTTGCCAGCAACGGCCTGATCGTG

CGTGACGGTGGCCGCGTGCTGGTTGTTGATACCGCCTGGACCGATGATCAGACGGCGCAGATTCT

GAATTGGATCAAACAAGAAATCAATCTGCCGGTTGCGCTGGCAGTGGTCACCCACGCGCACCAAG

ACAAAATGGGTGGCATGGACGCACTGCACGCGGCTGGTATTGCGACGTACGCAAATGCACTGAGC

AACCAGCTGGCACCGCAGGAGGGCATGGTTGCGGCGCAGCATAGCCTGACCTTTGCGGCGAATGG

TTGGGTGGAGCCGGCGACGGCTCCGAACTTCGGCCCGTTGAAAGTGTTCTATCCGGGTCCGGGTC

ACACCTCGGACAACATCACCGTCGGTATTGATGGCACCGACATTGCCTTCGGCGGCTGCCTGATC

AAAGACAGCAAGGCAAAGTCCCTGGGCAATCTGGGTGATGCGGACACTGAGCACTACGCCGCGAG

CGCACGCGCATTCGGTGCGGCATTTCCTAAGGCCTCCATGATTGTTATGAGCCATTCTGCGCCGG

ACAGCCGTGCCGCGATCACGCACACGGCGCGTATGGCTGACAAGCTGCGCTAATGA

Amino Acid Sequence: (STII leader amino acid sequence is shown in bold)
(SEQ ID NO: 23)
MKKNIAFLLA SMFVFSIATN AYAMETGDQR FGDLVFRQLA PNVWQHTSYL DMPGFGAVAS

NGLIVRDGGR VLVVDTAWTD DQTAQILNWI KQEINLPVAL AVVTHAHQDK MGGMDALHAA

GIATYANALS NQLAPQEGMV AAQHSLTFAA NGWVEPATAP NFGPLKVFYP GPGHTSDNIT

VGIDGTDIAF GGCLIKDSKA KSLGNLGDAD TEHYAASARA FGAAFPKASM IVMSHSAPDS

RAAITHTARM ADKLR

NDM_3_10 (plasmid pNDM-3, pMDM-6, pNDM-9, pNDM-12)-PelB leader + delta-38
Nucleic Acid Sequence:
(SEQ ID NO: 6)
ATGAAATACCTGCTGCCGACCGCTGCTGCTGGTCTGCTGCTCCTCGCTGCCCAGCCGGCGATGGC

CATGGAAACCGGTGATCAGCGTTTTGGTGATTTAGTCTTTCGTCAATTGGCCCCAAACGTCTGGC

AGCATACCAGCTATCTGGATATGCCGGGTTTCGGTGCTGTTGCCAGCAACGGCCTGATCGTGCGT

GACGGTGGCCGCGTGCTGGTTGTTGATACCGCCTGGACCGATGATCAGACGGCGCAGATTCTGAA

TTGGATCAAACAAGAAATCAATCTGCCGGTTGCGCTGGCAGTGGTCACCCACGCGCACCAAGACA

AAATGGGTGGCATGGACGCACTGCACGCGGCTGGTATTGCGACGTACGCAAATGCACTGAGCAAC

CAGCTGGCACCGCAGGAGGGCATGGTTGCGGCGCAGCATAGCCTGACCTTTGCGGCGAATGGTTG

GGTGGAGCCGGCGACGGCTCCGAACTTCGGCCCGTTGAAAGTGTTCTATCCGGGTCCGGGTCACA

CCTCGGACAACATCACCGTCGGTATTGATGGCACCGACATTGCCTTCGGCGGCTGCCTGATCAAA

GACAGCAAGGCAAAGTCCCTGGGCAATCTGGGTGATGCGGACACTGAGCACTACGCCGCGAGCGC

ACGCGCATTCGGTGCGGCATTTCCTAAGGCCTCCATGATTGTTATGAGCCATTCGCGCCGGACA

GCCGTGCCGCGATCACGCACACGGCGCGTATGGCTGACAAGCTGCGCTAATGA

Amino Acid Sequence: (PelB leader amino acid sequence is shown in bold)
(SEQ ID NO: 24)
MKYLLPTAAA GLLLLAAQPA MAMETGDQRF GDLVFRQLAP NVWQHTSYLD MPGFGAVASN

GLIVRDGGRV LVVDTAWTDD QTAQILNWIK QEINLPVALA VVTHAHQDKM GGMDALHAAG

IATYANALSN QLAPQEGMVA AQHSLTFAAN GWVEPATAPN FGPLKVFYPG PGHTSDNITV

GIDGTDIAFG GCLIKDSKAK SLGNLGDADT EHYAASARAF GAAFPKASMI VMSHSAPDSR

AAITHTARMA DKLR

NDM_4_13 (plasmid pNDM-13) Native + delta-37
Nucleic Acid Sequence:
(SEQ ID NO: 7)
ATGCAAATGGAAACCGGTGATCAGCGTTTTGGTGATTTAGTCTTTCGTCAATTGGCCCCAAACGT

CTGGCAGCATACCAGCTATCTGGATATGCCGGGTTTCGGTGCTGTTGCCAGCAACGGCCTGATCG

TGCGTGACGGTGGCCGCGTGCTGGTTGTTGATACCGCCTGGACCGATGATCAGACGGCGCAGATT

CTGAATTGGATCAAACAAGAAATCAATCTGCCGGTTGCGCTGGCAGTGGTCACCCACGCGCACCA

AGACAAAATGGGTGGCATGGACGCACTGCACGCGGCTGGTATTGCGACGTACGCAAATGCACTGA

GCAACCAGCTGGCACCGCAGGAGGGCATGGTTGCGGCGCAGCATAGCCTGACCTTTGCGGCGAAT

GGTTGGGTGGAGCCGGCGACGGCTCCGAACTTCGGCCCGTTGAAAGTGTTCTATCCGGGTCCGGG

TCACACCTCGGACAACATCACCGTCGGTATTGATGGCACCGACATTGCCTTCGGCGGCTGCCTGA

TCAAAGACAGCAAGGCAAAGTCCCTGGGCAATCTGGGTGATGCGGACACTGAGCACTACGCCGCG

AGCGCACGCGCATTCGGTGCGGCATTTCCTAAGGCCTCCATGATTGTTATGAGCCATTCGCGCC

GGACAGCCGTGCCGCGATCACGCACACGGCGCGTATGGCTGACAAGCTGCGCTAATGA

Amino Acid Sequence:
(SEQ ID NO: 25)
MQMETGDQRF GDLVFRQLAP NVWQHTSYLD MPGFGAVASN GLIVRDGGRV LVVDTAWTDD

QTAQILNWIK QEINLPVALA VVTHAHQDKM GGMDALHAAG IATYANALSN QLAPQEGMVA

AQHSLTFAAN GWVEPATAPN FGPLKVFYPG PGHTSDNITV GIDGTDIAFG GCLIKDSKAK

SLGNLGDADT EHYAASARAF GAAFPKASMI VMSHSAPDSR AAITHTARMA DKLR

NDM_5_13 (plasmid pNDM-14)-STII leader + delta-37
Nucleic Acid Sequence:
(SEQ ID NO: 8)
ATGAAAAAAACATTGCATTTCTGCTGGCGAGCATGTTTGTTTTTAGCATTGCAACCAATGCATA

TGCCCAAATGGAAACCGGTGATCAGCGTTTTGGTGATTTAGTCTTTCGTCAATTGGCCCCAAACG

```
TCTGGCAGCATACCAGCTATCTGGATATGCCGGGTTTCGGTGCTGTTGCCAGCAACGGCCTGATC

GTGCGTGACGGTGGCCGCGTGCTGGTTGTTGATACCGCCTGGACCGATGATCAGACGGCGCAGAT

TCTGAATTGGATCAAACAAGAAATCAATCTGCCGGTTGCGCTGGCAGTGGTCACCCACGCGCACC

AAGACAAATGGGTGGCATGGACGCACTGCACGCGGCTGGTATTGCGACGTACGCAAATGCACTG

AGCAACCAGCTGGCACCGCAGGAGGGCATGGTTGCGGCGCAGCATAGCCTGACCTTTGCGGCGAA

TGGTTGGGTGGAGCCGGCGACGGCTCCGAACTTCGGCCCGTTGAAAGTGTTCTATCCGGGTCCGG

GTCACACCTCGGACAACATCACCGTCGGTATTGATGGCACCGACATTGCCTTCGGCGGCTGCCTG

ATCAAAGACAGCAAGGCAAAGTCCCTGGGCAATCTGGGTGATGCGGACACTGAGCACTACGCCGC

GAGCGCACGCGCATTCGGTGCGGCATTTCCTAAGGCCTCCATGATTGTTATGAGCCATTCTGCGC

CGGACAGCCGTGCCGCGATCACGCACACGGCGCGTATGGCTGACAAGCTGCGCTAATGA
```

Amino Acid Sequence: (STII leader amino acid sequence is shown in bold)
(SEQ ID NO: 26)

MKKNIAFLLA SMFVFSIATN AYAQMETGDQ RFGDLVFRQL APNVWQHTSY LDMPGFGAVA

SNGLIVRDGG RVLVVDTAWT DDQTAQILNW IKQEINLPVA LAVVTHAHQD KMGGMDALHA

AGIATYANAL SNQLAPQEGM VAAQHSLTFA ANGWVEPATA PNFGPLKVFY PGPGHTSDNI

TVGIDGTDIA FGGCLIKDSK AKSLGNLGDA DTEHYAASAR AFGAAFPKAS MIVMSHSAPD

SRAAITHTAR MADKLR

NDM_6_13 (plasmid pNDM-15)-Native delta-35
Nucleic Acid Sequence:
(SEQ ID NO: 9)

```
ATGGGTCAACAAATGGAAACCGGTGATCAGCGTTTTGGTGATTTAGTCTTTCGTCAATTGGCCCC

AAACGTCTGGCAGCATACCAGCTATCTGGATATGCCGGGTTTCGGTGCTGTTGCCAGCAACGGCC

TGATCGTGCGTGACGGTGGCCGCGTGCTGGTTGTTGATACCGCCTGGACCGATGATCAGACGGCG

CAGATTCTGAATTGGATCAAACAAGAAATCAATCTGCCGGTTGCGCTGGCAGTGGTCACCCACGC

GCACCAAGACAAATGGGTGGCATGGACGCACTGCACGCGGCTGGTATTGCGACGTACGCAAATG

CACTGAGCAACCAGCTGGCACCGCAGGAGGGCATGGTTGCGGCGCAGCATAGCCTGACCTTTGCG

GCGAATGGTTGGGTGGAGCCGGCGACGGCTCCGAACTTCGGCCCGTTGAAAGTGTTCTATCCGGG

TCCGGGTCACACCTCGGACAACATCACCGTCGGTATTGATGGCACCGACATTGCCTTCGGCGGCT

GCCTGATCAAAGACAGCAAGGCAAAGTCCCTGGGCAATCTGGGTGATGCGGACACTGAGCACTAC

GCCGCGAGCGCACGCGCATTCGGTGCGGCATTTCCTAAGGCCTCCATGATTGTTATGAGCCATTC

TGCGCCGGACAGCCGTGCCGCGATCACGCACACGGCGCGTATGGCTGACAAGCTGCGCTAATGA
```

Amino Acid Sequence:
(SEQ ID NO: 27)

MGQQMETGDQ RFGDLVFRQL APNVWQHTSY LDMPGFGAVA SNGLIVRDGG RVLVVDTAWT

DDQTAQILNW IKQEINLPVA LAVVTHAHQD KMGGMDALHA AGIATYANAL SNQLAPQEGM

VAAQHSLTFA ANGWVEPATA PNFGPLKVFY PGPGHTSDNI TVGIDGTDIA FGGCLIKDSK

AKSLGNLGDA DTEHYAASAR AFGAAFPKAS MIVMSHSAPD SRAAITHTAR MADKLR

NDM_7_13 (plasmid pNDM-16)-STII leader + delta-35
Nucleic Acid Sequence:
(SEQ ID NO: 10)

```
ATGAAAAAAAACATTGCATTTCTGCTGGCGAGCATGTTTGTTTTTAGCATTGCAACCAATGCATA

TGCCGGTCAACAAATGGAAACCGGTGATCAGCGTTTTGGTGATTTAGTCTTTCGTCAATTGGCCC

CAAACGTCTGGCAGCATACCAGCTATCTGGATATGCCGGGTTTCGGTGCTGTTGCCAGCAACGGC

CTGATCGTGCGTGACGGTGGCCGCGTGCTGGTTGTTGATACCGCCTGGACCGATGATCAGACGGC

GCAGATTCTGAATTGGATCAAACAAGAAATCAATCTGCCGGTTGCGCTGGCAGTGGTCACCCACG
```

-continued

CGCACCAAGACAAAATGGGTGGCATGGACGCACTGCACGCGGCTGGTATTGCGACGTACGCAAAT

GCACTGAGCAACCAGCTGGCACCGCAGGAGGGCATGGTTGCGGCGCAGCATAGCCTGACCTTTGC

GGCGAATGGTTGGGTGGAGCCGGCGACGGCTCCGAACTTCGGCCCGTTGAAAGTGTTCTATCCGG

GTCCGGGTCACACCTCGGACAACATCACCGTCGGTATTGATGGCACCGACATTGCCTTCGGCGGC

TGCCTGATCAAAGACAGCAAGGCAAAGTCCCTGGGCAATCTGGGTGATGCGGACACTGAGCACTA

CGCCGCGAGCGCACGCGCATTCGGTGCGGCATTTCCTAAGGCCTCCATGATTGTTATGAGCCATT

CTGCGCCGGACAGCCGTGCCGCGATCACGCACACGGCGCGTATGGCTGACAAGCTGCGCTAATGA

Amino Acid Sequence: (STII leader amino acid sequence is shown in bold)
(SEQ ID NO: 28)
MKKNIAFLLA SMFVFSIATN AYAGQQMETG DQRFGDLVFR QLAPNVWQHT SYLDMPGFGA

VASNGLIVRD GGRVLVVDTA WTDDQTAQIL NWIKQEINLP VALAVVTHAH QDKMGGMDAL

HAAGIATYAN ALSNQLAPQE GMVAAQHSLT FAANGWVEPA TAPNFGPLKV FYPGPGHTSD

NITVGIDGTD IAFGGCLIKD SKAKSLGNLG DADTEHYAAS ARAFGAAFPK ASMIVMSHSA

PDSRAAITHT ARMADKLR

NDM_8_13 (plasmid pNDM-17)-Tat leader + delta-38
Nucleic Acid Sequence:
(SEQ ID NO: 11)
ATGAAGCAGGCATTACGAGTAGCATTTGGTTTTCTCATACTGTGGGCATCAGTTCTGCATGCTAT

GGAAACCGGTGATCAGCGTTTTGGTGATTTAGTCTTTCGTCAATTGGCCCCAAACGTCTGGCAGC

ATACCAGCTATCTGGATATGCCGGGTTTCGGTGCTGTTGCCAGCAACGGCCTGATCGTGCGTGAC

GGTGGCCGCGTGCTGGTTGTTGATACCGCCTGGACCGATGATCAGACGGCGCAGATTCTGAATTG

GATCAAACAAGAAATCAATCTGCCGGTTGCGCTGGCAGTGGTCACCCACGCGCACCAAGACAAAA

TGGGTGGCATGGACGCACTGCACGCGGCTGGTATTGCGACGTACGCAAATGCACTGAGCAACCAG

CTGGCACCGCAGGAGGGCATGGTTGCGGCGCAGCATAGCCTGACCTTTGCGGCGAATGGTTGGGT

GGAGCCGGCGACGGCTCCGAACTTCGGCCCGTTGAAAGTGTTCTATCCGGGTCCGGGTCACACCT

CGGACAACATCACCGTCGGTATTGATGGCACCGACATTGCCTTCGGCGGCTGCCTGATCAAAGAC

AGCAAGGCAAAGTCCCTGGGCAATCTGGGTGATGCGGACACTGAGCACTACGCCGCGAGCGCACG

CGCATTCGGTGCGGCATTTCCTAAGGCCTCCATGATTGTTATGAGCCATTCTGCGCCGGACAGCC

GTGCCGCGATCACGCACACGGCGCGTATGGCTGACAAGCTGCGCTAATGA

Amino Acid Sequence: (Tat leader amino acid sequence is shown in bold)
(SEQ ID NO: 29)
MKQALRVAFG FLILWASVLH AMETGDQRFG DLVFRQLAPN VWQHTSYLDM PGFGAVASNG

LIVRDGGRVL VVDTAWTDDQ TAQILNWIKQ EINLPVALAV VTHAHQDKMG GMDALHAAGI

ATYANALSNQ LAPQEGMVAA QHSLTFAANG WVEPATAPNF GPLKVFYPGP GHTSDNITVG

IDGTDIAFGG CLIKDSKAKS LGNLGDADTE HYAASARAFG AAFPKASMIV MSHSAPDSRA

AITHTARMAD KLR

KPC (SEQ ID NOs: 12-18): 7 gene variants, native, STII + native,
native delta 2, STII + native delta 2, native delta 8,
STII delta 8, Tat leader + native
KPC_1_10 (plasmid pKPC-1, pKPC-3, pKPC-5, pKPC-7)-Native
Nucleic Acid Sequence:
(SEQ ID NO: 12)
ATGGCAACCGCTCTGACCAATTTAGTTGCAGAACCTTTCGCGAAACTGGAGCAAGATTTTGGTGG

CTCCATTGGTGTGTATGCGATGGATACGGGCAGCGGCGCAACCGTTAGCTATCGCGCCGAGGAAC

GTTTTCCGCTGTGTTCCAGCTTCAAGGGTTTTCTGGCGGCTGCGGTCCTGGCGCGTAGCCAGCAG

CAAGCCGGCCTGCTGGACACCCCGATCCGTTACGGCAAAAATGCGCTGGTGCCGTGGAGCCCGAT

TAGCGAGAAGTACTTGACCACTGGTATGACGGTCGCCGAGCTGTCGGCCGCAGCGGTGCAGTACA

-continued

```
GCGACAACGCAGCGGCGAATCTGCTGTTGAAAGAACTGGGTGGCCCGGCAGGCCTGACGGCGTTT
ATGCGCAGCATCGGTGACACCACCTTCCGCCTGGACCGCTGGGAATTGGAGCTGAACTCTGCTAT
CCCGAGCGATGCCCGTGATACGTCTAGCCCGCGTGCGGTTACTGAGAGCCTGCAGAAACTTACGC
TGGGTAGCGCGCTGGCTGCGCCGCAACGTCAACAGTTCGTGGATTGGCTGAAGGGTAATACGACC
GGTAACCACCGTATTCGTGCCGCAGTTCCGGCGGACTGGGCTGTTGGCGACAAGACCGGCACGTG
CGGTGTCTACGGTACCGCGAATGACTATGCAGTGGTCTGGCCAACCGGTCGTGCGCCGATCGTTC
TGGCAGTTTACACCCGTGCTCCGAACAAAGATGACAAGCATAGCGAAGCCGTGATTGCAGCGGCA
GCGCGCCTGGCGCTGGAGGGTTTGGGTGTCAACGGCCAGTGATAA
```

Amino Acid Sequence:
(SEQ ID NO: 30)
```
MATALTNLVA EPFAKLEQDF GGSIGVYAMD TGSGATVSYR AEERFPLCSS FKGFLAAAVL
ARSQQQAGLL DTPIRYGKNA LVPWSPISEK YLTTGMTVAE LSAAAVQYSD NAAANLLLKE
LGGPAGLTAF MRSIGDTTFR LDRWELELNS AIPSDARDTS SPRAVTESLQ KLTLGSALAA
PQRQQFVDWL KGNTTGNHRI RAAVPADWAV GDKTGTCGVY GTANDYAVVW PTGRAPIVLA
VYTRAPNKDD KHSEAVIAAA ARLALEGLGV NGQ
```

KPC_2_10 (plasmid pKPC-2, pKPC-4, pKPC-6, pKPC-8)-STII leader + Native
Nucleic Acid Sequence:
(SEQ ID NO: 13)
```
ATGAAAAAGAACATTGCATTTCTGCTGGCGAGCATGTTTGTTTTTAGCATTGCAACCAATGCATA
TGCCGCAACCGCTCTGACCAATTTAGTTGCAGAACCTTTCGCGAAACTGGAGCAAGATTTTGGTG
GCTCCATTGGTGTGTATGCGATGGATACGGGCAGCGGCGCAACCGTTAGCTATCGCGCCGAGGAA
CGTTTTCCGCTGTGTTCCAGCTTCAAGGGTTTTCTGGCGGCTGCGGTCCTGGCGCGTAGCCAGCA
GCAAGCCGGCCTGCTGGACACCCCGATCCGTTACGGCAAAAATGCGCTGGTGCCGTGGAGCCCGA
TTAGCGAGAAGTACTTGACCACTGGTATGACGGTCGCCGAGCTGTCGGCCGCAGCGGTGCAGTAC
AGCGACAACGCAGCGGCGAATCTGCTGTTGAAAGAACTGGGTGGCCCGGCAGGCCTGACGGCGTT
TATGCGCAGCATCGGTGACACCACCTTCCGCCTGGACCGCTGGGAATTGGAGCTGAACTCTGCTA
TCCCGAGCGATGCCCGTGATACGTCTAGCCCGCGTGCGGTTACTGAGAGCCTGCAGAAACTTACG
CTGGGTAGCGCGCTGGCTGCGCCGCAACGTCAACAGTTCGTGGATTGGCTGAAGGGTAATACGAC
CGGTAACCACCGTATTCGTGCCGCAGTTCCGGCGGACTGGGCTGTTGGCGACAAGACCGGCACGT
GCGGTGTCTACGGTACCGCGAATGACTATGCAGTGGTCTGGCCAACCGGTCGTGCGCCGATCGTT
CTGGCAGTTTACACCCGTGCTCCGAACAAAGATGACAAGCATAGCGAAGCCGTGATTGCAGCGGC
AGCGCGCCTGGCGCTGGAGGGTTTGGGTGTCAACGGCCAGTGATAA
```

Amino Acid Sequence: (STII leader amino acid sequence is shown in bold)
(SEQ ID NO: 31)
MKKNIAFLLA SMFVFSIATN AYAATALTNL VAEPFAKLEQ DFGGSIGVYA MDTGSGATVS
YRAEERFPLC SSFKGFLAAA VLARSQQQAG LLDTPIRYGK NALVPWSPIS EKYLTTGMTV
AELSAAAVQY SDNAAANLLL KELGGPAGLT AFMRSIGDTT FRLDRWELEL NSAIPSDARD
TSSPRAVTES LQKLTLGSAL AAPQRQQFVD WLKGNTTGNH RIRAAVPADW AVGDKTGTCG
VYGTANDYAV VWPTGRAPIV LAVYTRAPNK DDKHSEAVIA AARLALEGL GVNGQ KPC_3_13 (plasmid pKPC-9)-Native delta 2
Nucleic Acid Sequence:
(SEQ ID NO: 14)
```
ATGGCTCTGACCAATTTAGTTGCAGAACCTTTCGCGAAACTGGAGCAAGATTTTGGTGGCTCCAT
TGGTGTGTATGCGATGGATACGGGCAGCGGCGCAACCGTTAGCTATCGCGCCGAGGAACGTTTTC
CGCTGTGTTCCAGCTTCAAGGGTTTTCTGGCGGCTGCGGTCCTGGCGCGTAGCCAGCAGCAAGCC
GGCCTGCTGGACACCCCGATCCGTTACGGCAAAAATGCGCTGGTGCCGTGGAGCCCGATTAGCGA
```

-continued

```
GAAGTACTTGACCACTGGTATGACGGTCGCCGAGCTGTCGGCCGCAGCGGTGCAGTACAGCGACA

ACGCAGCGGCGAATCTGCTGTTGAAAGAACTGGGTGGCCCGGCAGGCCTGACGGCGTTTATGCGC

AGCATCGGTGACACCACCTTCCGCCTGGACCGCTGGGAATTGGAGCTGAACTCTGCTATCCCGAG

CGATGCCCGTGATACGTCTAGCCCGCGTGCGGTTACTGAGAGCCTGCAGAAACTTACGCTGGGTA

GCGCGCTGGCTGCGCCGCAACGTCAACAGTTCGTGGATTGGCTGAAGGGTAATACGACCGGTAAC

CACCGTATTCGTGCCGCAGTTCCGGCGGACTGGGCTGTTGGCGACAAGACCGGCACGTGCGGTGT

CTACGGTACCGCGAATGACTATGCAGTGGTCTGGCCAACCGGTCGTGCGCCGATCGTTCTGGCAG

TTTACACCCGTGCTCCGAACAAAGATGACAAGCATAGCGAAGCCGTGATTGCAGCGGCAGCGCGC

CTGGCGCTGGAGGGTTTGGGTGTCAACGGCCAGTGATAA
```

Amino Acid Sequence:
(SEQ ID NO: 32)
```
MALTNLVAEP FAKLEQDFGG SIGVYAMDTG SGATVSYRAE ERFPLCSSFK GFLAAAVLAR

SQQQAGLLDT PIRYGKNALV PWSPISEKYL TTGMTVAELS AAAVQYSDNA AANLLLKELG

GPAGLTAFMR SIGDTTFRLD RWELELNSAI PSDARDTSSP RAVTESLQKL TLGSALAAPQ

RQQFVDWLKG NTTGNHRIRA AVPADWAVGD KTGTCGVYGT ANDYAVVWPT GRAPIVLAVY

TRAPNKDDKH SEAVIAAAAR LALEGLGVNG Q
```

KPC_4_13 (plasmid pKPC-10)-STII leader + delta 2
Nucleic Acid Sequence:
(SEQ ID NO: 15)
```
ATGAAAAAGAACATTGCATTTCTGCTGGCGAGCATGTTTGTTTTTAGCATTGCAACCAATGCATA

TGCCGCTCTGACCAATTTAGTTGCAGAACCTTTCGCGAAACTGGAGCAAGATTTTGGTGGCTCCA

TTGGTGTGTATGCGATGGATACGGGCAGCGGCGCAACCGTTAGCTATCGCGCCGAGGAACGTTTT

CCGCTGTGTTCCAGCTTCAAGGGTTTTCTGGCGGCTGCGGTCCTGGCGCGTAGCCAGCAGCAAGC

CGGCCTGCTGGACACCCCGATCCGTTACGGCAAAAATGCGCTGGTGCCGTGGAGCCCGATTAGCG

AGAAGTACTTGACCACTGGTATGACGGTCGCCGAGCTGTCGGCCGCAGCGGTGCAGTACAGCGAC

AACGCAGCGGCGAATCTGCTGTTGAAAGAACTGGGTGGCCCGGCAGGCCTGACGGCGTTTATGCG

CAGCATCGGTGACACCACCTTCCGCCTGGACCGCTGGGAATTGGAGCTGAACTCTGCTATCCCGA

GCGATGCCCGTGATACGTCTAGCCCGCGTGCGGTTACTGAGAGCCTGCAGAAACTTACGCTGGGT

AGCGCGCTGGCTGCGCCGCAACGTCAACAGTTCGTGGATTGGCTGAAGGGTAATACGACCGGTAA

CCACCGTATTCGTGCCGCAGTTCCGGCGGACTGGGCTGTTGGCGACAAGACCGGCACGTGCGGTG

TCTACGGTACCGCGAATGACTATGCAGTGGTCTGGCCAACCGGTCGTGCGCCGATCGTTCTGGCA

GTTTACACCCGTGCTCCGAACAAAGATGACAAGCATAGCGAAGCCGTGATTGCAGCGGCAGCGCG

CCTGGCGCTGGAGGGTTTGGGTGTCAACGGCCAGTGATAA
```

Amino Acid Sequence: (STII leader amino acid sequence is shown in bold)
(SEQ ID NO: 33)
MKKNIAFLLA SMFVFSIATN AYAALTNLVA EPFAKLEQDF GGSIGVYAMD TGSGATVSYR
```
AEERFPLCSS FKGFLAAAVL ARSQQQAGLL DTPIRYGKNA LVPWSPISEK YLTTGMTVAE

LSAAAVQYSD NAAANLLLKE LGGPAGLTAF MRSIGDTTFR LDRWELELNS AIPSDARDTS

SPRAVTESLQ KLTLGSALAA PQRQQFVDWL KGNTTGNHRI RAAVPADWAV GDKTGTCGVY

GTANDYAVVW PTGRAPIVLA VYTRAPNKDD KHSEAVIAAA ARLALEGLGV NGQ
```

KPC_5_13 (plasmid pKPC-11)-Native delta 8
Nucleic Acid Sequence:
(SEQ ID NO: 16)
```
ATGGCAGAACCTTTCGCGAAACTGGAGCAAGATTTTGGTGGCTCCATTGGTGTGTATGCGATGGA

TACGGGCAGCGGCGCAACCGTTAGCTATCGCGCCGAGGAACGTTTTCCGCTGTGTTCCAGCTTCA
```

-continued

```
AGGGTTTTCTGGCGGCTGCGGTCCTGGCGCGTAGCCAGCAGCAAGCCGGCCTGCTGGACACCCCG

ATCCGTTACGGCAAAAATGCGCTGGTGCCGTGGAGCCCGATTAGCGAGAAGTACTTGACCACTGG

TATGACGGTCGCCGAGCTGTCGGCCGCAGCGGTGCAGTACAGCGACAACGCAGCGGCGAATCTGC

TGTTGAAAGAACTGGGTGGCCCGGCAGGCCTGACGGCGTTTATGCGCAGCATCGGTGACACCACC

TTCCGCCTGGACCGCTGGGAATTGGAGCTGAACTCTGCTATCCCGAGCGATGCCCGTGATACGTC

TAGCCCGCGTGCGGTTACTGAGAGCCTGCAGAAACTTACGCTGGGTAGCGCGCTGGCTGCGCCGC

AACGTCAACAGTTCGTGGATTGGCTGAAGGGTAATACGACCGGTAACCACCGTATTCGTGCCGCA

GTTCCGGCGGACTGGGCTGTTGGCGACAAGACCGGCACGTGCGGTGTCTACGGTACCGCGAATGA

CTATGCAGTGGTCTGGCCAACCGGTCGTGCGCCGATCGTTCTGGCAGTTTACACCCGTGCTCCGA

ACAAAGATGACAAGCATAGCGAAGCCGTGATTGCAGCGGCAGCGCGCCTGGCGCTGGAGGGTTTG

GGTGTCAACGGCCAGTGATAA
```

Amino Acid Sequence:
(SEQ ID NO: 34)
```
MAEPFAKLEQ DFGGSIGVYA MDTGSGATVS YRAEERFPLC SSFKGFLAAA VLARSQQQAG

LLDTPIRYGK NALVPWSPIS EKYLTTGMTV AELSAAAVQY SDNAAANLLL KELGGPAGLT

AFMRSIGDTT FRLDRWELEL NSAIPSDARD TSSPRAVTES LQKLTLGSAL AAPQRQQFVD

WLKGNTTGNH RIRAAVPADW AVGDKTGTCG VYGTANDYAV VWPTGRAPIV LAVYTRAPNK

DDKHSEAVIA AARLALEGL GVNGQ
```

KPC_6_13 (plasmid pKPC-12)-STII leader + delta 8
Nucleic Acid Sequence:
(SEQ ID NO: 17)
```
ATGAAAAAGAACATTGCATTTCTGCTGGCGAGCATGTTTGTTTTTAGCATTGCAACCAATGCATA

TGCCGCAGAACCTTTCGCGAAACTGGAGCAAGATTTTGGTGGCTCCATTGGTGTGTATGCGATGG

ATACGGGCAGCGGCGCAACCGTTAGCTATCGCGCCGAGGAACGTTTTCCGCTGTGTTCCAGCTTC

AAGGGTTTTCTGGCGGCTGCGGTCCTGGCGCGTAGCCAGCAGCAAGCCGGCCTGCTGGACACCCC

GATCCGTTACGGCAAAAATGCGCTGGTGCCGTGGAGCCCGATTAGCGAGAAGTACTTGACCACTG

GTATGACGGTCGCCGAGCTGTCGGCCGCAGCGGTGCAGTACAGCGACAACGCAGCGGCGAATCTG

CTGTTGAAAGAACTGGGTGGCCCGGCAGGCCTGACGGCGTTTATGCGCAGCATCGGTGACACCAC

CTTCCGCCTGGACCGCTGGGAATTGGAGCTGAACTCTGCTATCCCGAGCGATGCCCGTGATACGT

CTAGCCCGCGTGCGGTTACTGAGAGCCTGCAGAAACTTACGCTGGGTAGCGCGCTGGCTGCGCCG

CAACGTCAACAGTTCGTGGATTGGCTGAAGGGTAATACGACCGGTAACCACCGTATTCGTGCCGC

AGTTCCGGCGGACTGGGCTGTTGGCGACAAGACCGGCACGTGCGGTGTCTACGGTACCGCGAATG

ACTATGCAGTGGTCTGGCCAACCGGTCGTGCGCCGATCGTTCTGGCAGTTTACACCCGTGCTCCG

AACAAAGATGACAAGCATAGCGAAGCCGTGATTGCAGCGGCAGCGCGCCTGGCGCTGGAGGGTTT

GGGTGTCAACGGCCAGTGATAA
```

Amino Acid Sequence: (STII leader amino acid sequence is shown in bold)
(SEQ ID NO: 35)
MKKNIAFLLA SMFVFSIATN AYAAEPFAKL EQDFGGSIGV YAMDTGSGAT VSYRAEERFP

LCSSFKGFLA AAVLARSQQQ AGLLDTPIRY GKNALVPWSP ISEKYLTTGM TVAELSAAAV

QYSDNAAANL LLKELGGPAG LTAFMRSIGD TTFRLDRWEL ELNSAIPSDA RDTSSPRAVT

ESLQKLTLGS ALAAPQRQQF VDWLKGNTTG NHRIRAAVPA DWAVGDKTGT CGVYGTANDY

AVVWPTGRAP

-continued

KPC_7 13 (plasmid pKPC-13)-Tat + native
Nucleic Acid Sequence:
(SEQ ID NO: 18)
ATGAAGCAGGCATTACGAGTAGCATTTGGTTTTCTCATACTGTGGGCATCAGTTCTGCATGCTGC

AACCGCTCTGACCAATTTAGTTGCAGAACCTTTCGCGAAACTGGAGCAAGATTTTGGTGGCTCCA

TTGGTGTGTATGCGATGGATACGGGCAGCGGCGCAACCGTTAGCTATCGCGCCGAGGAACGTTTT

CCGCTGTGTTCCAGCTTCAAGGGTTTTCTGGCGGCTGCGGTCCTGGCGCGTAGCCAGCAGCAAGC

CGGCCTGCTGGACACCCCGATCCGTTACGGCAAAAATGCGCTGGTGCCGTGGAGCCCGATTAGCG

AGAAGTACTTGACCACTGGTATGACGGTCGCCGAGCTGTCGGCCGCAGCGGTGCAGTACAGCGAC

AACGCAGCGGCGAATCTGCTGTTGAAAGAACTGGGTGGCCCGGCAGGCCTGACGGCGTTTATGCG

CAGCATCGGTGACACCACCTTCCGCCTGGACCGCTGGGAATTGGAGCTGAACTCTGCTATCCCGA

GCGATGCCCGTGATACGTCTAGCCCGCGTGCGGTTACTGAGAGCCTGCAGAAACTTACGCTGGGT

AGCGCGCTGGCTGCGCCGCAACGTCAACAGTTCGTGGATTGGCTGAAGGGTAATACGACCGGTAA

CCACCGTATTCGTGCCGCAGTTCCGGCGGACTGGGCTGTTGGCGACAAGACCGGCACGTGCGGTG

TCTACGGTACCGCGAATGACTATGCAGTGGTCTGGCCAACCGGTCGTGCGCCGATCGTTCTGGCA

GTTTACACCCGTGCTCCGAACAAAGATGACAAGCATAGCGAAGCCGTGATTGCAGCGGCAGCGCG

CCTGGCGCTGGAGGGTTTGGGTGTCAACGGCCAGTGATAA

Amino Acid Sequence: (Tat leader amino acid sequence is shown in bold)
(SEQ ID NO: 36)
MKQALRVAFG FLILWASVLH AATALTNLVA EPFAKLEQDF GGSIGVYAMD TGSGATVSYR

AEERFPLCSS FKGFLAAAVL ARSQQQAGLL DTPIRYGKNA LVPWSPISEK YLTTGMTVAE

LSAAAVQYSD NAAANLLLKE LGGPAGLTAF MRSIGDTTFR LDRWELELNS AIPSDARDTS

SPRAVTESLQ KLTLGSALAA PQRQQFVDWL KGNTTGNHRI RAAVPADWAV GDKTGTCGVY

GTANDYAVVW PTGRAPIVLA VYTRAPNKDD KHSEAVIAAA ARLALEGLGV NGQ

TABLE 1

Characteristics of Various P2A Bacterial Strains.

| Strain # | Plasmid # | Vector | N-Terminal Variant | Predicted N-Terminal | Host Name | Cellular Compartment |
|---|---|---|---|---|---|---|
| SYT-PS0100-01 | pP2A-1 | pCYT10 (high T7) | Native | METGT | BL21 | cyto |
| SYT-PS0200-02 | pP2A-2 | pCYT10 (high T7) | STII | ETGT | BL21 | peri |
| SYT-PS0300-03 | pP2A-3 | pCYT11 (med T7) | Native | METGT | BL21 | cyto |
| SYT-PS0400-04 | pP2A-4 | pCYT11 (med T7) | STII | ETGT | BL21 | peri |
| SYT-PP0500-05 | pP2A-5 | pCYT12 (high phoA) | Native | METGT | BL21 | cyto |
| SYT-PP0600-06 | pP2A-6 | pCYT12 (high phoA) | STII | ETGT | BL21 | peri |
| SYT-PP0700-07 | pP2A-7 | pCYT13 (med phoA) | Native | METGT | BL21 | cyto |
| SYT-PP0800-08 | pP2A-8 | pCYT13 (med phoA) | STII | ETGT | BL21 | peri |
| SYT-PP0900-09 | pP2A-9 | pCYT13 (med phoA) | Tat | ETGT | BL21 | peri |
| SYT-PS0104-10 | pP2A-1 | pCYT10 (high T7) | Native | METGT | BL21 T7 LysY | cyto |
| SYT-PS0205-11 | pP2A-2 | pCYT10 (high T7) | STII | ETGT | BL21 T7 LysY degP | peri |
| SYT-PS0304-12 | pP2A-3 | pCYT11 (med T7) | Native | METGT | BL21 T7 LysY | cyto |
| SYT-PS0405-13 | pP2A-4 | pCYT11 (med T7) | STII | ETGT | BL21 T7 LysY degP | peri |
| SYT-PP0601-14 | pP2A-6 | pCYT12 (high phoA) | STII | ETGT | BL21 degP | peri |

TABLE 1-continued

Characteristics of Various P2A Bacterial Strains.

| Strain # | Plasmid # | Vector | N-Terminal Variant | Predicted N-Terminal | Host Name | Cellular Compartment |
|---|---|---|---|---|---|---|
| SYT-PP0801-15 | pP2A-8 | pCYT13 (med phoA) | STII | ETGT | B121 degP | peri |
| SYT-PS0103-16 | pP2A-1 | pCYT10 (high T7) | Native | METGT | MG1655 T7+ | cyto |
| SYT-PS0203-17 | pP2A-2 | pCYT10 (high T7) | STII | ETGT | MG1655 T7+ | peri |
| SYT-PS0303-18 | pP2A-3 | pCYT11 (med T7) | Native | N1ETGT | MG1655 T7+ | cyto |
| SYT-PS0403-19 | pP2A-4 | pCYT11 (med T7) | STII | ETGT | MG1655 T7+ | peri |
| SYT-PP0502-20 | pP2A-5 | pCYT12 (high phoA) | Native | METGT | W3110 degP | cyto |
| SYT-PP0602-21♀ | pP2A-6♀ | pCYT12 (high phoA)♀ | STII♀ | ETGT♀ | W3110 degP♀ | peri♀ |
| SYT-PP0702-22 | pP2A-7 | p pCYT13 (med phoA) | Native | METGT | W3110 degP | cyto |
| SYT-PP0802-23 | pP2A-8 | pCYT13 (med phoA) | STII | ETGT | W3110 degP | peri |
| SYT-PP0901-24 | pP2A-9 | pCYT13 (med phoA) | Tat | ETGT | BL21 degP | peri |
| SYT-PP0902-25 | pP2A-9 | pCYT13 (med phoA) | Tat | ETGT | W3110 degP | peri |

♀Chosen for shake flask and fermentation testing

TABLE 2

Characteristics of Various NDM-1 Bacterial Strains

| Strain # | Plasmid # | Vector | N-Terminal Variant | Predicted N-Terminal | Host Name | Cellular Compartment |
|---|---|---|---|---|---|---|
| STY-NS0100-26 | pNDM-1 | pCYT10 (high T7) | Native (D38) | METG | BL21 | cyto |
| STY-NS0200-27 | pNDM-2 | pCYT10 (high T7) | STII (D38) | METG | BL21 | peri |
| STY-NS0300-28 | pNDM-3 | pCYT10 (high T7) | PelB (D38) | METG | BL21 | peri |
| STY-NS0400-29 | pNDM-4 | pCYT11 (med T7) | Native (D38) | METG | 9121 | cyto |
| STY-NS0500-30 | pNDM-5 | pCYT11 (med T7) | SiII (D38) | METG | BL21 | peri |
| STY-NS0600-31 | pNDM-6 | pCYT11 (med T7) | PelB (D38) | METG | B121 | peri |
| STY-NP0700-32 | pNDM-7 | pCYT12 (high phoA) | Native (D38) | METG | BL21 | cyto |
| STY-NP0800-33 | pNDM-8 | pCYT12 (high phoA) | STII (D38) | METG | BL21 | peri |
| STY-NP0900-34 | pNDM-9 | pCYT12 (high phoA) | PelB(D38) | METG | BL21 | peri |
| STY-NP1000-35 | pNDM-10 | pCYT13 (med phoA) | Native (D38) | METG | BL21 | cyto |
| STY-NP1100-36 | pNDM-11 | pCYT13 (med phoA) | STII (D38) | METG | BL21 | peri |
| STY-NP1200-37 | pNDM-12 | pCYT13 (med phoA) | PelB (D38) | METG | BL21 | peri |
| STY-NP1300-38 | pNDM-13 | pCYT13 (med phoA) | Native (Δ37) | MQMETG | BL21 | cyto |
| STY-NP1400-39 | pNDM-14 | pCYT13 (med phoA) | STII (Δ37) | QMETG | BL21 | peri |
| STY-NP1500-40 | pNDM-15 | pCYT13 (med phoA) | Native (Δ35) | M/GQQMETG | BL21 | cyto |
| STY-NP1600-41 | pNDM-16 | pCYT13 (med phoA) | STII (Δ35) | GQQMETG | BL21 | peri |
| STY-NP1700-42 | pNDM-17 | pCYT13 (med phoA) | Tat (D38) | METG | BL21 | peri |
| STY-NS0104-43 | pNDM-1 | pCYT10 (high T7) | Native (D38) | METG | BL21 T7 LysY | cyto |
| STY-NS0205-44 | pNDM-2 | pCYT10 (high T7) | STII (D38) | METG | BL21 T7 LysY degP | peri |
| STY-NS0305-45 | pNDM-3 | pCYT10 (high T7) | PelB (D38) | METG | BL21 T7 LysY degP | peri |
| STY-NS0404-46 | pNDM-4 | pCYT11 (med T7) | Native (D38) | METG | BL21 T7 LysY | cyto |
| STY-NS0505-47 | pNDM-5 | pCYT11 (med T7) | STII (D38) | METG | BL21 T7 LysY degP | peri |
| STY-NS0605-48 | pNDM-6 | pCYT11 (med T7) | PelB (D38) | METG | BL21 T7 LysY degP | peri |
| STY-NP0801-49 | pNDM-8 | pCYT12 (high phoA) | STII (D38) | METG | BL21 degP | peri |
| STY-NP0901-50 | pNDM-9 | pCYT12 (high phoA) | PelB (D38) | METG | BL21 degP | peri |
| STY-NP1101-51 | pNDM-11 | pCYT13 (med phoA) | STII (D38) | METG | BL21 degP | peri |
| STY-NP1201-52 | pNDM-12 | pCYT13 (med phoA) | PelB (D38) | METG | BL21 degP | peri |
| STY-NS0103-53 | pNDM-1 | pCYT10 (high T7) | Native (D38) | METG | MG1655 T7+ | cyto |
| STY-NS0203-54 | pNDM-2 | pCYT10 (high T7) | STII (D38) | METG | MG1655 T7+ | peri |
| STY-NS0303-55 | pNDM-3 | pCYT10 (high T7) | PelB (D38) | METG | MG1655 T7+ | peri |
| STY-NS0403-56 | pNDM-4 | pCYT11 (med T7) | Native (D38) | METG | MG1655 T7+ | cyto |
| STY-NS0503-57 | pNDM-5 | pCYT11 (med T7) | STII (D38) | mETG | MG1655 T7+ | per. |
| STY-NS0603-58 | pNDM-6 | pCYT11 (med T7) | PelB (D38) | mETG | MG1655 T7+ | peri |
| STY-NP0702-59 | pNDM-7 | pCYT12 (high phoA) | Native (D38) | METG | W3110 degP | cyto |

TABLE 2-continued

Characteristics of Various NDM-1 Bacterial Strains

| Strain # | Plasmid # | Vector | N-Terminal Variant | Predicted N-Terminal | Host Name | Cellular Compartment |
|---|---|---|---|---|---|---|
| STY-NP0802-60 | pNDM-8 | pCYT12 (high phoA) | STII (D38) | METG | W3110 degP | peri |
| STY-NP0902-61 | pNDM-9 | pCYT12 (high phoA) | PelB (D38) | METG | W3110 degP | peri |
| STY-NP1002-62 | pNDM-10 | pCYT13 (med phoA) | Native (D38) | METG | W3110 degP | cyto |
| STY-NP1102-63* | pNDM-11* | pCYT13 (med phoA)* | STII (D38)* | METG* | W3110 degP* | peri* |
| STY-NP1203-64 | pNDM-12 | pCYT13 (med phoA) | PelB (D38) | METG | W3110 degP | peri |
| STY-NP1302-65 | pNDM-13 | pCYT13 (med phoA) | Native (Δ37) | MQMETG | W3110 degP | cyto |
| STY-NP1402-66 | pNDM-14 | pCYT13 (med phoA) | STII (Δ37) | QMETG | W3110 degP | peri |
| STY-NP1502-67 | pNDM-15 | pCYT13 (med phoA) | Native (Δ35) | M/GQQMETG | W3110 degP | cyot |
| STY-NP1602-68♀ | pNDM-16♀ | pCYT13 (med phoA)♀ | STII (Δ35)♀ | GQQMETG♀ | W3110 degP♀ | peri♀ |
| STY-NP1702-69* | pNDM-17* | pCYT13 (med phoA)* | Tat (D38)* | METG* | W3110 degP* | peri* |

*Chosen for shake flask testing
♀Chosen for shake flask and fermentation testing

TABLE 3

Characteristics of Various KPC-1/2 Bacterial Strains.

| Strain # | Plasmid # | Vector | N-Terminal Variant | Predicted N-Terminal | HostName | Cellular Compartment |
|---|---|---|---|---|---|---|
| SYT-KS0100-70 | pKPC-1 | pCYT10 (high T7) | Native | M/ATAL | BL21 | cyto |
| SYT-KS0200-71 | pKPC-2 | pCYT10 (high T7) | STII | ATAL | BL21 | peri |
| SYT-KS0300-72 | pKPC-3 | pCYT11 (med T7) | Native | M/ATAL | BL21 | cyto |
| SYT-KS0400-73 | pKPC-4 | pCYT11 (med T7) | STII | ATAL | BL21 | peri |
| SYT-KP0500-74 | pKPC-5 | pCYT12 (high phoA) | Native | M/ATAL | BL21 | cyto |
| SYT-KP0600-75 | pKPC-6 | pCYT12 (high phoA) | STII | ATAL | BL21 | peri |
| SYT-KP0700-76 | pKPC-7 | pCYT13 (mod phoA) | Native | M/ATAL | BL21 | cyto |
| SYT-KP0800-77 | pKPC-8 | pCYT13 (med phoA) | STII | ATAL | BL21 | peri |
| SYT-KP0900-78 | pKPC-9 | pCYT13 (med phoA) | Native (Δ2) | M/ALTN | BL21 | cyto |
| SYT-KP1000-79 | pKPC-10 | pCYT13 (med phoA) | STII (Δ2) | ALTN | BL21 | peri |
| SYT-KP1100-80 | pKPC-11 | pCYT13 (med phoA) | Native (Δ8) | AEPF | BL21 | cyto |
| SYT-KP1200-81 | pKPC-12 | pCYT13 (med phoA) | STII (Δ8) | AEPF | BL21 | peri |
| SYT-KP1300-82 | pKPC-13 | pCYT13 (med phoA) | Tat | ATAL | BL21 | peri |
| SYT-KS0104-83 | pKPC-1 | pCYT10 (high T7) | Native | M/ATAL | BL21 T7 LysY | cyto |
| SYT-KS0205-84 | pKPC-2 | pCYT10 (high T7) | STII | ATAL | BL21 T7 LysY degP | peri |
| SYT-KS0304-85 | pKPC-3 | pCYT11 (med T7) | Native | M/ATAL | BL21 T7 LysY | cyto |
| SYT-KS0405-86 | pKPC-4 | pCYT11 (med T7) | STII | ATAL | BL21 T7 LysY degP | peri |
| SYT-KP0601-87 | pKPC-6 | pCYT12 (high phoA) | STII | ATAL | BL21 degP | peri |
| SYT-KP0101-88 | pKPC-8 | pCYT13 (med phoA) | STII | ATAL | BL21 degP | peri |
| SYT-KS0103-89 | pKPC-1 | pCYT10 (high 77) | Native | M/ATAL | MG165577+ | cyto |
| SYT-KS0203-90 | pKPC-2 | pCYT10 (high 77) | STII | ATAL | MG165517+ | peri |
| SYT-KS0303-91 | pKPC-3 | pCYT11 (med T7) | Native | M/ATAL | MG165517+ | cyto |
| SYT-KS0403-92 | pKPC-4 | pCYT11 (med T7) | STII | ATAL | MG165577+ | peri |
| SYT-KP0502-93 | pKPC-5 | pCYT12 (high phoA) | Native | M/ATAL | W3110 degP | cyto |
| SYT-KP0602-94 | pKPC-6 | pCYT12 (high phoA) | STII | ATAL | W3110 degP | peri |
| SYT-KP0702-95 | pKPC-7 | pCYT13 (med phoA) | Native | M/ATAL | W3110 degP | cyto |
| SYT-KP0302-96 | pKPC-8 | pCYT13 (med phoA) | STII | ATAL | W3110 degP | peri |
| SYT-KS0107-97 | pKPC-1 | pCYT10 (high T7) | Native | M/ATAL | Shuffle T7 | cyto |
| SYT-KS0307-98 | pKPC-3 | pCYT11 (med T7) | Native | M/ATAL | Shuffle 17 | cyto |
| SYT-KP0506-99 | pKPC-5 | pCYT12 (high phoA) | Native | M/ATAL | Shuffle | cyto |
| SYT-KP0706-100 | pKPC-7 | pCYT13 (med phoA) | Native | M/ATAL | Shuffle | cyto |
| SYT-KP0906-101♀ | pKPC-9♀ | pCYT13 (med phoA)♀ | Native (Δ2)♀ | M/ALTN♀ | Shuffle♀ | cyto♀ |
| SYT-KP1106-102* | pKPC-11* | pCYT13 (med phoA)* | Native (Δ8)* | AEPF* | Shuffle* | cyto* |
| SYT-KP1202-103 | pKPC-12 | pCYT13 (med phoA) | STII (Δ8) | AEPF | W3110 degP | peri |
| SYT-KP1306-104 | pKPC-13 | pCYT13 (med phoA) | Tat | ATAL | Shuffle | peri |

*Chosen for shake flask testing
♀Chosen for shake flask and fermentation testing

TABLE 4 below shows the various plasmid vectors.

| Plasmid Vector | Copy # | Promoter | Antibiotic Resistance |
|---|---|---|---|
| pCYT10 | High (pUC) | T7 | tet |
| pCYT11 | Med (pBR322) | T7 | tet |
| pCYT12 | High (pUG) | phoA | tet |
| pCYT13 | Med (pBR322) | phoA | tet |

Example 2: Screening Various P2A, NDM, and KPC-Encoding Bacterial Strains

Experiments were carried out, inter alia, to identify bacterial strains that result in sufficient expression of one or more biologically active carbapenemases, among other purposes.

A total of 104 transformed bacterial strains, 25 P2A strains, 44 NDM strains, and 35 KPC strains (as shown in Tables 1-3) were assessed for carbapenemase protein expression in a screening assay. Colonies of the 104 transformed strains were picked, grown overnight, diluted 1:50 into 24 well dishes (3 ml volume per well), and grown overnight. A total of 2×1.0 ml sample were saved per strain. Bacteria were lysed with Bug Buster protein extraction reagent (EMD Millipore, Cat #70584). The soluble and insoluble fractions were analyzed using SDS-PAGE. The data from the initial screen of P2A and NDM bacterial strains is summarized in Tables 5 and 6. 8 out of 25 P2A strains produced a soluble or insoluble band (Table 5), and 14 out of 44 NMD strains produced a soluble or insoluble band (Table 6). Because the metallo-beta-lactamases including P2A and NDM require zinc ions for activity (Queenan and Bush, Clin. Micro. Rev. (2007) 20:440-458)], a second round of screening was performed with supplementation of the bacterial growth media with 100 uM $ZnSO_4$.

TABLE 5

Initial Expression Screen of P2A Strains (Grown without Zinc in Media)

| Plasmid # | Vector | Variant | Strain # | Host Name | Sol | Insol | Media Supe |
|---|---|---|---|---|---|---|---|
| pP2A-1 | pCYT10 (high T7) | 1 (native) | SYT-PS0100-01 | BL21 | ** | ** | ** |
| pP2A-2 | pCYT10 (high T7) | 2 (STII) | SYT-PS0200-02 | BL21 | ** | ** | ** |
| pP2A-3 | pCYT11 (med T7) | 1 (native) | SYT-PS0300-03 | BL21 | ** | ** | ** |
| pP2A-4 | pCYT11 (med T7) | 2 (STII) | SYT-PS0400-04 | BL21 | ** | ** | ** |
| pP2A-5 | pCYT12 (high phoA) | 1 (native) | SYT-PS0500-05 | BL21 | ** | ‡ | ** |
| pP2A-6 | pCYT12 (high phoA) | 2 (STII) | SYT-PS0600-06 | BL21 | ** | ** | ** |
| pP2A-7 | pCYT13 (med phoA) | 1 (native) | SYT-PS0700-07 | BL21 | ** | ** | ** |
| pP2A-8 | pCYT13 (med phoA) | 2 (STII) | SYT-PS0800-08 | BL21 | ** | ** | ** |
| pP2A-9 | pCYT13 (med phoA) | 3 (tat) | SYT-PS0900-09 | BL21 | ** | ** | ** |
| pP2A-1 | pCYT10 (high T7) | 1 (native) | SYT-PS0104-10 | BL21 T7 LysY | ** | ** | ** |
| pP2A-2 | pCYT10 (high T7) | 2 (STII) | SYT-PS0205-11 | BL21 T7 LysY degP | ** | ** | ** |
| pP2A-3 | pCYT11 (med T7) | 1 (native) | SYT-PS0304-12 | BL21 T7 LysY | ** | ** | * |
| pP2A-4 | pCYT11 (med T7) | 2 (STII) | SYT-PS0405-13 | BL21 T7 LysY degP | ** | ** | ** |
| pP2A-6 | pCYT12 (high phoA) | 2 (STII) | SYT-PP0601-14 | BL21 degP | ** | ** | ** |
| pP2A-8 | pCYT13 (med phoA) | 2 (STII) | SYT-PP0801-15 | BL21 degP | * | * | ** |
| pP2A-1 | pCYT10 (high T7) | 1 (native) | SYT-PS0103-16 | MG1655 T7+ | ** | ‡ | ** |
| pP2A-2 | pCYT10 (high T7) | 2 (STII) | SYT-PS0203-17 | MG1655 T7+ | ** | ** | ** |
| pP2A-3 | pCYT11 (med T7) | 1 (native) | SYT-PS0303-18 | MG1655 T7+ | ** | ** | ** |
| pP2A-4 | pCYT11 (med T) | 2 (STII) | SYT-PS0403-19 | MG1655 T7+ | ** | ** | ** |
| pP2A-5 | pCYT12 (high phoA) | 1 (native) | SYT-PP0502-20 | W3110 degP | * | ‡ | ** |
| pP2A-6 | pCYT12 (high phoA) | 2 (STII) | SYT-PP0602-21 | W3110 degP | * | † | ** |
| pP2A-7 | pCYT13 (med phoA) | 1 (native) | SYT-PP0702-22 | W3110 degP | high MW?; † | high MW?; † | ** |
| pP2A-8 | pCYT13 (med phoA) | 2 (STII) | SYT-PP0802-23 | W3110 degP | ‡ | † | ** |

TABLE 5-continued

Initial Expression Screen of P2A Strains (Grown without Zinc in Media)

| Plasmid # | Vector | Variant | Strain # | Host Name | Sol | Insol | Media Supe |
|---|---|---|---|---|---|---|---|
| pP2A-9 | pCYT13 (med phoA) | 3 (tat) | SYT-PP0901-24 | BL21 degP | ** | ** | ** |
| pP2A-9 | pCYT13 (med phoA) | 3 (tat) | SYT-PP0902-25 | W3110 degP | high MW?; † | high MW?; † | ** |

†Very high expression level
‡Medium expression level
*Detectable band
**No detectable band

TABLE 6

Initial Expression Screen of NDM Strains (Grown without Zinc in Media)

| Plasmid # | Vector | Variant | Strain # | Host Name | Sol | Insol | Media Supe |
|---|---|---|---|---|---|---|---|
| pNDM-1 | pCYT10 (high T7) | 1 (native) | SYT-NS0100-26 | BL21 | ** | ** | ** |
| pNDM-2 | pCYT10 (high T7) | 2 (STII) | SYT-NS0200-27 | BL21 | ** | ** | ** |
| pNDM-3 | pCYT10 (high T7) | 3 (PelB) | SYT-NS0300-28 | BL21 | ** | ** | ** |
| pNDM-4 | pCYT11 (med T7) | 1 (native) | SYT-NS0400-29 | BL21 | ** | ** | ** |
| pNDM-5 | pCYT11 (med T7) | 2 (STII) | SYT-NS0500-30 | BL21 | ** | ** | ** |
| pNDM-6 | pCYT11 (med T7) | 3 (PelB) | SYT-NS0600-31 | BL21 | ** | ** | ** |
| pNDM-7 | pCYT12 (high phoA) | 1 (native) | SYT-NP0700-32 | BL21 | ** | ‡ | ** |
| pNDM-8 | pCYT12 (high phoA) | 2 (STII) | SYT-NP0800-33 | BL21 | ** | ** | ** |
| pNDM-9 | pCYT12 (high phoA) | 3 (PelB) | SYT-NP0900-34 | BL21 | ** | ** | ** |
| pNDM-10 | pCYT13 (med phoA) | 1 (native) | SYT-NP1000-35 | BL21 | ** | ‡ | ** |
| pNDM-11 | pCYT13 (med phoA) | 2 (STII) | SYT-NP1100-36 | BL21 | ** | ** | ** |
| pNDM-12 | pCYT13 (med phoA) | 3 (PelB) | SYT-NP1200-37 | BL21 | ** | ** | ** |
| pNDM-13 | pCYT13 (med phoA) | 4 (Δ37) | SYT-NP1300-38 | BL21 | ** | ** | ** |
| pNDM-14 | pCYT13 (med phoA) | 5 (STII-Δ37) | SYT-NP1400-39 | BL21 | ** | ** | ** |
| pNDM-15 | pCYT13 (med phoA) | 6 (Δ35) | SYT-NP1500-40 | BL21 | ** | ** | ** |
| pNDM-16 | pCYT13 (med phoA) | 7 (STII-Δ35) | SYT-NP1600-41 | BL21 | ** | ** | ** |
| pNDM-17 | pCYT13 (med phoA) | 8 (tat) | SYT-NP1700-42 | BL21 | ** | ** | ** |
| pNDM-1 | pCYT10 (high T7) | 1 (native) | SYT-NS0104-43 | BL21 T7 LysY | ** | ** | ** |
| pNDM-2 | pCYT10 (high T7) | 2 (STII) | SYT-NS0205-44 | BL21 T7 LysY degP | ** | ** | ** |
| pNDM-3 | pCYT10 (high T7) | 3 (PelB) | SYT-NS0305-45 | BL21 T7 LysY degP | * | ** | ** |
| pNDM-4 | pCYT11 (med T7) | 1 (native) | SYT-NS0404-46 | BL21 T7 LysY | * | ** | ** |
| pNDM-5 | pCYT11 (med T7) | 2 (STII) | SYT-NS0505-47 | BL21 T7 LysY degP | * | ** | ** |
| pNDM-6 | pCYT11 (med T7) | 3 PeB) | SYT-NS0605-48 | BL21 T7 LysY degP | * | ** | ** |
| pNDM-8 | pCYT12 (high phoA) | 2 (STII) | SYT-NP0801-49 | BL21 degP | ** | ** | ** |
| pNDM-9 | pCYT12 (high phoA) | 3 (PelB) | SYT-NP0901-50 | BL21 degP | ** | ** | ** |
| pNDM-11 | pCYT13 (med phoA) | 2 (STII) | SYT-NP1101-51 | BL21 degP | ** | ** | ** |
| pNDM-12 | pCYT13 (med phoA) | 3 (PelB) | SYT-NP1201-52 | BL21 degP | ** | ** | ** |
| pNDM-1 | pCYT10 (high T7) | 1 (native) | SYT-NS0103-53 | MG1655T7+ | ** | * | ** |
| pNDM-2 | pCYT10 (high T7) | 2 (STII) | SYT-NS0203-54 | MG1655T7+ | ** | ** | ** |
| pNDM-3 | pCYT11 (med T7) | 3 (PelB) | SYT-NS0303-55 | MG1655T7+ | ** | ** | ** |
| pNDM-4 | pCYT11 (med T7) | 1 (native) | SYT-NS0403-56 | MG1655T7+ | ** | ** | ** |
| pNDM-5 | pCYT11 (med T7) | 2 (STII) | SYT-NS0503-57 | MG1655T7+ | ** | ** | ** |
| pNDM-6 | pCYT11 (med T7) | 3 (PelB) | SYT-NS0603-58 | MG1655T7+ | * | ** | ** |
| pNDM-7 | pCYT12 (high phoA) | 1 (native) | SYT-NP0720-59 | W3110 degP | ** | ** | ** |
| pNDM-8 | pCYT12 (high phoA) | 2 (STII) | SYT-NP0802-60 | W3110 degP | ** | ** | ** |
| pNDM-9 | pCYT12 (high phoA) | 3 (PelB) | SYT-NP0902-61 | W3110 degP | ** | ** | ** |
| pNDM-10 | pCYT13 (med phoA) | 1 (native) | SYT-NP1002-62 | W3110 degP | ** | * | ** |
| pNDM-11 | pCYT13 (med phoA) | 2 (STII) | SYT-NP1002-63 | W3110 degP | ‡ | † | ** |
| pNDM-12 | pCYT13 (med phoA) | 3 (PelB) | SYT-NP1202-64 | W3110 degP | ** | ** | ** |
| pNDM-13 | pCYT13 (med phoA) | 4 (Δ37) | SYT-NP1302-65 | W3110 degP | ** | ** | ** |
| pNDM-14 | pCYT13 (med phoA) | 5 (STII-Δ37) | SYT-NP1402-66 | W3110 degP | ** | ‡ | ** |
| pNDM-15 | pCYT13 (med phoA) | 6 (Δ35) | SYT-NP1502-67 | W3110 degP | * | * | ** |
| pNDM-16 | pCYT13 (med phoA) | 7 (STII-Δ35) | SYT-NSP1602-68 | W3110 degP | ‡ | ‡ | ** |
| pNDM-17 | pCYT13 (med phoA) | 8 (tat) | SYT-NP1702-69 | W3110 degP | * | * | ** |

Figure 2:
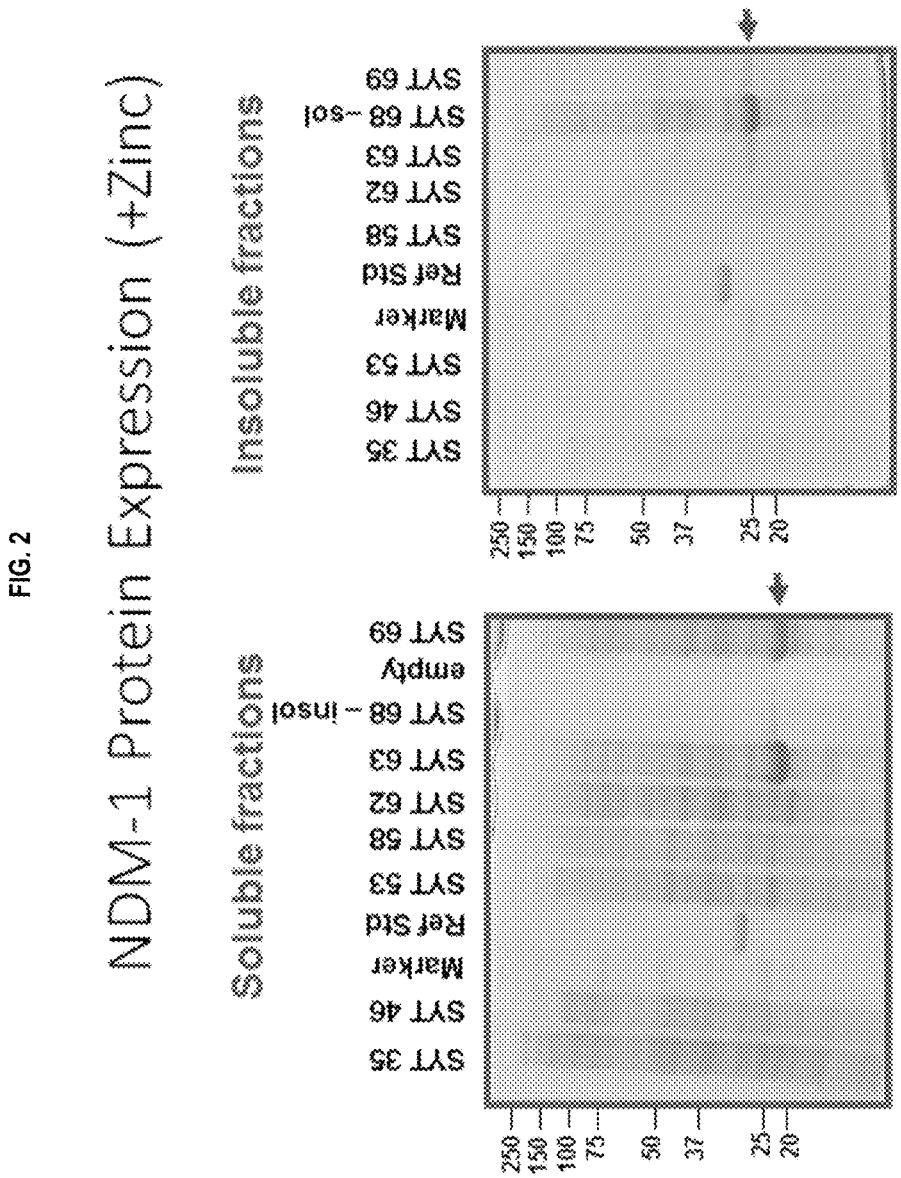
FIG. 2 shows NDM protein expression. Bacterial strains were grown in media supplemented with 100 uM $ZnSO_4$. Equal volumes of cell lysates from the soluble (left panel) or insoluble (right panel) fractions were analyzed by SDS-PAGE. The STY-68 insoluble fraction was run on the soluble fraction gel, and the STY-68 insoluble fraction was run on the insoluble gel. The protein size marker was Precision Plus Protein Prestained Standards (Marker) (Bio-Rad), and the reference standard (Ref Std) was the beta-lactamase protein, P3A. The NDM product is indicated with an arrow.

Screening was performed using the P2A strains that showed some enzyme production (i.e., strain # s: 5, 15, 16, 17, 20, 21, 22, 23, and 25—Table 7), and with the NDM strains that showed some enzyme production (i.e., strain # s: 35, 46, 53, 58, 62, 63, 68, and 69—Table 8). The SDS-PAGE analyses are displayed in FIG. 1 and FIG. 2.

Surprisingly, the addition of ZnSO$_4$ to the media resulted in higher protein expression levels and unexpectedly, a shift in the intracellular localization and the solubility of the enzymes. Addition of zinc shifted expression of the enzyme from inclusion bodies to the soluble fractions. Specifically, the presence of zinc increased the amount of proteins in the soluble fraction and reduced the amount of protein detected in inclusion bodies. In many instances, protein was detected in inclusion bodies (IB) without zinc, but was soluble in the cytoplasm or periplasmic space in the presence of zinc. Further, as shown in Tables 7 and 8, the "$" cells represent a shift from the expected intracellular localization to a different localization.

TABLE 7

Comparison of P2A Expression with and without Zinc Supplementation in Media

| Vector | Variant | Strain # | Host Name | Relative Expression Sol | Insol | Expected Comp | Ob-served | Expression with Zinc Sol | Insol | Expected Comp | Ob-served |
|---|---|---|---|---|---|---|---|---|---|---|---|
| pCYT12 (high phoA) | 1 (native) | SYT-PP0500-05 | BL21 | ** | ‡ | SOL; $ | IB; $ | ‡ | * | SOL | SOL |
| pCYT13 (med phoA) | 2 (STII) | SYT-PP0801-15 | BL21 degP | * | ‡ | PPL-SOL; $ | SOL/IB; $ | ‡ | * | PPL-SOL | PPL-SOL |
| pCYT10 (high 17) | 1 (native) | SYT-PS0103-16 | MG1655 T7+ | * | ** | SOL/IB | IB | ** | ** | SOL/IB | SOL/IB |
| pCYT12 (high phoA) | 1 (native) | SYT-PP0502-20 | W3110 degP | ** | * | SOL | SOL/IB | ‡ | * | SOL | SOL |
| pCYT12 (high phoA) | 2 (STII) | SYT-PP0602-21 | W3110 degP | * | | PPL-SOL | SOL/IB | ‡ | * | PPL-SOL | PPL-SOL |
| pCYT13 (med phoA) | 1 (native) | SYT-PP0702-22 | W3110 degP | ** | ** | SOL | SOL/IB | ** | ** | SOL | SOL |
| pCYT13 (med phoA) | 2 (STII) | SYT-PP0802-23 | W3110 degP | ‡ | † | PPL-SOL | SOL/IB | ‡ | more insol; ‡ | PPL-SOL | PPL-SOL |
| pCYT13 (med phoA) | 3 (tat) | SYT-PP0902-25 | W3110 degP | high MW?; † | high MW?; † | SOL | SOL/IB | | | SOL | SOL |

TABLE 8

Comparison of NDM Expression with and without Zinc Supplementation in Media

| Plasmid # | Vector | Variant | Strain # | Host Name | Relative Expression Sol | Insol | Expected Comp | Ob-served | Expression with Zinc Sol | Insol | Expected Comp | Ob-served |
|---|---|---|---|---|---|---|---|---|---|---|---|---|
| pNDM-7 | pCYT12 (high phoA) | 1 (native) | SYT-NP0700-32 | BL21 | ** | ‡ | SOL; $ | IB; $ | | | | |
| pNDM-10 | pCYT13 (med phoA) | 1 (native) | SYT-NP1000-35 | BL21 | * | ‡ | SOL; $ | IB; $ | ** | ** | SOL | none |
| pNDM-3 | pCYT10 (high T7) | 3 (PelB) | SYT-NS0305-45 | BL21 LysYdegP | * | ** | PPL-SOL | PPL-SOL | | | | |
| pNDM-4 | pCYT11 (med T7) | 1 (native) | SYT-NS0404-46 | W3110 degP | * | * | IB; $ | SOL; $ | ** | ** | IB | none |
| pNDM-5 | pCYT11 (med T7) | 2 (STII) | SYT-NS0505-47 | W3110 degP | * | | PPL-SOL | SOL | | | | |
| pNDM-6 | pCYT11 (med T7) | 3 (PelB) | SYT-NS0605-48 | W3110 degP | ** | * | PPL-SOL | SOL | | | | |
| pNDM-1 | pCYT10 (high T7) | 1 (native) | SYT-NS0103-53 | W3110 degP | * | ** | IB | IB | * | * | IB; $ | Both; $ |
| pNDM-6 | pCYT11 (med T7) | 3 (PelB) | SYT-NS0603-58 | W3110 degP | ** | * | PPL-SOL | SOL | * | ** | PPL-SOL | sol |
| pNDM-10 | pCYT13 (med phoA) | 1 (native) | SYT-NP-1002-62 | W3110 degP | ** | ** | SOL; $ | IB; $ | doublet?; * | ** | SOL | sol |
| pNDM-11 | pCYT13 (med phoA) | 2 (STII) | SYT-NP-1102-63 | W3110 degP | ‡ | | PPL-SOL; $ | IB/SOL; $ | † | *; * | PPL-SOL | sol |
| pNDM-14 | pCYT13 (med phoA) | 5 (STII) Δ37 | SYT-NP1402-66 | W3110 degP | ** | ‡ | PPL-SOL; | IB; $ | | | | |
| pNDM-15 | pCYT13 (med phoA) | 6 (Δ35) | SYT-NP1502-67 | W3110 degP | * | ** | SOL | SOL | | | | |

TABLE 8-continued

Comparison of NDM Expression with and without Zinc Supplementation in Media

| Plasmid # | Vector | Variant | Strain # | Host Name | Relative Expression | | | | Expression with Zinc | | | |
|---|---|---|---|---|---|---|---|---|---|---|---|---|
| | | | | | Sol | Insol | Expected Comp | Observed | Sol | Insol | Expected Comp | Observed |
| pNDM-16 | pCYT13 (med phoA) | 7 (STII Δ35) | SYT-NP1602-68 | W3110 degP | ‡ | ‡ | PPL-SOL; $ | IB/SOL; $ | ‡ | * | PPL-SOL | sol |
| pNDM-17 | pCYT13 (med phoA) | 8 (tat) | SYT-NP1702-69 | W3110 degP | * | ** | PPL-SOL | SOL | † | * | PPL-SOL | sol |

Figure 3:
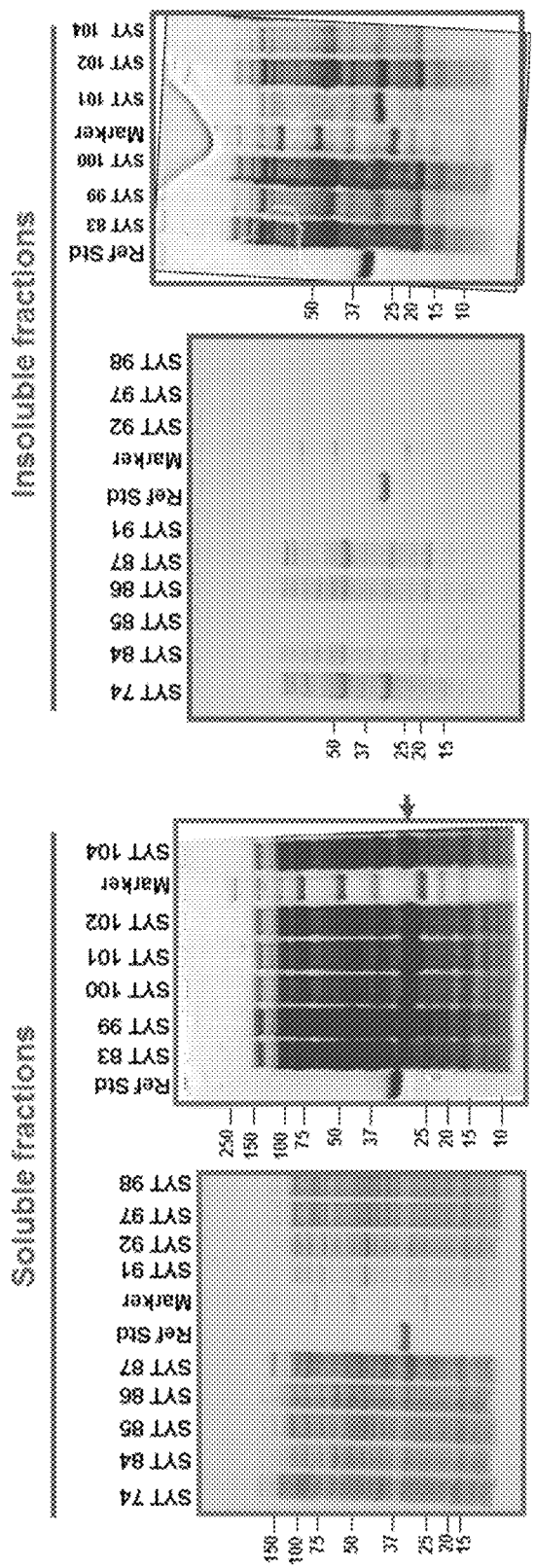
FIG. 3 shows KPC protein expression. Bacterial strains were grown in media without zinc supplementation. Equal volumes of cell lysates from the soluble (left panels) or insoluble (right panels) fractions were analyzed by SDS-PAGE. The protein size marker was Precision Plus Protein Prestained Standards (Marker) (Bio-Rad), and the reference standard (Ref Std) was the beta-lactamase protein, P3A. The KPC product is indicated with an arrow.

The metallo-beta-lactamases including P2A and NDM require zinc ions for activity. However, there are no reports that demonstrate that addition of zinc to the bacterial growth media results in a shift in intracellular localization and/or the solubility of NDM-1 when produced in *E. coli*. T Initial screening of the KPC strains demonstrated very high protein expression levels in 17 of the 35 strains (Table 9) with secondary screening of the highest expressing strains (i.e., strain #s 74, 83, 86, 87, 88, 89, 90, 93, 94, 95, 96, 99, 100, 101, 102, 103, and 104) confirming these results (Table 10). As KPC does not require zinc as a cofactor, zinc was not used in the bacterial growth media. Interestingly, in all cases, KPC protein was detected in the predicted cellular compartment (Table 10). However, inclusion bodies were observed in some cases where KPC expression was extremely high (Table 10). The SDS-PAGE analyses are displayed in FIG. 3

TABLE 9

Initial Expression Screen of KPC Strains

| Plasmid # | Vector | Variant | Strain # | Host Name | Sol | Insol | Media Supe |
|---|---|---|---|---|---|---|---|
| pkPC-1 | pCYT10 (high T7) | 1 (active) | SYT-KS0100-70 | BL21 | ** | ** | ** |
| pkPC-2 | pCYT10 (high T7) | 2 (STII) | SYT-KS0200-71 | BL21 | ** | ** | ** |
| pkPC-3 | pCYT11 (med T7) | 1 (native) | SYT-KS0300-72 | BL21 | ** | ** | ** |
| pkPC-4 | pCYT12 (high phoA) | 2 (STII) | SYT-KS0400-73 | BL21 | ** | ** | ** |
| pkPC-5 | pCYT12 (med phoA) | 1 (native) | SYT-KP0500-74 | BL21 | ** | ‡ | ** |
| pkPC-6 | pCYT13 (high phoA) | 2 (STII) | SYT-KP0600-75 | BL21 | ** | ** | ** |
| pkPC-7 | pCYT13 (med phoA) | 1 (native) | SYT-KP0700-76 | BL21 | ** | ** | ** |
| pkPC-8 | pCYT13 (med phoA) | 2 (STII) | SYT-KP0800-77 | BL21 | ** | ** | ** |
| pkPC-9 | pCYT13 (med phoA) | 3 (Δ2) | SYT-KP0900-78 | BL21 | ** | ** | ** |
| pkPC-10 | pCYT13 (med phoA) | 4 (STII-Δ2) | SYT-KP1000-79 | BL21 | ** | ** | ** |
| pkPC-11 | pCYT13 (med phoA) | 5 (Δ8) | SYT-KP1100-80 | BL21 | ** | ** | ** |
| pkPC-12 | pCYT13 (med phoA) | 6 (STII-Δ8) | SYT-KP1200-81 | BL21 | ** | ** | ** |
| pkPC-13 | pCYT13 (med phoA) | 7 (tat) | SYT-KP1300-82 | BL21 | ** | ** | ** |
| pkPC-1 | pCYT13 (med phoA) | 1 (native) | SYT-KS0104-83 | BL21 T7 LysY | * | *; ** | ** |
| pkPC-2 | pCYT10 (med phoA) | 2 (STII) | SYT-KS0205-84 | BL21 T7 LysY degP | ** | ** | ** |
| pkPC-3 | pCYT11 (med phoA) | 1 (native) | SYT-KS0304-85 | BL21 T7 LysY | ** | ** | ** |
| pkPC-4 | pCYT11 (med phoA) | 2 (STII) | SYT-KS0405-86 | BL21 T7 LysY degP | ** | * | ** |
| pkPC-6 | pCYT12 (high phoA) | 2 (STII) | SYT-KP0601-87 | BL21 degP | ‡ | * | ** |
| pkPC-8 | pCYT13 (med phoA) | 2 (STII) | SYT-KP0801-88 | BL21 degP | * | * | * |
| pkPC-1 | pCYT10 (high T7) | 1 (native) | SYT-KS0103-89 | MG1655 T7+ | * | ** | * |
| pkPC-2 | pCYT10 (high T7) | 2 (STII) | SYT-KS0203-90 | MG1655 T7+ | * | ** | * |
| pkPC-3 | pCYT11 (med T7) | 1 (native) | SYT-KS0303-91 | MG1655 T7+ | ** | ** | ** |
| pkPC-4 | pCYT11 (med T7) | 2 (STII) | SYT-KS0403-92 | MG1655 T7+ | ** | ** | ** |
| pkPC-5 | pCYT12 (high phoA) | 1 (native) | SYT-KP0502-93 | W3110 degP | * | * | * |
| pkPC-6 | pCYT12 (high phoA) | 2 (STII) | SYT-KP0602-94 | W3110 degP | Doublet; † | doublet?; ‡ | * |
| pkPC-7 | pCYT13 (med phoA) | 1 (native) | SYT-KP0702-95 | W3110 degP | * | ** | * |
| pkPC-8 | pCYT13 (med phoA) | 2 (STII) | SYT-KP0802-96 | W3110 degP | Doublet; † | Doublet; ‡ | * |
| pkPC-1 | pCYT10 (high T7) | 1 (native) | SYT-KS0107-97 | Shuffle T7 | ** | ** | ** |
| pkPC-3 | pCYT11 (med T7) | 1 (native) | SYT-KS0307-98 | Shuffle T7 | ** | ** | ** |
| pkPC-5 | pCYT12 (high phoA) | 1 (native) | SYT-KP0506-99 | Shuffle | † | * | ** |
| pkPC-7 | pCYT13 (med phoA) | 1 (native) | SYT-KP0706-100 | Shuffle | † | * | ** |
| pkPC-9 | pCYT13 (med phoA) | 3 (Δ2) | SYT-KP-0906-101 | Shuffle | Doublet; † | ‡ | ** |
| pkPC-11 | pCYT13 (med phoA) | 5 (Δ8) | SYT-KP1106-102 | Shuffle | Doublet; † | *; ‡ | ** |
| pkPC-12 | pCYT13 (med phoA) | 6 (STII-Δ8) | SYT-KP1202-103 | W3110 degP | Doublet; † | Doublet; ‡ | ? |
| pkPC-13 | pCYT13 (med phoA) | 7 (tat) | SYT-KP1306-104 | Shuffle | Doublet; † | * | ** |

TABLE 10

Secondary Expression Screen of KPC strains

| Plasmid # | Vector | Variant | Strain # | Host Name | Sol | Insol | Expected Comp | Observed |
|---|---|---|---|---|---|---|---|---|
| pkPC-5 | pCYT12 (high phoA) | 1 (native) | SYT-KP0500-74 | BL21 | ** | ‡ | IB | IB |
| pkPC-6 | pCYT12 (high phoA) | 2 (STII) | SYT-KP0601-87 | BL21 degP | ‡ | * | PPL-SOL; $ | PPL-SOL/IB; $ |
| pkPC-8 | pCYT13 (med phoA) | 2 (STII) | SYT-KP0801-88 | BL21 degP | * | * | PPL-SOL; $ | PPL-SOL/IB; $ |
| pkPC-1 | pCYT10 (high T7) | 1 (native) | SYT-KS0104-83 | BL21 T7 LysY | * | *; ** | IB; $ | SOL; $ |
| pkPC-4 | pCYT11 (med 17) | 2 (STII) | SYT-KS0405-86 | BL21 T7 LysY degP | ** | * | PPL-SOL; $ | PPL-IB; $ |
| pkPC-1 | pCYT10 (high T7) | 1 (native) | SYT-KS0103-89 | MG1655 T7+ | * | ** | IB; $ | SOL; $ |
| pkPC-2 | pCYT10 (high 17) | 2 (STII) | SYT-KS0203-90 | MG1655 T7+ | * | ** | PPL-SOL | PPL-SOL |
| pkPC-5 | pCYT12 (high phoA) | 1 (native) | SYT-KP0506-99 | Shuffle | † | * | SOL; $ | SOL-IB; $ |
| pkPC-7 | pCYT13 (med phoA) | 1 (native) | SYT-KP0706-100 | Shuffle | † | *; * | SOL; $ | SOL-IB; $ |
| pkPC-9 | pCYT13 (med phoA) | 3 (Δ2) | SYT-KP0906-101 | Shuffle | † | ‡ | SOL; $ | SOL-IB; $ |
| pkPC-11 | pCYT13 (med phoA) | 5 (Δ8) | SYT-KP1106-102 | Shuffle | † | *; ‡ | SOL; $ | SOL-IB; $ |
| pkPC-13 | pCYT13 (med phoA) | 7 (tat) | SYT-KP1306-104 | Shuffle | † | * | PPL-SOL; $ | PPL-SOL/IB; $ |
| pkPC-5 | pCYT12 (high phoA) | 1 (native) | SYT-KP0502-93 | W3110 degP | * | * | IB; $ | SOL/IB; $ |
| pkPC-7 | pCYT13 (med phoA) | 1 (native) | SYT-KP0702-95 | W3110 degP | * | ** | IB; $ | SOL; $ |
| pkPC-6 | pCYT12 (high phoA) | 2 (STII) | SYT-KP0602-94 | W3110 degP | Doublet; † | doublet?; ‡ | PPL-SOL; $ | PPL-SOL/IB; $ |
| pkPC-8 | pCYT13 (med phoA) | 2 (STII) | SYT-KP0802-96 | W3110 degP | Doublet; † | Doublet; ‡ | PPL-SOL; $ | PPL-SOL/IB; $ |
| pkPC-12 | pCYT13 (med phoA) | 6 (STII-Δ8) | SYT-KP1202-103 | W3110 degP | Doublet; † | Doublet; ‡ | PPL-SOL; $ | PPL-SOL/IB; $ |

Biological activity of the carbapenemases, P2A, NDM, and KPC, present in the E. coli cell lysates were evaluated in a microtiter plate assay using CENTA as the chromogenic substrate (Bebrone et al. Antimicrob. Agents Chemother (2001) 45:1868-1871; van Berkel et al., J. Med. Chem. (2013) 56:6945-6953). Briefly, the assay was performed in a 50 mM NaH$_2$PO$_4$ buffer, pH 7.0 with supplementation of 100 uM ZnSO$_4$, with CENTA (Calbiochem Cat #219475) at 50 ug/ml. The assays were run using purified P3A protein for the standard curve at protein concentrations of 0 ng/ml, 3 ng/ml, 6 ng/ml, 8 ng/ml, 10 ng/ml, 15 ng/ml, 20 ng/ml and 40 ng·ml. The plates were read at 405 nm after a 30 minute incubation using a microtiter plate reader. Cell lysates from the bacterial strains showing the highest protein expression levels by SDS-PAGE were evaluated for biological activity, which included P2A strains 5, 15, 20, 21, and 23, NDM strains 53, 58, 63, 68, and 69, and KPC strains 94, 96, 99, 100, 101, 102, 103, and 104 (Table 11). In addition, fresh lysate, frozen (−80° C.) lysate, or lysate stored overnight at 4° C. from strain P2A-21 were compared, and fresh and frozen (−80° C.) lysates from strain NDM-63 were compared to assess the stability of enzyme activity under differing storage conditions. All other lysates were kept frozen at −80° C. until assayed (Table 11). The strains that displayed the highest biological activities were P2A 21, NDM 63, 68, and 69, and KPC 101 and 102. No difference in activity was detected under the different storage conditions for P2A and NDM.

TABLE 11

Biological Activity of Bacterial Cell Lysates from P2A, NDM, and KPC Strains

| Strain # | Molecule | Construct | Compartment | Promoter | OD | Activity (mg/mL) |
|---|---|---|---|---|---|---|
| 21 (fresh) | P2A | STII | peri | phoA | 3.4 | 19.6 |
| 21 | P2A | STII | peri | phoA | 3.3 | 17.0 |
| 21 (4 ON) | P2A | STII | peri | phoA | 3.4 | 20.6 |
| 5 | P2A | native | cyto | phoA | 5.1 | 2.7 |
| 15 | P2A | STII | peri | phoA | 3.9 | 4.0 |
| 20 | P2A | native | cyto | phoA | 4.2 | 2.5 |
| 23 | P2A | STII | peri | phoA | 2.7 | 7.7 |
| 63 | NDM | STII | peri | phoA | 5.5 | 206.9 |
| 63 (fresh) | NDM | STII | peri | phoA | 4.5 | 163.6 |
| 68 | NDM | STII-Δ35 | peri | phoA | 4.6 | 162.4 |
| 69 | NDM | tat | peri | phoA | 4.3 | 90.2 |
| 53 | NDM | native | cyto | T7 | 1.3 | 17.5 |
| 58 | NDM | PelB | peri | T7 | 0.616 | 13.6 |
| 94 | KPC | STII | peri | phoA | 5.6 | 38.3 |
| 96 | KPC | STII | peri | phoA | 4.7 | 38.1 |
| 99 | KPC | native | cyto | phoA | 4.9 | 22.7 |
| 100 | KPC | native | cyto | phoA | 4.8 | 27.9 |
| 101 | KPC | Δ2 | cyto | phoA | 5.2 | 107.1 |
| 102 | KPC | Δ8 | cyto | phoA | 5.6 | 64.2 |
| 103 | KPC | STII-Δ8 | peri | phoA | 4.4 | 31.2 |
| 104 | KPC | Tat | cyto | phoA | 4.6 | 37.9 |

Example 3: Evaluation of Enzyme Expression Levels, Biological Activity, and Reproducibility Experiments were carried out, inter alia, to evaluate the growth and enzyme production characteristics of the E. coli carbapenemase-expressing strains when scaled up from 24-well plates into shake flasks.

The strains chosen for scale-up into shake flasks were P2A-21, NDM-63, NDM-68, and NDM-69, and KPC-101 and KPC-102, based on protein expression levels and biological activities. All strains were streaked onto LB agar plates containing tetracycline (tet) (12.5 ug/ml) and incubated at 30° C. for approximately 18 hours. For each strain, an isolated colony was used to inoculate a 2 ml pre-culture in LB tet broth (12.5 ug/ml) and incubated at 30° C. overnight. The pre-culture was inoculated 1/50 into 50 ml LB tet (12.5 ug/ml) supplemented with 100 uM $ZnSO_4$ in two, 500 ml baffled flasks with ventilated caps and incubated at 30° C. with shaking for approximately 24 hours. 1 ml aliquots were centrifuged and decanted. Bacterial pellets were stored at −20° C. One pellet from each strain was prepared immediately for biological activity assay, and a second pellet prepared for SDS-PAGE analysis. The OD600 values of the shake flask cultures were similar to those obtained in the 24-well dish cultures (Table 12).

TABLE 12

OD600 Values for Bacterial Strains Grown in Shake Flasks Versus 24-well Plate

| | P2A-21 | NDM-63 | NDM-68 | NDM-69 | KPC-101 | KPC-102 |
|---|---|---|---|---|---|---|
| Flask A | 2.75 | 3.65 | 3.48 | 3.26 | 4.60 | 5.01 |
| Flask B | 2.60 | 3.58 | 3.65 | 3.17 | 4.64 | 4.50 |
| Average | 2.68 | 3.62 | 3.57 | 3.23 | 4.62 | 4.78 |
| 24-well | 3.24 | 2.16 | 1.80 | 2.39 | 5.23 | 5.61 |

Figure 4:
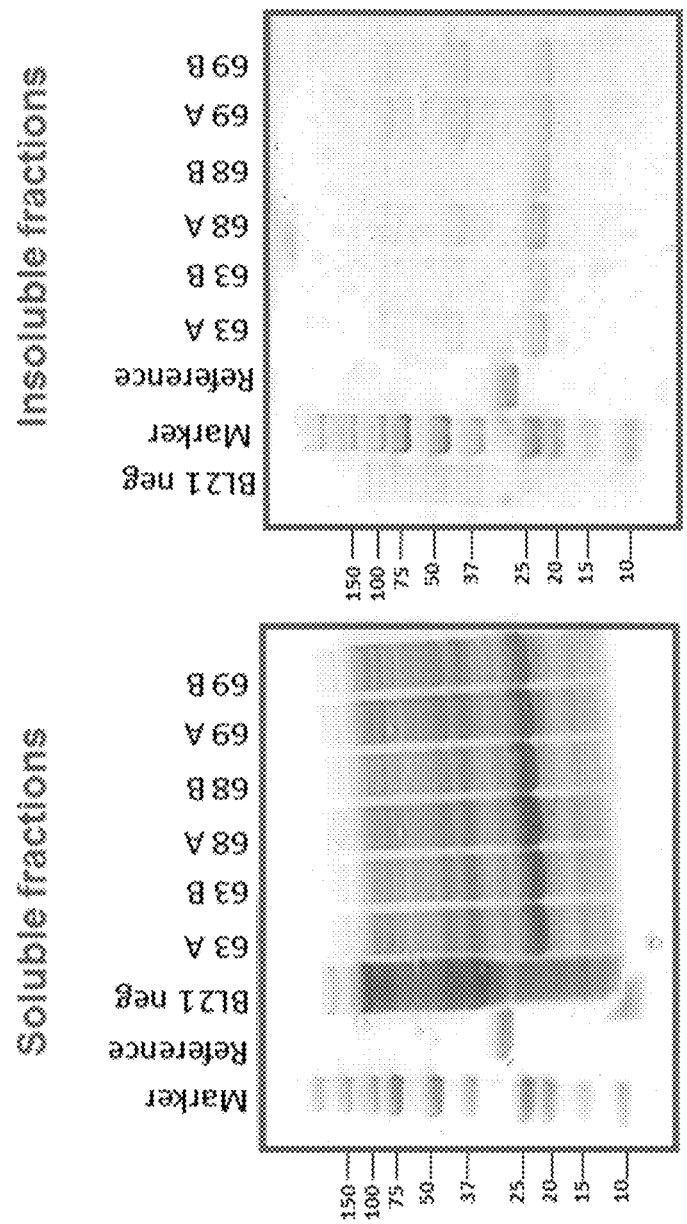
FIG. 4 shows NDM protein expression from shake flasks. Bacterial strains were grown in media with 100 uM $ZnSO_4$ supplementation. Equal volumes of cell lysates from the soluble (left panels) or insoluble (right panels) fractions were analyzed by SDS-PAGE. The protein size marker was Precision Plus Protein Prestained Standards (Marker) (Bio-Rad), and the reference standard (Reference) was the beta-lactamase protein, P3A. Duplicate shake flasks are designated A and B.
Figure 5:
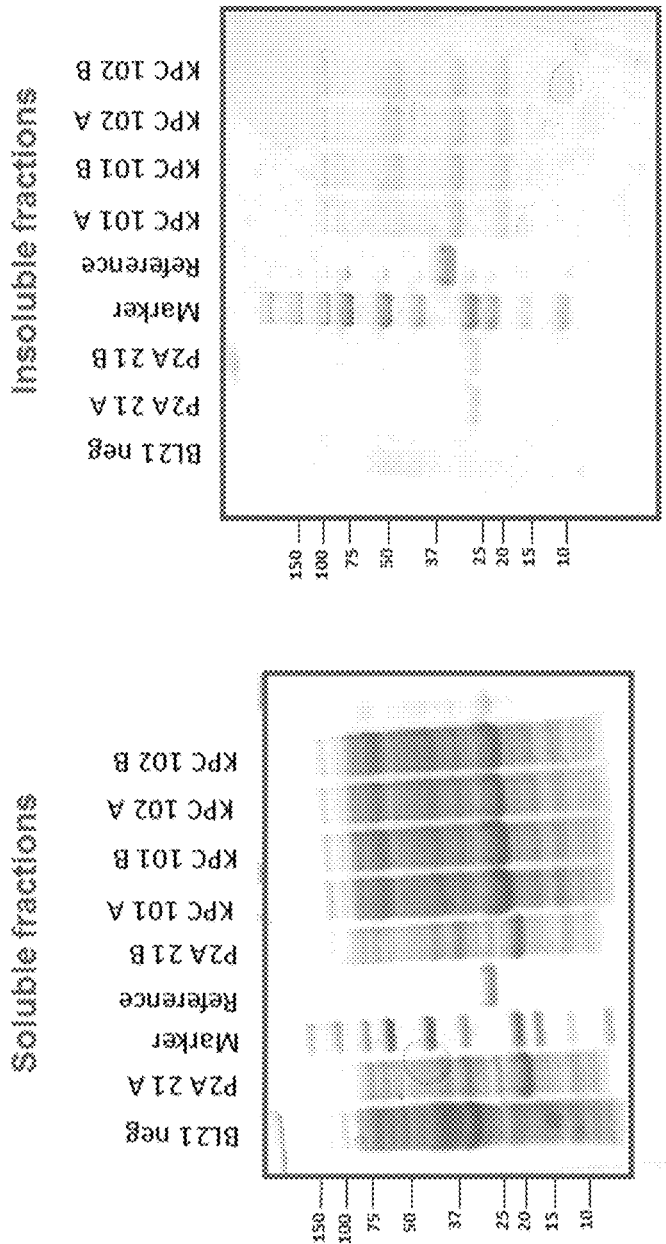
FIG. 5 shows P2A and KPC protein expression from shake flasks. Bacterial strains were grown in media with 100 uM $ZnSO_4$ supplementation. Equal volumes of cell lysates from the soluble (left panels) or insoluble (right panels) fractions were analyzed by SDS-PAGE. The protein size marker was Precision Plus Protein Prestained Standards (Marker) (Bio-Rad), and the reference standard (Reference) was the beta-lactamase protein, P3A, and BL21 neg was cell lysate from the untransformed cell line. Duplicate shake flasks are designated A and B.

Bacterial lysates were analyzed for protein expression by SDS-PAGE. Strong NDM expression was detected in all strains with good reproducibility between shake flasks (FIG. 4). Strong expression of P2A and KPC was also detected with good reproducibility between shake flasks (FIG. 5). In all cases, the vast majority of the protein was detected in the soluble fractions (FIG. 4 and FIG. 5). Biological activity was assessed in the cell lysates using the CENTA assay as described with P3A as the standard. All enzymes displayed biological activity (Table 13). The highest biological activity for NDM was from strain NDM-68. KPC-101 and KPC-102 showed similar biological activities.

TABLE 13

Biological Activity of P2A, NDM, and KPC Produced in Shake Flask Culture

| P2A | | NDM | | KPC | |
|---|---|---|---|---|---|
| Strain | Acitivity (mg/L) | Strain | Acitivity (mg/L) | Strain | Acitivity (mg/L) |
| P2A-21, Flask A | 19.6 | NDM 68, Flask A | 344.5 | KPC 101, Flask A | 128.5 |
| P2A-21, Flask B | 17.0 | NDM 68, Flask B | 346.1 | KPC 101, Flask B | 99.2 |
| Neg | 0.00 | NDM 68, Flask A | 198.9 | KPC 101, Flask A | 100.2 |
| | | NDM 68, Flask B | 199.3 | KPC 101, Flask B | 130.0 |
| | | NDM 68, Flask A | 160.5 | Neg | 0.00 |
| | | NDM 68, Flask B | 187.1 | | |
| | | Neg | 0.00 | | |

Example 4: Fermentation Studies with Selected P2A, NDM, and KPC Expressing Bacterial Strains Experiments were carried out to evaluate the growth and enzyme production characteristics of the E. coli carbapenemase-expressing strains when scaled up into 5 liter bioreactors.

Strains chosen for the fermentation studies were P2A-21, NDM-68, and KPC-101, based on protein expression levels and biological activities observed with the shake flask scale-up studies. A total of four 5 liter bioreactors were used. NDM-68 was grown under different conditions in two bioreactors. The fermentation conditions used were low phosphate bacterial growth media (CRAP), with a 50% glucose, 2 mM $ZnSO_4$ feed, salt supplement of 1 M $MgSO_4$ (when OD600 reached ~40), $ZnSO_4$ supplementation of P2A and NDM fermenters. The initial batch volume was 3 liters with an inoculum ratio of 1%, run at 30° C. with 750 rpm fixed agitation, and 4.5 liters LPM airflow, with dissolved oxygen levels kept greater than or equal to 35 ppm, and pH kept at 6.8+0.01. The P2A, first NDM, and KPC fermenters used standard phosphate doses (17 mM), while the second NDM fermenter was dosed with extra zinc (final concentration 740 uM) and extra phosphate (34 mM) as it was uncertain if the zinc in the reactor would chelate the phosphate making it unavailable to cell growth. A summary of the fermenter runs is shown below in Table 14.

TABLE 14

Fermentation Run Summary

| Process Parameter | Ferm A | Ferm B | Ferm C | Ferm D |
|---|---|---|---|---|
| Strain | SYT 21 | SYT 68 | SYT 68 | SYT 101 |
| Molecule | P2A | NDM | NDM | KPC |
| Inoculum OD | 6.02 | 6.63 | | 1.78 |
| Volume of Inoculum (mL) | 34 | 34 | 34 | 34 |
| EFT at DO spike (hr) | 9.0 | 9.3 | 9.6 | 18.6 |
| OD at DO spike | 24 | 28 | 22 | 11 |
| Glucose feed* used (mL) | 781 | 779 | 771 | 585 |
| Phosphate feed delivered (mL) | 0 | 0 | 100 | 0 |
| Acid used (mL) | 8 | 11 | 2 | 4 |
| Base used (mL) | 227 | 221 | 261 | 153 |
| Total EFT (hr) | 48 | 48 | 48 | 48 |
| Harvest OD | 86 | 145 | 124 | 50 |
| Harvest Biomass (g/L) | 195 | 205 | 246 | 120 |
| Harvest PO4 (mM - calculated) | 17 | 17 | 36 | 18 |

Figure 6:
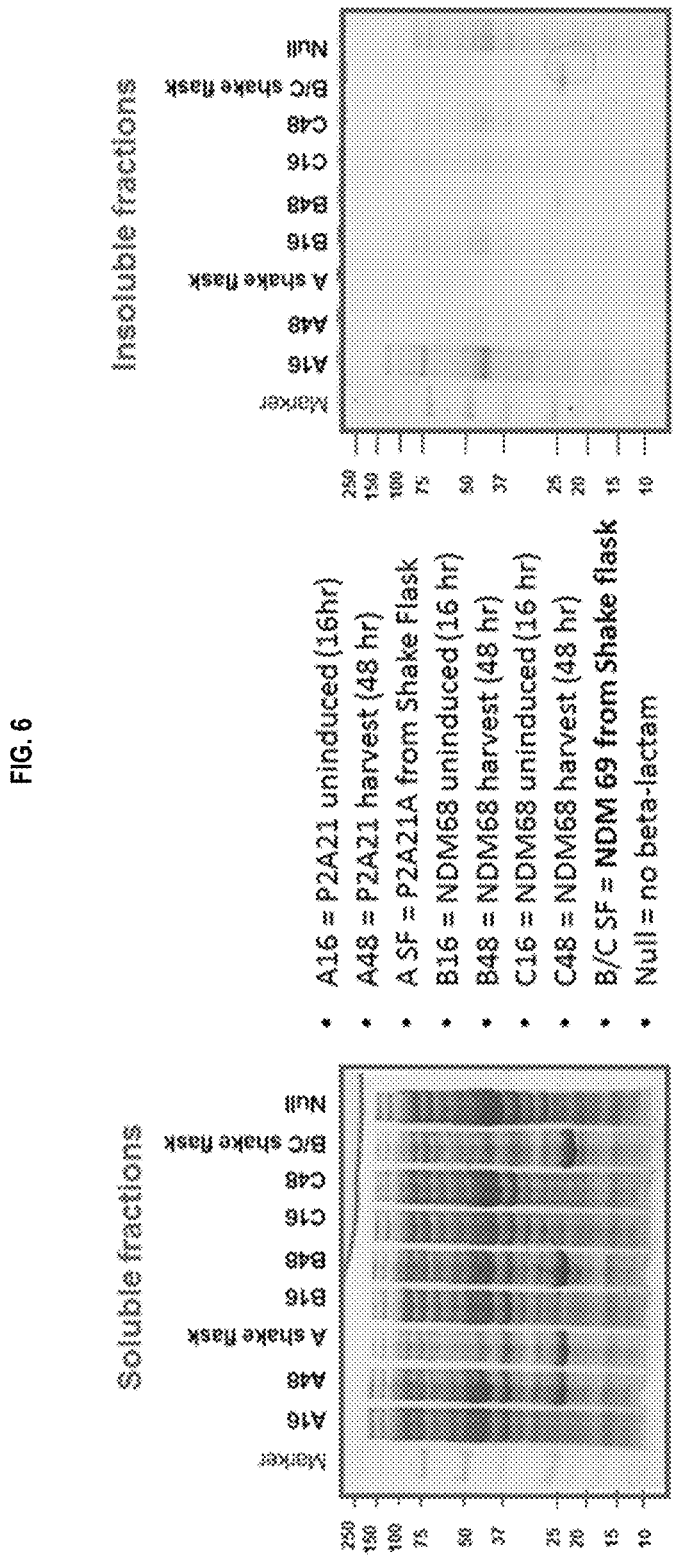
FIG. 6 shows P2A and NDM protein expression from fermenters. Bacterial strains were grown in fermenters. Lysates were prepared from bacteria collected at 16 hours and at 48 hours. Equal volumes of cell lysates from the soluble (left panels) or insoluble (right panels) fractions were analyzed by SDS-PAGE and compared to cell lysates from the shake flask study. NDM-69 was used as the shake flask comparison instead of NDM-68. The protein size marker was Precision Plus Protein Prestained Standards (Marker) (Bio-Rad), and Null was from a cell lysate from the untransformed cell line.
Figure 7:
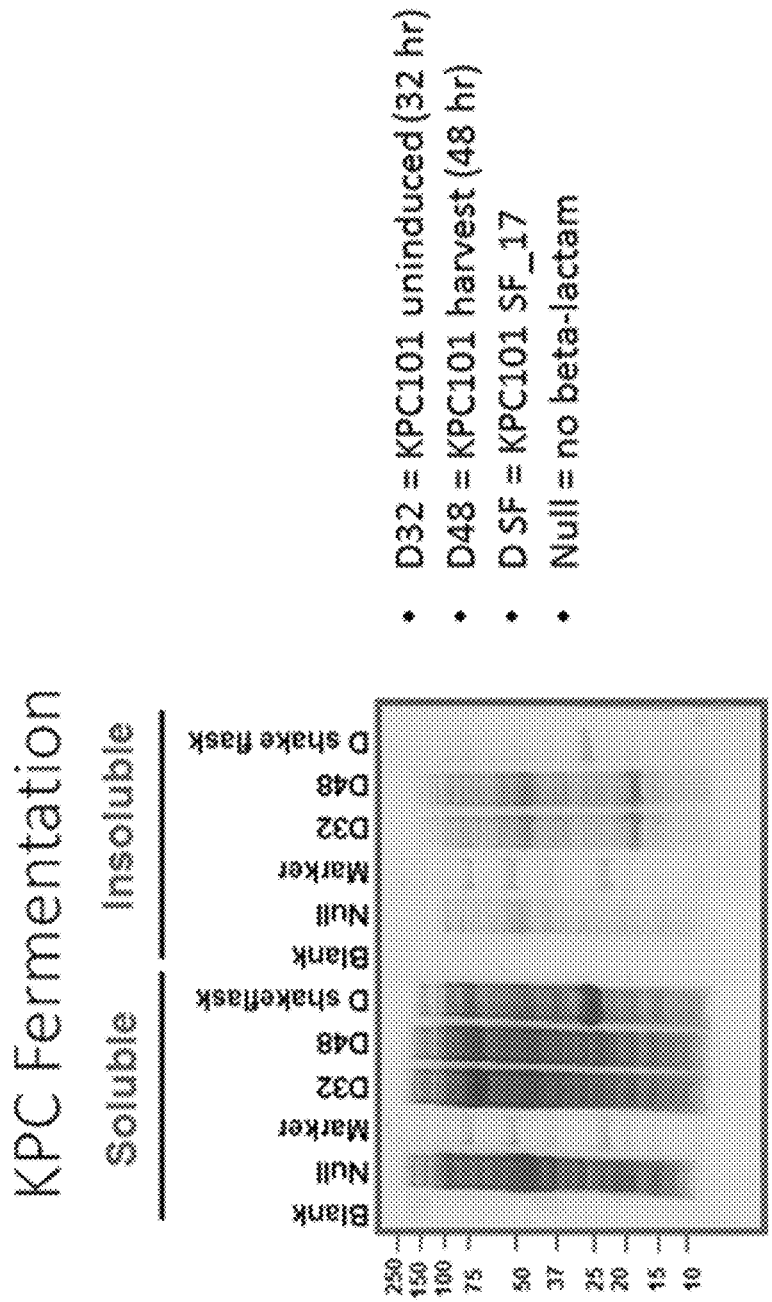
FIG. 7 shows KPC protein expression from fermenters. Bacterial strain KPC-101 was grown in a fermenter. As the cells grew slowly, the early collection was delayed until 32 hours, compared to 16 hours for the other fermenters. Lysates were prepared from bacteria collected at 32 hours and at 48 hours. Equal volumes of cell lysates from the soluble or insoluble fractions were analyzed by SDS-PAGE and compared to cell lysate from the shake flask study. The protein size marker was Precision Plus Protein Prestained Standards (Marker) (Bio-Rad), and Null was from a cell lysate from the untransformed cell line.

DO-dissolved oxygen
EFT-elapsed fermentation time
*Glucose feed initiated at DO spike Aliquots of bacteria were collected early in the fermentation cycle, 16 hours, for P2A and NDM, and 32 hours for KPC, prior to enzyme expression induction, and late in the cycle (48 hours) and subjected to SDS-PAGE (FIG. 6 and FIG. 7) and biological activity analyses (Table 15). Fermenter D that contained KPC-101 did not reach a high OD. Fermenters A, B, and C, reached high ODs. Specifically, Fermenters A and B, P2A and NDM yielded a specific productivity comparable to the shake flasks. The additional phosphate in Fermenter C inhibited enzyme production although biomass was improved by approximately 15%, suggesting that more phosphate with the addition of longer fermentation times might improve total yields. Fermenter D did not achieve sufficient biomass to induce KPC as strongly as observed in the shake flasks. Bioreactor expression is achieved by changing of growth conditions, lowering phosphate conditions, and/or changing the promoter.

TABLE 15

Biological Activity of Bacterial Cell Lysates Isolated from the Fermenters
Activity of Fermenter Samples

| Strain | Bioreactor | Time (hr) | Activity (mg/L) |
| --- | --- | --- | --- |
| P2A-21 | A | 16 | 3.2 |
|  |  | 48 | 59.7 |
| NDM 68 | B | 16 | 6.6 |
|  |  | 48 | 520.0 |
| NDM 68 | C | 16 | 5.8 |
|  |  | 48 | 14.1 |
| KPC 101 | D | 32 | 2.0 |
|  |  | 48 | 2.2 |
| Neg | N/A |  | 0.00 |

Example 5: Characterization of the Biological Activities of Carbapenemase Enzymes Purified from Fermenter (P2A and NDM) or Shake Flask (KPC) Cultures Experiments were carried out to evaluate, among others, whether the carbapenemase enzymes, P2A, NDM, and KPC can be purified with retention of biological activity.

Figure 8:
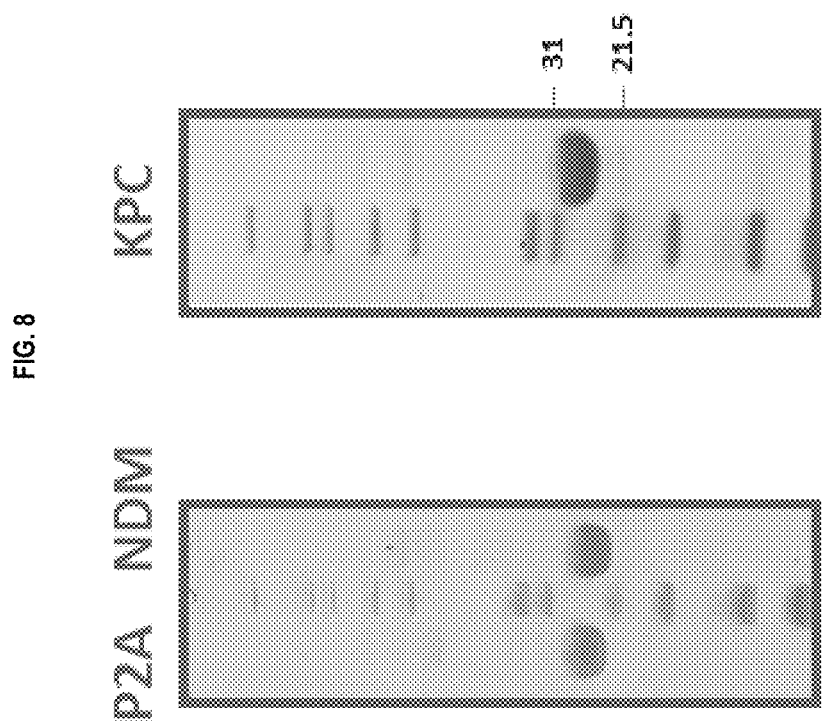
FIG. 8 shows purified carbapenemases, P2A, NDM, and KPC. Cleared cell lysates were subjected to cation-exchange chromatography using an SP-sepharose column. NDM was subjected to an additional purification step using a hydrophobic column, phenyl sepharose. Enzymes were formulated in 20 mM HEPES, pH 7.5, 150 mM NaCl buffer. The P2A and NDM samples were supplemented with 100 uM $ZnSO_4$ in all steps of the purification process, including in the final formulation.

Frozen cell pellets retained from the fermenter studies, Fermenter A, P2A, Fermenter B, NDM, or from the shake flask studies, shake flask A, KPC, were lysed at 3×7000 psi in a Panda table top cell homogenizer. The lysate was spun at 45000 g for 1 hour, supernatants collected and pH adjusted to 5.5 with 1 M MES. The supernatants were spun at 45000 g for 30 minutes, to remove precipitated debris and filtered through a 0.45 um filter. The filtered supernatants were subjected to cation-exchange chromatography using an SP-sepharose column. NDM was subjected to an additional purification step using a hydrophobic column, phenyl sepharose. The fractions containing the peak levels of protein were concentrated and dialyzed against a 20 mM HEPES, pH 7.5, 150 mM NaCl buffer. The P2A and NDM samples were supplemented with 100 uM $ZnSO_4$ in all steps of the purification process. Purified enzymes yields were calculated to be approximately 600 mg of protein per liter. Purified proteins were analyzed by SDS-PAGE (FIG. 8) and for biological activity (Table 16). Strong protein bands of the expected size, with little observable contamination with other proteins, were observed for all enzymes by SDS-PAGE (FIG. 8). Biological activity analyses revealed that the purified proteins retained their biological activity (Table 16). These data demonstrate that the carbapenemase enzymes P2A, NDM, and KPC can be produced and purified from E. coli while retaining their biological activity.

TABLE 16

Biological activity of the Purified Carbapenemases, P2A, NDM, and KPC

| Sample | Con (mg/mL) | Lot # | ß-Lactamase (mg/L) |
| --- | --- | --- | --- |
| P2A-21 | 2.8 | 272-10 | 317.7 |
| NDM-68 | 3.3 | 272-9 | 1703.8 |
| KPC-101 | 4.8 | 272-16 | 1219.2 |

Figure 9:
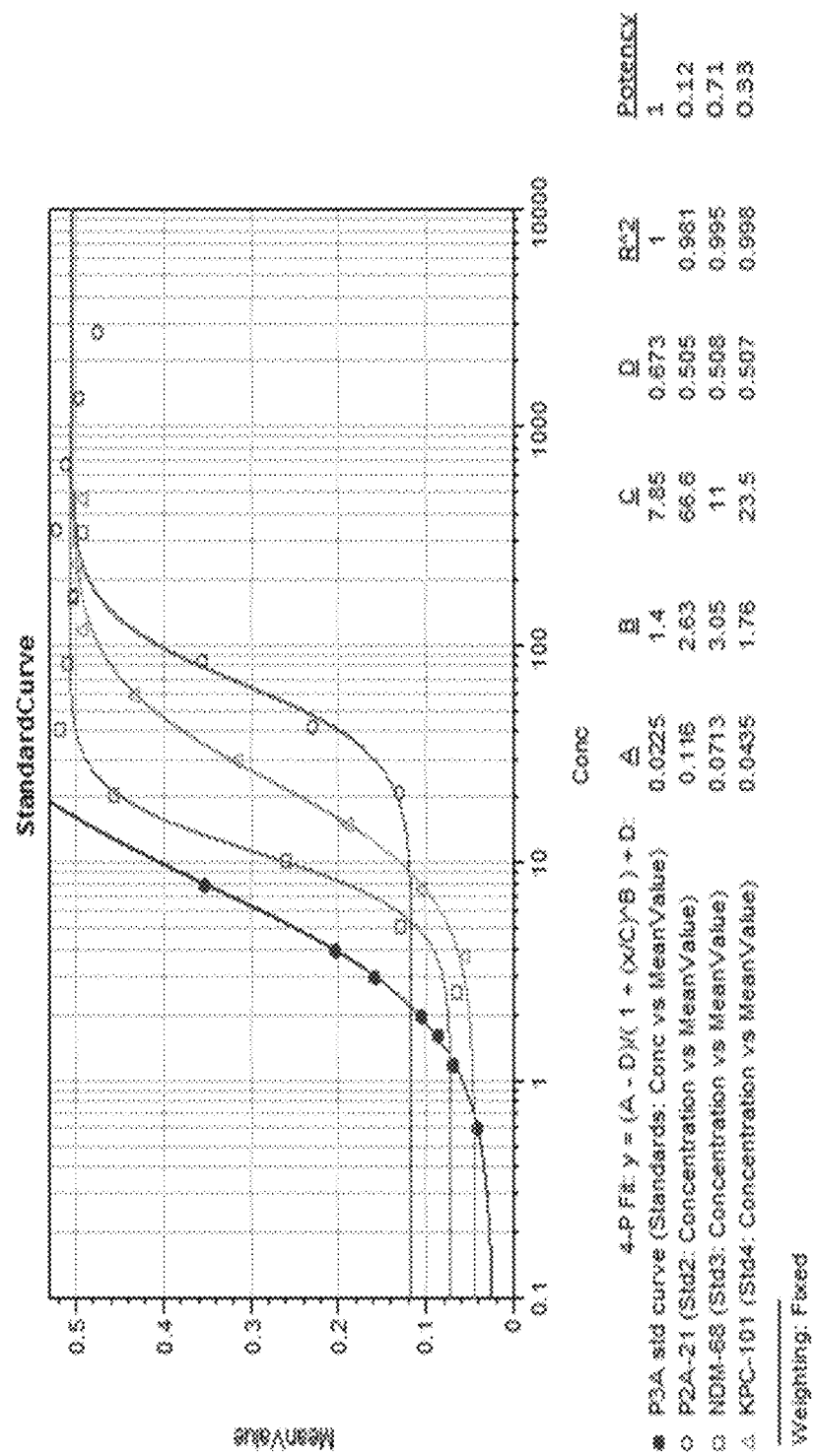
FIG. 9 shows relative specific activities of P3A, P2A, NDM, and KPC against CENTA. Data were plotted with the protein concentrations of the purified beta-lactamase on the X-axis and the $OD_{405}$ plotted on the Y-axis. The relative potency of each enzyme is displayed in the yellow box and was P3A>NDM-68>KPC-101>P2A-21 (from left to right).

As different beta-lactamase enzymes display differential affinity and kinetics with diverse substrates, including antibiotics and the CENTA reagent, it was possible to determine the relative specific activities of P2A, NDM, and KPC compared to P3A for CENTA as a substrate now that purified proteins were available and therefore, protein concentrations were known. To compare the relative activity of P2A, NDM, and KPC to that of P3A, the data from the CENTA assay was plotted using the protein concentration of each beta-lactamase on the X-axis and the OD405 reading (relating to degradation of the CENTA substrate) on the Y-axis to obtain a series of sigmoid curves (FIG. 9). The midpoint of each curve provides the relative potency of each enzyme for CENTA degradation. Using this analysis, the relative potencies of the beta-lactamases were: P3A=1.0; NDM-68=0.71, KPC-101=0.33 and P2A-21=0.12 (FIG. 9). This in the CENTA assay, quantification of the three carbapenemases using a P3A standard curve will underestimate the amounts of the three carbapenemases. This is most exaggerated with P2A, in which the amounts are underestimated by a factor of about 8.

Example 6. Generation of IPTG-Inducible P2A Cell Lines in the BL21 (DE3) E. Coli Strain Because the phoA promoter in the SYT21-P2A plasmid is difficult to work with, two new E coli strains encoding the P2A gene under the control of the T7 promoter inducible system were generated. The P2A coding region was cloned into the pET30a vector (Promega, Madison, Wis.) with the STII leader (to direct secretion to the periplasmic space) and without the leader for cytoplasmic expression. The two plasmids, pET30a-P2AL (P2A with the STII leader) and pET30a-P2A (P2A without the leader) were used to transform the E coli strain BL21 (DE3) (New England Biolabs, Ipswich, Mass.). P2A amino acid and DNA sequences are provided below:

```
P2A amino acid sequence with STII leader (leader sequence is
indicated by underlining)
                                                   (SEQ ID NO 66)
MKKNIAFLLA SMFVFSIATN AYAETGTISI SQLNKNVWVH TELGYFNGEA VPSNGLVLNT

SKGLVLVDSS WDNKLTKELI EMVEKKFQKR VTDVIITHAH ADRIGGITAL KERGIKAHST
```

-continued

ALTAELAKNS GYEEPLGDLQ TITSLKFGNT KVETFYPGKG HTEDNIVVWL PQYQILAGGC

LVKSAEAKDL GNVADAYVNE WSTSIENVLK RYGNINSVVP GHGEVGDKGL LLHTLDLLK

P2A DNA sequence with leader (underlining: NdeI restriction site; bold: XhoI restriction site)

(SEQ ID NO: 67)

<u>CATATG</u>AAAAAAAACATTGCATTTCTGCTGGCGAGCATGTTTGTTTTTAGCATTGCAACCAATGCATACGC

CGAAACGGGCACCATTAGCATTAGCCAACTCAACAAAAACGTTTGGGTCCACACCGA

GTTAGGCTATTTCAACGGTGAAGCCGTGCCGAGCAATGGTTTGGTTCTGAATACGTCCAAGGGTCTGGTGT

GGTAGACTCCAGCTGGGACAATAAGCTGACCAAAGAACTGATCGAAATGGTTGAGAAAAAGTTCCAGAAGC

GTGTGACTGATGTCATTATCACCCATGCGCACGCGGACCGCATCGGTGGCATTACCGCGCTGAAAGAGCGT

GGCATTAAAGCACATAGCACGGCACTGACGGCTGAGCTGGCGAAGAACAGCGGCTACGAAGAACCGCTGGG

TGATCTGCAGACCATCACGTCGCTGAAGTTTGGCAACACCAAAGTCGAGACTTTTTACCCAGGTAAGGGTC

ATACCGAAGATAACATCGTGGTTTGGCTGCCGCAGTACCAAATCCTGGCCGGTGGCTGCCTGGTTAAGAGC

GCAGAGGCGAAAGATCTGGGTAATGTCGCGGACGCTTATGTGAACGAGTGGAGCACCTCTATTGAAAATGT

TTTGAAACGTTATGGTAATATCAATAGCGTTGTGCCGGGTCACGGTGAGGTCGGCGACAAAGGTCTGCTGT

TGCACACGCTGGATCTGCTGAAGTGATAACTCGAG

P2A amino acid sequence no leader (SEQ ID NO: 68)

METGTISISQ LNKNVWVHTE LGYFNGEAVP SNGLVLNTSK GLVLVDSSWD NKLTKELIEM

VEKKFQKRVT DVIITHAHAD RIGGITALKE RGIKAHSTAL TAELAKNSGY EEPLGDLQTI

TSLKFGNTKV ETFYPGKGHT EDNIVVWLPQ YQILAGGCLV KSAEAKDLGN VADAYVNEWS

TSIENVLKRY GNINSVVPGH GEVGDKGLLL HTLDLLK

P2A DNA sequence no leader (SEQ ID NO: 69)

<u>CATATG</u>GAAACGGGCACCATTAGCATTAGCCAACTCAACAAAAACGTTTGGGTCCACACCGAGTTAGGCTA

TTTCAACGGTGAAGCCGTGCCGAGCAATGGTTTGGTTCTGAATACGTCCAAGGGTCTGGTGTTGGTAGACT

CCAGCTGGGACAATAAGCTGACCAAAGAACTGATCGAAATGGTTGAGAAAAAGTTCCAGAAGCGTGTGACT

GATGTCATTATCACCCATGCGCACGCGGACCGCATCGGTGGCATTACCGCGCTGAAAGAGCGTGGCATTAA

AGCACATAGCACGGCACTGACGGCTGAGCTGGCGAAGAACAGCGGCTACGAAGAACCGCTGGGTGATCTGC

AGACCATCACGTCGCTGAAGTTTGGCAACACCAAAGTCGAGACTTTTTACCCAGGTAAGGGTCATACCGAA

GATAACATCGTGGTTTGGCTGCCGCAGTACCAAATCCTGGCCGGTGGCTGCCTGGTTAAGAGCGCAGAGGC

GAAAGATCTGGGTAATGTCGCGGACGCTTATGTGAACGAGTGGAGCACCTCTATTGAAAATGTTTTGAAAC

GTTATGGTAATATCAATAGCGTTGTGCCGGGTCACGGTGAGGTCGGCGACAAAGGTCTGCTGTTGCACACG

CTGGATCTGCTGAAGTGATAACTCGAG

Figure 10:
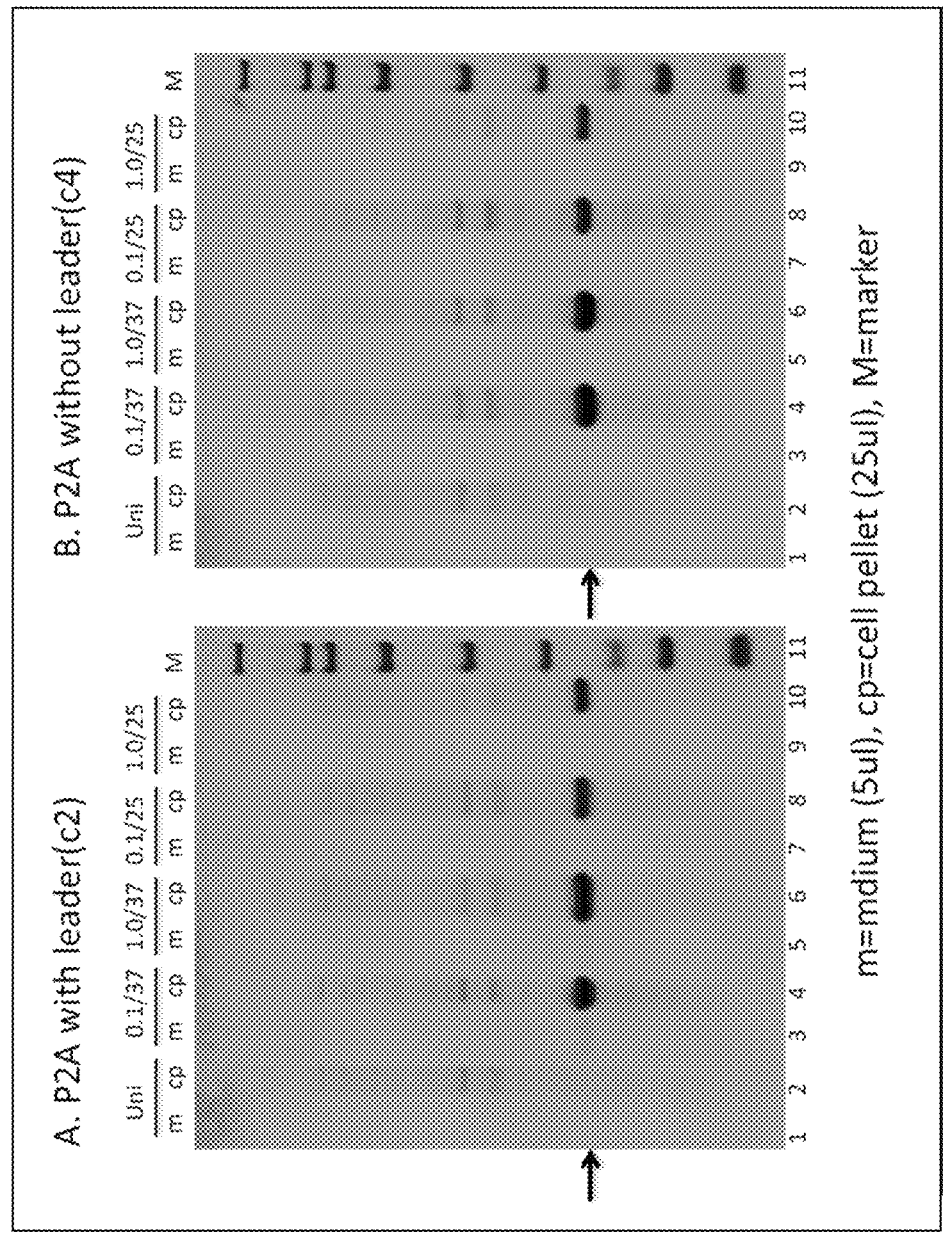
FIG. 10 shows P2A protein induction testing. The pET30a-P2AL (panel A) or the pET30a-P2A (panel B) BL21 (DE3) *E coli* strains were evaluated under different IPTG induction (0.1 mM or 1.0 mM IPTG) and growth conditions (37° C. or 25° C.). Tissue culture media (m) or whole cell lysates (CP) were analyzed via SDS/PAGE and visualized by Coomassie blue staining. Uni=uninduced cells, m=culture media, cp=cell pellet, M=protein size marker. Arrow indicates the P2A protein.

Individual colonies were screened for the presence of the P2A plasmids by restriction mapping. The integrity of the plasmids was then verified by sequencing analyses. P2A protein expression was evaluated under different induction conditions. The cells were cultured in LB media with the addition of 100 uM ZnSO$_4$ for 16 hours at 37° C. and then induced for 4 hours with 0.1 mM or 1.0 mM IPTG at 37° C. or 25° C. Aliquots of the media and of the cell pellets were incubated with SDS/PAGE gel loading buffer and denatured at 95° C. for 5 minutes prior to loading onto an SDS/PAGE gel (FIG. 10).

Strong induction of P2A expression was detected under all IPTG induction conditions. The optimal induction condition for P2A was 37° C., although P2A expression at 25° C. was at only slightly lower levels. No difference in P2A expression was detected with 1.0 versus 0.1 mM IPTG. Secreted P2A was detectable in the tissue culture media (faint band) for pET30a-P2AL (with the leader) but not detectable from pET30a-P2A (without the leader). P2A expression in the cell pellet fractions was estimated to be >50% of the total protein in the E coli cells.

To determine what fraction of the total P2A protein produced was in the soluble vs insoluble (inclusion bodies) fraction, the next study was performed. pET30a-P2AL (clone 2) and pET30a-P2A (clone 4) were grown for 16 hours in LB plus 100 uM ZnSO$_4$ and induced with 0.1 mM IPTG at 25° C. for 4 hours. For comparison, the phoA promoted P2A cell line, SYT21-P2A was grown in APS-LB media plus 100 uM ZnSO$_4$ for 16 hours and then was induced by incubating at 25° C. overnight. At the time of harvest, the cell density of each culture was measured using OD600.

Figure 11:
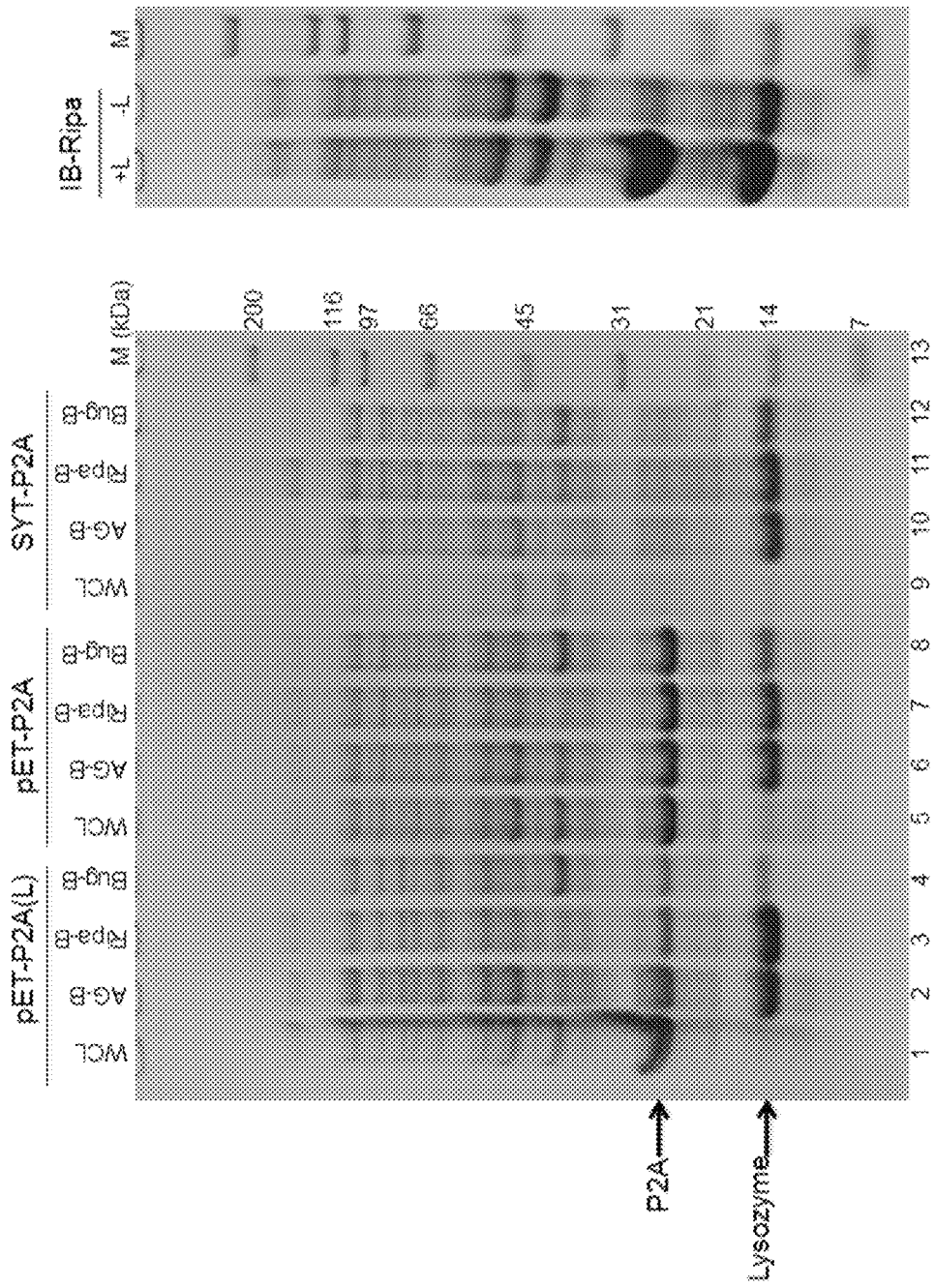
FIG. 11 depicts P2A expression and solubility testing. The total protein from 7.5 ul of induced cell culture (WCL) and equivalent (7.5 ul culture) of soluble lysate from each buffer system (AG-B, Ripa-B, or Bug-B) were analyzed via SDS/PAGE and visualized by Coomassie blue staining. The panel on the right displays the insoluble fraction from inclusion bodies (IB) after lysis in the Ripa-B buffer. +L indicates P2A with leader, and −L indicates P2A without leader.

Three 1 ml culture from each strain was collected and spun down to remove the media. The cell pellets were resuspended in 200 ul of 1) AG-B lysis buffer (50 mM HEPES, pH 7.9; 150 mM NaCl, 0.2% Triton X100, 2% glycerol, 100 uM $ZnSO_4$, and 1 mM $MgCl_2$), RIPA Buffer (Sigma R0278), and BugBuster buffer (Novagen #70584-4). Lysozyme was added to each buffer to a final concentration of 0.5 mg/mL. Cells were lysed by thawing at 37° C. and freezing at −80° C. for 3 cycles. Soluble proteins and insoluble proteins were recovered by centrifugation in a microfuge for 10 min and analyzed by SDS/PAGE (FIG. 11).

The expression of P2A was greatly induced in the presence of IPTG using the pET30a-P2AL (clone 2) and pET30a-P2A (clone 4) strains. P2A was not induced to the same extent using the phoA system with the SYT21-P2A *E coli* strain. The induced P2A protein was soluble using the three different lysis buffers with the pET30a-P2AL (clone 2) strain expressing less soluble protein than the pET30a-P2A (clone 4) strain. The estimated P2A expression levels and solubility are summarized in Table 17.

TABLE 17

P2A Estimated Expression Levels and Solubility

|  | pET30a-P2AL (clone 2) | pET30a-P2A (clone 4) | SYT-P2A |
|---|---|---|---|
| $OD_{600}$ | 1.845 | 1.551 | 1.394 |
| P2A Expression (mg/mL) | >200 | >200 | ND |
| Solubility AG-B | 50% | >90% | ND |
| Solubility Ripa-B | 25% | >90% | ND |
| Solubility BugBuster-B | 15% | >90% | ND |

P2A expression level was much higher with the IPTG inducible system than with the phoA inducible system. In addition, the pET30a-P2A (without the leader) expressed more soluble protein than the pER30a-P2AL (with the leader).

To achieve an estimate of the amount of P2A protein in each of the lysates, dilutions of the lysates (5 ul, 2.5 ul, 1.3 ul, and 0.63 ul) were evaluated on SDS/PAGE compared to dilutions of a purified P2A standard protein (2.0 ug, 1.0 ug, 0.5 ug, 0.25 ug, 0.13 ug). Based on the P2A protein band intensities, an estimate of the amount of P2A protein in each of the lysates was obtained. The biological activity of the P2A protein in the cell lysates under the different lysing conditions was evaluated using the CENTA chromogenic assay compared to the biological activity of the P2A protein standard. The biological activity was normalized based on the P2A protein concentration estimate and an estimated P2A specific activity was obtained. The specific activity is displayed as % activity compared to the P2A standard (100%). These data are summarized in Table 18. All lysates displayed biological activity. The lysates from the pET30a-P2A (no leader) cells showed higher specific activity compared to the pET30a-P2AL cells. The P2A expression cassette without the leader will be used for future studies.

TABLE 18

P2A Concentrations and Specific Activity in Cell Lysates

| Sample | Description | P2A conc (mg/mL) | Relative beta-lactamase Activity (mg/mL) CENTA | % Activity Compared to P2A standard |
|---|---|---|---|---|
| C2-1 | P2A + L, AG buff | 0.3 | 0.24 | 80 |
| C2-2 | P2A + L, Ripa buff | 0.4 | 0.36 | 90 |
| C2-3 | P2A + L, BugBuster | 0.2 | 0.15 | 75 |
| C4-1 | P2A, AG buff | 0.8 | 0.96 | 120 |
| C4-2 | P2A, Ripa buff | 1.6 | 1.9 | 119 |
| C4-3 | P2A, BugBuster | 0.8 | 0.94 | 118 |

Figure 12:
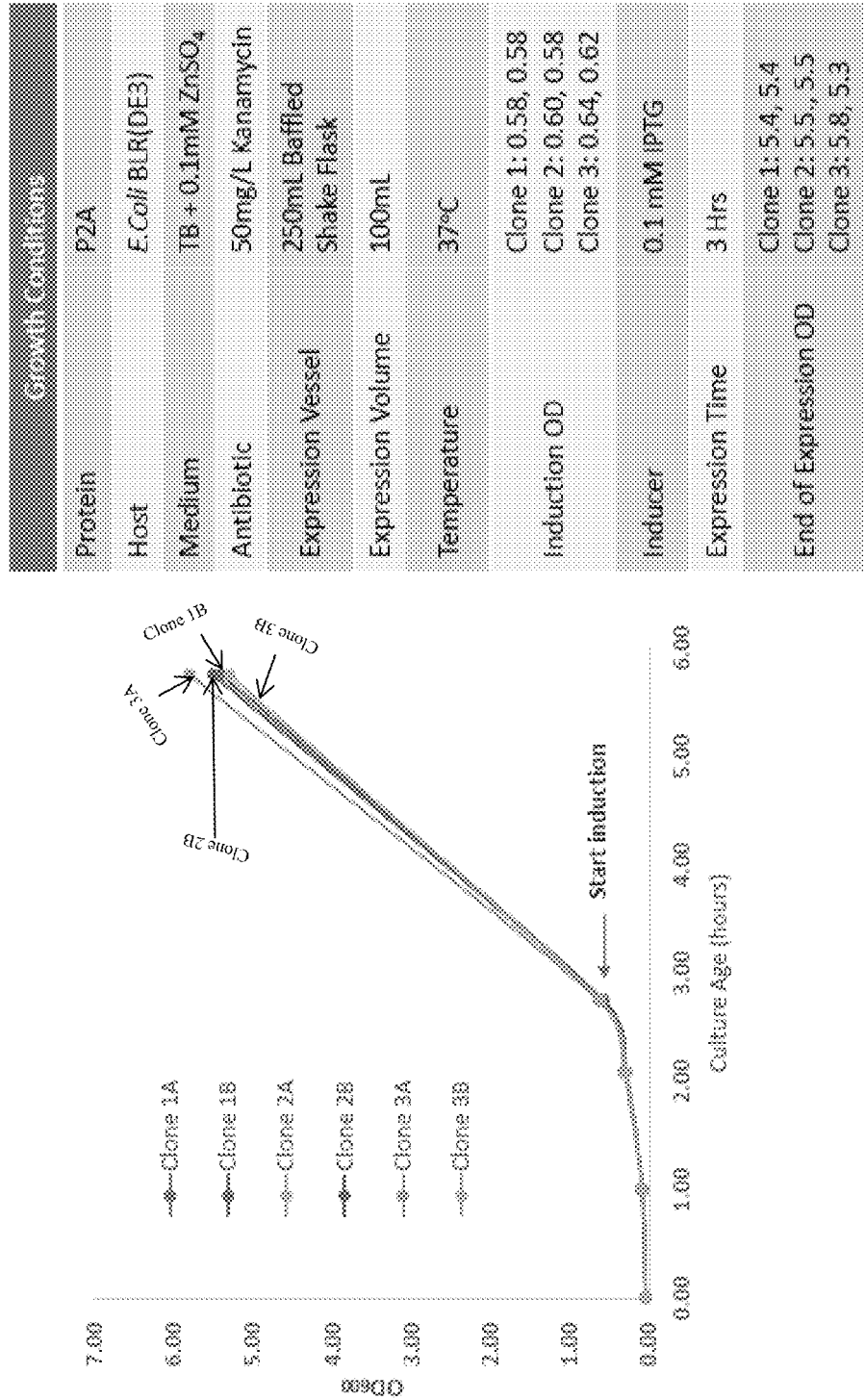
FIG. 12 shows growth curve for each of the 3 clones of the BLR(DE3) *E. coli* strain expressing P2A. The growth conditions are summarized in the adjacent table.

Example 7. Generation of IPTG-Inducible P2A Cell Lines in the BLR (DE3) *E. Coli* Strain Because the *E coli* cell line BLR (DE3) (New England Biolabs, Ipswich, Mass.) is similar to BL21 (DE3) cell line except that the BLR (DE3) cell line is recA−. A recA− cell line is a preferred cell line for growth under bioreactor conditions as it reduces the chances for recombination. Therefore, the pET30a-P2A (without leader) plasmid was used to transform *E coli* BLR (DE3) cells. Three colonies were chosen and grown up in duplicate overnight in 50 mL of LB media supplemented with 50 mg/L of Kanamycin. The 50 mL cultures were used to inoculate 100 mL of TB media supplemented with 0.1 mM $ZnSO_4$ and Kanamycin (50 mg/L) to an $OD_{600}$ of ~0.05. Cells were allowed to grow until they reached an $OD_{600}$ of ~0.6. A total of 6 mL of culture was removed and used to prepare glycerol stocks. The remaining culture was induced with 0.1 mM IPTG and grown at 37° C. for an additional 3 hrs. Cell pellets (from 1 mL culture media and cells) were prepared and kept frozen at −80° C. The growth curves of these cultures is displayed in FIG. 12.

Figure 13:
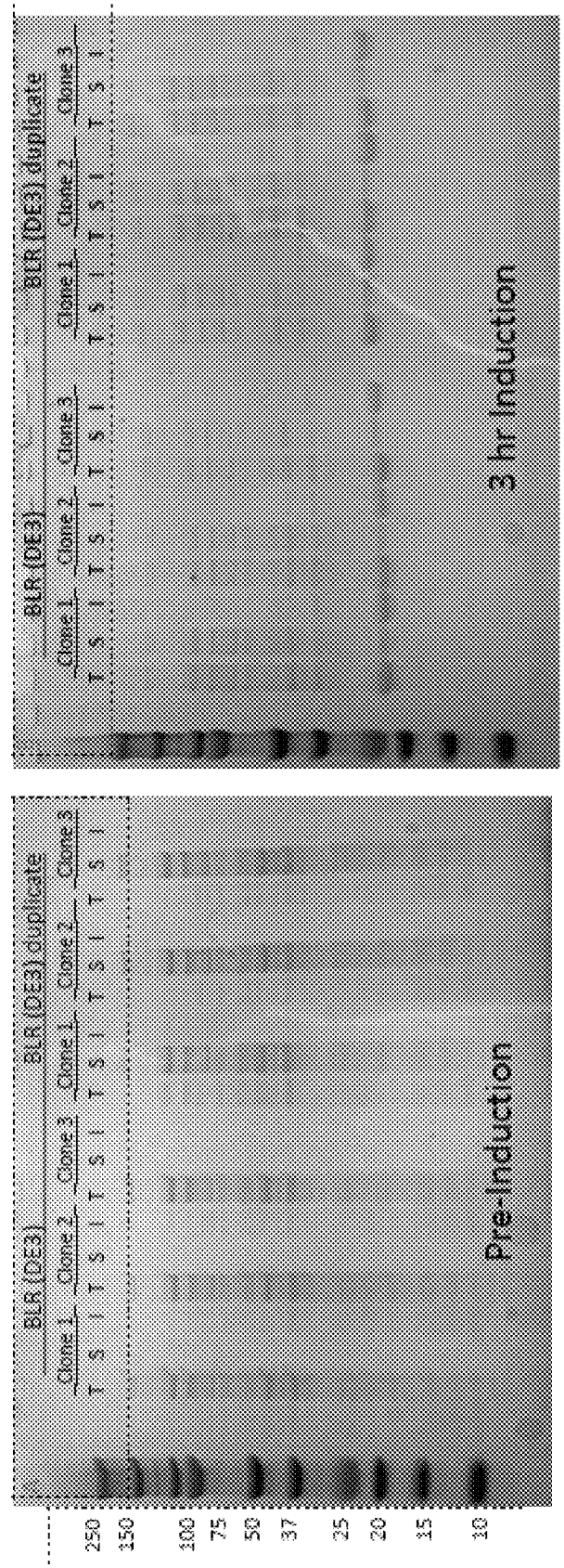
FIG. 13 shows SDS/PAGE analyses of the 3 clones of the BLR(DE3) *E. coli* strain expressing P2A. The total cell lysate (T), soluble (S), and insoluble (IS) fractions are displayed. Pre-induction expression levels are displayed on the gel on the left (Gel A), and after the 3 hour induction with 0.1 mM IPTG at 37° C. is displayed on the gel on the right (Gel B).
Figure 14:
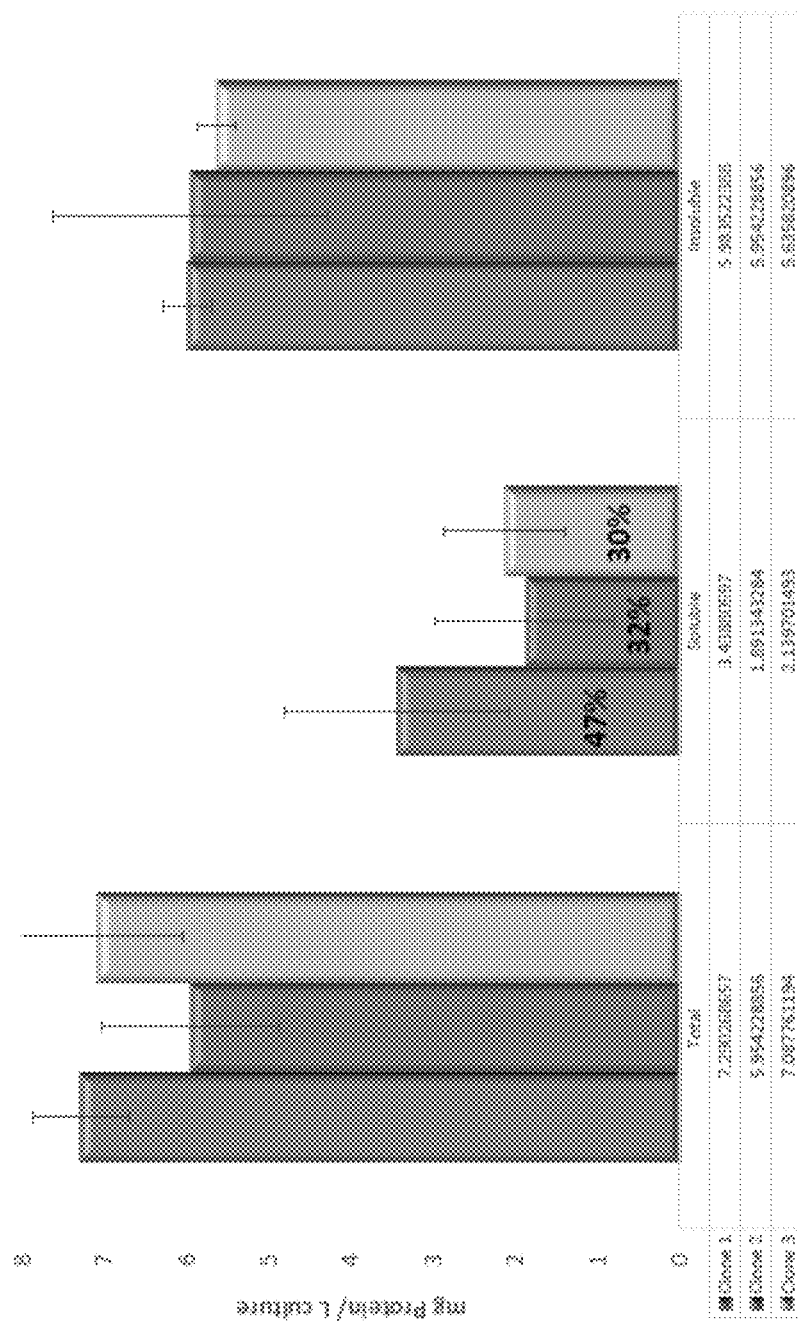
FIG. 14 provides estimated P2A protein concentration using the band intensities from the SDS/PAGE displayed in FIG. 13. Total, soluble, and insoluble fractions were estimated for Clone 1 (first bar), Clone 2 (middle bar), and Clone 3 (3rd bar). The % of soluble protein is displayed on the bars for the appropriate clone.

Cell pellets were thawed and lysed. Aliquots of the total cell lysate were taken. The cell lysate was then centrifuged, and aliquots of the soluble (supernatant) and insoluble (cell pellet) fractions were obtained. The total cell lysate, soluble, and insoluble fractions were analyzed by SDS/PAGE. Samples collected preinduction and after the 3 hour induction with 0.1 mM IPTG are shown in FIG. 13. A high level of P2A protein was induced in all three clones and duplicates. Much of the P2A protein produced was in the insoluble fraction. The P2A protein concentrations in each of the bands in the gel displayed in FIG. 13 was estimated based on band intensity. The estimated expression levels for each clone of total, soluble, or insoluble protein is displayed in FIG. 14. Clone 1 displayed the highest total P2A expression at 7.3 mg/L and the highest percentage of soluble protein (47%).

Example 8. Optimization of the Induction Conditions for BLR (DE3) P2A-Expression Cell Line, Clone 1

The expression levels of P2A protein produced from BLR (DE3) P2A cell line, Clone 1, were compared under different induction temperatures and induction durations.

Figure 15:
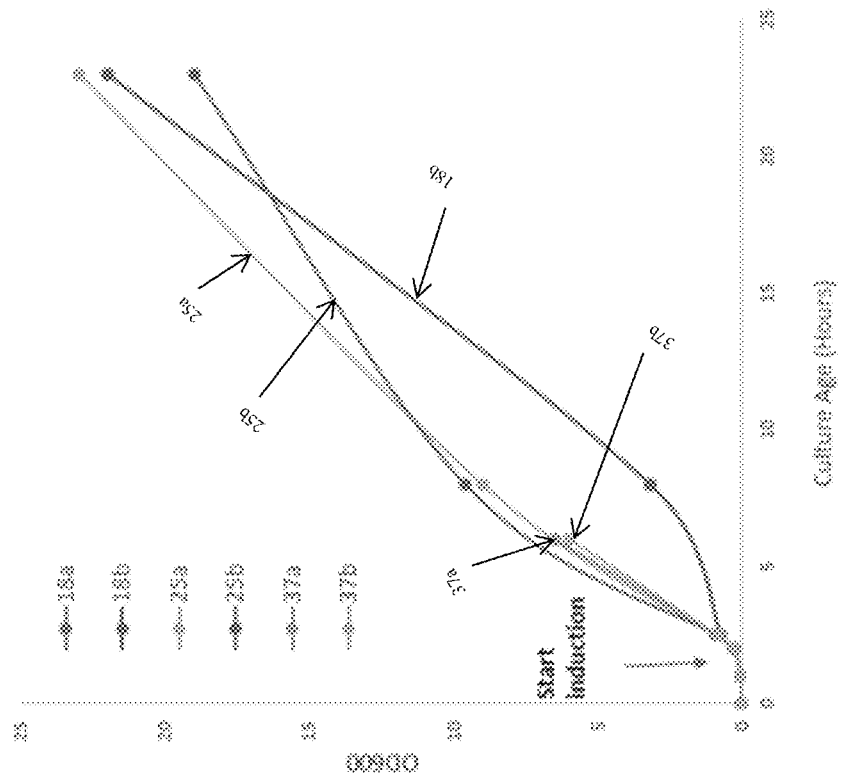
FIG. 15 depicts growth curves for each induction condition. The growth conditions are summarized in the adjacent table.
Figure 16:
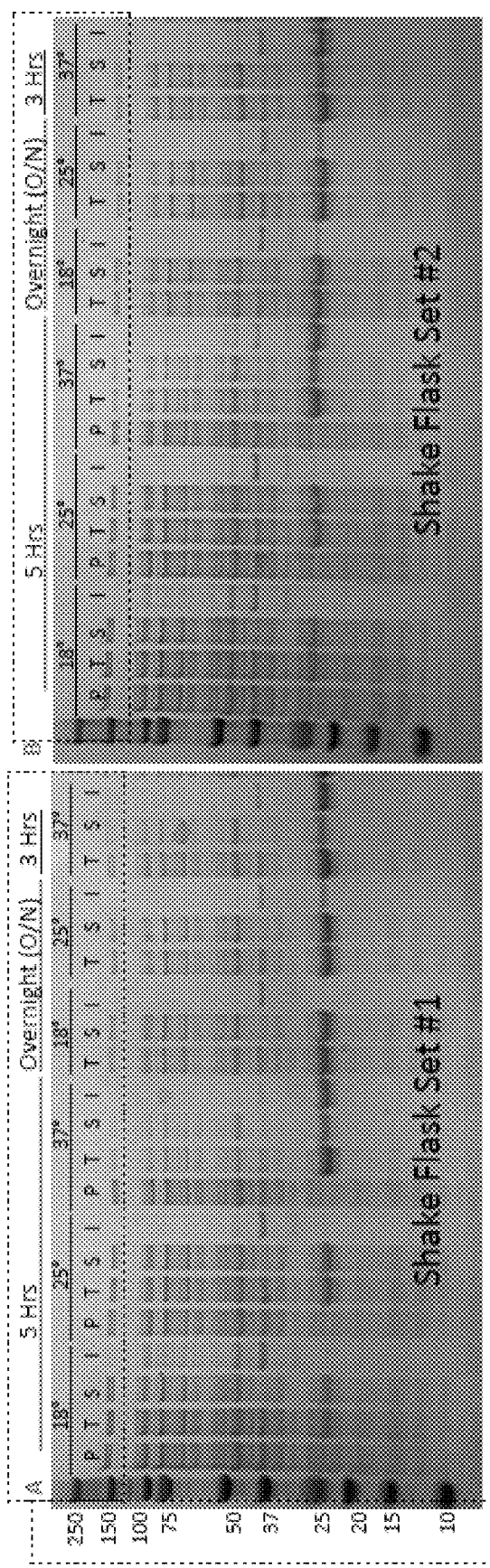
FIG. 16 depicts SDS/PAGE analyses of P2A expression under different induction conditions. The preinduction (P), total cell lysate (T), soluble (S), and insoluble (IS) fractions are displayed. The gel on the right side (Gel A) and the gel on the left side (Gel B) display duplicate samples.
Figure 17:
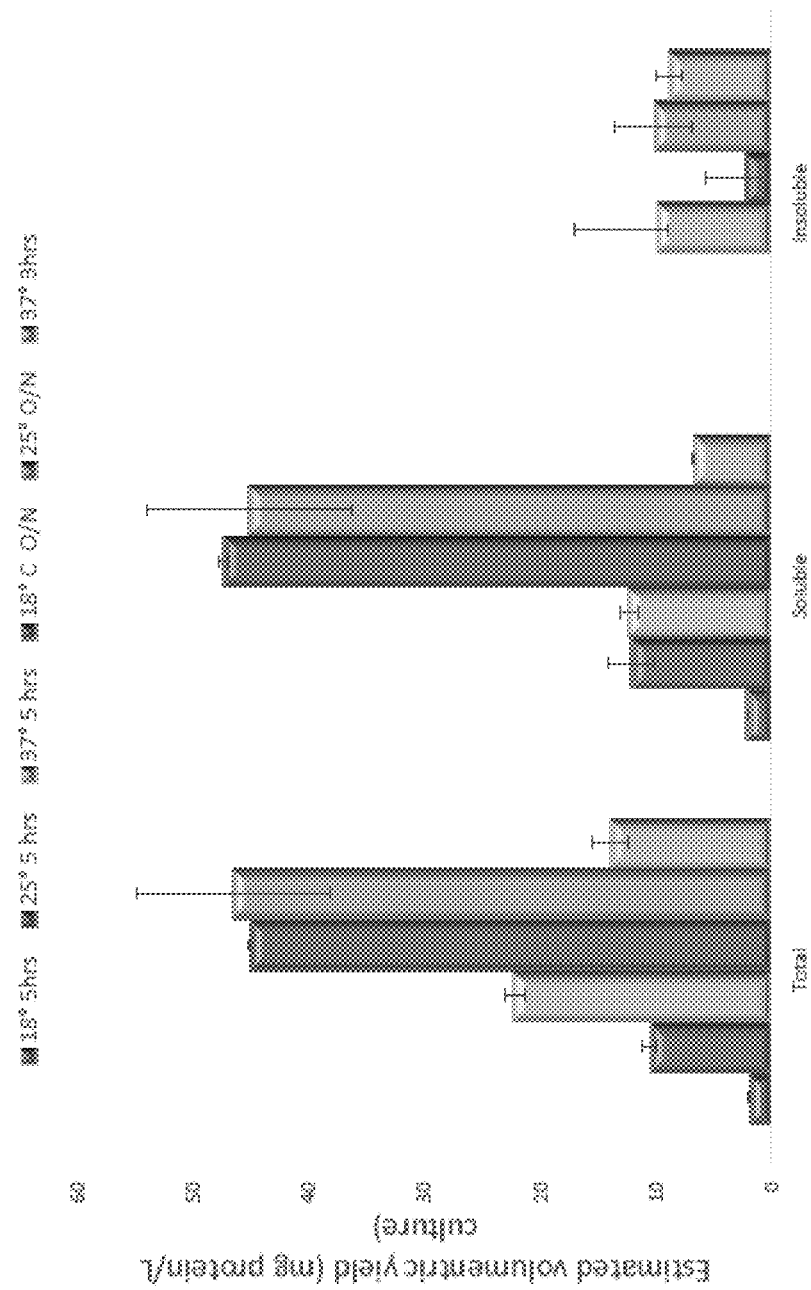
FIG. 17 provides estimated P2A protein concentration using the band intensities from the SDS/PAGE displayed in FIG. 16. Total, soluble, and insoluble fractions were estimated for the different induction conditions, first bar, 18° C. for 5 hours, second bar, 25° C. for 5 hours, third bar, 37° C. for 5 hours, fourth bar, 18° C. overnight, fifth bar, 25° C. overnight, and sixth bar, 37° C. for 3 hrs.

A total of 50 mL of LB media supplemented with 50 mg/L of Kanamycin was inoculated with *E coli* BLR (DE3) P2A Clone 1 and allowed to grow overnight at 37° C. This overnight seed culture was used to inoculate 6×100 mL TB media supplemented with 0.1 mM ZnSO$_4$ and Kanamycin (50 mg/L) to OD$_{600}$ of ~0.07-0.09. The cultures were induced with 0.1 mM IPTG and incubated at 18° C., 25° C., or 37° C. at 250 rpm for 5 hours or 20 hours (overnight). The 37° C. for 3 hour condition was repeated to compare to the first conditions tested. Following the induction at the indicated conditions, cell pellets were collected and stored at −80° C. until processed. FIG. 15 shows the growth curve of the cultures under the different growth and induction conditions. Cell pellets were thawed and lysed. Aliquots of the preinduction and post induction total cell lysates were taken. The cell lysate was then centrifuged, and aliquots of the soluble (supernatant) and insoluble (cell pellet) fractions were obtained. The total cell lysate, soluble, and insoluble fractions were analyzed by SDS/PAGE (FIG. 16). A high level of P2A protein was induced under all conditions. Interestingly, reducing the induction temperature to 18° C. or 25° C. and induction overnight displayed both high level protein expression but also shifted the protein from mainly in the insoluble fraction to the soluble fraction. The P2A protein concentrations in each of the bands in the gel displayed in FIG. 16 was estimated based on band intensity. The estimated expression levels under each induction condition are displayed in FIG. 17. The highest P2A expression level and the condition that produced the most soluble protein was the 18° C. induction overnight. However, the 25° C. induction overnight also gave good soluble protein expression.

To achieve an estimate of the amount of P2A protein in each of the soluble lysates from the 3 clones displayed in FIG. 13, and the soluble lysates from the samples subjected to different induction conditions (FIG. 16), dilutions of the lysates (2.5 ul, 1.3 ul, 0.63 ul, and 0.31 ul) were evaluated on SDS/PAGE compared to dilutions of a purified P2A standard protein (2.0 ug, 1.0 ug, 0.5 ug, 0.25 ug, 0.13 ug). Based on the P2A protein band intensities, an estimate of the amount of P2A protein in each of the lysates was obtained. The biological activity of the P2A protein in these cell lysates was evaluated using the CENTA chromogenic assay compared to the biological activity of the P2A protein standard. The biological activity was normalized based on the P2A protein concentration estimate and an estimated P2A specific activity was obtained. The specific activity is displayed as % activity compared to the P2A standard (100%). These data are summarized in Table 19. All lysates displayed biological activity.

TABLE 19

P2A Concentrations and Specific Activity in Cell Lysates
Relative P2A activity mg/mL Lysate

| Lysate | Replicate | P2A lactamase Activity (mg/mL) | Concentration (mg/mL) | % Activity Compared to P2A standard |
|---|---|---|---|---|
| Clone 1 | 1 | 0.09 | 0.1 | 90 |
|  | 2 | 0.12 | 0.1 | 120 |
| Clone 2 | 1 | 0.1 | 0.1 | 100 |
|  | 2 | 0.15 | 0.1 | 150 |
| Clone 3 | 1 | 0.13 | 0.1 | 130 |
|  | 2 | 0.13 | 0.1 | 130 |
| 18 o/n | 1 | 0.21 | 0.2 | 103 |
|  | 2 | 0.16 | 0.1 | 156 |
| 25 on | 1 | 0.30 | 0.2 | 148 |
|  | 2 | 0.27 | 0.2 | 135 |

TABLE 19-continued

P2A Concentrations and Specific Activity in Cell Lysates
Relative P2A activity mg/mL Lysate

| Lysate | Replicate | P2A lactamase Activity (mg/mL) | Concentration (mg/mL) | % Activity Compared to P2A standard |
|---|---|---|---|---|
| 37 3 hrs | 1 | 0.13 | 0.1 | 131 |
|  | 2 | 0.18 | 0.1 | 182 |

Example 9. Fermentation of the *E. Coli* BLR (DE3) P2A-Cell Line, Clone 1

Figure 18:
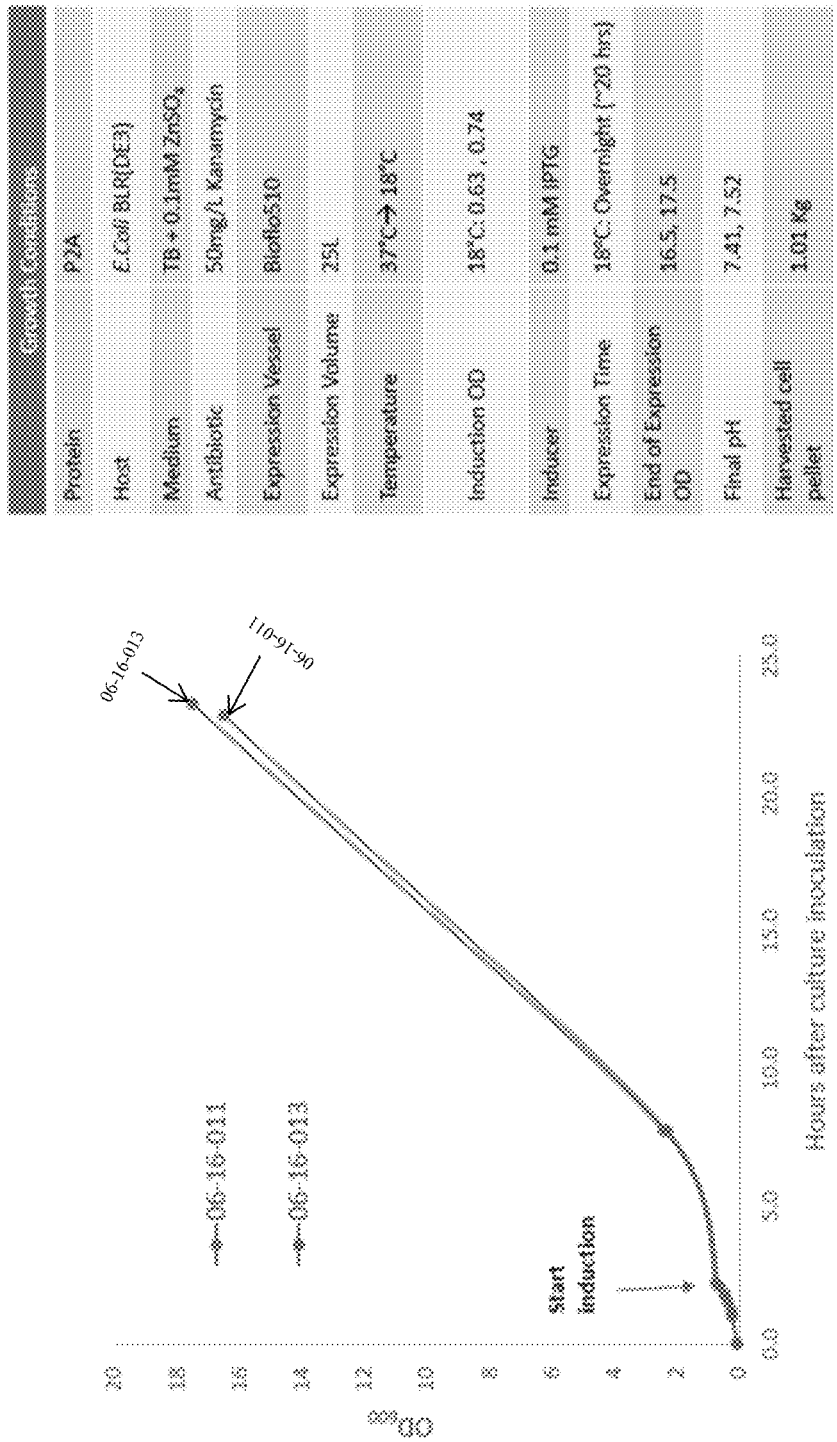
FIG. 18 provides growth curve for *E coli* BLR(DE3) P2A clone 1. The two 25 L runs are Lot 06-16-011 and Lot 06-16-013. The growth conditions are summarized in the adjacent table.
Figure 19:
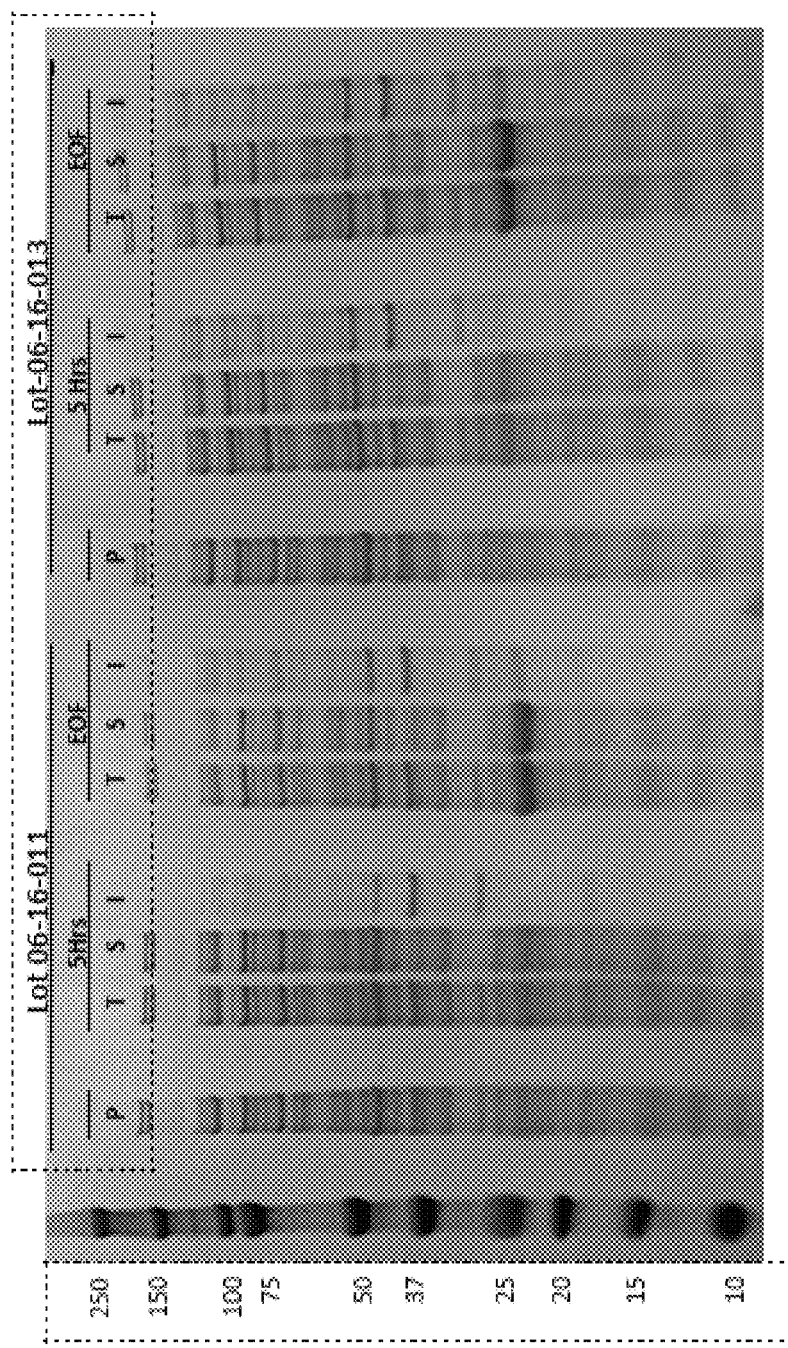
FIG. 19 depicts SDS/PAGE analyses of P2A expression under the different induction conditions. The preinduction (P), total cell lysate (T), soluble (S), and insoluble (IS) fractions are displayed. The right hand side of the gel displays Lot 06-16-011 and the left had side of the gel displays Lot 06-16-013.
Figure 20:
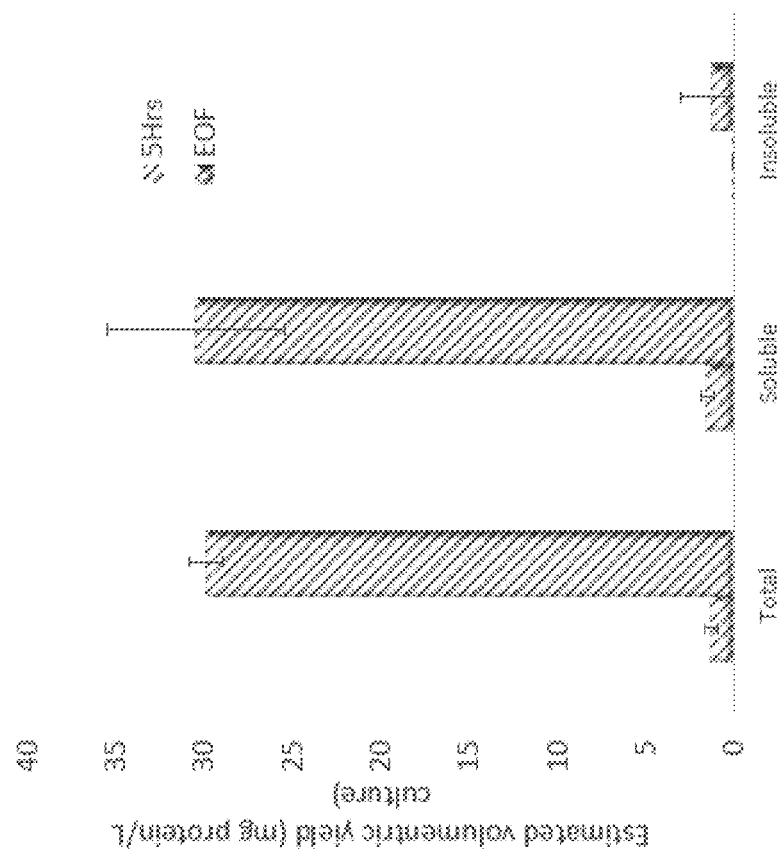
FIG. 20 provides estimated P2A protein concentration using the band intensities from the SDS/PAGE displayed in FIG. 19. Total, soluble, and insoluble fractions were estimated at 5 hours (first bars) and end of fermentation (EOF), second bars.

Using the optimized induction and growth conditions, a fermentation of 2×25 L was performed. One liter of LB media supplemented with 50 mg/L of Kanamycin was inoculated with *E coli* BLR(DE3) P2A clone 1 and allowed to grow overnight at 37° C. The overnight seed culture was used to inoculated 25 L of TB media supplemented with 0.1 mM ZnSO$_4$ and 50 mg/L Kanamycin. Cultures were induced with 0.1 mM IPTG at an OD of ~0.06-0.08 and the temperature was reduced to 18° C. Aliquots were taken at 5 hours and 20+ hours after induction and cell pellets were isolated and stored at −80° C. until use (FIG. 18). Cells were lysed and preinduction, total, soluble, and insoluble fractions were evaluated by SDS/PAGE (FIG. 19). Both lots showed good induction of P2A expression at the end of fermentation compared to the preinduction levels. In addition, the majority of the P2A protein was recovered in the soluble fraction. The P2A protein concentrations in each of the bands in the gel displayed in FIG. 19 was estimated based on band intensity. The estimated expression levels under each induction condition are displayed in FIG. 20. The majority of the P2A protein was recovered in the soluble fraction. A total of 1.01 kg of cell paste was collected and stored at −80° C.

Example 10. Characterization of Enzymatic Activity In Vitro

Figure 21A:
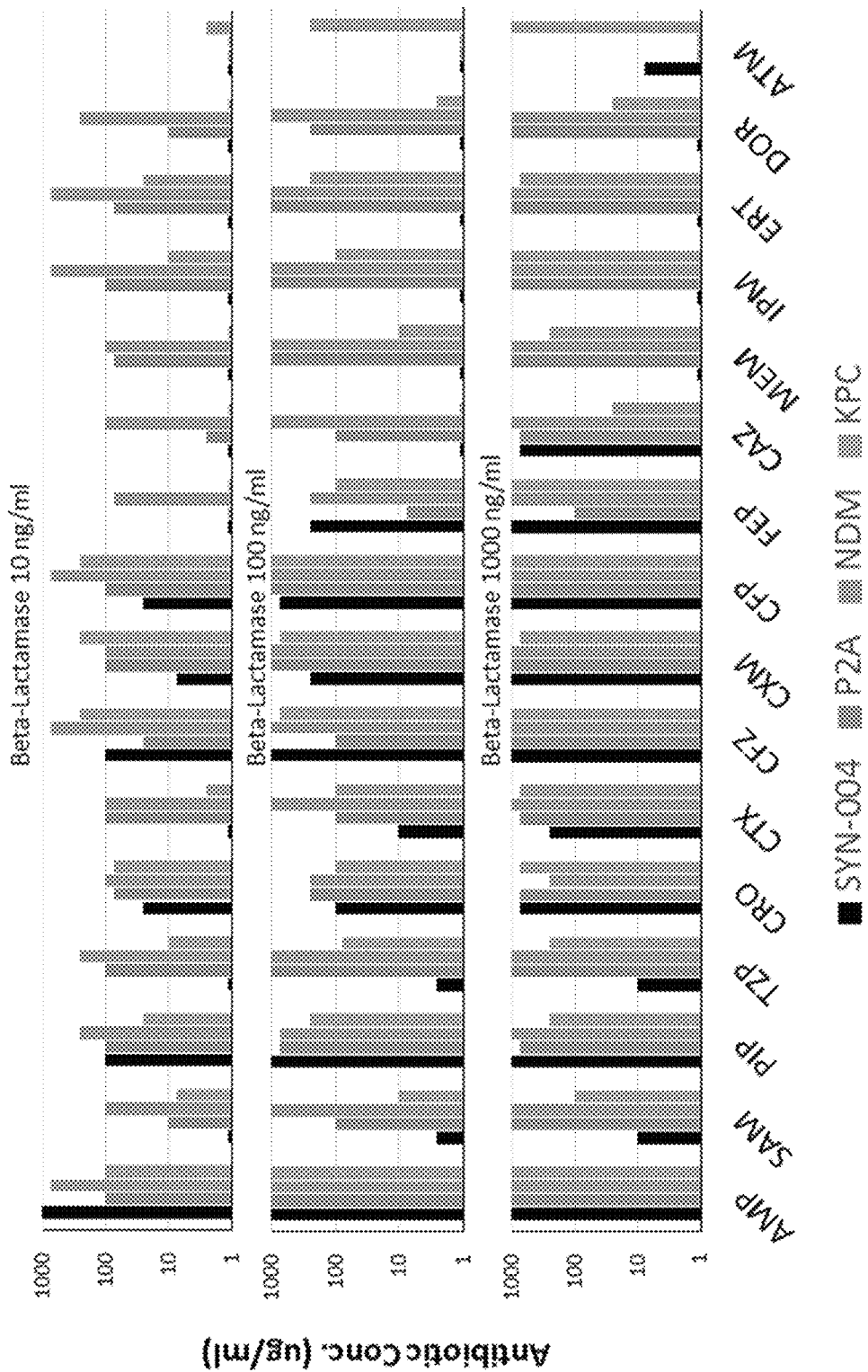
Figure 21B:
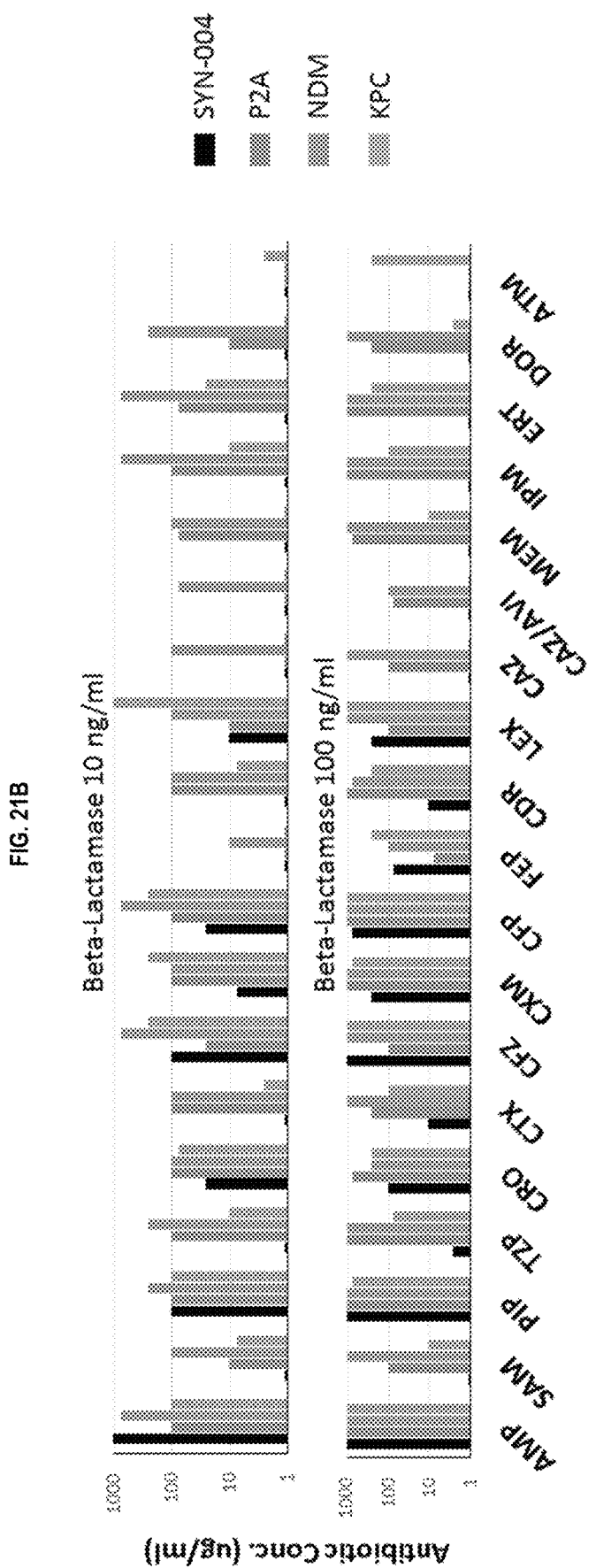

To mimic the activity of the carbapenemase enzymes, P2A, NDM, and KPC in the gut in the presence of high antibiotic concentrations, a novel screening assay was performed using a 96 well plate format. The assay was performed by mixing 10, 100 or 1000 μg/ml of the antibiotics, AMP: ampicillin, SAM: ampicillin/sulbactam, PIP: pipercillin, TZP: pipercillin/taxobactam, CRO: ceftriaxone, CTX: cefotaxime, CFZ: cefozolin, CXM: cefuroxime, CFP: cefoperazone, FEP: cefepime, CAZ: ceftazidime, MEM: meropenem, IPM: imipenem, ERT: ertapenem, DOR: doripenem, ATM: aztreonam, CDR: cefdinir; LEX: cephalexin; and CAZ/AVI: cefoperazone/avibactam with purified P2A, NDM, KPC, and P3A at concentrations of 10, 100, or 1000 ng/ml in each well of a 96 well microtiter plate. *E. coli* (ATCC 25922) was added immediately after the addition of the beta-lactamase enzymes, and the plates were incubated overnight. Bacterial growth was quantified by measuring the absorbance at 625 nm (OD625) in a Spectramax 384 Plus plate reader. The analysis was performed twice for each antibiotic. The beta-lactamase activity was determined as positive or negative based on the appearance of bacterial growth in the individual wells. An OD625 of 1.0 or greater indicated maximal bacterial growth, therefore complete antibiotic degradation and beta-lactamase activity. An OD625 of less than 1.0 indicated low bacterial growth therefore incomplete antibiotic degradation, hence low beta-lactamase activity. FIGS. 21A, 21B, and 21C display the comparison of the four beta-lactamases, P3A (SYN-004), P2A, NDM, and KPC with all 16 antibiotics at beta-lactamase concentrations of 10, 100, or 1000 ng/ml.

The data demonstrate that the carbapenemases P2A, NDM, and KPC all displayed a broader degradation profile than P3A which included activity against carbapenems. NDM appeared to be the most potent beta-lactamase and efficiently degraded all tested cephalosporins and carbapenems. P2A displayed good activity against all carbapenems and most cephalosporins, however, compared to NDM, activity was reduced against the cephalosporins, cefepime and ceftazidime. Compared to SYN-004, P2A, NDM, and KPC were demonstrated to be potent carbapenemases that efficiently degraded meropenem, imipenem, ertapenem, and doripenem, and the metallo-beta-lactamases, P2A and NDM, were resistant to inhibition by sulbactam, tazobactum, and avibactam (FIGS. 21A and 21B). KPC was the only beta-lactamase that displayed activity against the monobactam, aztreonam. While all three carbapenemases displayed resistance to the beta-lactamase inhibitors sulbactam and tazobactam, NDM was the least affected by sulbactam.

These data indicate that all three carbapenemases have sufficient potency to be developed into oral therapeutics. Each has the potential to protect the microbiome from most, if not all beta-lactam antibiotics and provide prophylaxis for *Clostridium difficile* infection.

Additionally, the stability of the carbapenemase enzymes in various buffers and chyme were also carried out. Enzyme kinetics was also assessed.

Example 11. P2A Stability in Human Chyme

The stability of purified P2A when incubated in human chyme at 37° C. was evaluated by assessing aliquots withdrawn from incubated samples at 0, 0.5, 1, 2, 3, 4, 5, and 6 hours for beta-lactamase activity using a CENTA beta-lactamase substrate. Five different chyme specimens were used for evaluation of stability. The mixed chyme sample contained equal volumes of each of the five chime specimens mixed together. Chyme samples were characterized for pH, liquid content, and protease activity (Table 20).

TABLE 20 pH, Liquid Content, and Protease Activity of Individual Human Chyme Specimens

| Specimen | pH | % Liquid | Protease activity (mU/mL) |
|---|---|---|---|
| Chyme 1 | 6.42 | 55 | 5.57 |
| Chyme 2 | 5.98 | 57 | 8.96 |
| Chyme 3 | 5.58 | 57 | 6.63 |
| Chyme 4 | 6.26 | 66 | 6.21 |
| Chyme 5 | 6.56 | 78 | 6.56 |

Figure 22:
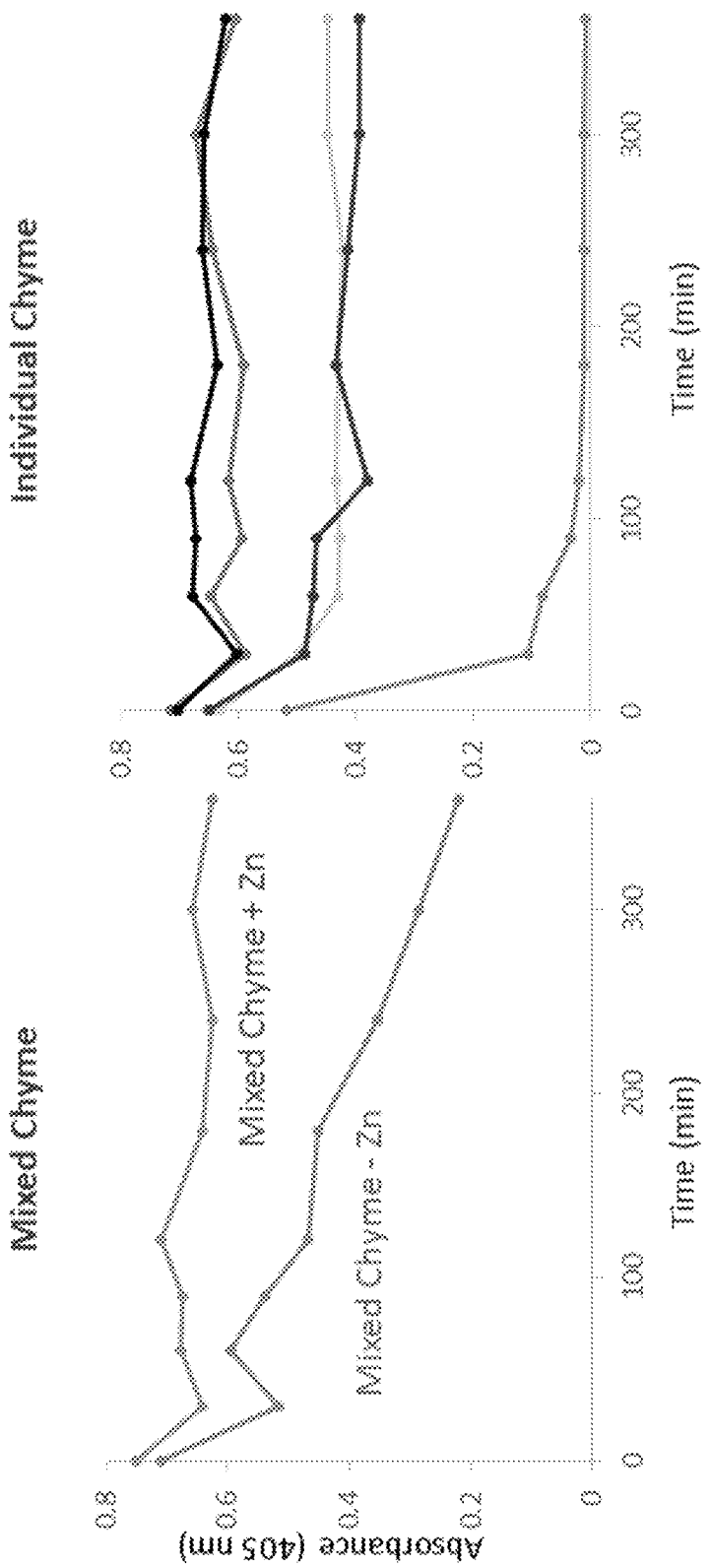
FIG. 22 shows stability of P2A activity in human chyme. The left panel shows mixed chyme with or without Zn. In the right panel, P2A pellets were incubated in chyme samples from five different donors. Aliquots were taken at 0, 30, 60, 120, 180, 240, 300, and 360 minutes and beta-lactamase activity was measured using the CENTA assay.
Figure 23:
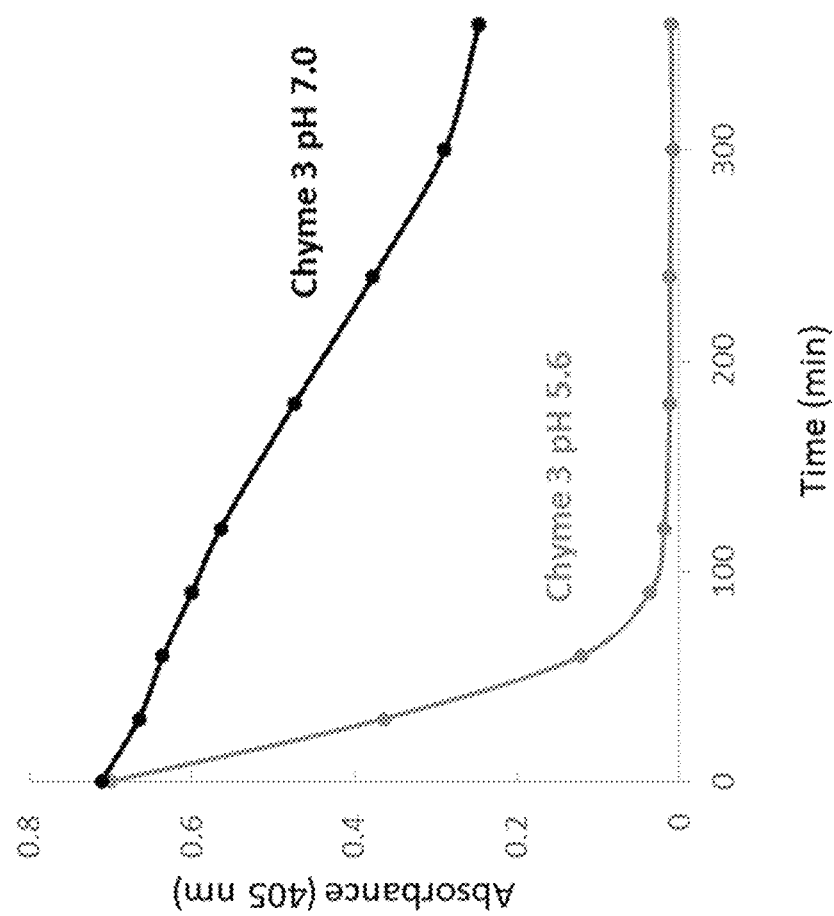
FIG. 23 shows stability of P2A activity in pH-adjusted human chyme 3. Purified P2A was incubated in chyme 3 at pH 5.6 and chyme 3 pH 7.0. pH was adjusted using NaOH. Aliquots were taken at 0, 30, 60, 120, 180, 240, 300, and 360 minutes and beta-lactamase activity was measured using the CENTA assay.

P2A beta-lactamase activity was stable over 6 hrs, the longest time tested in the study, when evaluated in the mixed chyme in the presence of 100 uM $ZnSO_4$, while activity declined more rapidly when additional zinc was not included in the mixed chyme. For all subsequent studies, 100 uM $ZnSO_4$ was added to all chyme specimens. P2A beta-lactamase activity was also relatively stable in four of five individual chyme samples (FIG. 22). However, P2A activity rapidly declined when incubated in the chyme 3 sample (FIG. 22). Unexpectedly, when the pH of chyme 3 was adjusted to pH 7.0 using NaOH, the stability of P2A in the pH-adjusted chyme 3 was improved (FIG. 23).

Example 12: KPC and NDM Stability in Human Chyme

The stability of KPC and NDM in human chyme at 37° C. was evaluated by adding purified KPC or NDM (final concentration of 80 ng/mL) to mixed human chyme that contained equal volumes of each of five human chyme specimens collected from five different donors. $ZnSO_4$ was added to the mixed chyme for a final concentration of 100 µM $ZnSO_4$. Aliquots of the enzyme/chyme mixture were collected at 0, 30, 60, 120, 180, and 240 minutes of incubation and evaluated for beta-lactamase activity with a chromogenic assay using the CENTA reagent as the substrate. The biological activity of the enzymes in the mixed chyme was compared to the activity in buffer (HEPES buffer, 100 µM $ZnSO_4$ pH 6.2).

Figure 24:
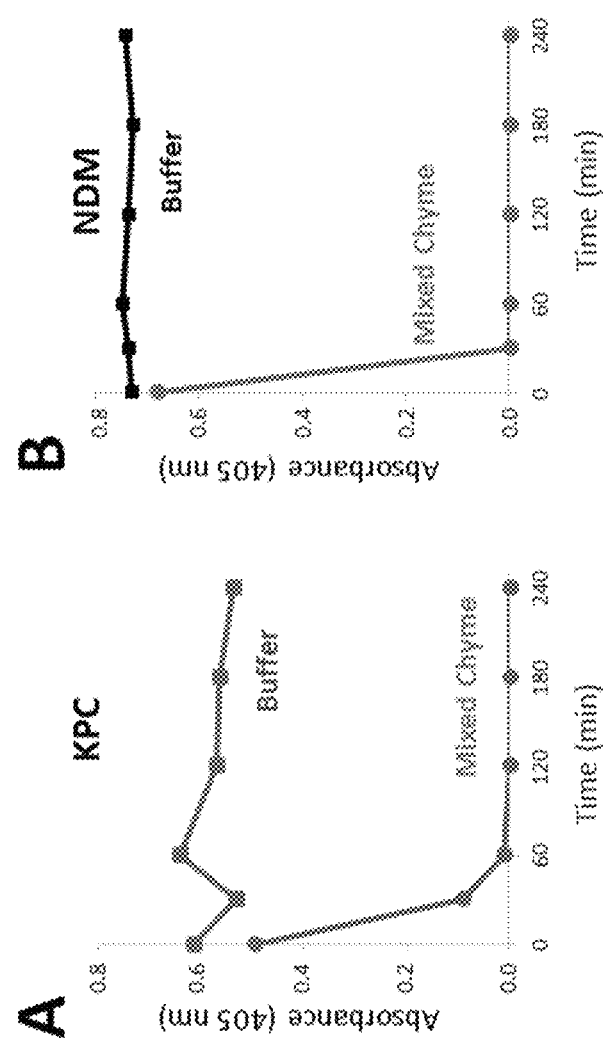
FIG. 24 shows the stability of KPC and NDM activity in human chyme. Purified KPC (Panel A) or NDM (Panel B), both in PBS, pH 7.5 were incubated in buffer (HEPES buffer, 100 uM $ZnSO_4$ pH 6.2) or mixed human chyme supplemented with 100 uM $ZnSO_4$. The final concentration of KPC and NDM in the samples was 80 ng/mL. Aliquots were taken at 0, 30, 60, 120, 180, and 240 minutes and evaluated for beta-lactamase activity using a CENTA beta-lactamase substrate. The activity in buffer is indicated by the squares and the activity in chyme is indicated by the circles.

Both KPC and NDM showed stable activity when incubated in buffer for at least 4 hours. In contrast, KPC and NDM lost biological activity when incubated in the mixed human chyme. All NDM activity was lost by the first time point of 30 minutes while KPC activity was not detectable by 60 minutes (FIG. 24).

Example 13: Loss of NDM Activity in Human Chyme is Due to Proteolytic Cleavage of the NDM NDM activity was lost immediately upon incubation in the mixed human chyme (FIG. 24). To determine if the loss in activity was due to digestion by proteases present in the human chyme, purified NDM (100 ug/ml) was incubated for 30 minutes with dilutions of human mixed chyme ranging from 100% to 0% chyme in the absence or presence of a serine protease inhibitor cocktail (SigmaFAST protease inhibitors cocktail without EDTA (Sigma-Aldrich catalog number S8830). All incubations were performed in the presence of 100 µM $ZnSO_4$ (final concentration). Samples removed at 30 minutes were transferred to lamelli sample buffer containing beta mercaptoethanol for analysis of protein degradation by gel electrophoreses and staining with coomassie blue. The remaining samples were snap frozen and used for evaluation of beta lactamase activity using a CENTA substrate (FIG. 25). The results demonstrate that intact NDM protein could be detected with chyme dilutions of 6.25% or less, and that the NDM could be easily distinguished from the endogenous proteins present in the chyme at dilutions of 3.13% or less (FIG. 25, panel A). In addition, most of the activity of NDM was retained at chyme dilutions of 3.13% or less (FIG. 25, panel A). In the presence of protease inhibitors, the majority of the NDM activity was retained at chyme dilutions of 50% or less. These data demonstrate that the loss of activity of NDM in chyme was due to the proteolytic cleavage of the NDM protein by endogenous serine proteases present in human chyme (FIG. 25, panel B).

Figure 26:
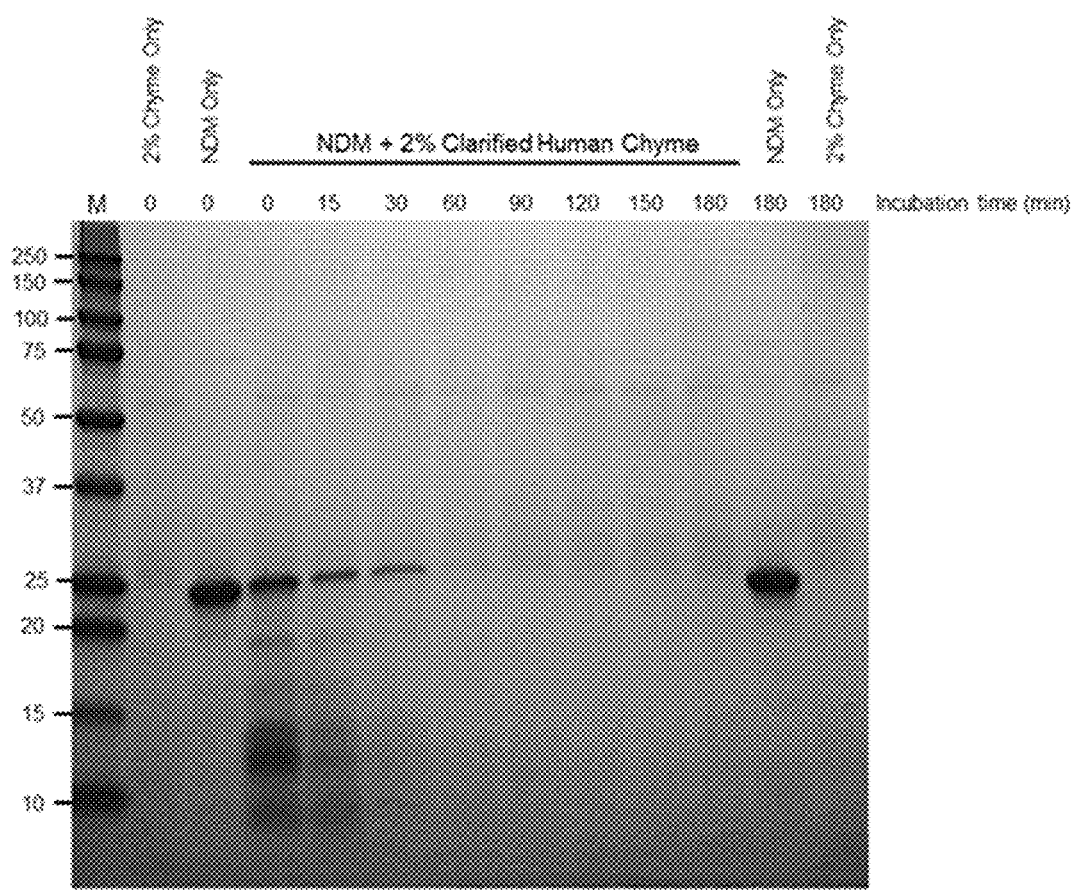
FIG. 26 shows proteolytic cleavage fragments of NDM incubated in 2% human chyme. NDM at a concentration of 500 μg/mL was incubated in 2% chyme for times ranging from 0-180 minutes. Incubation times are displayed above the lanes. M is the indicated molecular mass markers, sizes in kDa (Bio-Rad Precision Plus Protein Standards).

Example 14: Characterization of the Proteolytic Cleavage Products of NDM Following Incubation in Mixed Chyme The loss of NDM activity upon incubation with human chyme was due to the proteolytic cleavage of NDM by endogenous proteases present in human chyme. To map the cleavage sites within the NDM protein, NDM (500 ug/mL) was incubated with 2% mixed human chyme (human chyme diluted with incubation buffer, 20 mM Hepes pH 6.2; 150 mM NaCl, 100 uM $ZnSO_4$) for times ranging from 0 to 180 minutes. Twenty microliters of each sample (1 ug) was removed and transferred to 20 μL of 2× denaturing sample buffer for a final concentration of 25 ng/μL. The samples were boiled and 10 μL (250 ng of NDM) was subjected to analysis by SDS-PAGE. NDM was rapidly degraded, in 0-15 minutes, into 5 distinct cleavage fragments (FIG. 26). NDM and these fragments were further degraded during the course of the incubation and were undetectable between 60-90 minutes (FIG. 26). These data demonstrate that the protease(s) in chyme cleave NDM in at least 3 distinct sites.

Figure 27:
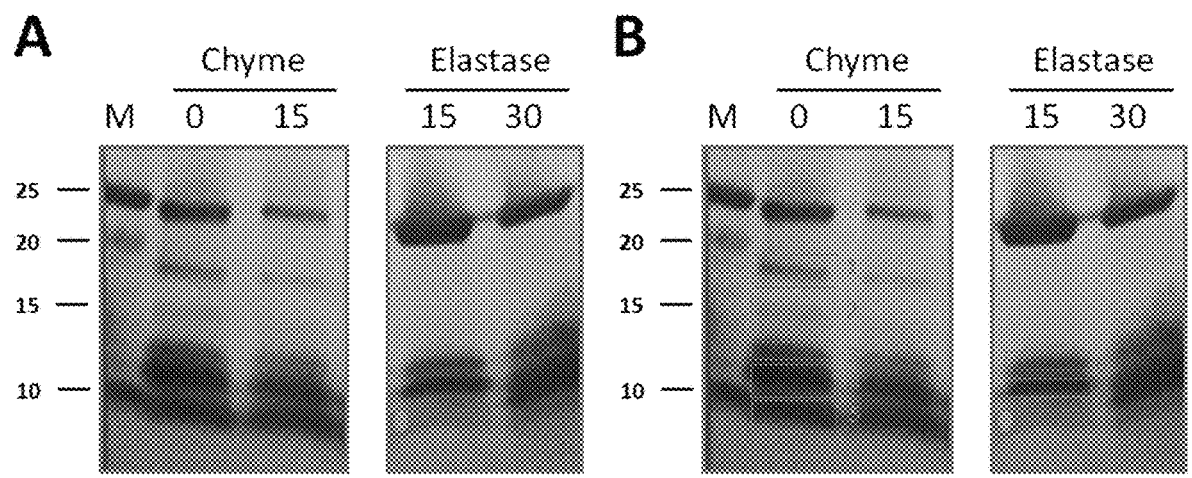
FIG. 27 shows Coomassie-stained PVDF membrane containing the proteolytic cleavage fragments of NDM. NDM was incubated in 2% human chyme or purified porcine pancreatic elastase (0.25 U/mL), analyzed by SDS/PAGE and proteins transferred to PVDF membrane and stained with Coomassie. Panel A shows stained PVDF membranes containing the protein fragments and protein size markers. The left panel (Chyme) displays the products of digestion in 2% human mixed chyme and the right panel displays the products of elastase digestion. Panel B shows stained PVDF membrane as displayed in A with the fragments that were isolated indicated by the numbered boxes. The fragments were subjected to N-terminal amino acid sequencing.
Figure 31:
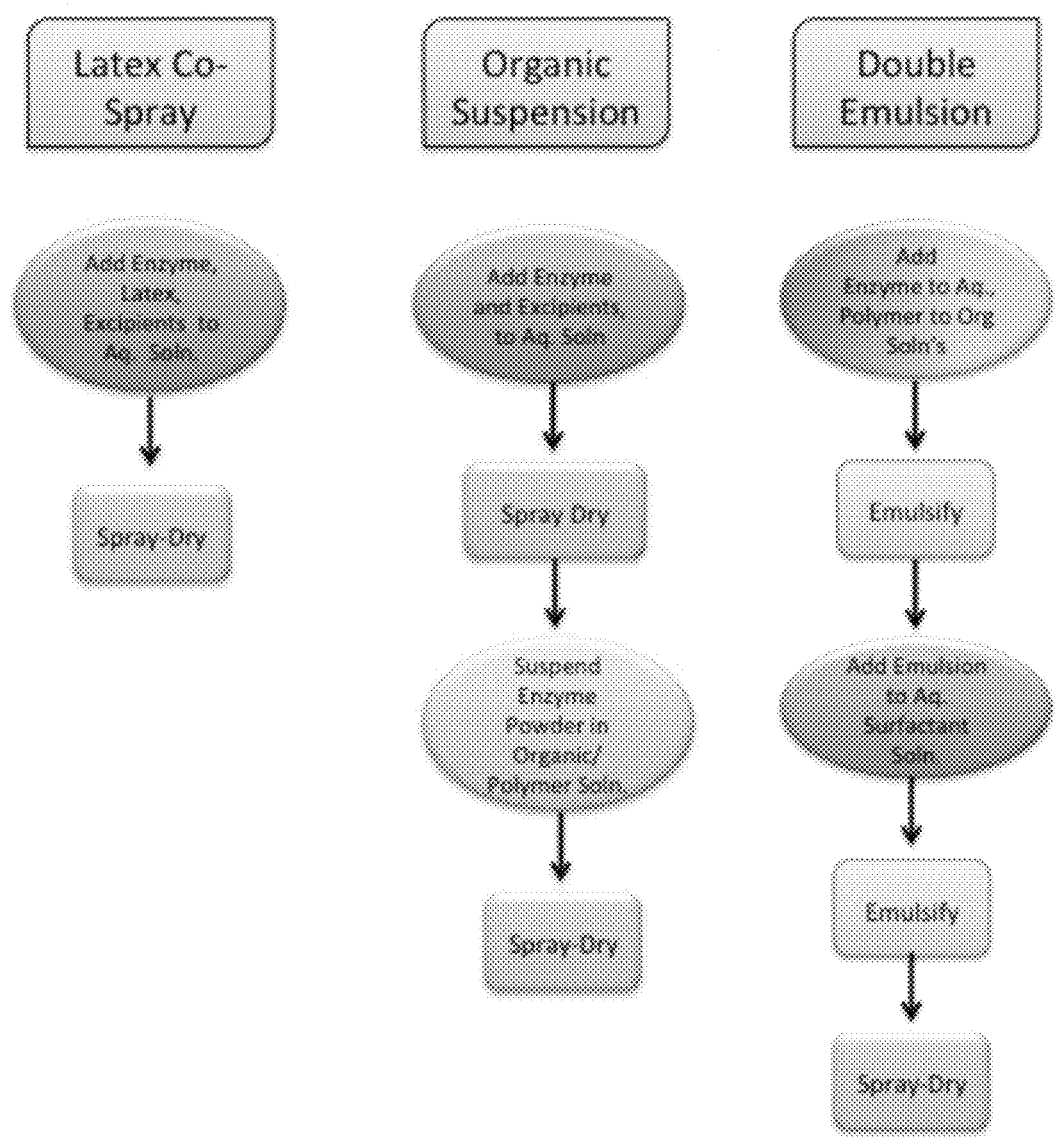
FIG. 31 depicts various non-limiting embodiments for manufacturing delayed-release capsules containing antibiotic-degrading agents (e.g. a broad spectrum carbapenemase such as P2A, NDM-1, and KPC-1/2).
Figure 32:
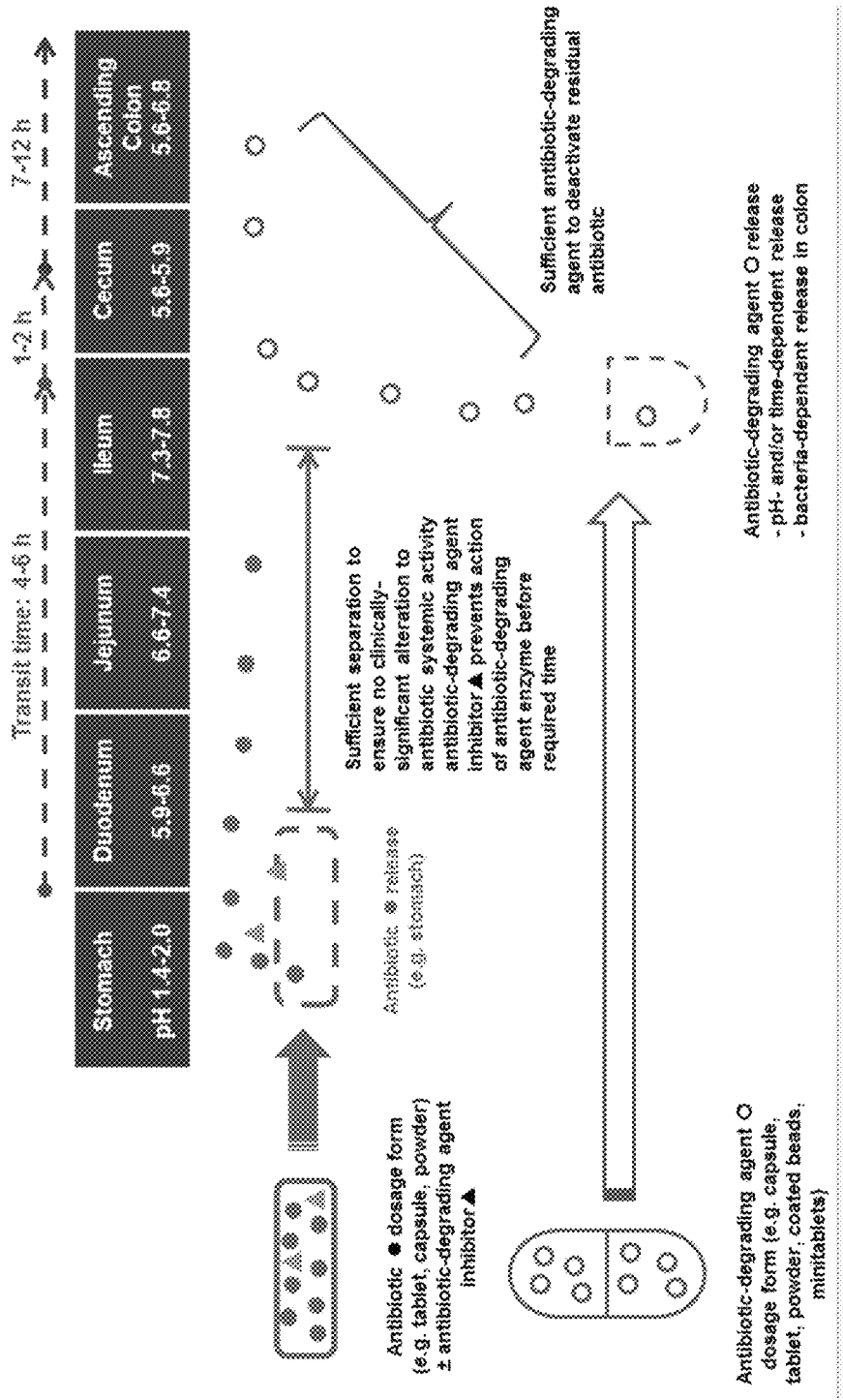
FIG. 32 shows various non-limiting formulation approaches for segregating antibiotic and/or antibiotic-degrading agent inhibitor and antibiotic-degrading agent release.
Figure 33:
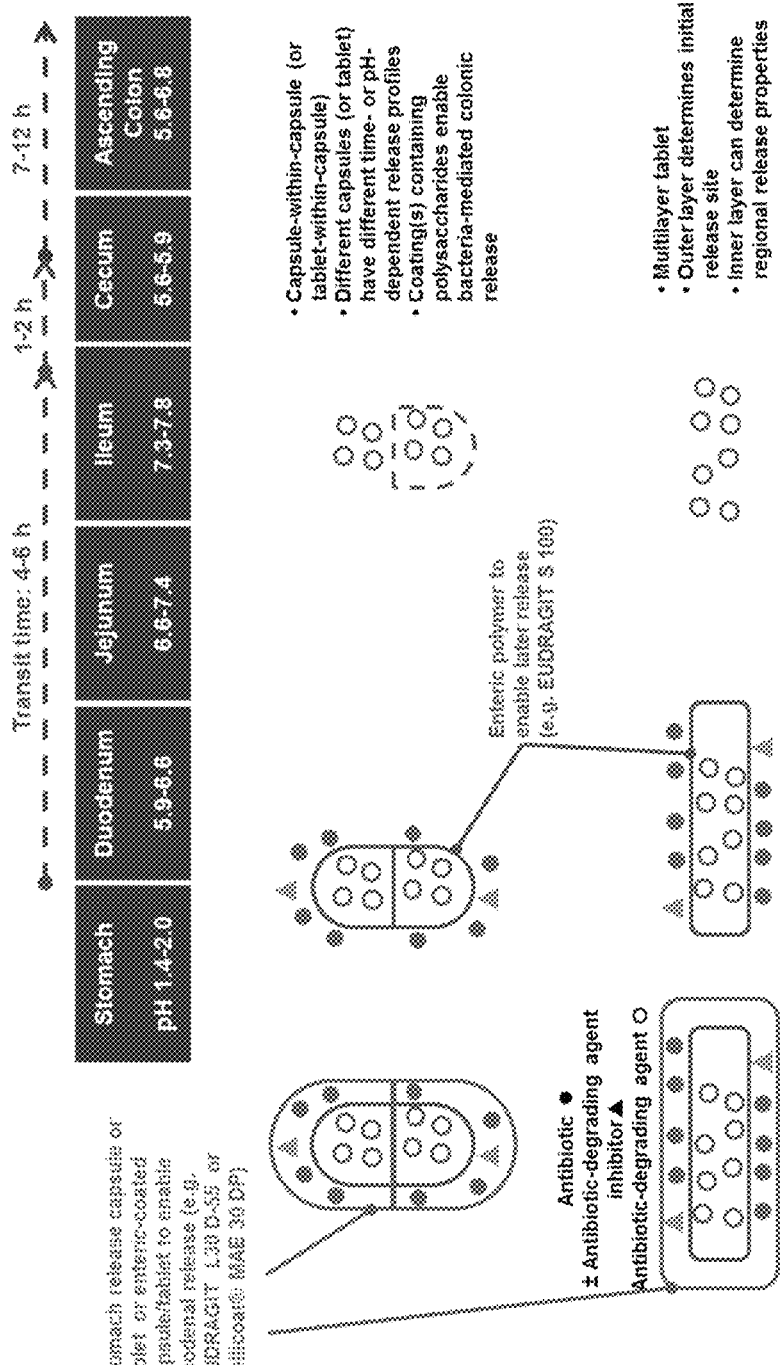
FIG. 33 shows various non-limiting combination dosage forms.
Figure 34:
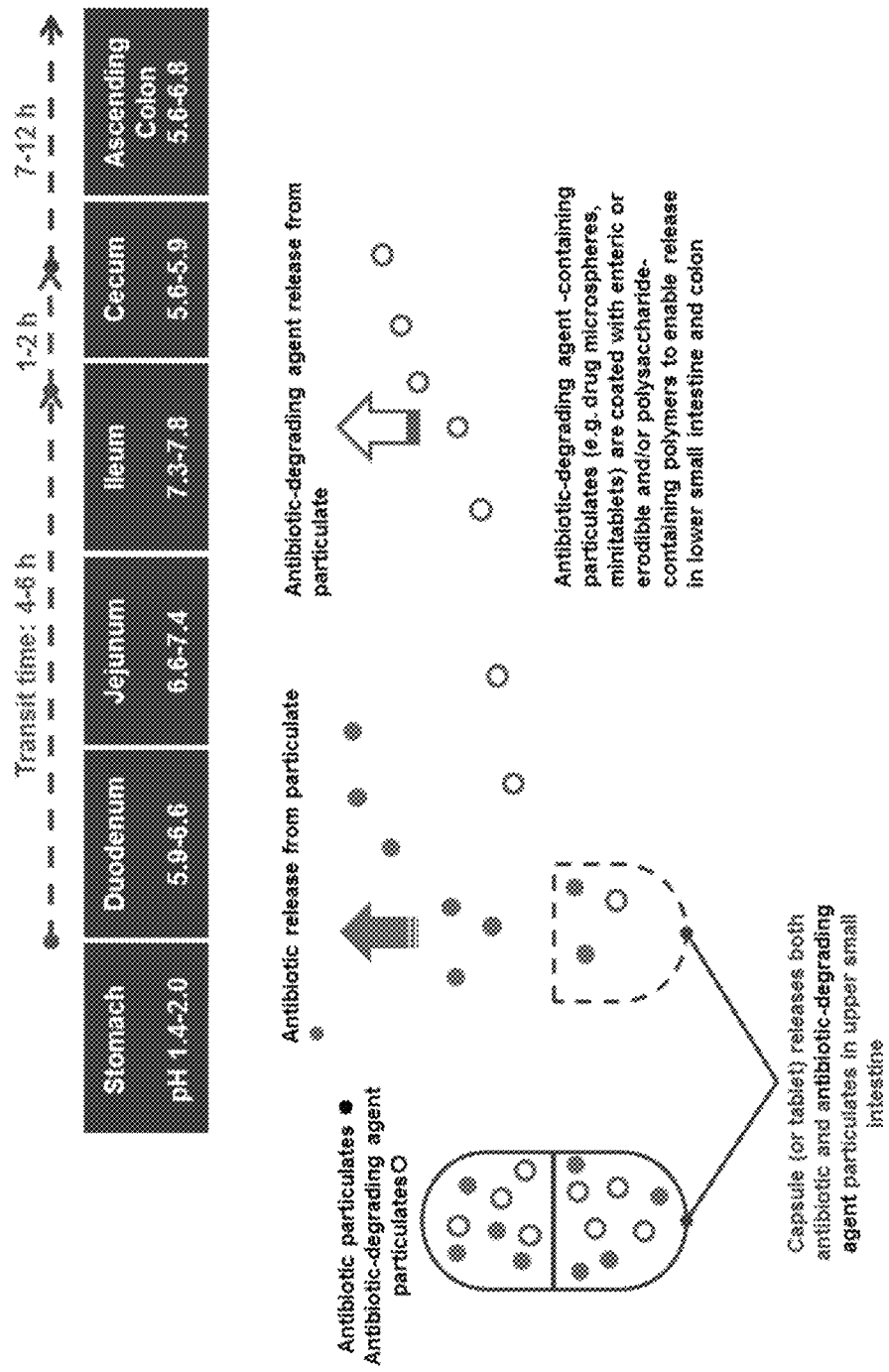
FIG. 34 shows various non-limiting microparticulate dosage forms.
Figure 35:
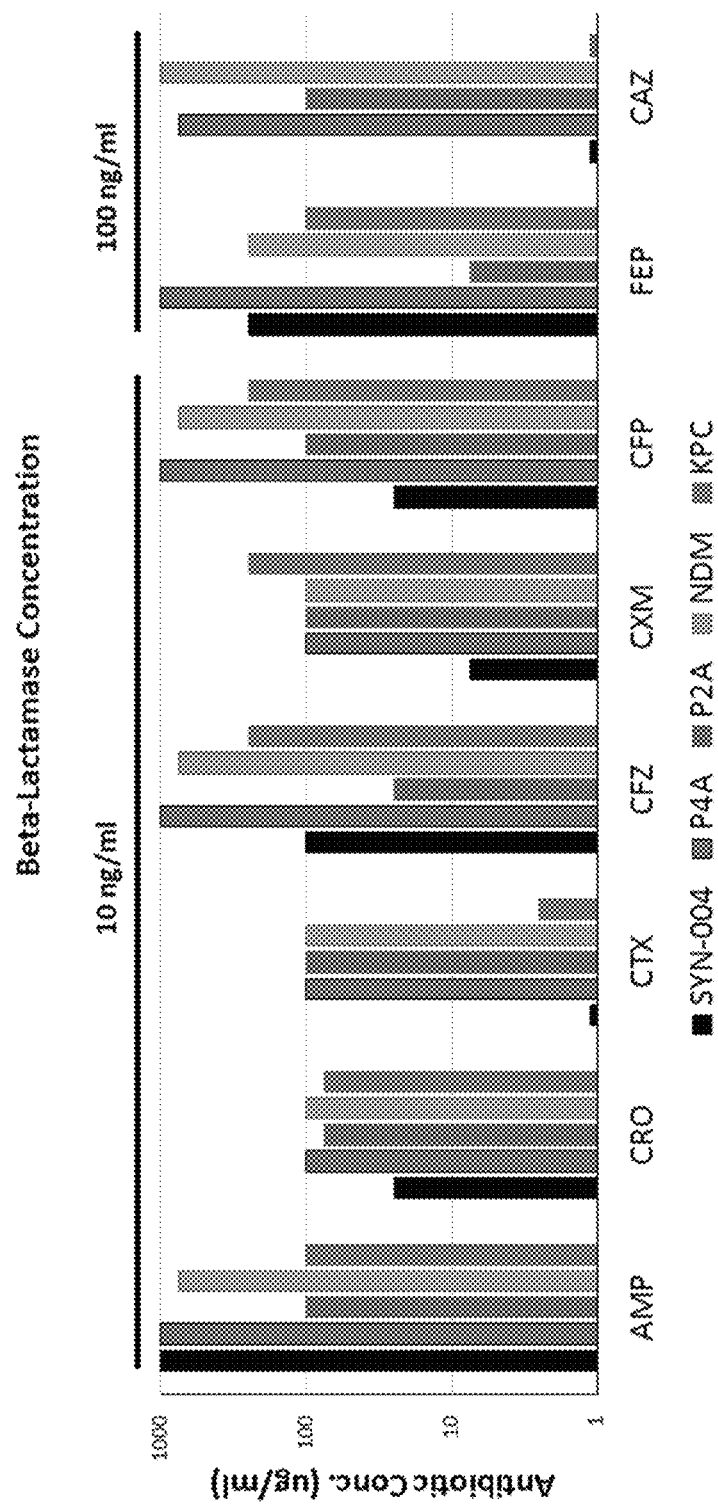
FIG. 35 shows a comparison of P3A (i.e. SYN-004), P4A, P2A, NDM, and KPC antibiotic inactivation activities via assessment of bacterial growth. The graph displays bacterial growth in the presence of 10 ng/ml or 100 ng/ml of the beta-lactamase enzymes. The abbreviations for the antibiotics are as follows: AMP: ampicillin, CRO: ceftriaxone, CTX: cefotaxime, CFZ: cefozolin, CXM: cefuroxime, CFP: cefoperazone, FEP: cefepime, and CAZ: ceftazidime. The order of histograms for each set of data is, from left to right, SYN-004, P4A, P2A, NDM, and KPC.

To map the proteolytic cleavage sites of the NDM fragments, NDM was incubated with 2% mixed human chyme as described for 0 or 15 minutes. As elastase is a serine protease present in human chyme, NDM was incubated with purified porcine pancreatic elastase (Sigma-Aldrich, Cat # E1250) at a concentration of 0.25 U/mL for 15 or 30 minutes. The NDM digestions were analyzed by SDS/PAGE, the gel equilibrated in 1×Tris-Glycine transfer buffer and the proteins were transferred to an equilibrated Sequi-Blot PVDF membrane by wet transfer in Tris-glycine buffer. Following transfer, the membrane was stained with Coomassie brilliant blue R-250 0.025% in 40% methanol for 15 minutes at ambient temperature. The membrane was destained in 50% methanol, air dried and bands were excised and placed into individual 1.5 mL tubes (FIG. 27). The isolated fragments were analyzed by N-terminal sequencing of the first 5 amino acids using a Perkin Elmer Applied Biosystems Model 494 Procise protein/peptide sequencer with an on-line Perkin Elmer Applied Biosystems Model 140C PTH Amino Acid Analyzer. The chemical process employed by the protein sequencer to determine the amino acid sequence is derived from the degradation method developed by Edman.

The results of N-terminal sequence analysis are presented in Table 21 and FIGS. 28 and 29. The NDM cleavage fragments were identified using the fragment sizes (FIG. 27), the N-terminus sequencing data, and the NDM sequence. Three cleavages were identified (FIG. 27), with two of the cleavage sites mapped to specific amino acids. The mapped cleavage sites are displayed in FIG. 28 and correspond to an elastase cleavage site (Chyme fragments 3 and 4 are identical to Elastase fragments 6 and 7), and a chyme cleavage site (Fragment 1 and 5). Fragment 5 is composed of at least two fragments as the predicted cleavages predict fragments of 6.1 and 5.4 kDa (FIG. 29) and both N-terminal sequences were detected after the Edmond degradation reactions (Table 28). Fragment 2, which appears to be a minor fragment of approximately 15 kDa (FIG. 27) had an N-terminus of the native NDM (GQQME). Based on the size of Fragment 2, the predicted cleavage site is expected to be between the mapped elastase and the mapped chyme cleavage sites (FIG. 28, underline). However, the other fragment from this cleavage was not detected, and it is expected to be quite small, as the elastase and chyme cleavages appear to be much stronger. The cleavage site of Fragment 2 may require more investigation for more accurate mapping. These data demonstrate that the proteases present in human chyme act on a limited number of specific cleavage sites within NDM. Three cleavage sites were identified in NDM, one of which corresponds to an elastase cleavage site. Without wishing to be bound by theory, removal of these sites, by modification of the amino acid sequence surrounding the cleavage site, may prevent cleavage and thereby improve the stability of NDM in chyme.

TABLE 21

Results of N-terminal sequence analysis. Amino acids at position 1 through 5 of each digested product were determined by Edmond degradation reactions, NDM amino acid sequence, and fragment sizes. The fragment numbers correspond to FIG. 27.

| Fragment Number | MW (kDa) | Amino Acid Position | | | | |
| --- | --- | --- | --- | --- | --- | --- |
| | | 1 | 2 | 3 | 4 | 5 |
| Full-Length | 24.8 | G | Q | Q | M | E |
| 1 | 19.5 | G | Q | Q | M | E |
| 2 | ~15 | G | Q | Q | M | E |
| 3 | 13.4 | G | Q | Q | M | E |
| 4 | 11.5 | S | L | T | F | A |
| 5 | 6.1 | S | L | T | F | A |
| | 5.4 | N | L | G | D | A |
| 6 | 13.4 | G | Q | Q | M | E |
| 7 | 11.5 | S | L | T | F | A |

Example 15: Modification of the Amino Acid Sequence of NDM Proximal to the Mapped Cleavage Sites to Improve the Stability of NDM in Chyme without Adversely Affecting NDM Biological Activity Three cleavage sites were identified in NDM, one of which corresponds to an elastase cleavage site. Removal of these sites, by modification of the amino acid sequence surrounding the cleavage site, may prevent cleavage and thereby improve the stability of NDM in chyme. Because the metallo-beta-lactamase, P2A, is stable in human chyme for at least 6 hours an alignment of the NDM and P2A amino acid sequences was performed (FIG. 30).

The amino acids proximal to the chyme cleavage sites are changed to amino acids that correspond to the P2A sequence in these regions. For example, the NDM amino acid sequence surrounding the SLTFA elastase cleavage site is changed to: YEEPLG. Multiple amino acids are substituted at each of these sites. The designed NDM coding regions are synthesized and cloned into *E. coli* expression plasmids. The new NDM proteins are synthesized and purified as described and the biological activity and stability in chyme are evaluated. NDM molecules that display biological activity and stability in chyme are subjected to bioreactor fermentation, purification, and formulation as described.

Example 16. Manufacturing of P2A, NDM, and/or KPC-Containing Enteric Coated Pellets P2A, NDM, and/or KPC formulations including P2A, NDM, and/or KPC enteric-coated pellets are produced. Specifically, P2A, NDM, and/or KPC are formulated into enteric-coated pellets of approximated 1.0 to 1.3 mm in diameter. Briefly, the enzyme is spray-coated onto a sucrose core and spray-dried with an enteric layer, Eudragit L30 D-55, to protect the active pharmaceutical ingredient from the acidic conditions of the stomach. The Eudragit L30 D55 polymer begins to depolymerize when the pH rises to 5.5 and above in the small intestine, releasing the active drug from the pellet.

For example, delayed-release capsules including P2A, NDM, and/or KPC enteric-coated pellets are manufactured in a GMP process. Specifically, the GMP manufacture of P2A, NDM, and/or KPC Delayed-Release Capsule is a three stage sequential process including: 1) P2A, NDM, and/or KPC drug layering onto sucrose core pellets by spray application, 2) enteric coating with EUDRAGIT L30 D-55 using spray application, and 3) encapsulation of pellets into hard gelatin capsules size 0.

P2A, NDM, and/or KPC layered pellets are produced by spray application of P2A, NDM, and/or KPC drug substance using hydroxypropylcellulose (HPC) as a binder excipient, water as a solvent, and sucrose spheres as starting material. The spray application is performed using a fluid bed system over six work shifts, in order to achieve a final active pharmaceutical agent (API) percentage of at least 15%. After the sixth work shift of spray application of the P2A, NDM, and/or KPC/HPC mixture, the P2A, NDM, and/or KPC layered pellets are dried overnight at room temperature on trays, then sifted through a 1.4 mm sieve prior to bulk packaging in polyethylene (PE) bags and PE containers. The drug-layered pellets are stored at about 5±3° C. for further processing.

In a subsequent process, the P2A, NDM, and/or KPC layered pellets are coated with methacrylic acid ethyl acrylate copolymer (EUDRAGIT L 30 D-55) as an enteric polymer, triethyl citrate as a plasticizer, glyceryl monostearate as a glidant, polysorbate-80 as an emulsifier, and water as a diluent. The coating is performed using a fluid bed system in a single work shift. The enteric coated P2A, NDM, and/or KPC layered pellets are dried overnight at room temperature on trays and sifted through a 1.6 mm sieve prior to packaging as bulk pellets in PE bags and PE containers. The enteric coated P2A, NDM, and/or KPC layered pellets are stored at about 5±3° C. for further processing.

The enteric coated P2A, NDM, and/or KPC layered pellets are encapsulated in hard gelatin capsules using an automated capsule filler with a capsule transport and dosing unit for filling size 0 capsules. The final P2A, NDM, and/or KPC delayed-release capsules, 75 mg, are packed as bulk Drug Product in PE bags and PE containers, and stored at about 5±3° C. ready for shipment.

In a separate manual process to manufacture P2A, NDM, and/or KPC delayed-release capsules, 25 mg, the enteric P2A, NDM, and/or KPC layered pellets are encapsulated in hard gelatin capsules using an analytical balance, capsule filling funnel for filling size 0 capsules. The final P2A, NDM, and/or KPC delayed-release capsule, 25 mg are packed as bulk Drug Product in PE bags and PE containers, and stored at 5±3° C. ready for shipment.

For example, P2A, NDM, and/or KPC delayed-release capsules, intended for use in clinical trials and stability studies, are packaged in a 100 cc high density polyethylene (HDPE) round bottle with 38 mm polypropylene (PP) child resistant closures, with an induction seal.

The formulations of the present invention may also take the form of those as described in PCT/US15/54606 and PCT/US15/00228, the entire contents of all of which are incorporated herein by reference.

Example 17. Additional P2A, NDM, and/or KPC Formulations

The carbapenemase enzymes, P2A, NDM, and KPC are formulated for release in a location in the GI tract in which it deactivates residual oral antibiotic residue, specifically for release in a location in the GI tract that is distal to the release of the orally administered antibiotic.

P2A, NDM, and/or KPC are formulated by combining the enzyme with a latex, or other polymer, and a particulate, micro-encapsulated enzyme preparation is formed. The microspheres may then be covered with a pH-dependent enteric coating. No sucrose core is required and this allows for higher drug loading per pellet and therefore a smaller capsule size for therapy. Formulations are developed to produce particles that have enteric functionality (not released in the stomach, complete release in the distal small intestine) built into the matrix itself, to reduce excipient load. If the formulation shows good retention of activity and stability, but insufficient protection from acidic conditions, enteric coating is applied to the particulates.

A variety of approaches for generating particulates (such as microspheres, aggregates, other) that are amenable to the inclusion of proteins may be used. These approaches involve at least two phases, one containing the protein, and one containing a polymer that forms the backbone of the particulate. For example, coacervation, where the polymer is made to separate from its solvent phase by addition of a third component, or multiple phase emulsions, such as water in oil in water (w/o/w) emulsion where the inner water phase contains the protein, the intermediate organic phase contains the polymer, and the external water phase stabilizers that support the w/o/w double emulsion until the solvents can be removed to form the microspheres may be used.

In another approach, the protein and stabilizing excipients (e.g., hydroxyproplyl methylcellulose acetate succinate (HPMCAS) type MF; Aquacoat (FMC), sodium stearyl fumarate; trehalose, mannitol, Tween 80, polyvinyl alcohol, and/or others) are combined and then the mixture from aqueous solution is sprayed, particles form and are collected. The particles are then suspended in a dry, water immiscible organic solvent containing polymer and release modifying compounds, and the suspension sonicated to disperse the particles. For example, two formulations of P3A were developed using this method (Tables 22 and 23), and similar formulations are developed for P2A, NDM, and KPC. Notably, HPMCAS-MF was used as the pore forming reagent as it is water insoluble at low pH (i.e., forms a gel), and become water soluble at high pH. At least 80% P3A activity was recovered after dissolution of the P3A particles made using these formulations as measured by the CENTA chromatogenic assay (Tables 22 and 23) (Bebrone et al., Antimicrobial Agents and Chemotherapy; (2001) 45:1868).

TABLE 22

Illustrative formulation 1

| Component | Item | Amt (g) in 500 ml | % Total | % |
|---|---|---|---|---|
| API | P3A | 2.50 | 0.5 | 9.77 |
| Pore Former | HPMCAS-MF | 1.67 | 0.3 | 6.53 |
| Matrix | Aquacoat (FMC) | 50.00 | 10.1 | 58.62 |
| Lube | Sodium-Stearyl Fumarate | 0.83 | 0.2 | 3.24 |
| Buffer | Sodium Hydrogen Phosphate | 0.59 | 0.1 | 2.31 |
| Protectant | Trehalose | 5.00 | 1.0 | 19.54 |
| Water | | 440.00 | 88.8 | |
| Total Water | | 489.85 | | |
| Total Solids | | 25.59 | | 100.00 |
| Solids in Matrix | | | | 30.00 |
| Activity Recovered | | | | 82.00 |

TABLE 23

Illustrative formulation 2

| Component | Item | Amt (g) in 500 ml | % Total | % |
|---|---|---|---|---|
| API | P3A | 11.25 | 2.30 | 39.37 |
| Pore Former | HPMCAS-MF | 1.50 | 0.30 | 5.25 |
| Matrix | Aquacoat (FMC) | 50.00 | 10.00 | 52.49 |
| Lube | Sodium-Stearyl Fumarate | 0.33 | 0.10 | 1.14 |
| Buffer | Sodium Hydrogen Phosphate | 0.50 | 0.10 | 1.75 |
| Protectant | Trehalose | 0.00 | 0.00 | 0.00 |
| Water | | 437.50 | 87.50 | |
| Total Water | | 472.50 | | |
| Total Solids | | 28.58 | | 100.00 |
| Solids in Matrix | | | | 30.00 |
| Activity Recovered | | | | 80.00 |

Another approach uses aqueous phases but no organic solvent. Here, the enzyme, buffer components, a polymer latex, and stabilizing and release-modifying excipients are dissolved/dispersed in water. The aqueous dispersion is spray-dried, leading to coalescence of the latex, and incorporation of the protein and excipients in particles of the coalesced latex. If the release modifiers are insoluble at acidic conditions but soluble at higher pHs (such as carboxylic acidic) then release from the matrix should be inhibited in the gastric environment.

Illustrative formulation approaches are shown in FIGS. 31-34.

It is expected that using one or more of these strategies will result in P2A, NDM, and KPC formulation(s) useful for oral delivery.

Example 18. Illustrative Formulations

Formulation approaches for segregating antibiotic and/or antibiotic-degrading agent inhibitor and antibiotic-degrading agent release are undertaken to allow the antibiotic to retain its anti-microbial function while also preserving the GI microbiome from damaging effects of excess antibiotic. FIG. 32 shows various non-limiting approaches. FIG. 33 shows various non-limiting combination dosage forms. FIG. 34 shows various non-limiting microparticulate dosage forms.

Example 19. Characterization of Enzymatic Activity in Vitro—Comparison of P3A, P4A, P2A, NDM, and KPC Activity Against Cephalosporins To provide protection against the broadest spectrum of antibiotics, the carbapenemases, such as P2A, NDM, and/or KPC, are used together with one or more additional beta-lactamases, to provide protection against most penicillins, cephalosporins, and carbapenems. Two or more antibiotic-degrading enzymes, such as P2A and P4A, are co-formulated into one pill or capsule, or are used at the same time but delivered in separate pills or capsules. Co-formulation of the two or more enzymes is performed as described in Examples 16-18. Using the *E. coli* growth inhibition assay as described in Example 10, P2A was demonstrated to be a potent carbapenemase that efficiently degraded meropenem, imipenem, ertapenem, and doripenem (FIGS. 21A and 21B), and was resistant to inhibition by sulbactam and tazobactum (FIGS. 21A and 21B). However, P2A was not as active against the cephalosporins, cefozolin, cefoperazone, cefepime, and ceftazidime (FIG. 35), compared to SYN-004 or P4A. Additionally, at low beta-lactamase concentrations, SYN-004 and P4A displayed higher activity against ampicillin than did P2A (FIGS. 21A, 21B and 35). Whereas SYN-004 and P4A have excellent cephalosporin activity, they are known to be devoid of carbapenemase activity. Therefore, the co-administration of P2A and P4A provides protection against most penicillins, cephalosporins, and carbapenems. If protection against the monobactam, aztreonam is required, then KPC is co-administered with P2A and P4A, as KPC was the only beta-lactamase that degraded aztreonam (FIGS. 21A and 21B). The same combination studies are undertaken with P4A with NDM and/or KPC. The same combination studies are undertaken with P3A (a/k/a SYN-004) with P2A and/or NDM and/or KPC.

Example 20. In Vivo Evaluation of an Enteric Formulation and/or a Modified-Release Formulation of P2A, NDM, and/or KPC Experiments are performed to evaluate the activity of oral formulations of the carbapenemases, P2A NDM, and/or KPC, to degrade a parenterally-delivered carbapenem antibiotic, such as meropenem, in dogs and/or pigs.

Chosen oral formulation(s) of P2A, NDM, or KPC and parenteral meropenem are delivered to cohorts (n=3-5) of normal young pigs (~50 lbs) or Beagle dogs. Animals are treated with P2A, NDM, or KPC and the antibiotic for 5-7 consecutive days (Table 19). P2A, NDM, or KPC treatment is started 1 day prior to antibiotic delivery. Plasma and stool is collected daily, beginning the day prior to treatment (Day −1). A cohort of animals is treated with clindamycin as a positive control for microbiome damage. Plasma is monitored for meropenem levels and stool is subjected to 16S RNA sequencing and/or shotgun DNA sequencing to monitor the diversity of the microbiome. Antibiotic levels in the stool are also measured. It is expected that at one or both of the meropenem/P2A, NDM, or KPC doses, the plasma levels of meropenem are not affected while the microbiome is protected, indicating that the P2A, NDM, or KPC degraded the meropenem excreted into the intestine following IV meropenem delivery. Other carbapenem and cephalosporin antibiotics are evaluated in an analogous manner. Table 24 below shows the experimental design.

TABLE 24

| Treatment of Normal Pigs or Dogs with Meropenem and P2A, NDM, or KPC | | |
|---|---|---|
| Cohort (n = 3-5) | Antibiotic Intraperitoneal | P2A, NDM, or KPC (oral) |
| 1 | none | none |
| 2 | Clindamycin (IP) (30 mg/kg) | none |
| 3 | Meropenem (IP) (15 mg/kg BID) | P2A, NDM, KPC High dose (12.5 mg/kg QID) |
| 4 | Meropenem (IP) (15 mg/kg BID) | P2A, NDM, KPC Low dose (0.5 mg/kg QID) |
| 5 | Meropenem (IP) (15 mg/kg BID) | none |
| 6 | Meropenem (IP) (30 mg/kg BID) | P2A, NDM, KPC High dose (12.5 mg/kg QID) |

TABLE 24-continued Treatment of Normal Pigs or Dogs with
Meropenem and P2A, NDM, or KPC

| Cohort (n = 3-5) | Antibiotic Intraperitoneal | P2A, NDM, or KPC (oral) |
|---|---|---|
| 7 | Meropenem (IP) (30 mg/kg BID) | P2A, NDM, KPC Low dose (0.5 mg/kg QID) |
| 8 | Meropenem (IP) (30 mg/kg BID) | none |

Example 21. In Vivo Evaluation of Enteric Formulations and/or a Modified-Release Formulations of P2A and P4A Experiments are performed to evaluate the activity of oral formulations of the carbapenemase, P2A, used concurrently with the cephalosporinase, P4A, to degrade a parenterally-delivered antibiotic combination including a carbapenem antibiotic, meropenem, and a cephalosporin antibiotic, cefepime, in dogs and/or pigs.

Chosen oral formulation(s) of P2A and P4A, and parenteral meropenem plus cefepime are delivered to cohorts (n=3-5) of normal young pigs (~50 lbs) or Beagle dogs. Animals are treated with P2A plus P4A and the antibiotics for 5-7 consecutive days (Table 25). P2A and P4A treatment is started 1 day prior to antibiotic delivery (or concurrently). Plasma and stool is collected daily, beginning the day prior to treatment (Day −1). A cohort of animals is treated with clindamycin as a positive control for microbiome damage. Plasma is monitored for meropenem and cefepime levels and stool is subjected to 16S RNA sequencing and/or shotgun DNA sequencing to monitor the diversity of the microbiome. Antibiotic levels in the stool are also measured. It is expected that at one or both of the meropenem/cefepime plus P2A/P4A doses, the plasma levels of meropenem and cefepime are not affected while the microbiome is protected, indicating that the P2A and the P4A degraded the antibiotics excreted into the intestine following antibiotic delivery. Other carbapenem and cephalosporin antibiotics and antibiotic degrading enzyme combinations are evaluated in an analogous manner. Table 25 below shows the experimental design.

TABLE 25

Treatment of Normal Pigs or Dogs with
Meropenem and Cefepime plus P2A and P4A

| Cohort (n = 3-5) | Antibiotic Intraperitoneal | P2A and P4A (oral) |
|---|---|---|
| 1 | none | none |
| 2 | Clindamycin (IP) (30 mg/kg) | none |
| 3 | Meropenem and Cefepime (IP) (15 mg/kg BID of each) | P2A + P4A High dose (12.5 mg/kg QID of each) |
| 4 | Meropenem and Cefepime (IP) (15 mg/kg BID of each) | P2A + P4A Low dose (0.5 mg/kg QID of each) |
| 5 | Meropenem and Cefepime (IP) (15 mg/kg BID of each) | none |
| 6 | Meropenem and Cefepime (IP) (30 mg/kg BID of each) | P2A + P4A High dose (12.5 mg/kg QID of each) |
| 7 | Meropenem + Cefepime (IP) (30 mg/kg BID of each) | P2A + P4A Low dose (0.5 mg/kg QID of each) |
| 8 | Meropenem and Cefepime (IP) (30 mg/kg BID of each) | none |

Example 22. Oral P2A Degrades Ampicillin in the Dog Gastrointestinal (GI) Tract The ability of P2A to degrade ampicillin in the dog intestinal tract was evaluated using laboratory beagles that had permanent jejunal fistulas. The fistulas allowed the repeated collection of jejunal chyme specimens from these animals. Dogs were treated with peroral P2A (1 mg/kg) in a liquid formulation (PBS buffer), and/or intravenous ampicillin (40 mg/kg). Serum samples were collected and serum ampicillin levels quantified. Jejunal chyme samples were collected and ampicillin and P2A levels were quantified. Ampicillin levels in serum and chyme were measured using a standard reverse phase HPLC method. P2A activity levels in chyme were determined spectrophotometrically using meropenem as a substrate. Meropenem hydrolysis was monitored at a wavelength of 297 nm.

Figure 36:
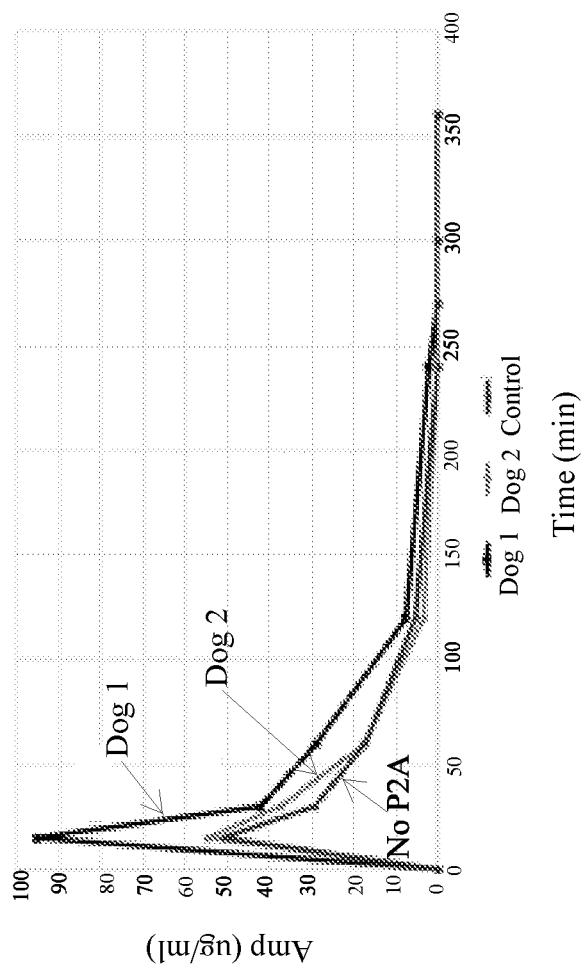
FIG. 36 shows serum levels of ampicillin in P2A-treated and control dogs. The curves labeled Dog 1 (at peak, this is the top curve) and Dog 2 (at peak, this is the middle curve) represent animals treated with both ampicillin and P2A. The curve labeled No P2A (at peak, this is the bottom curve) represents a dog that was treated only with ampicillin.
Figure 37:
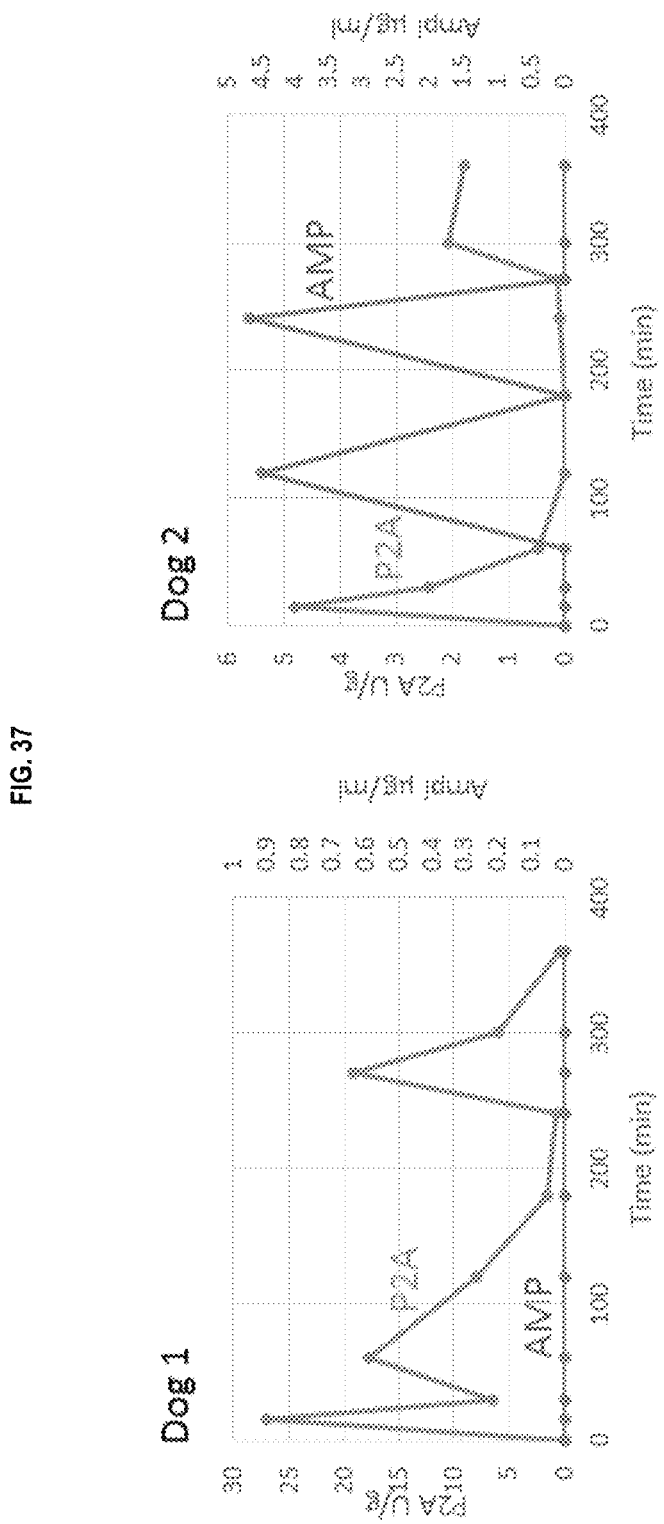
FIG. 37 shows jejunal levels of P2A and ampicillin in dogs. Both ampicillin and P2A were measured in the jejunal chyme samples obtained at the indicated times (in both panels, the P2A curve is the one with the first peak). Each dog (Dog 1, left panel; Dog 2, right panel) received both ampicillin and P2A as described.

The serum levels of ampicillin were similar with the three treated dogs (FIG. 36). Dog 1 and Dog 2 received both ampicillin and P2A while the dog represented by the curve labeled "No P2A" received only ampicillin. These data demonstrate that orally-delivered P2A does not reduce serum levels of ampicillin, suggesting that P2A will not affect the efficacy of systemically-delivered ampicillin. The levels of ampicillin and P2A were also measured in jejunal chyme collected from dogs treated with both ampicillin and P2A (FIG. 37). In Dog 1, the ampicillin levels in the chyme were very low or undetectable while the levels of P2A were well above the detection limit. In Dog 2, when P2A was detected in the chyme, ampicillin levels were undetectable, and when P2A levels were low or undetectable, ampicillin levels were high. These data demonstrated that orally delivered P2A degraded ampicillin in the dog intestinal tract.

Example 23. Oral P2A Degrades Ceftriaxone in the Dog GI Tract

The ability of P2A to degrade ceftriaxone in the dog intestinal tract was evaluated using laboratory beagles that had permanent jejunal fistulas. The fistulas allowed the repeated collection of jejunal chyme specimens from these animals. Dogs were treated with peroral P2A (2.5 mg/kg) in a liquid formulation (PBS buffer), and/or intravenous ceftriaxone (30 mg/kg). A single dose of omeprazole (10 mg) was delivered orally to each dog prior to treatment with ceftriaxone and/or P2A to inhibit the HCl activity in the stomach to potentially reduce P2A degradation. Serum samples were collected and serum ceftriaxone levels quantified. Jejunal chyme samples were collected and ceftriaxone and P2A levels were quantified. Ceftriaxone levels in serum and chyme were measured using a plate diffusion method using ceftriaxone susceptible *Micrococcus luteus* TS504 as the test strain. P2A activity levels in chyme were determined spectrophotometrically using meropenem as a substrate. Meropenem hydrolysis was monitored at a wavelength of 297 nm.

Figure 38:
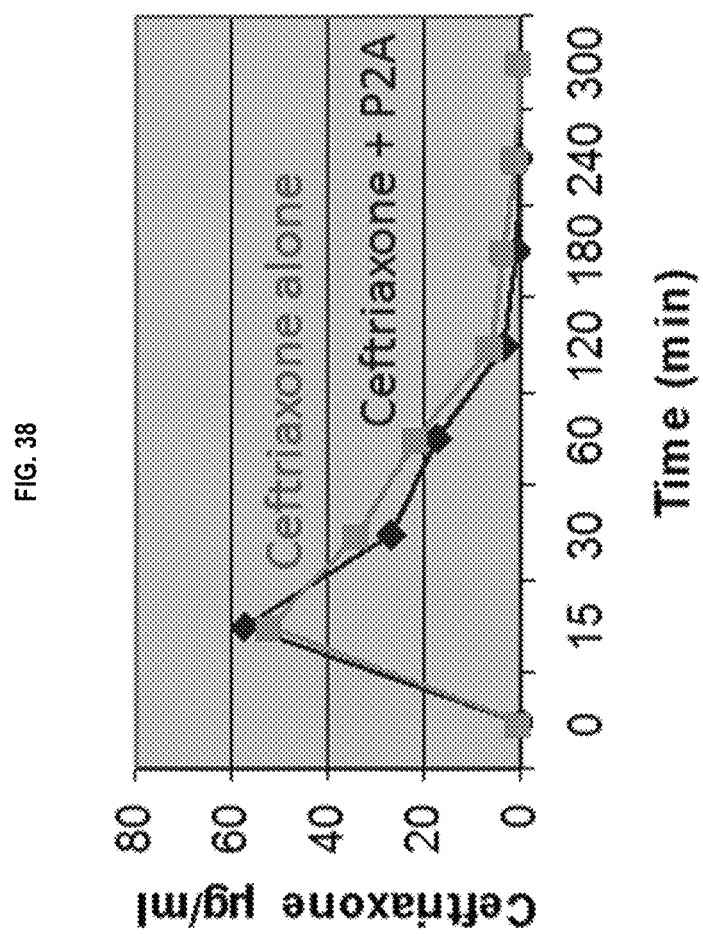
FIG. 38 shows serum levels of ceftriaxone in P2A-treated and control dogs. The graph displayed the mean serum levels of ceftriaxone in dogs treated with ceftriaxone alone (■) or in dogs treated with ceftriaxone+P2A (♦).
Figure 39:
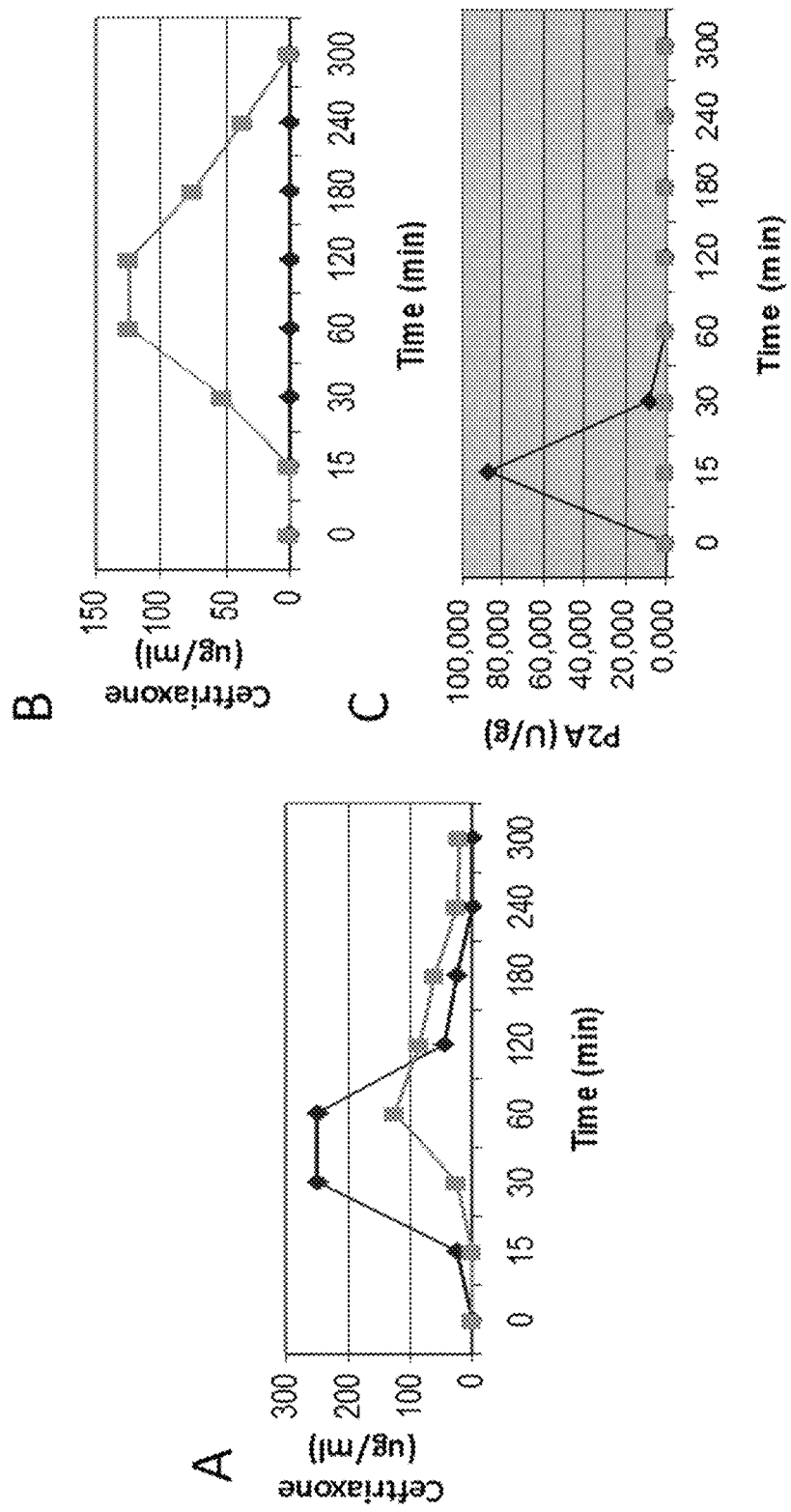
FIG. 39 shows jejunal levels of P2A and ceftriaxone in dogs. P2A and/or ceftriaxone were measured in jejunal chyme samples obtained at the indicated times. Panel A: Ceftriaxone levels in chyme from two dogs treated with ceftriaxone alone. Panel B: Ceftriaxone levels in chyme from two dogs treated with ceftriaxone+P2A. Panel C: P2A levels in chyme from the two dogs in B treated with ceftriaxone+P2A.

The serum levels of ceftriaxone were similar in dogs treated with ceftriaxone alone or with the combination of ceftriaxone and P2A (FIG. 38). These data demonstrate that orally-delivered P2A does not reduce serum levels of ceftriaxone, suggesting that P2A will not affect the efficacy of systemically-delivered ceftriaxone. The levels of ceftriaxone and/or P2A were also measured in jejunal chyme collected from dogs treated with ceftriaxone alone or ceftriaxone and P2A (FIG. 39). Ceftriaxone was readily measured in the chyme from dogs treated with ceftriaxone alone. Of two dogs treated with ceftriaxone and P2A, one animal displayed little or no P2A in the chyme while the other animal displayed high levels of intestinal P2A (FIG. 39). The dog with detectable P2A in the chyme showed little or no ceftriaxone in the chyme, while the animal without detectable P2A displayed similar ceftriaxone levels as the ceftriaxone alone treated dogs. These data demonstrated that orally delivered P2A, when present in the intestinal tract, degraded ceftriaxone.

Example 24. Oral P2A Degrades Meropenem in the Dog GI Tract

The ability of P2A to degrade meropenem in the dog intestinal tract was evaluated using laboratory beagles that had permanent jejunal fistulas. The fistulas allowed the repeated collection of jejunal chyme specimens from these animals. Dogs were treated with peroral P2A (1 mg/kg) in a liquid formulation (PBS buffer), and/or intravenous meropenem (30 mg/kg). Serum samples were collected and serum meropenem levels quantified. Jejunal chyme samples were collected and meropenem and P2A levels were quantified. Meropenem levels in serum and chyme were measured using a plate diffusion method using meropenem susceptible *Micrococcus luteus* TS504 as the test strain. P2A activity levels in chyme were determined spectrophotometrically using meropenem as a substrate. Meropenem hydrolysis was monitored at a wavelength of 297 nm.

Figure 40:
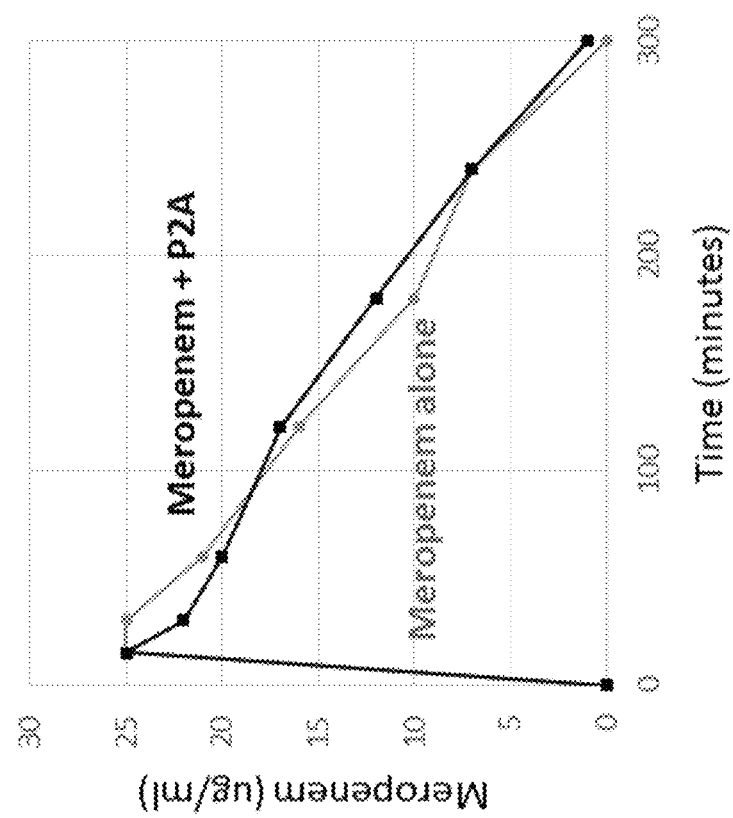
FIG. 40 shows serum levels of meropenem in P2A-treated and control dogs. The graph displayed the mean serum levels of meropenem in dogs (n=3) treated with meropenem alone (circles) or in dogs treated with meropenem+P2A (squares), (n=3).

The serum levels of meropenem were similar in dogs treated with ceftriaxone alone or with the combination of ceftriaxone and P2A (FIG. 40). These data demonstrate that orally-delivered P2A does not reduce serum levels of meropenem, suggesting that P2A will not affect the efficacy of systemically-delivered meropenem. The levels of meropenem and/or P2A were also measured in jejunal chyme collected from dogs treated with meropenem alone or meropenem and P2A (Table 26). At jejunal P2A concentrations of at least 0.5 U/g, meropenem was not detected in the intestinal samples. These data demonstrated that orally delivered P2A, when present in the intestinal tract, degraded meropenem.

TABLE 26

Peak P2A and Meropenem Levels in Dog Jejunum

| Cohort (n = 3) | Treatment | Dog | P2A (U/g) | Meropenem (ug/ml) |
|---|---|---|---|---|
| Antibiotic alone | Meropenem (30 mg/kg, IV) | 1 | — | 3.0 |
| | | 2 | — | 3.2 |
| | | 3 | — | 3.0 |
| P2A + Antibiotic | Meropenem (30 mg/kg, IV) + P2A (1 mg/kg, PO) | 4 | 80 | 0 |
| | | 5 | 0.5 | 0 |
| | | 6 | 0.2 | 2.0 |

Example 25. Oral P2A Degrades Cefotaxime in the Dog GI Tract

The ability of P2A to degrade cefotaxime in the dog intestinal tract was evaluated using laboratory beagles that had permanent jejunal fistulas. The fistulas allowed the repeated collection of jejunal chyme specimens from these animals. Dogs were treated with peroral P2A (1 mg/kg) in a liquid formulation (PBS buffer), and/or intravenous cefotaxime (60 mg/kg). A single dose of omeprazole (10 mg) was delivered orally to each dog prior to treatment with ceftriaxone and/or P2A to inhibit the HCl activity in the stomach to potentially reduce P2A degradation. Serum samples were collected and serum cefotaxime levels quantified. Jejunal chyme samples were collected and cefotaxime and P2A levels were quantified. Cefotaxime levels in serum and chyme were measured using a plate diffusion method using cefotaxime susceptible *Micrococcus luteus* TS504 as the test strain. P2A activity levels in chyme were determined spectrophotometrically using meropenem as a substrate. Meropenem hydrolysis was monitored at a wavelength of 297 nm.

Figure 41:
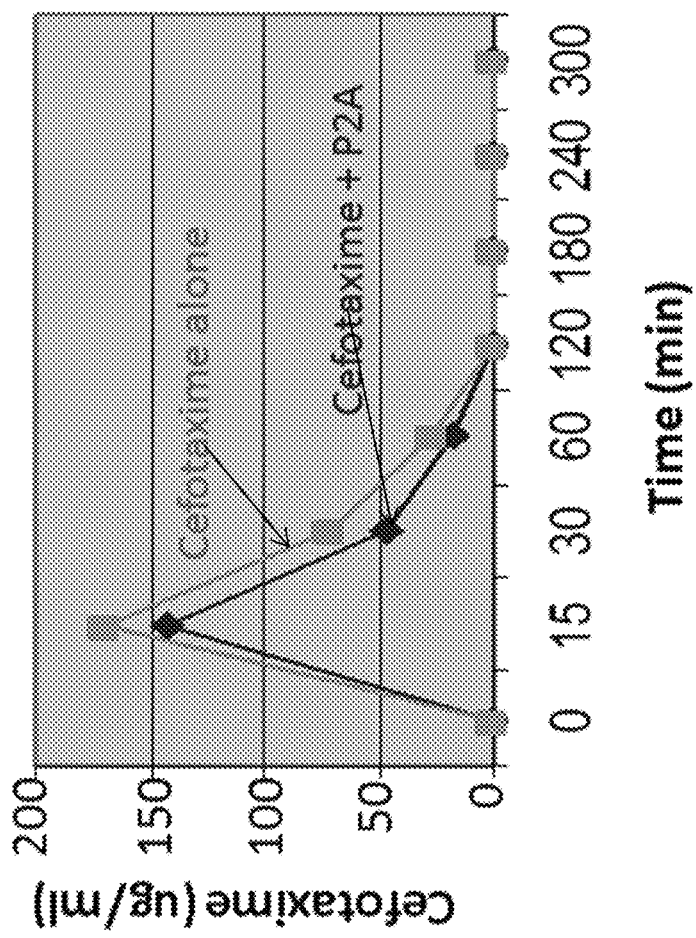
FIG. 41 shows serum levels of cefotaxime in P2A-treated and control dogs. The graph displayed the mean serum levels of cefotaxime in dogs treated with cefotaxime alone (■) or in dogs treated with cefotaxime+P2A (♦).
Figure 42:
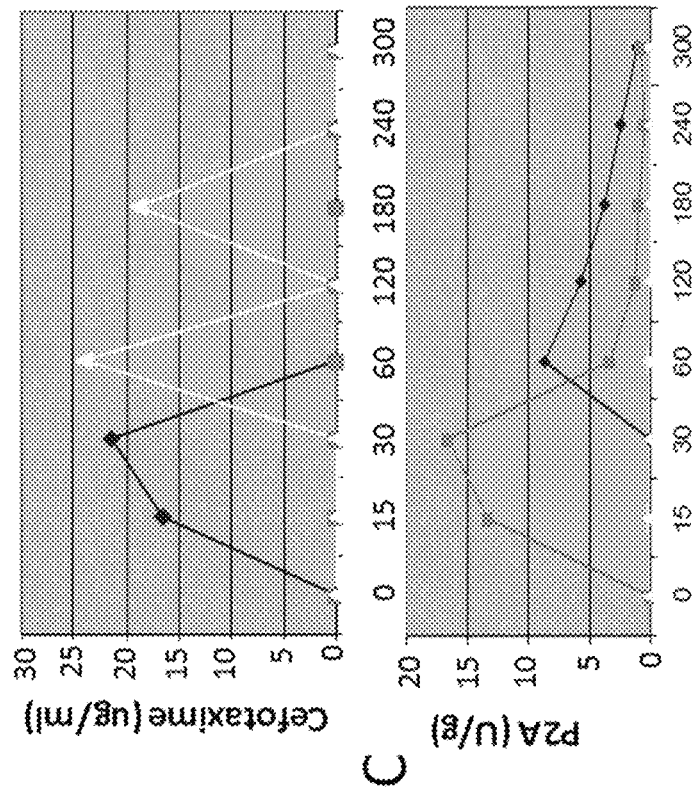
FIG. 42 shows jejunal levels of P2A and cefotaxime in dogs. P2A and/or cefotaxime were measured in jejunal chyme samples obtained at the indicated times. Panel A: Cefotaxime levels in chyme from two dogs treated with cefotaxime alone. Panel B: Cefotaxime levels in chyme from three dogs treated with cefotaxime+P2A. Panel C: P2A levels in chyme from the three dogs in B treated with cefotaxime+P2A.

The serum levels of cefotaxime were similar in dogs treated with cefotaxime alone or with the combination of cefotaxime and P2A (FIG. 41). These data demonstrate that orally-delivered P2A does not reduce serum levels of cefotaxime, suggesting that P2A will not affect the efficacy of systemically-delivered cefotaxime. The levels of cefotaxime and/or P2A were also measured in jejunal chyme collected from dogs treated with cefotaxime alone or cefotaxime and P2A (FIG. 42). Cefotaxime was readily measured in the chyme from dogs treated with cefotaxime alone. Of three dogs treated with cefotaxime and P2A, one animal displayed little or no P2A in the chyme while the other two animals displayed high levels of intestinal P2A (FIG. 42). The dogs with detectable P2A in the chyme showed little or no cefotaxime in the chyme during the time when P2A was present, while the animal without detectable P2A showed variable levels of ceftriaxone in the GI tract. These data demonstrated that orally delivered P2A, when present in the intestinal tract, degraded cefotaxime.

Example 26. Evaluation of P2A Enteric-Coated Particles for Degradation of Cefotaxime in the Dog GI Tract An enteric-coated pellet formulation of P2A was produced using methods similar to that used successfully for the production of the P1A enteric-coated pellets (e.g. sucrose core particles, pH-dependent polymer Eudragit L 30 D-55 coating, see Tarkkanen, Antimicrobial Agents and Chemotherapy, June 2009, p. 2455-2462, the entire contents of which are hereby incorporated by reference).

The ability of P2A to degrade cefotaxime in the dog intestinal tract was evaluated using laboratory beagles that had permanent jejunal fistulas. The fistulas allowed the repeated collection of jejunal chyme specimens from these animals. Dogs were treated with peroral P2A enteric-coated pellets at two doses, 0.5 mg/kg or 0.25 mg/kg of P2A content and/or intravenous cefotaxime (120 mg/kg). The dosing was performed twice. Animals were fed 20 minutes before P2A was delivered orally. Each animal received 3-5 P2A capsules, dependent on the P2A dose and the body weight. Cefotaxime was delivered intravenously 10 minutes after P2A administration. Chyme samples were collected at the indicated times ranging from 15 minutes after cefotaxime delivery. A second feeding was given to the animals at 5 hours and 40 minutes after cefotaxime delivery, followed 10 minutes later by P2A delivery, and 10 minutes later, a second cefotaxime treatment. Cefotaxime levels in chyme were measured using a plate diffusion method using cefotaxime susceptible *Micrococcus luteus* TS504 as the test strain. P2A activity levels in chyme were determined spectrophotometrically using meropenem as a substrate. Meropenem hydrolysis was monitored at a wavelength of 297 nm.

Figure 43:
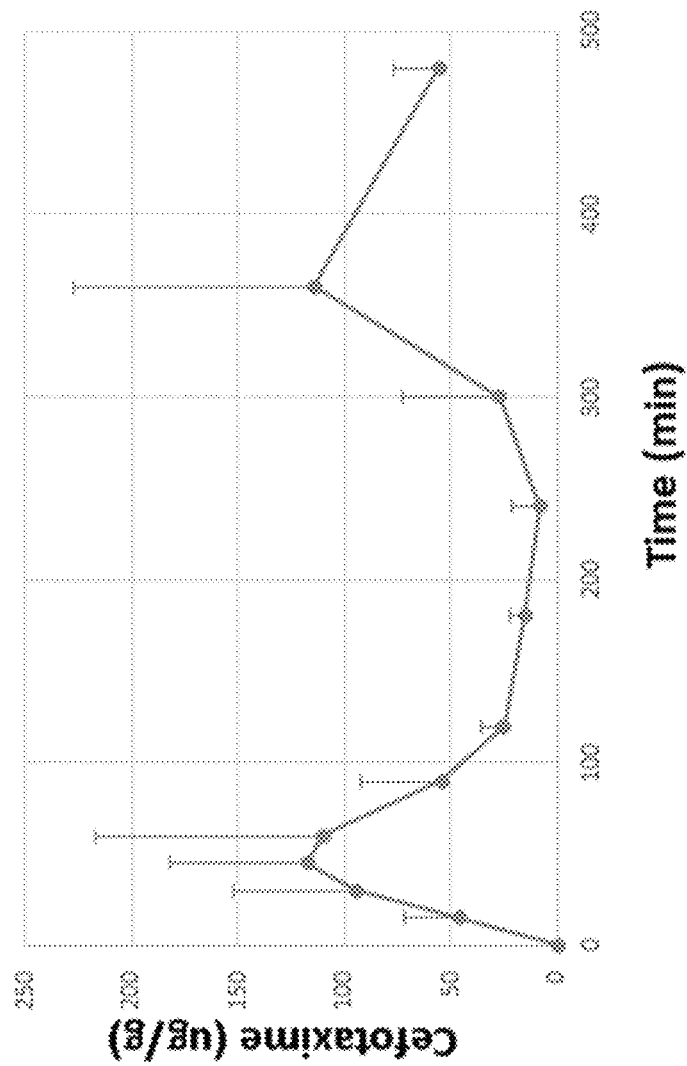
FIG. 43 shows jejunal levels of cefotaxime in dogs treated with cefotaxime alone. The graph displays the mean values and standard deviations from 6 dogs. Cefotaxime was administered at Time 0 and at Time 300.
Figure 44:
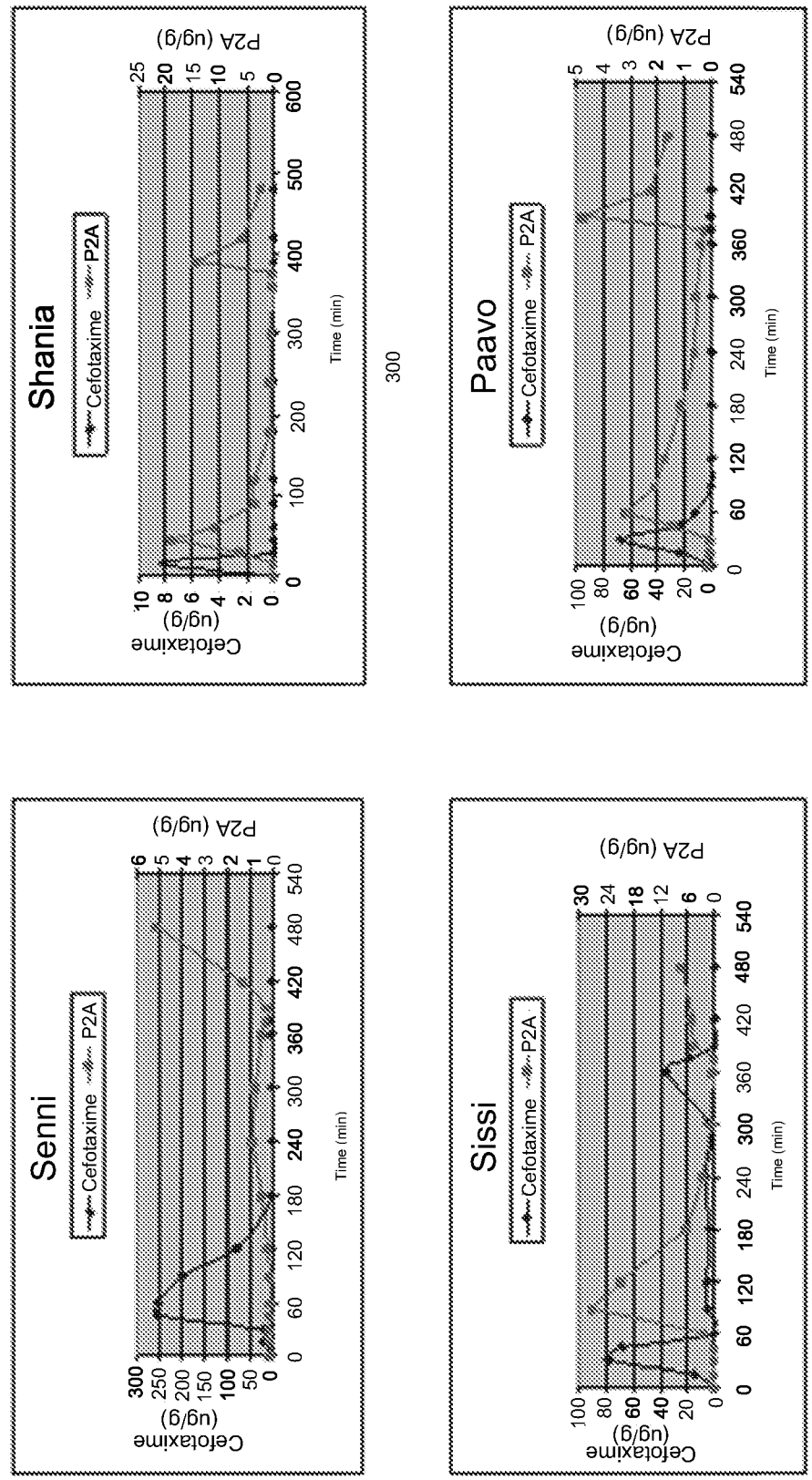
FIG. 44 shows jejunal levels of cefotaxime and P2A in four representative treated dogs. The graphs display the cefotaxime levels in (diamonds, in all four panels, the curve with the first peak in time) and the P2A levels in pink (squares) for individual dogs. The dogs Senni and Sissi (left panels) received cefotaxime (120 mg/kg) and 0.5 mg/kg of P2A. The dogs Shania and Paavo (right panels) received cefotaxime (120 mg/kg) and 0.25 mg/kg of P2A.

High levels of cefotaxime was measured in the chyme from dogs treated with cefotaxime alone, as the cefotaxime dose used of 120 mg/kg was 4 times the clinical dose (FIG. 43). Dogs treated with both cefotaxime and P2A (0.5 mg/kg or 0.25 mg/kg doses) displayed lower overall levels of cefotaxime in their chyme compared to the cefotaxime alone levels. Cefotaxime and P2A chyme levels of individual animals show a clear pattern (FIG. 44). When P2A was detectable in the chyme, cefotaxime was not detected, and vice versa, when P2A was not detectable, then cefotaxime levels were measured (FIG. 44). These data demonstrated that orally delivered P2A, when present in the intestinal tract, degraded cefotaxime.

Example 27. Evaluation of Carbapenemases as a Prophylactic to Prevent C. difficile Disease (CDI) Following Antibiotic Treatment in Hamsters These studies evaluate the efficacy of carbapenemases, P2A NDM, and/or KPC (for example, enteric formulations or modified-release formulations of these enzymes) in the prevention of CDI in a hamster disease model.

Oral formulations, including enteric and/or other modified-release formulations of P2A, NDM, and/or KPC are tested in a rodent model of CDI. Rodent models include the Syrian Golden hamster (*Mesocricetus auratus*) *C. difficile* model (Sambol and Tang, 2001; J. Infect. Disease 183: 1760). The hamster model has been referred to as "the gold standard" small animal model for the evaluation of the efficacy of a variety of prophylactic and therapeutic interventions against CDI. CDI is induced in the hamsters using the following protocol. Male Golden Syrian hamsters, purchased from Harlan (Indianapolis, Ind.) are pretreated 5 days or 24 hours prior to infection with a single subcutaneous injection of clindamycin at 10 or 30 mg/kg to deplete the animal's microbiome and predispose them to *C. difficile* infection. As the use of any antibiotic is a risk factor for *C. difficile* infection (Freeman and Wilcox, Microbes Infect. (1999) 1:377-384, meropenem is used in place of clindamycin to predispose the animals to *C. difficile* infection. On the day of infection, animals are inoculated by oral gavage with $10^6$ *C. difficile* (ATCC 43255) vegetative cells per hamster. The *C. difficile* inoculum is prepared by growing the bacteria in Difco reinforced clostridial medium with 1% Oxyrase for 24 hours under anaerobic conditions. The optical density at 600 nm is adjusted to 1.5 and then diluted 1:10. The hamsters are given 0.75 ml of this suspension orally via gavage. An aliquot of the inoculum is then serially diluted, plated on *Brucella* agar supplemented with hemin and vitamin K1 (Remel, Lenexa, Kans.), and incubated anaerobically for 48 hours in an airtight container (Pack-Anaero MGC) to determine the infection titer. Animals are observed twice daily during the first 24 hours postinfection and then every 2 hours for the following 24 hours during the acute phase of the disease, followed by twice daily for the remainder of the study. Signs of CDI include signs of mortality and morbidity, presence of diarrhea as indicated by a wet tail, and overall appearance including activity, general response to handling, touch, or ruffled fur. Body weights are monitored every 2 to 3 days.

To evaluate the prophylactic potential of P2A, NDM, and/or KPC, the carbapenemase enzyme is administered orally beginning at the time of antibiotic administration, 1 day prior to *C. difficile* infection, and continued for the duration of the studies, up to 28 days. Disease is compared in animals that receive clindamycin or meropenem (Antibiotic). The efficacy of the enzyme treatment groups are compared to control animals that receive no treatment, animals that receive the standard of care, vancomycin (20 mg/kg orally daily beginning 24 hours after infection and continued for 5 days), or animals that receive both vancomycin and enzyme treatment. Plasma is monitored for antibiotic levels and stool is subjected to 16S RNA sequencing to monitor the diversity of the microbiome. Stool is analyzed for the presence of meropenem. Efficacy evaluations include mortality and evaluation of *C. difficile* bacteria titers and/or *C. difficile* toxins A and B in cecal contents, at the time of death or at the end of the study following euthanasia. It is expected that treatment with meropenem and P2A, NMD, or KPC does not affect blood levels of the antibiotic and protects the animals from CDI, indicating that P2A, NDM, or KPC degrades the meropenem antibiotic excreted into the intestine following antibiotic absorption. Table 27 below shows the experimental design.

TABLE 27

C. difficile Efficacy Hamster Study Treatment Groups

| Cohort (n = 6-10) | Antibiotic Intraperitoneal | C. diff innoculation | Treatment |
|---|---|---|---|
| 1 | none | None | none |
| 2 | Clindamycin (30 mg/kg) | + | none |
| 3 | Meropenem 30 mg/kg BID | + | none |
| 4 | Meropenem 30 mg/kg BID | + | vancomycin |
| 5 | Meropenem 30 mg/kg BID | + | P2A, NDM, or KPC High dose (12.5 mg/kg QID) |
| 6 | Meropenem 15 mg/kg BID | + | P2A, NDM, or KPC Low dose (0.5 mg/kg QID) |
| 7 | Meropenem 15 mg/kg BID | + | Vancomycin + P2A, NDM, or KPC High dose (12.5 mg/kg QID) |

Example 28. Evaluation of Carbapenemases as a Prophylactic to Prevent C. difficile Disease (CDI) Following Antibiotic Treatment in Humanized Pigs These studies evaluate the efficacy of carbapenemases, P2A NDM, and/or KPC in the prevention of CDI in humanized pigs.

P2A, NDM, or KPC is tested in a humanized pig model of CDI. The humanized pig model is a model of the human gastrointestinal tract where the gnotobiotic pigs are reconstituted with human fecal homogenates (Zhang et al., Gut Microbes (2013) 4:193). The humanized pigs are treated with antibiotics (clindamycin or meropenem) to disrupt their intestinal microbiome and then exposed to *C. difficile* after which they develop CDI including *C. difficile* associated diarrhea (CDAD).

To test the prophylactic potential of P2A, NDM, or KPC, P2A, NDM, or KPC is administered one day prior to (or concurrently with) antibiotic treatment (Day −1), and maintained for the duration of the antibiotic treatment. Clindamycin is delivered 1 to 5 days prior to *C. difficile* inoculation and serves as the positive control cohort for microbiome damage. Meropenem or another antibiotic is delivered beginning 1 to 5 days prior to *C. difficile* inoculation, and maintained for 5-7 days. The antibiotics are used to disrupt the intestinal microbiome to predispose the animals to *C. difficile* infection. *C. difficile* vegetative cells or spores are administered, at doses ranging from $10^6$ to $10^8$, and animals are monitored for CDI symptoms including CDAD. Animals exposed to *C. difficile* are expected to develop disease symptoms within 48 hours of bacterial inoculation (Steele et al., 2010; J. Infect. Dis 201:428). CDI is compared in animals that receive clindamycin or meropenem (Antibiotic). The efficacy of the P2A, NDM, or KPC treatment groups are compared to control animals that receive no treatment, animals that receive the standard of care, vancomycin (20 mg/kg orally daily beginning 24 hours after infection and continued for 5 days), or animals that receive both vancomycin and P2A, NDM, or KPC. It is expected that treatment with meropenem and P2A, NMD, or KPC, does not affect blood levels of the antibiotic and protects the animals from CDI, indicating that the P2A, NDM, or KPC degrades the meropenem antibiotic excreted into the intestine following antibiotic absorption. Table 28 shows the experimental design.

TABLE 28

P2A, NDM, or KPC *C. difficile* Efficacy
Humanized Pig Study Treatment Groups

| Cohort (n = 2-3) | Antibiotic Intraperitoneal | *C. diff* innoculation | Treatment |
|---|---|---|---|
| 1 | none | None | none |
| 2 | Clindamycin (30 mg/kg) | + | none |
| 3 | Meropenem 30 mg/kg BID | + | none |
| 4 | Meropenem 30 mg/kg BID | + | vancomycin |
| 5 | Meropenem 30 mg/kg BID | + | P2A, NDM, or KPC High dose (12.5 mg/kg QID) |
| 6 | Meropenem 15 mg/kg BID | + | P2A, NDM, or KPC Low dose (0.5 mg/kg QID) |
| 7 | Meropenem 15 mg/kg BID | + | Vancomycin + P2A, NDM, or KPC Low dose (0.5 mg/kg QID) |

Example 29. Development of a Pig Model of Carbapenem-Mediated Disruption of the Gut Microbiome P2A is a potent carbapenemase being developed to degrade carbapenem antibiotics such as ertapenem, meropenem, imipenem, and doripenem in the GI tract to protect the gut microbiome and prevent carbapenem-mediated dysbiosis. A pig model of ertapenem-mediated dysbiosis was established. This pig model will be used to evaluate the efficacy of oral delivery of enteric-coated or other formulations of P2A to degrade ertapenem in the pig GI tract and to prevent dysbiosis. To develop the pig model as study was performed using normal piglets to determine if ertapenem causes gut dysbiosis.

TABLE 29

Piglet study design

| Group (N = 5) | Antibiotic | Antibiotic Delivery |
|---|---|---|
| Pig 11, 12, 13, 14, 15 | Ertapenem (30 mg/kg) | IV, 1X per day 12 pm |

A total of five, two month old Yorkshire piglets, approximately 20 kg each, were used for this study. The animals were treated with ertapenem (30 mg/kg) via intravenous infusion one a day for a total of 7 days.

Two pre-treatment fecal samples were obtained, the first 4 days after the animals arrived at the animal treatment facility (Day −7), and the second 7 days after arrival (Day −4). An additional 3 fecal samples were collected at Day 4, Day 8, and Day 9. The fecal samples were collected using the OMNIgene GUT sample collection kits (OMR-200, DNA Genotek, Ontario, Canada) and stored at room temperature away from light until all samples were collected. DNA isolated from the fecal samples was subjected to deep sequencing of the intestinal microbiome and analyses.

On Day 2, after 3 ertapenem doses, animals were bled and serum collected. Blood was collected aseptically from the vena cava from anesthetized animals. Three blood draws were performed, at 1 hour, 3 hours, and 8 hours after amoxicillin administration. A Telazol cocktail was administered intramuscularly at a minimal dose (1 mL or less per 50 lbs) to achieve light anesthesia/sedations. At each timepoint, approximately 9 mL of blood was collected into a serum separator vacutainer tube. After coagulation, samples were centrifuged and the serum was transferred to a cryovial and stored at −80° C. until shipment to the evaluation laboratory (Center for Anti-Infective Research and Development, Hartford Hospital, Hartford, Conn.).

Ertapenem levels in the pig serum were quantified using a modification of a validated HPLC-based assay (Xuan et al. (2002). Pharmacodynamic assessment of ertapenem (MK-0826) against *Streptococcus pneumoniae* in a murine neutropenic thigh infection model. Antimicrobial Agents and Chemotherapy, 46:2990-2999). The standard curve was comprised of 6 points ranging from 0.25 to 50 µg/ml for the ertapenem. The standard curve was prepared in the blank pig serum. The Quality Control (QC): 0.5 µg/ml (QC Low), and 40.0 µg/ml (QC High). The assay was linear over a range of 0.25 to 50 µg/mL (R=0.999). Interday coefficients of variation for the low (0.5 µg/mL) and high (40 µg/mL) quality control samples were 5.2% and 7.1%, respectively. Interday coefficients of variation were 4.7% and 3.8%, respectively. Peak height was used to integrate all the peaks. Sigma Plot was used to calculate drug concentrations and a −1 weighting factor was used. All standard curves were acceptable.

Figure 45:
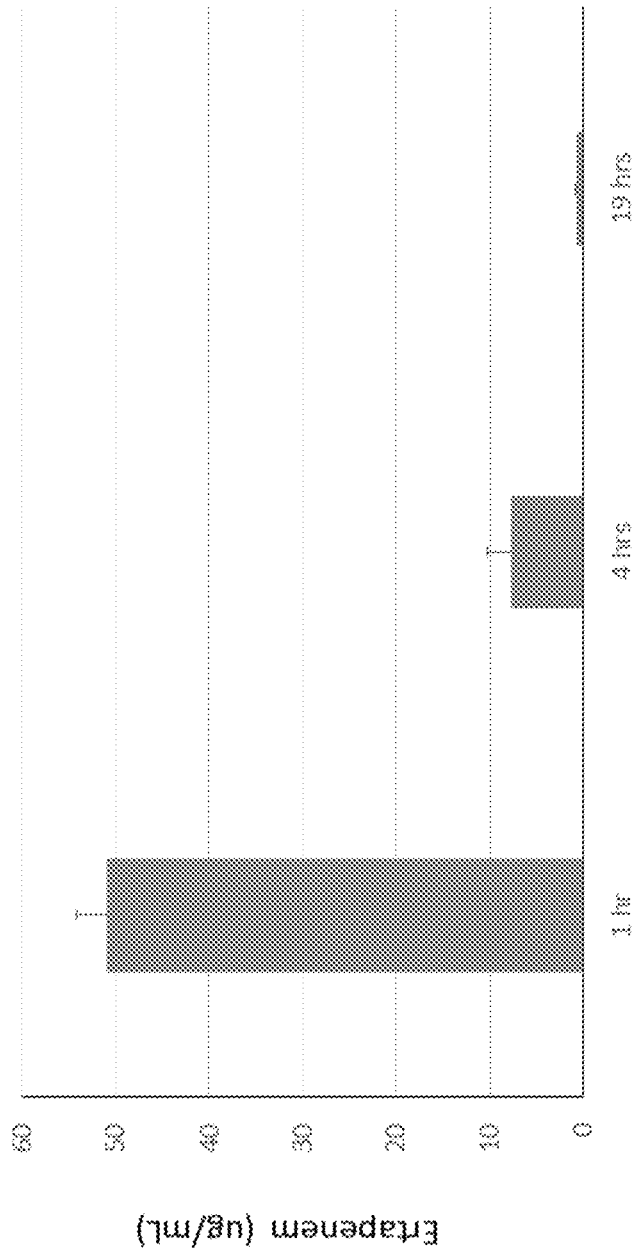
FIG. 45 depicts ertapenem levels in the pig serum. Ertapenem was quantified in the pig serum using an HPLC-based assay (Xuan et al., 2002). The data are displayed as the mean+standard deviation.

The limit of detection of the assay was 0.5 ug/mL. The ertapenem levels were reported as the mean and standard deviation (FIG. 45).

DNA was isolated from the fecal samples and subjected to whole genome shotgun sequencing using an Illumina HiSeq system with a target of 20 million 100 bp single reads per sample. DNA isolation and sequencing were performed. Sequenced datasets were taxonomically classified using the GENIUS® software package (Hasan et al., 2014, Lax et al., 2014) by CosmosID, Inc. (Rockville, Md.).

Figure 46:
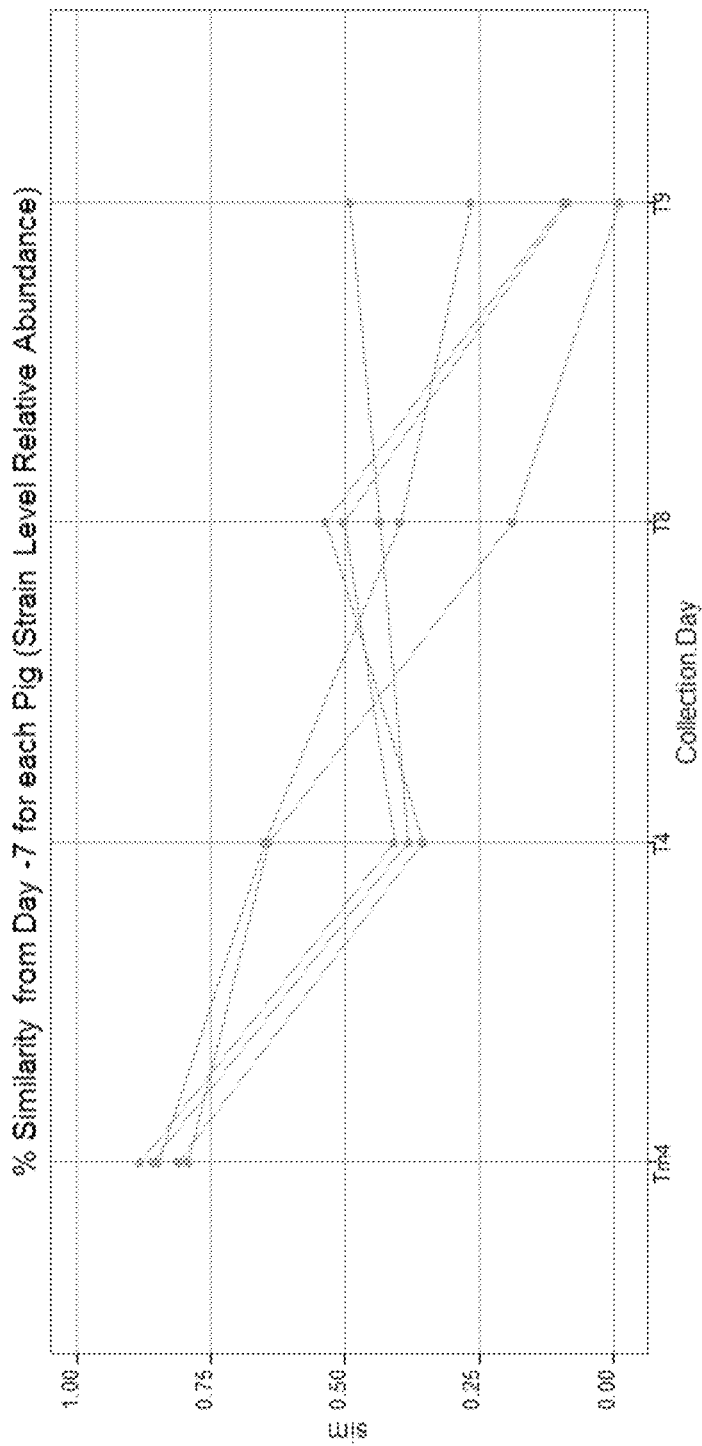
FIG. 46 shows strain relative abundance percent similarity. The percent similarity based on the relative abundance of the bacterial strains identified from sequence analysis of the fecal DNA samples was compared for the ertapenem treated animals (n=5) Day −7 to Day 9.

The percent similarity based on the relative bacterial strain abundance was calculated. The percent similarity from Day −7 to Day 9 of the ertapenem-treated animals was compared for each day, Day −7, Day −4, Day 4, Day 8 and Day 9 (FIG. 46). The diversity of the microbiome decreased from Day −7 to Day −4 in both groups. As the animals were in the process of acclimating and were not yet treated at Day −4, these data suggest that the microbiome was changing based on the new environment. Animals began ertapenem treatment on Day 1 and the percent similarity decreased every day the animals were evaluated. These data demonstrate that ertapenem causes a loss of diversity in the microbiome of treated pigs.

Figure 47:
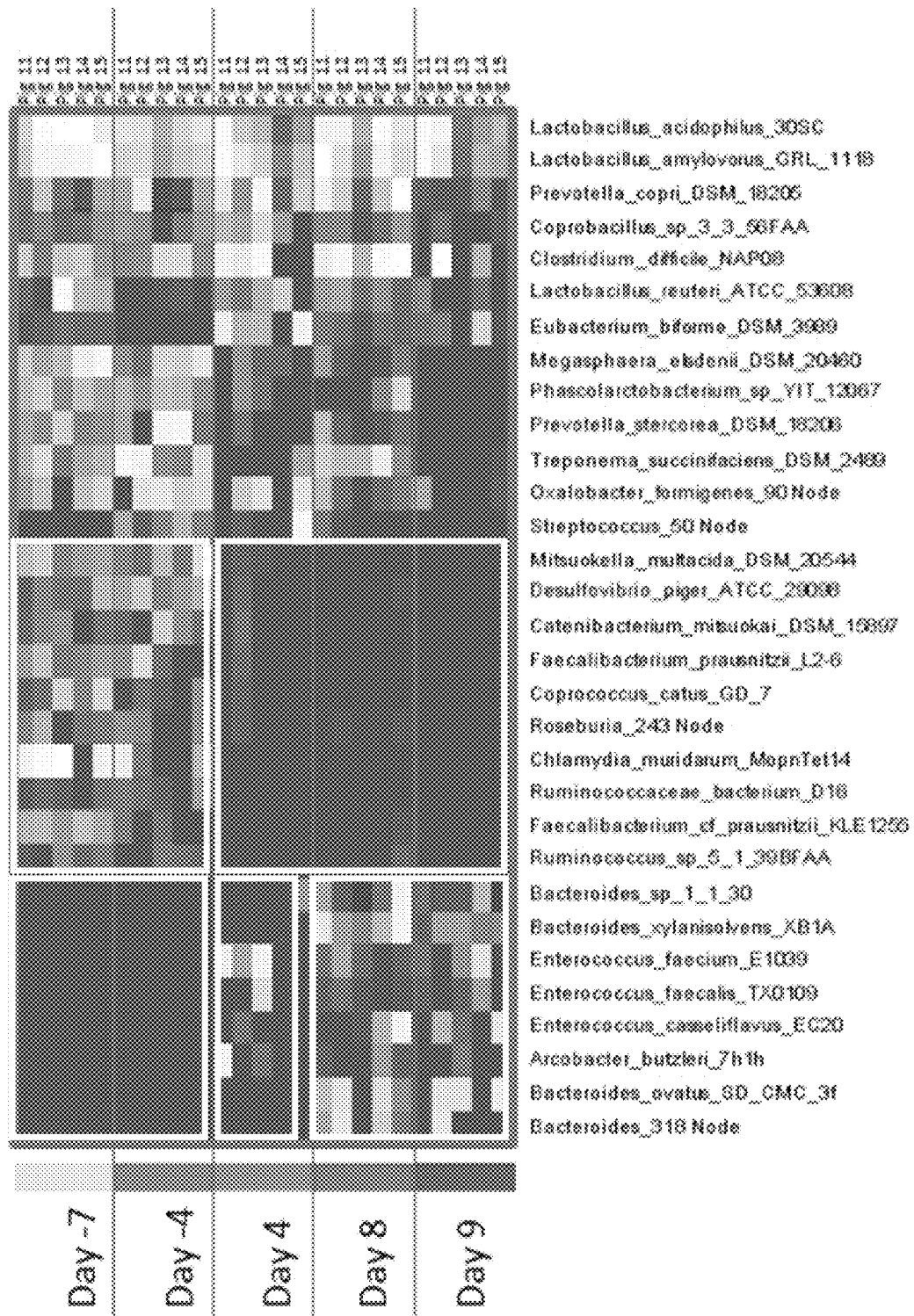
FIG. 47 depicts strain abundance heat map. Heatmaps of the bacterial taxa were constructed based on the relative abundance of each bacterial strain and organized chronologically by study day. The pigs are labeled on the right side of the figure, and the study days are indicated by the different colored bars on the right side of the figure. The individual bacterial strains are displayed on the bottom. The lighter boxes on the right side of the figure indicate bacterial strains that were decreased in the ertapenem treated group. The white boxes on the left side of the figure indicate bacterial strains that became more abundant in the ertapenmen treated animals.

Heatmaps of the bacterial taxa were constructed based on the relative abundance of each bacterial strain and organized chronologically by study day and by animal (FIG. 47). The abundance of some bacterial species decreased in the ertapenem-treated pigs by Day 4. Similarly, some bacterial species increased in abundance in the ertapenem-treated pigs. These data demonstrate that ertapenem disrupts the microflora in the pig gut.

A statistical analysis was performed to determine the probability that the microbiomes before and after antibiotic treatment remained the same or were different. The microbiome sequence data were analyzed using a parameterization of the Dirichlet-Multinomial distribution (La Rosa et al., 2012) to perform a Likelihood Ratio Test. The pretreatment Day −4 and the posttreatment Day 8 and Day 9 microbiomes of the ertapenem-treated pigs were compared. The p value obtained comparing the Day 4 microbiomes to the Day −4 microbiomes was $1.7 \times 10^{-19}$. The p value obtained comparing the Day 8 microbiomes to the Day −4 microbiomes was $<1.0 \times 10^{-25}$. The p value obtained comparing the Day 9 microbiomes to the Day −4 microbiomes was $7.0 \times 10^{-16}$. These data demonstrate that ertapenem significantly alters the bacterial populations in the pig gut.

Example 30. Evaluation of Oral Delivery of P2A to Pigs to Protect the Microbiome from the Effects of Ertapenem A study is performed using normal piglets to determine if P2A, when delivered orally with IV ertapenem functions to protect the microbiome from ertapenem-induced dysbiosis. The study also tests if P2A affects the serum levels of ertapenem (Table 30).

TABLE 30

Piglet study design

| Group (N = 5) | Antibiotic | Antibiotic Delivery | P2A |
|---|---|---|---|
| 1 Pig 1, 2, 3, 4, 5 | Ertapenem (30 mg/kg) | IV, 1X per day 12 pm | None |
| 2 Pig 6, 7, 8, 9, 10 | Ertapenem (30 mg/kg) | IV, 1X per day 12 pm | 1 size 0 capsule (75 mg), QID 7am, 12 5 pm, 10 pm pm |

A total of ten, two month old Yorkshire piglets, approximately 20 kg each, are used for this study. All 10 animals are treated with IV ertapenem once a day for a total of 7 days, and one cohort of 5 animals is also treated with oral P2A four times a day for a total of 9 days. The P2A treatment is started the day before ertapenem treatment and continued for a day after ertapenem is stopped.

Two pre-treatment fecal samples are obtained, the first 4 days after the animals arrive at the animal treatment facility (Day −7), and the second 7 days after arrival (Day −4). An additional 3 fecal samples are collected at Day 4, Day 8, and Day 9. The fecal samples are collected using the OMNIgene GUT sample collection kits (OMR-200, DNA Genotek, Ontario, Canada) and stored at room temperature away from light until all samples are collected. DNA isolated from the fecal samples is subjected to deep sequencing of the intestinal microbiome and analyses.

On Day 2, after 2 ertapenem doses, animals are bled and serum collected. Blood is collected aseptically from the vena cava from anesthetized animals. Three blood draws are performed, at 1 hour, 4 hours, and 10 hours after ertapenem administration. A Telazol cocktail is administered intramuscularly at a minimal dose (1 mL or less per 50 lbs) to achieve light anesthesia/sedations. At each timepoint, approximately 9 mL of blood is collected into a serum separator vacutainer tube. After coagulation, samples are centrifuged and the serum is transferred to a cryovial and stored at −80° C. until shipment to the evaluation laboratory (Sannova Analytical, Inc., Somerset, N.J.).

It is expected that administration of P2A protects the microbiome from the effects of ertapenem and that P2A does not affect the serum levels of ertapenem. The data supports the use of P2A as a therapy to prevent carbapenem-mediated gut dysbiosis.

Example 31. Genetically-Modified Yeast for Delivery of Carbapenemases to the Intestinal Tract Genetically-modified microorganisms are tested as a delivery vehicle to administer carbapenemases, P2A NDM, and/or KPC, to the intestinal track to protect the microbiome while not affecting antibiotic absorption and therefore, antibiotic efficacy.

Yeasts genetically-modified to produce the antibiotic-degrading enzymes, P2A, NDM, and/or KPC, are produced similarly to that described for the *C. difficile* toxin-binding proteins in PCT/US15/58967, the contents of which are hereby incorporated by reference in their entirety. Briefly, the P2A, NDM, or KPC coding region is codon optimized for expression in the yeast, *S. cerevasiae*, modified to reduced DNA homologies, and evaluated for the presence of N-linked glycosylation sites, synthesized and cloned into the yeast expression plasmid, pD1214 (DNA 2.0) that contains the strong, constitutive TEF promoter, and a selectable URA3+ marker. Different *S. cerevasiae* leader sequences that facilitate secretion are known and are utilized to mediate P2A, NDM, or KPC secretion. A series of *S. cerevasiae* secretion vectors are available which contain a panel of different leader sequences to facilitate secretion. An illustrative secretion signal is the yeast mating factor alpha (MAT alpha) signal, which is a 89 amino acid sequence composed of the signal and the prosequence which is cleaved in the Golgi by Kex2, an endogenous yeast protease, to yield the mature, secreted protein. The invertase and other signal sequences are naturally cleaved during translocation and secretion of the protein by signal peptidase and do not require additional protease cleavage steps.

At least two strategies are used to generate *S. cerevasiae*, substrain *boulardii*, transformants that secrete P2A, NDM, or KPC.

One strategy is the production of a *S. boulardii* URA3 knockout strain to allow the use of the P2A NDM, and/or KPC expression plasmids that contain the URA3 selectable marker to generate transformants (non-integrated, containing the plasmids) to use in efficacy evaluation in rodents and/or pigs. The *S. boulardii* URA3 knockout was generated using the CRISPR recombination system (DiCarlo et al, 2013, Nucleic Acids Res. 41:4436). The *S. boulardii* strain, designation Sb48 (ATCC Product # MYA-796) submitted to ATCC by D. A. Stevens (McCullough et al., 1998; J. Clinical Microbiology, 36:2613) was used for these studies. Three potential wild-type Cas9 cleavage sites in the upstream region of the URA3 gene were identified and approximately 500 bp of the regions surrounding these target sites are sequenced to ensure the presence of the sites in this yeast strain. A homology construct was designed that contains an approximate 10 bp region in the middle replaced by an insert that contains multiple stop codons in all frames ensuring that the first stop codon is in the URA3 reading frame. The CRISPR system was used to create the recombination/insertion and the URA3-clones are selected on FOA (5-fluoroorotic acid) media. 5-FOA allows the selection for URA3-mutants, as an active URA3 gene (encodes orotidine 5-phosphate decarboxylase) converts FOA into a toxic compound causing cell death. The selected clones were then tested to ensure that they will not grow on media without uracil. Selected clones were sequenced to verify the expected integration.

Once the S. boulardii strain is confirmed to be URA3−, the yeast are transformed with the P2A, NDM, or KPC encoding plasmids. Clones are identified by plating on media without uracil. The resulting transformants are screened for secretion of P2A, NDM, or KPC using SDS/PAGE. Filtered yeast supernatants are evaluated for activity using the CENTA beta-lactamase biological activity assay (Bebrone et al., Antimicrob. Agents Chemother (2001) 45:1868-1871).

The second strategy generates stable integrants in the wild-type S. boulardii strain using a neomycin resistance gene (neo) as the selectable marker. Without neo expression, S. boulardii is sensitive to G418. The S. boulardii strain, designation Sb48 (ATCC Product # MYA-796) submitted to ATCC by D. A. Stevens (McCullough et al., 1998; J. Clinical Microbiology, 36:2613), or commercially available ATCC, is used for these studies. Integration regions are chosen based on Flagfeldt et al (2009, Yeast 26:545), where chromosomal integration sites were screened for high level heterologous gene expression. The integration sites that show the highest expression levels, Regions 20, 21, and 19 are sequenced in the wild-type S. boulardii strain to verify their presence. Once verified, a region is chosen and plasmids containing integration cassettes are designed. The integration cassettes containing the P2A, NDM, or KPC expression cassette, a neo expression cassette, at least 500 bp of homology sequence from the upstream part of the integration region and at least 500 bp of homology sequence from the downstream part of the integration region so that the integration region is deleted via the homologous recombination event. The wild-type S. boulardii is transformed with the integration cassettes and clones are selected for G418 resistance. Clones are picked, cultures grown, and supernatants screened for the presence of the P2A, NDM, or KPC protein via SDS/PAGE. Filtered yeast supernatants are evaluated for biological activity using the CENTA beta-lactamase biological activity assay [Bebrone et al., Antimicrob. Agents Chemother (2001) 45:1868-1871). Clones are chosen, based on protein expression levels and biological activity, and the insert is sequenced to verify the integrity of the integrated sequence.

The P2A, NDM, or KPC-expressing yeast are tested in a rodent, pig, and/or dog model(s) to determine if the carbapenem-degrading yeast are efficacious in the degradation of an antibiotic, without affecting antibiotic absorption. For pig or dog studies, cohorts (n=3-5) of normal young pigs or beagle dogs are treated with the genetically modified yeast and the antibiotic, such as meropenem for 5-7 consecutive days (Table 20). Yeast treatment is started 3 days prior to antibiotic treatment (or concurrently with) and maintained throughout the antibiotic treatment period. Plasma and stool is collected daily, beginning the day prior to treatment yeast treatment (Day −4) and prior to antibiotic treatment (Day −1). A cohort of animals is treated with clindamycin as a positive control for microbiome damage. Plasma is monitored for meropenem levels and stool is subjected to 16S RNA sequencing and/or shotgun DNA sequencing to monitor the diversity of the microbiome. Antibiotic levels in the stool are also measured. It is expected that at one or both of the meropenem/yeast doses, the plasma levels of meropenem are not affected while the microbiome is protected, indicating that the P2A, NDM, or KPC degraded the meropenem excreted into the intestine following IV meropenem delivery. Other carbapenem and cephalosporin antibiotics are evaluated in an analogous manner. See Table 31 for experimental design.

TABLE 31

Treatment of Normal Pigs and/or Dogs with S. boulardii expressing P2A, NDM, or KPC and a Parenteral Antibiotic (Meropenem)

| Cohort (n = 3-5) | Antibiotic Intraperitoneal | S. boulardii oral |
|---|---|---|
| 1 | none | none |
| 2 | Clindamycin (IP) (30 mg/kg) | none |
| 3 | Meropenem (IP) High dose (30 mg/kg BID) | S. boulardii wt $3 \times 10^{10}$ cfu BID |
| 4 | Meropenem (IP) High dose (30 mg/kg BID) | S. boulardii P2A, NDM, or KPC-expressing $3 \times 10^{10}$ cfu BID |
| 5 | Meropenem (IP) High dose (30 mg/kg BID) | none |
| 6 | Meropenem (IP) Low Dose (15 mg/kg BID) | S. boulardii wt $3 \times 10^{10}$ cfu BID |
| 7 | Meropenem (IP) Low Dose (15 mg/kg BID) | S. boulardii P2A, NDM, or KPC-expressing $3 \times 10^{10}$ cfu BID |
| 8 | Meropenem (IP) Low Dose (15 mg/kg BID) | none |

Example 32. In Vivo Analysis of Yeast-Expressed P2A, NDM, or KPC in Hamster CDI Model P2A, NDM, or KPC-expressing yeast is evaluated in the prevention of C. difficile infection and disease in a hamster model of C. difficile disease.

The S. boulardii transformants expressing P2A, NDM, and/or KPC are evaluated in rodent models of C. difficile disease (CDI), including the Syrian Golden hamster (Mesocricetus auratus) C. difficile model (Sambol and Tang, 2001; J. Infect. Disease 183:1760) as described in Example 12.

To evaluate the prophylactic potential of the S. boulardii transformants expressing P2A, NMD, or KPC, the yeast are administered, via oral gavage, at doses ranging $2 \times 10^8$ to $2 \times 10^{10}$ cfu/animal daily beginning at the time of antibiotic administration, 5 or 1 day prior to C. difficile infection, and continued for the duration of the studies, up to 28 days. As yeast are not sensitive to antibiotics, the yeast will remain viable even in the presence of antibiotics. Disease is compared in animals that receive clindamycin or meropenem (Antibiotic). The efficacy of the P2A, NDM, or KPC-expressing yeast are compared to control animals that receive no treatment, animals that receive the standard of care, vancomycin (20 mg/kg orally daily beginning at 24 hours after infection and continued for 5 days), or animals that receive both vancomycin and the yeast. Efficacy evaluations include mortality and evaluation of *C. difficile* bacteria titers and/or *C. difficile* toxins A and B in cecal contents, at the time of death or at the end of the study following euthanasia. It is expected that administration of meropenem and the P2A, NMD, or KPC-expressing yeast does not affect blood levels of the antibiotic and protects the animals from CDI, indicating that the yeast expressed the antibiotic-inactivating enzyme which functioned to degrade meropenem antibiotic excreted into the intestine following antibiotic absorption. Table 32 below shows the experimental design.

TABLE 32

P2A, NDM, or KPC-Expressing Yeast *C. difficile* Efficacy Hamster Study Treatment Groups

| Cohort (n = 6-10) | Antibiotic Intraperitoneal | *C. diff* innoculation | Treatment |
|---|---|---|---|
| 1 | none | None | none |
| 2 | Clindamycin (30 mg/kg) | + | none |
| 3 | Meropenem 30 mg/kg BID | + | none |
| 4 | Meropenem 30 mg/kg BID | + | vancomycin |
| 5 | Meropenem 30 mg/kg BID | + | wt yeast High dose ($10^{10}$ cfu BID) |
| 6 | Meropenem 15 mg/kg BID | + | P2A, NDM, or KPC yeast High dose ($10^{10}$ cfu BID) |
| 7 | Meropenem 15 mg/kg BID | + | P2A, NDM, or KPC yeast Low dose ($10^{8}$ BID) |
| 8 | Meropenem 30 mg/kg BID | + | Vancomycin + P2A, NDM, or KPC yeast High dose ($10^{10}$ cfu BID) |

Example 33. In Vivo Analysis of Yeast-Expressed P2A, NDM, or KPC in Porcine Model of CDI P2A, NDM, or KPC-expressing yeast is evaluated in the prevention of *C. difficile* infection and disease in a humanized pig model of *C. difficile* disease.

The *S. boulardii* transformants expressing P2A, NDM, and/or KPC are tested in a humanized pig model of CDI. The humanized pig model is described in Example 13. The humanized pigs are treated with antibiotics (clindamycin or merpenemen) to disrupt their intestinal microbiome and then exposed to *C. difficile* after which they develop CDI including *C. difficile* associated diarrhea (CDAD).

To test the prophylactic potential of P2A, NDM, and/or KPC-expressing yeast, the yeast are administered one day prior to antibiotic treatment (Day −1), or at the same time as, and delivered BID for the duration of the antibiotic treatment. Yeast are given at doses ranging from $5 \times 10^9$ to $6 \times 10^{10}$ cfu/animal. Clindamycin is delivered 1 to 5 days prior to *C. difficile* inoculation and serves as the positive control for microbiome damage and *C. difficile* infection. Meropenem is delivered beginning 1 to 5 days prior to *C. difficile* inoculation, and maintained for 5-7 days. The antibiotics are used to disrupt the intestinal microbiome to predispose the animals to *C. difficile* infection. *C. difficile* vegetative cells or spores are administered, at doses ranging from $10^6$ to $10^8$, and animals are monitored for CDI symptoms including CDAD. CDI is compared in animals that receive clindamycin or meropenem (Antibiotic). The efficacy of the P2A, NDM, and/or KPC-expressing yeast treatment groups are compared to control animals that receive no treatment, animals that receive the standard of care, vancomycin (20 mg/kg orally daily beginning 24 hours after infection and continued for 5 days), or animals that receive both vancomycin and P2A, NDM, and/or KPC-expressing yeast. It is expected that treatment with meropenem and the P2A, NMD, or KPC-expressing yeast does not affect blood levels of the antibiotic and protects the animals from CDI, indicating that the yeast expressed the antibiotic-inactivating enzyme which functioned to degrade meropenem antibiotic excreted into the intestine following antibiotic absorption. Table 33 below shows the experimental design.

TABLE 33

P2A, NDM, or KPC-Expressing Yeast *C. difficile* Efficacy Pig Study Treatment Groups

| Cohort (n = 2-3) | Antibiotic | *C. diff* innoculation | Treatment |
|---|---|---|---|
| 1 | none | None | none |
| 2 | Clindamycin (30 mg/kg) | + | none |
| 3 | Meropenem 30 mg/kg BID | + | none |
| 4 | Meropenem 30 mg/kg BID | + | vancomycin |
| 5 | Meropenem 30 mg/kg BID | + | Wt yeast High dose ($3 \times 10^{10}$ cfu BID) |
| 6 | Meropenem 15 mg/kg BID | + | P2A, NDM, or KPC yeast High dose ($3 \times 10^{10}$ cfu BID) |
| 7 | Meropenem 15 mg/kg BID | + | P2A, NDM, or KPC yeast Low dose ($2.5\ 10^9$ BID) |
| 8 | Meropenem 30 mg/kg BID | + | Vancomycin + P2A, NDM, or KPC yeast High dose ($3 \times 10^{10}$ cfu BID) |

EQUIVALENTS

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

Those skilled in the art will recognize, or be able to ascertain, using no more than routine experimentation, numerous equivalents to the specific embodiments described specifically herein. Such equivalents are intended to be encompassed in the scope of the following claims.

INCORPORATION BY REFERENCE

All patents and publications referenced herein are hereby incorporated by reference in their entireties.

The publications discussed herein are provided solely for their disclosure prior to the filing date of the present application. Nothing herein is to be construed as an admission that the present invention is not entitled to antedate such publication by virtue of prior invention.

As used herein, all headings are simply for organization and are not intended to limit the disclosure in any manner. The content of any individual section may be equally applicable to all sections.

REFERENCES

The following references are hereby incorporated by reference in their entireties:

Bebrone, C, Lassaux, P, Vercheval, L, Sohier, J S, Jehaes, A, Sauvage, E, Galleni, M. (2010). Current challenges in antimicrobial chemotherapy: focus on beta-lactamase inhibition. Drugs 70:651-679.

Bebrone, C, Moall, C, Mahy, G, Rival, S, Docquier, J D<Rossolini, G M, Fastrez, J, Pratt, R F, Frere, J-M, Galleni, M. (2001). CENTA as a chromogenic substrate for studying beta-lactamases. Antimicrob Agents and Chemo. 45:1868-1871.

Bevan, A, Brenner, C, Fuller, R S. (1998). Quantitative assessment of enzyme specificity in vivo: P2 recognition by KEx2 protease defined in a genetic system. PNAS 95:10384-10389.

DiCarlo, J E, Norville, J E, Mali, P, Rios, X, Aach, J, Church, G M. (2013). Genome engineering in *Saccharomyces cerevisiae* using CRISPR-Cas systems. Nucl. Acids Res. 41: 4333.

Edwards-Ingram, L, Gitsham, P, Burton, N, Warhurst, g, Clarke, I, Hoyle, D, Oliver, S G, Stateva, L. (2007). Genotypic and physiological characterization of *Saccharomyces boulardii*, the probiotic strain of *Saccharomyces cerevisiae*. Appl. Environ. Microbiol. 73:2458.

Flagfeldt, D B, Siewers, V, Huang, L, Nielsen, J. (2009). Characterization of chromosomal integration sites for heterologous gene expression in *Saccharomyces cerevisiae*. Yeast 26:545.

Freeman, J, Wilcox, M H. (1999). Antibioitics and *Clostridium difficile*. Microbes Infect. 1:377-384.

Garrait, G, Jarrige, J F, Blanquet-Diot, S, Alric, M. (2009). Genetically engineered yeasts as a new delivery vehicle of active compounds to the digestive tract: In vivo validation of the concept in the rat. Metabolic Engineering 11:148-154.

Graff, S, Chaumeil, J-C, Boy, P, Lai-Kuen, R, Charrueau, C. (2008). Influence of pH conditions on the viability of *Saccharomyces boulardii* yeast. J. Gen. Appl. Microbiol. 54:221-227.

Green, V L, Verma, A, Owens, R J, Phillips, S E V, Carr, S B. (2011). Structure of New Delhi metallo-beta-lactamase I (NDM-1). Acta Cryst. F67:1160-1164.

Hatoum R, Labrie, St, Fliss, I. (2012). Antimicrobial and probiotic properties of yeasts: from fundamental to novel applications. Frontiers in Microbiology 3: 421-421.

Hou, J, Tyo, K E J, Liu, Z, Petranovic, D, Nielsen, J. (2012). Metabolic engineering of recombinant protein secretion by *Saccharomyces cerevisiae*. FEMS Yeast Res. 12:491-510.

Kelesidis, T, Pothoulakis, C. (2012). Efficacy and safety of the probiotic *Saccharomyces boulardii* for the prevention and therapy of gastrointestinal disorders. Therapeutic Advances in Gastroenterology 5:111.

Kim, Y, Cunningham, M A, Mire, J, Tesar, C, Sacchettini, J, Joachimiak, A. (2013). NDM-1, the ultimate promiscuous enzyme: substrate recognition and catalytic mechanism. FASEB J. 27:1917-1927.

Kim, Y, Tesar, C, mire, J, Jedrzejczak, R, Bindowski, A, Babnigg, G., Sacchettini, J, Joachimaik, A. (2011). Structure of Apo- and monometalated forms of NDM-1; A highly potent carbapenem-hydrolyzing metallo-beta-lactamase. PLOS One 6:e24621.

King, D, Strynadka, N. (2011). Crystal structure of New Delhi metallo-beta-lactamase reveals molecular basis for antibiotic resistance. Protein Sci. 20:1484-1491.

Klein, S M, Elmer, G W, McFarland, L V, Surawicz, C M, Levy, R H. (1993). Recovery and elimination of the biotherapeutic agent, *Saccharomyces boulardii*, in healthy human volunteers. Pharm Res. 10:1615-1619.

LaRosa, P. S. et al. (2012). Hypothesis testing and power calculations for taxonomic-Based human microbiome data. PLoS ONE 7, e52078.

Li, T, Wang, Q, Chen, F, Li, X, Luo, S, Fang, H, Wang, D, Li, Z, Hou, X, Wnag, H. (2013). Biochemical characteristics of New Delhi Metallo-beta-lactamase-1 show unexpected difference to other MBLs. PLOS One 8:e61914.

Liang, Z, Li, L, Wang, Y, Chen, L, Kong, X, Hong, Y, Lan, I, Zheng, M, Guang-Yang, C, Liu, H, Shen, X, Luo, C, Li, K K, Chen, K, Kiang, H. (2011). Molecular basis of NDM-1, a new antibiotic resistance determinant. PLOS One 6:e23606.

Liu, F, Moreno, P, Basit, A W. (2010). A novel double-coating approach for improved pH-triggered delivery to the ileo-colonic region of the gastrointestinal tract. European J. Pharm. Bioparrma. 74:311-315.

Makena, A, Brem, J, Pferrer, I, Geffen, R E J, Wilkins, S E, Tarhonskaya, H, Flashman, E, Phee, L M, Wareham, D W, Schofield, C J. (2015). Biochemical characterization of New Delhi metallo-beta-lactamase variants reveals differences in protein stability. J. Antimicrob, Chemother. 70:463-469.

McCoullough, M J, Clemons, K V, McCusker, J H, Stevens, D A. (1998). Species identification and virulence attributes of *Saccharomyces boulardii*. J. Clin. Microbiol. 36:2613.

Nakamura, A, Nakazawa, K, Miyakowawa, I, Mizukoshi, S, Tsurubuchi, K, Nakagawa, M, O'Hara, K, Sawai, T. (2000). Macrolide esterase-producing *Escherichia coli* clinically isolated in Japan. J. Antibiotics 53:516-524.

Otten, S L, Rosazza, J P. (1983). Oxidative ring fission of the naphthoquinones lapachol and dichloroallyl lowsone by *Penicillium notatum*. J. Biol. Chem. 258:1610-1613.

Papp-Wallace, K M, Bethel, C R, Kistler, A M, Kasuboski, C., Taracila, M., Bonomo, R A. (2010). Inhibitor resistance in the KPC-2 beta-lactamase, a preeminent property of this class A beta-lactamase. Antimicrobial Agents and Chemotherapy 54:890-897.

Parshikov, I A, Sutherland, J B. (2012). Microbial transformations of antimicrobial quinolones and related drugs. J. Ind. Microbiol. Biotechnol. 39:1731-1740.

Queenan, A M, Bush, K. (2007). Carbapenemases: the versatile beta-lactamases. Clin. Micro. Rev. 20:440-458.

Sambol, S P, Tang, J K. (2001). Infection of hamsters with epidemiologically important strains of *Clostridium difficile*. J. Infect. Diseases 183:1760.

Shen, B, Yu, Y, Chen, H, Cao, X, Lao, X, Fang, Y, Shi, Y, Chen, J, Zheng, H. (2013). Inhibitor discovers of full-length New Delhi Metallo-beta-lactamase-1 (NDM-1). PLOS One 8:e62955.

Steele, J, Feng, H, Parry, N, Tzipori, S. (2010). Piglet models for acute or chronic *Clostridium difficile* illness (CDI). J. Infect. Dis. 201:428.

Thomas, P W, Zheng, M, Wu, S, Guo, H, Liu, D, Xu, D, Fast, W. (2011). Characterization of purified New Helhi Metallo-beta-lactamase-1. Biochemistry 50:10102-10113.

Varum, F J O, Hatton, G B, Freire, A C, Basit, A W. (2013). A novel coating for ileo-colonic drug targeting: Proof of concept in humans using scintigraphy. European J. Pharm. Bioparrma. 84:573-577.

Van Berkel, S, Brem, J, Rydzik, A M, Salimraj, R, Cain, R, Verma, A, Owens, R J, Gishwick, C W G, Spencer, J, Schofield, C J. (2013). Assay platform for clinically relevant metallo-beta-lactamases. J. Med. Chem. 56:6945-6953.

Wetzstein, H-G, Schneider, J, Karl, W. (2012). Metabolite providing fungal cleavage of the aromatic core part of a fluoroquinolone antibiotic. AMB Express 2:3.

Xuan et al. (2002). Pharmacodynamic assessment of ertapenem (MK-0826) against *Streptococcus pneumoniae* in a murine neutropenic thigh infection model, Antimicrobial Agents and Chemotherapy, 46:2990-2999.

Yang, H, Aitha, M, Hetrick, A M, Richmond, T K, Tierney, D L, Crowder, M W. (2012). Mechanistic and spectroscopic studies of metallo-beta-lactamase NDM-1. Biochemistry 51:3839-3847.

Yigit, H, Queenan, A M, Anderson, G J, Domenech-Sanchez, A, Biddle, J W, Steward, C D, Alberti, S, Bush, K, Tenover, F C. (2001), Novel carbapenem-hydrolyzing beta-lactamase, KPC-1, from a carbapenem-resistant strain of *Klebsiella pneumoniae*. Antimicrobial Agents and Chemotherapy 45:1151-1161.

Yigit, H, Queenan, A M, Rasheed, J K<Biddle, J W, Domenech-Sanchez, A, Alberti, S, Bush, K, Tenover, F C. (2003). Carbapenem-resistant strain of *Klebsiella oxytoca* harboring carbapenem-hydrolyzing beta-lactamase KPC-2. Antimicrobial Agents and Chemotherapy 47:3881-3889.

Yong, D, Toleman, M A, Giske, C G, Cho, H S, Sundman, K, Lee, K, Walsh, T R. (2009). Characterization of a new metallo-beta-lactamase gene, blaNDM-1, and a novel erythromycin esterase gene carried on a unique genetic structure in *Klebsiella pneumoniae* sequence type 14 from India. Antimicrobial Agents and Chemotherapy 53:5046-5054, Zhang, H, Hao, Q. (2011). Crystal structure of NDM-1 reveals a common beta-lactam hydrolysis mechanism. FASEB J. 25:2574-2582.

Zhang, Q, Widmer, G, Tzipori, S. (2013). A pig model of the human gastrointestinal tract. Gut Microbes 4:193.

---

What is claimed is:

1. A method for producing a recombinant carbapenemase in *Escherichia coli* (*E. coli*), comprising:
   (a) providing a host *E. coli* cell transformed with a vector comprising a sequence encoding the carbapenemase;
   (b) culturing the *E. coli* cell to induce expression of the carbapenemase; and
   (c) recovering the carbapenemase from a soluble fraction prepared from the cytoplasm or periplasmic space of the *E. coli* cell, wherein:
   the carbapenemase comprises at least 95% sequence identity with the amino acid sequence of SEQ ID NO: 68 (P2A), and
   the culturing is in the presence of about 100 µM zinc, such that the amount of carbapenemase in the soluble fraction is increased and the amount of carbapenemase in inclusion bodies is reduced, relative to culturing in the absence of zinc.

2. The method of claim 1, wherein the carbapenemase has the amino acid sequence of SEQ ID NO: 68 (P2A).

3. The method of claim 1, wherein the method yields about 10 grams of active carbapenemase per liter of culture.

4. The method of claim 1, wherein the method yields about 15 grams of active carbapenemase per liter of culture.

5. The method of claim 1, wherein the zinc is in the form of $ZnSO_4$.

6. The method of claim 1, wherein the culturing is in a bioreactor or a shake flask.

7. The method of claim 1, wherein the *E. coli* cell is induced to express the carbapenemase using isopropyl β-D-1-thiogalactopyranoside (IPTG).

8. A method for producing a recombinant carbapenemase in *Escherichia coli* (*E. coli*), comprising:
   (a) providing a host *E. coli* cell transformed with a vector comprising a sequence encoding the carbapenemase;
   (b) culturing the *E. coli* cell to induce expression of the carbapenemase; and
   (c) recovering the carbapenemase from a soluble fraction prepared from the cytoplasm or periplasmic space of the *E. coli* cell, wherein:
   the carbapenemase comprises at least 95% sequence identity with the amino acid of SEQ ID NO: 53 (NDM-1), and
   the culturing is in the presence of about 100 µM zinc, such that the amount of carbapenemase in the soluble fraction is increased and the amount of carbapenemase in inclusion bodies is reduced, relative to culturing in the absence of zinc.

9. The method of claim 8, wherein the carbapenemase has the amino acid sequence of SEQ ID NO: 53 (NDM-1).

10. The method of claim 8, wherein the method yields about 10 grams of active carbapenemase per liter of culture.

11. The method of claim 8, wherein the method yields about 15 grams of active carbapenemase per liter of culture.

12. The method of claim 8, wherein the zinc is in the form of $ZnSO_4$.

13. The method of claim 8, wherein the culturing is in a bioreactor or a shake flask.

14. The method of claim 8, wherein the *E. coli* cell is induced to express the carbapenemase using isopropyl β-D-1-thiogalactopyranoside (IPTG).

* * * * *

SEQUENCE LISTING

```
<160> NUMBER OF SEQ ID NOS: 78

<210> SEQ ID NO 1
<211> LENGTH: 657
<212> TYPE: DNA
<213> ORGANISM: Artificial Sequence
<220> FEATURE:
<223> OTHER INFORMATION: Synthetic sequence

<400> SEQUENCE: 1
atggaaacgg gcaccattag cattagccaa ctcaacaaaa acgtttgggt ccacaccgag      60
ttaggctatt tcaacggtga agccgtgccg agcaatggtt tggttctgaa tacgtccaag     120
ggtctggtgt tggtagactc cagctgggac aataagctga ccaaagaact gatcgaaatg     180
gttgagaaaa agttccagaa gcgtgtgact gatgtcatta tcacccatgc gcacgcggac     240
cgcatcggtg gcattaccgc gctgaaagag cgtggcatta aagcacatag cacggcactg     300
acggctgagc tggcgaagaa cagcggctac gaagaaccgc tgggtgatct gcagaccatc     360
acgtcgctga agtttggcaa caccaaagtc gagacttttt acccaggtaa gggtcatacc     420
gaagataaca tcgtggtttg gctgccgcag taccaaatcc tggccggtgg ctgcctggtt     480
aagagcgcag aggcgaaaga tctgggtaat gtcgcggacg cttatgtgaa cgagtggagc     540
acctctattg aaaatgtttt gaaacgttat ggtaatatca atagcgttgt gccgggtcac     600
ggtgaggtcg gcgacaaagg tctgctgttg cacacgctgg atctgctgaa gtgataa       657

<210> SEQ ID NO 2
<211> LENGTH: 723
<212> TYPE: DNA
<213> ORGANISM: Artificial Sequence
<220> FEATURE:
<223> OTHER INFORMATION: Synthetic sequence

<400> SEQUENCE: 2
```

| | |
|---|---|
| atgaaaaaaa acattgcatt tctgctggcg agcatgtttg tttttagcat tgcaaccaat | 60 |
| gcatatgccg aaacgggcac cattagcatt agccaactca acaaaaacgt ttgggtccac | 120 |
| accgagttag gctatttcaa cggtgaagcc gtgccgagca atggtttggt tctgaatacg | 180 |
| tccaagggtc tggtgttggt agactccagc tgggacaata agctgaccaa agaactgatc | 240 |
| gaaatggttg agaaaaagtt ccagaagcgt gtgactgatg tcattatcac ccatgcgcac | 300 |
| gcggaccgca tcggtggcat taccgcgctg aaagagcgtg gcattaaagc acatagcacg | 360 |
| gcactgacgg ctgagctggc gaagaacagc ggctacgaag aaccgctggg tgatctgcag | 420 |
| accatcacgt cgctgaagtt tggcaacacc aaagtcgaga cttttacccc aggtaagggt | 480 |
| cataccgaag ataacatcgt ggtttggctg ccgcagtacc aaatcctggc cggtggctgc | 540 |
| ctggttaaga gcgcagaggc gaaagatctg ggtaatgtcg cggacgctta tgtgaacgag | 600 |
| tggagcacct ctattgaaaa tgttttgaaa cgttatggta atatcaatag cgttgtgccg | 660 |
| ggtcacggtg aggtcggcga caaaggtctg ctgttgcaca cgctggatct gctgaagtga | 720 |
| taa | 723 |

<210> SEQ ID NO 3
<211> LENGTH: 717
<212> TYPE: DNA
<213> ORGANISM: Artificial Sequence
<220> FEATURE:
<223> OTHER INFORMATION: Synthetic sequence

<400> SEQUENCE: 3

| | |
|---|---|
| atgaagcagg cattacgagt agcatttggt tttctcatac tgtgggcatc agttctgcat | 60 |
| gctgaaacgg gcaccattag cattagccaa ctcaacaaaa acgtttgggt ccacaccgag | 120 |
| ttaggctatt tcaacggtga agccgtgccg agcaatggtt tggttctgaa tacgtccaag | 180 |
| ggtctggtgt tggtagactc cagctgggac aataagctga ccaaagaact gatcgaaatg | 240 |
| gttgagaaaa agttccagaa gcgtgtgact gatgtcatta tcacccatgc gcacgcggac | 300 |
| cgcatcggtg gcattaccgc gctgaaagag cgtggcatta aagcacatag cacggcactg | 360 |
| acggctgagc tggcgaagaa cagcggctac gaagaaccgc tgggtgatct gcagaccatc | 420 |
| acgtcgctga agtttggcaa caccaaagtc gagactttt acccaggtaa gggtcatacc | 480 |
| gaagataaca tcgtggtttg gctgccgcag taccaaatcc tggccggtgg ctgcctggtt | 540 |
| aagagcgcag aggcgaaaga tctgggtaat gtcgcggacg cttatgtgaa cgagtggagc | 600 |
| acctctattg aaaatgtttt gaaacgttat ggtaatatca atagcgttgt gccgggtcac | 660 |
| ggtgaggtcg gcgacaaagg tctgctgttg cacacgctgg atctgctgaa gtgataa | 717 |

<210> SEQ ID NO 4
<211> LENGTH: 702
<212> TYPE: DNA
<213> ORGANISM: Artificial Sequence
<220> FEATURE:
<223> OTHER INFORMATION: Synthetic sequence

<400> SEQUENCE: 4

| | |
|---|---|
| atggaaaccg gtgatcagcg ttttggtgat ttagtctttc gtcaattggc cccaaacgtc | 60 |
| tggcagcata ccagctatct ggatatgccg ggtttcggtg ctgttgccag caacggcctg | 120 |
| atcgtgcgtg acgtggccgg cgtgctggtt gttgataccg cctggaccga tgatcagacg | 180 |
| gcgcagattc tgaattggat caaacaagaa atcaatctgc cggttgcgct ggcagtggtc | 240 |
| acccacgcgc accaagacaa aatgggtggc atggacgcac tgcacgcggc tggtattgcg | 300 |

| | |
|---|---|
| acgtacgcaa atgcactgag caaccagctg gcaccgcagg agggcatggt tgcggcgcag | 360 |
| catagcctga cctttgcggc gaatggttgg gtggagccgg cgacggctcc gaacttcggc | 420 |
| ccgttgaaag tgttctatcc gggtccgggt cacacctcgg acaacatcac cgtcggtatt | 480 |
| gatggcaccg acattgcctt cggcggctgc ctgatcaaag acagcaaggc aaagtccctg | 540 |
| ggcaatctgg gtgatgcgga cactgagcac tacgccgcga gcgcacgcgc attcggtgcg | 600 |
| gcatttccta aggcctccat gattgttatg agccattctg cgccggacag ccgtgccgcg | 660 |
| atcacgcaca cggcgcgtat ggctgacaag ctgcgctaat ga | 702 |

<210> SEQ ID NO 5
<211> LENGTH: 771
<212> TYPE: DNA
<213> ORGANISM: Artificial Sequence
<220> FEATURE:
<223> OTHER INFORMATION: Synthetic sequence

<400> SEQUENCE: 5

| | |
|---|---|
| atgaaaaaaa acattgcatt tctgctggcg agcatgtttg tttttagcat tgcaaccaat | 60 |
| gcatatgcca tggaaaccgg tgatcagcgt tttggtgatt tagtcttcg tcaattggcc | 120 |
| ccaaacgtct ggcagcatac cagctatctg gatatgccgg gtttcggtgc tgttgccagc | 180 |
| aacggcctga tcgtgcgtga cggtggccgc gtgctggttg ttgataccgc ctggaccgat | 240 |
| gatcagacgg cgcagattct gaattggatc aaacaagaaa tcaatctgcc ggttgcgctg | 300 |
| gcagtggtca cccacgcgca ccaagacaaa atgggtggca tggacgcact gcacgcggct | 360 |
| ggtattgcga cgtacgcaaa tgcactgagc aaccagctgg caccgcagga gggcatggtt | 420 |
| gcggcgcagc atagcctgac ctttgcggcg aatggttggg tggagccggc gacggctccg | 480 |
| aacttcggcc cgttgaaagt gttctatccg ggtccgggtc acacctcgga caacatcacc | 540 |
| gtcggtattg atggcaccga cattgccttc ggcggctgcc tgatcaaaga cagcaaggca | 600 |
| aagtccctgg gcaatctggg tgatgcggac actgagcact acgccgcgag cgcacgcgca | 660 |
| ttcggtgcgg catttcctaa ggcctccatg attgttatga ccattctgc gccggacagc | 720 |
| cgtgccgcga tcacgcacac ggcgcgtatg gctgacaagc tgcgctaatg a | 771 |

<210> SEQ ID NO 6
<211> LENGTH: 768
<212> TYPE: DNA
<213> ORGANISM: Artificial Sequence
<220> FEATURE:
<223> OTHER INFORMATION: Synthetic sequence

<400> SEQUENCE: 6

| | |
|---|---|
| atgaaatacc tgctgccgac cgctgctgct ggtctgctgc tcctcgctgc ccagccggcg | 60 |
| atggccatgg aaaccggtga tcagcgtttt ggtgatttag tctttcgtca attggcccca | 120 |
| aacgtctggc agcataccag ctatctggat atgccgggtt tcggtgctgt tgccagcaac | 180 |
| ggcctgatcg tgcgtgacgg tggccgcgtg ctggttgttg ataccgcctg gaccgatgat | 240 |
| cagacggcgc agattctgaa ttggatcaaa caagaaatca atctgccggt tgcgctggca | 300 |
| gtggtcaccc acgcgcacca agacaaaatg ggtggcatgg acgcactgca cgcggctggt | 360 |
| attgcgacgt acgcaaatgc actgagcaac cagctggcac cgcaggaggg catggttgcg | 420 |
| gcgcagcata gcctgacctt tgcggcgaat ggttgggtgg agccggcgac ggctccgaac | 480 |
| ttcggcccgt tgaaagtgtt ctatccgggt ccgggtcaca cctcggacaa catcaccgtc | 540 |

```
ggtattgatg gcaccgacat tgccttcggc ggctgcctga tcaaagacag caaggcaaag      600
tccctgggca atctgggtga tgcggacact gagcactacg ccgcgagcgc acgcgcattc      660
ggtgcggcat ttcctaaggc ctccatgatt gttatgagcc attctgcgcc ggacagccgt      720
gccgcgatca cgcacacggc gcgtatggct gacaagctgc gctaatga                  768
```

<210> SEQ ID NO 7
<211> LENGTH: 708
<212> TYPE: DNA
<213> ORGANISM: Artificial Sequence
<220> FEATURE:
<223> OTHER INFORMATION: Synthetic sequence

<400> SEQUENCE: 7

```
atgcaaatgg aaaccggtga tcagcgtttt ggtgatttag tctttcgtca attggcccca       60
aacgtctggc agcataccag ctatctggat atgccgggtt tcggtgctgt tgccagcaac      120
ggcctgatcg tgcgtgacgg tggccgcgtg ctggttgttg ataccgcctg gaccgatgat      180
cagacggcgc agattctgaa ttggatcaaa caagaaatca atctgccggt tgcgctggca      240
gtggtcaccc acgcgcacca agacaaaatg ggtggcatgg acgcactgca cgcggctggt      300
attgcgacgt acgcaaatgc actgagcaac cagctggcac gcaggaggg catggttgcg       360 gcgcagcata gcctgacctt tgcggcgaat ggttgggtgg agccggcgac ggctccgaac      420
ttcggcccgt tgaaagtgtt ctatccgggt ccgggtcaca cctcggacaa catcaccgtc      480
ggtattgatg gcaccgacat tgccttcggc ggctgcctga tcaaagacag caaggcaaag      540
tccctgggca atctgggtga tgcggacact gagcactacg ccgcgagcgc acgcgcattc      600
ggtgcggcat ttcctaaggc ctccatgatt gttatgagcc attctgcgcc ggacagccgt      660
gccgcgatca cgcacacggc gcgtatggct gacaagctgc gctaatga                  708
```

<210> SEQ ID NO 8
<211> LENGTH: 774
<212> TYPE: DNA
<213> ORGANISM: Artificial Sequence
<220> FEATURE:
<223> OTHER INFORMATION: Synthetic sequence

<400> SEQUENCE: 8

```
atgaaaaaaa acattgcatt tctgctggcg agcatgtttg tttttagcat tgcaaccaat       60
gcatatgccc aaatggaaac cggtgatcag cgttttggtg atttagtctt tcgtcaattg      120
gccccaaacg tctggcagca taccagctat ctggatatgc cgggtttcgg tgctgttgcc      180
agcaacggcc tgatcgtgcg tgacggtggc cgcgtgctgg ttgttgatac cgcctggacc      240
gatgatcaga cggcgcagat tctgaattgg atcaaacaag aaatcaatct gccggttgcg      300
ctggcagtgg tcacccacgc gcaccaagac aaaatgggtg gcatggacgc actgcacgcg      360
gctggtattg cgacgtacgc aaatgcactg agcaaccagc tggcaccgca ggagggcatg      420
gttgcggcgc agcatagcct gacctttgcg gcgaatggtt gggtggagcc ggcgacggct      480
ccgaacttcg gcccgttgaa agtgttctat ccgggtccgg gtcacacctc ggacaacatc      540
accgtcggta ttgatggcac cgacattgcc ttcggcggct gcctgatcaa agacagcaag      600
gcaaagtccc tgggcaatct gggtgatgcg gacactgagc actacgccgc gagcgcacgc      660
gcattcggtg cggcatttcc taaggcctcc atgattgtta tgagccattc tgcgccggac      720
agccgtgccg cgatcacgca cacggcgcgt atggctgaca agctgcgcta atga            774
```

<210> SEQ ID NO 9
<211> LENGTH: 714
<212> TYPE: DNA
<213> ORGANISM: Artificial Sequence
<220> FEATURE:
<223> OTHER INFORMATION: Synthetic sequence

<400> SEQUENCE: 9

```
atgggtcaac aaatggaaac cggtgatcag cgttttggtg atttagtctt tcgtcaattg      60
gccccaaacg tctggcagca taccagctat ctggatatgc cgggtttcgg tgctgttgcc     120
agcaacggcc tgatcgtgcg tgacggtggc cgcgtgctgg ttgttgatac cgcctggacc     180
gatgatcaga cggcgcagat tctgaattgg atcaaacaag aaatcaatct gccggttgcg     240
ctggcagtgg tcacccacgc gcaccaagac aaaatgggtg gcatggacgc actgcacgcg     300
gctggtattg cgacgtacgc aaatgcactg agcaaccagc tggcaccgca ggagggcatg     360
gttgcggcgc agcatagcct gacctttgcg gcgaatggtt gggtggagcc ggcgacggct     420
ccgaacttcg gcccgttgaa agtgttctat ccgggtccgg tcacacctc ggacaacatc     480
accgtcggta ttgatggcac cgacattgcc ttcgcggct gcctgatcaa agacagcaag     540
gcaaagtccc tggcaatct gggtgatgcg gacactgagc actacgccgc gagcgcacgc     600
gcattcggtg cggcatttcc taaggcctcc atgattgtta tgagccattc tgcgccggac     660
agccgtgccg cgatcacgca cacggcgcgt atggctgaca agctgcgcta atga           714
```

<210> SEQ ID NO 10
<211> LENGTH: 780
<212> TYPE: DNA
<213> ORGANISM: Artificial Sequence
<220> FEATURE:
<223> OTHER INFORMATION: Synthetic sequence

<400> SEQUENCE: 10

```
atgaaaaaaa acattgcatt tctgctggcg agcatgtttg tttttagcat tgcaaccaat      60
gcatatgccg gtcaacaaat ggaaaccggt gatcagcgtt ttggtgattt agtctttcgt     120
caattggccc caaacgtctg gcagcatacc agctatctgg atatgccggg tttcggtgct     180
gttgccagca acggcctgat cgtgcgtgac ggtggccgcg tgctggttgt tgataccgcc     240
tggaccgatg atcagacggc gcagattctg aattggatca acaagaaat caatctgccg     300
gttgcgctgg cagtggtcac ccacgcgcac caagacaaaa tgggtggcat ggacgcactg     360
cacgcggctg gtattgcgac gtacgcaaat gcactgagca accagctggc accgcaggag     420
ggcatggttg cggcgcagca tagcctgacc tttgcggcga atggttgggt ggagccggcg     480
acggctccga acttcggccc gttgaaagtg ttctatccgg gtccgggtca cacctcggac     540
aacatcaccg tcggtattga tggcaccgac attgccttcg cggctgcct gatcaaagac     600
agcaaggcaa agtccctggg caatctgggt gatgcggaca ctgagcacta cgccgcgagc     660
gcacgcgcat tcggtgcggc atttcctaag gcctccatga ttgttatgag ccattctgcg     720
ccggacagcc gtgccgcgat cacgcacacg gcgcgtatgg ctgacaagct gcgctaatga     780
```

<210> SEQ ID NO 11
<211> LENGTH: 765
<212> TYPE: DNA
<213> ORGANISM: Artificial Sequence
<220> FEATURE:
<223> OTHER INFORMATION: Synthetic sequence

<400> SEQUENCE: 11

| | |
|---|---|
| atgaagcagg cattacgagt agcatttggt tttctcatac tgtgggcatc agttctgcat | 60 |
| gctatggaaa ccggtgatca gcgttttggt gatttagtct ttcgtcaatt ggccccaaac | 120 |
| gtctggcagc ataccagcta tctggatatg ccgggtttcg gtgctgttgc cagcaacggc | 180 |
| ctgatcgtgc gtgacggtgg ccgcgtgctg gttgttgata ccgcctggac cgatgatcag | 240 |
| acggcgcaga ttctgaattg gatcaaacaa gaaatcaatc tgccggttgc gctggcagtg | 300 |
| gtcacccacg cgcaccaaga caaaatgggt ggcatggacg cactgcacgc ggctggtatt | 360 |
| gcgacgtacg caaatgcact gagcaaccag ctggcaccgc aggagggcat ggttgcggcg | 420 |
| cagcatagcc tgacctttgc ggcgaatggt tgggtggagc cggcgacggc tccgaacttc | 480 |
| ggcccgttga agtgttccta tccgggtccg ggtcacacct cggacaacat caccgtcggt | 540 |
| attgatggca ccgacattgc cttcggcggc tgcctgatca agacagcaa ggcaaagtcc | 600 |
| ctgggcaatc tgggtgatgc ggacactgag cactacgccg cgagcgcacg cgcattcggt | 660 |
| gcggcatttc ctaaggcctc catgattgtt atgagccatt ctgcgccgga cagccgtgcc | 720 |
| gcgatcacgc acacggcgcg tatggctgac aagctgcgct aatga | 765 |

<210> SEQ ID NO 12
<211> LENGTH: 825
<212> TYPE: DNA
<213> ORGANISM: Artificial Sequence
<220> FEATURE:
<223> OTHER INFORMATION: Synthetic sequence

<400> SEQUENCE: 12

| | |
|---|---|
| atggcaaccg ctctgaccaa tttagttgca gaaccttttcg cgaaactgga gcaagatttt | 60 |
| ggtggctcca ttggtgtgta tgcgatggat acgggcagcg gcgcaaccgt tagctatcgc | 120 |
| gccgaggaac gttttccgct gtgttccagc ttcaagggtt ttctggcggc tgcggtcctg | 180 |
| gcgcgtagcc agcagcaagc cggcctgctg acaccccga tccgttacgg caaaaatgcg | 240 |
| ctggtgccgt ggagcccgat tagcgagaag tacttgacca ctggtatgac ggtcgccgag | 300 |
| ctgtcggccg cagcggtgca gtacagcgac aacgcagcgg cgaatctgct gttgaaagaa | 360 |
| ctgggtggcc cggcaggcct gacggcgttt atgcgcagca tcggtgacac caccttccgc | 420 |
| ctggaccgct gggaattgga gctgaactct gctatcccga gcgatgcccg tgatacgtct | 480 |
| agcccgcgtg cggttactga gagcctgcag aaacttacgc tgggtagcgc gctggctgcg | 540 |
| ccgcaacgtc aacagttcgt ggattggctg aagggtaata cgaccggtaa ccaccgtatt | 600 |
| cgtgccgcag ttccggcgga ctgggctgtt ggcgacaaga ccggcacgtg cggtgtctac | 660 |
| ggtaccgcga atgactatgc agtggtctgg ccaaccggtc gtgcgccgat cgttctggca | 720 |
| gtttacaccc gtgctccgaa caaagatgac aagcatagcg aagccgtgat tgcagcggca | 780 |
| gcgcgcctgg cgctggaggg tttgggtgtc aacggccagt gataa | 825 |

<210> SEQ ID NO 13
<211> LENGTH: 891
<212> TYPE: DNA
<213> ORGANISM: Artificial Sequence
<220> FEATURE:
<223> OTHER INFORMATION: Synthetic sequence

<400> SEQUENCE: 13

| | |
|---|---|
| atgaaaaaaa acattgcatt tctgctggcg agcatgtttg tttttagcat tgcaaccaat | 60 |
| gcatatgccg caaccgctct gaccaattta gttgcagaac ctttcgcgaa actggagcaa | 120 |
| gattttggtg gctccattgg tgtgtatgcg atggatacgg gcagcggcgc aaccgttagc | 180 |

```
tatcgcgccg aggaacgttt tccgctgtgt tccagcttca agggttttct ggcggctgcg      240
gtcctggcgc gtagccagca gcaagccggc ctgctggaca ccccgatccg ttacggcaaa      300
aatgcgctgg tgccgtggag cccgattagc gagaagtact tgaccactgg tatgacggtc      360
gccgagctgt cggccgcagc ggtgcagtac agcgacaacg cagcggcgaa tctgctgttg      420
aaagaactgg gtggcccggc aggcctgacg gcgtttatgc gcagcatcgg tgacaccacc      480
ttccgcctgg accgctggga attggagctg aactctgcta tcccgagcga tgcccgtgat      540
acgtctagcc cgcgtgcggt tactgagagc ctgcagaaac ttacgctggg tagcgcgctg      600
gctgcgccgc aacgtcaaca gttcgtggat tggctgaagg gtaatacgac cggtaaccac      660
cgtattcgtg ccgcagttcc ggcggactgg gctgttggcg acaagaccgg cacgtgcggt      720
gtctacggta ccgcgaatga ctatgcagtg gtctggccaa ccggtcgtgc cgatcgtt       780 ctggcagttt acacccgtgc tccgaacaaa gatgacaagc atagcgaagc cgtgattgca      840
gcggcagcgc gcctggcgct ggagggtttg ggtgtcaacg gccagtgata a               891
```

<210> SEQ ID NO 14
<211> LENGTH: 819
<212> TYPE: DNA
<213> ORGANISM: Artificial Sequence
<220> FEATURE:
<223> OTHER INFORMATION: Synthetic sequence

<400> SEQUENCE: 14

```
atggctctga ccaatttagt tgcagaacct ttcgcgaaac tggagcaaga ttttggtggc       60
tccattggtg tgtatgcgat ggatacgggc agcggcgcaa ccgttagcta tcgcgccgag      120
gaacgttttc cgctgtgttc cagcttcaag ggttttctgg cggctgcggt cctggcgcgt      180
agccagcagc aagccggcct gctggacacc ccgatccgtt acggcaaaaa tgcgctggtg      240
ccgtggagcc cgattagcga agaagtacttg accactggta tgacggtcgc cgagctgtcg      300
gccgcagcgg tgcagtacag cgacaacgca gcggcgaatc tgctgttgaa agaactgggt      360
ggcccggcag gcctgacggc gtttatgcgc agcatcggtg acaccacctt ccgcctggac      420
cgctgggaat tggagctgaa ctctgctatc ccgagcgatg cccgtgatac gtctagcccg      480
cgtgcggtta ctgagagcct gcagaaactt acgctgggta gcgcgctggc tgcgccgcaa      540
cgtcaacagt tcgtggattg gctgaagggt aatacgaccg gtaaccaccg tattcgtgcc      600
gcagttccgg cggactgggc tgttggcgac aagaccggca cgtgcggtgt ctacggtacc      660
gcgaatgact atgcagtggt ctggccaacc ggtcgtgcgc cgatcgttct ggcagtttac      720
acccgtgctc cgaacaaaga tgacaagcat agcgaagccg tgattgcagc ggcagcgcgc      780
ctggcgctgg agggtttggg tgtcaacggc cagtgataa                             819
```

<210> SEQ ID NO 15
<211> LENGTH: 885
<212> TYPE: DNA
<213> ORGANISM: Artificial Sequence
<220> FEATURE:
<223> OTHER INFORMATION: Synthetic sequence

<400> SEQUENCE: 15

```
atgaaaaaaa acattgcatt tctgctggcg agcatgtttg tttttagcat gcaaccaat        60 gcatatgccg ctctgaccaa tttagttgca gaacctttcg cgaaactgga gcaagatttt      120
ggtggctcca ttggtgtgta tgcgatggat acgggcagcg gcgcaaccgt tagctatcgc      180
```

```
gccgaggaac gttttccgct gtgttccagc ttcaagggtt ttctggcggc tgcggtcctg   240
gcgcgtagcc agcagcaagc cggcctgctg gacaccccga tccgttacgg caaaaatgcg   300
ctggtgccgt ggagcccgat tagcgagaag tacttgacca ctggtatgac ggtcgccgag   360
ctgtcggccg cagcggtgca gtacagcgac aacgcagcgg cgaatctgct gttgaaagaa   420
ctgggtggcc cggcaggcct gacggcgttt atgcgcagca tcggtgacac caccttccgc   480
ctggaccgct gggaattgga gctgaactct gctatcccga gcgatgcccg tgatacgtct   540
agcccgcgtg cggttactga gagcctgcag aaacttacgc tgggtagcgc gctggctgcg   600
ccgcaacgtc aacagttcgt ggattggctg aagggtaata cgaccggtaa ccaccgtatt   660
cgtgccgcag ttccggcgga ctgggctgtt ggcgacaaga ccggcacgtg cggtgtctac   720
ggtaccgcga atgactatgc agtggtctgg ccaaccggtc gtgcgccgat cgttctggca   780
gtttacaccc gtgctccgaa caaagatgac aagcatagcg aagccgtgat tgcagcggca   840
gcgcgcctgg cgctggaggg tttgggtgtc aacggccagt gataa                   885

<210> SEQ ID NO 16
<211> LENGTH: 801
<212> TYPE: DNA
<213> ORGANISM: Artificial Sequence
<220> FEATURE:
<223> OTHER INFORMATION: Synthetic sequence

<400> SEQUENCE: 16
atggcagaac ctttcgcgaa actggagcaa gattttggtg gctccattgg tgtgtatgcg    60
atggatacgg gcagcggcgc aaccgttagc tatcgcgccg aggaacgttt tccgctgtgt   120
tccagcttca agggttttct ggcggctgcg gtcctggcgc gtagccagca gcaagccggc   180
ctgctggaca ccccgatccg ttacggcaaa aatgcgctgg tgccgtggag cccgattagc   240
gagaagtact tgaccactgg tatgacggtc gccgagctgt cggccgcagc ggtgcagtac   300
agcgacaacg cagcggcgaa tctgctgttg aaagaactgg gtggcccggc aggcctgacg   360
gcgtttatgc gcagcatcgg tgacaccacc ttccgcctgg accgctggga attggagctg   420
aactctgcta tcccgagcga tgcccgtgat acgtctagcc cgcgtgcggt tactgagagc   480
ctgcagaaac ttacgctggg tagcgcgctg gctgcgccgc aacgtcaaca gttcgtggat   540
tggctgaagg gtaatacgac cggtaaccac cgtattcgtg ccgcagttcc ggcggactgg   600
gctgttggcg acaagaccgg cacgtgcggt gtctacggta ccgcgaatga ctatgcagtg   660
gtctggccaa ccggtcgtgc gccgatcgtt ctggcagttt acaccgtgc tccgaacaaa   720 gatgacaagc atagcgaagc cgtgattgca gcggcagcgc gcctggcgct ggagggtttg   780
ggtgtcaacg gccagtgata a                                              801

<210> SEQ ID NO 17
<211> LENGTH: 867
<212> TYPE: DNA
<213> ORGANISM: Artificial Sequence
<220> FEATURE:
<223> OTHER INFORMATION: Synthetic sequence

<400> SEQUENCE: 17
atgaaaaaaa acattgcatt tctgctggcg agcatgtttg ttttagcat tgcaaccaat    60 gcatatgccg cagaaccttt cgcgaaactg agcaagatt ttggtggctc cattggtgtg   120
tatgcgatga tacgggcag cggcgcaacc gttagctatc gcgccgagga acgttttccg   180
ctgtgttcca gcttcaaggg ttttctggcg gctgcggtcc tggcgcgtag ccagcagcaa   240
```

```
gccggcctgc tggacacccc gatccgttac ggcaaaaatg cgctggtgcc gtggagcccg    300
attagcgaga agtacttgac cactggtatg acggtcgccg agctgtcggc cgcagcggtg    360
cagtacagcg acaacgcagc ggcgaatctg ctgttgaaag aactgggtgg cccggcaggc    420
ctgacggcgt ttatgcgcag catcggtgac accaccttcc gcctggaccg ctgggaattg    480
gagctgaact ctgctatccc gagcgatgcc cgtgatacgt ctagcccgcg tgcggttact    540
gagagcctgc agaaacttac gctgggtagc gcgctggctg cgccgcaacg tcaacagttc    600
gtggattggc tgaagggtaa tacgaccggt aaccaccgta ttcgtgccgc agttccggcg    660
gactgggctg ttggcgacaa gaccggcacg tgcggtgtct acggtaccgc gaatgactat    720
gcagtggtct ggccaaccgg tcgtgcgccg atcgttctgg cagtttacac ccgtgctccg    780
aacaaagatg acaagcatag cgaagccgtg attgcagcgg cagcgcgcct ggcgctggag    840
ggtttgggtg tcaacggcca gtgataa                                        867
```

<210> SEQ ID NO 18
<211> LENGTH: 885
<212> TYPE: DNA
<213> ORGANISM: Artificial Sequence
<220> FEATURE:
<223> OTHER INFORMATION: Synthetic sequence

<400> SEQUENCE: 18

```
atgaagcagg cattacgagt agcatttggt tttctcatac tgtgggcatc agttctgcat     60
gctgcaaccg ctctgaccaa tttagttgca gaacctttcg cgaaactgga gcaagatttt    120
ggtggctcca ttggtgtgta tgcgatggat acgggcagcg gcgcaaccgt tagctatcgc    180
gccgaggaac gttttccgct gtgttccagc ttcaagggtt ttctggcggc tgcggtcctg    240
gcgcgtagcc agcagcaagc cggcctgctg gacaccccga tccgttacgg caaaaatgcg    300
ctggtgccgt ggagcccgat tagcgagaag tacttgacca ctggtatgac ggtcgccgag    360
ctgtcggccg cagcggtgca gtacagcgac aacgcagcgg cgaatctgct gttgaaagaa    420
ctgggtggcc cggcaggcct gacggcgttt atgcgcagca tcggtgacac caccttccgc    480
ctggaccgct gggaattgga gctgaactct gctatcccga gcgatgcccg tgatacgtct    540
agcccgcgtg cggttactga gagcctgcag aaacttacgc tgggtagcgc gctggctgcg    600
ccgcaacgtc aacagttcgt ggattggctg aagggtaata cgaccggtaa ccaccgtatt    660
cgtgccgcag ttccggcgga ctgggctgtt ggcgacaaga ccggcacgtg cggtgtctac    720
ggtaccgcga atgactatgc agtggtctgg ccaaccggtc gtgcgccgat cgttctggca    780
gtttacaccc gtgctccgaa caaagatgac aagcatagcg aagccgtgat tgcagcggca    840
gcgcgcctgg cgctggaggg tttgggtgtc aacggccagt gataa                    885
```

<210> SEQ ID NO 19
<211> LENGTH: 217
<212> TYPE: PRT
<213> ORGANISM: Artificial Sequence
<220> FEATURE:
<223> OTHER INFORMATION: Synthetic sequence

<400> SEQUENCE: 19

Met Glu Thr Gly Thr Ile Ser Ile Ser Gln Leu Asn Lys Asn Val Trp
1               5                   10                  15

Val His Thr Glu Leu Gly Tyr Phe Asn Gly Glu Ala Val Pro Ser Asn
            20                  25                  30

Gly Leu Val Leu Asn Thr Ser Lys Gly Leu Val Leu Asp Ser Ser
            35                  40                  45

Trp Asp Asn Lys Leu Thr Lys Glu Leu Ile Glu Met Val Glu Lys Lys
 50                  55                  60

Phe Gln Lys Arg Val Thr Asp Val Ile Ile Thr His Ala His Ala Asp
 65                  70                  75                  80

Arg Ile Gly Gly Ile Thr Ala Leu Lys Glu Arg Gly Ile Lys Ala His
                    85                  90                  95

Ser Thr Ala Leu Thr Ala Glu Leu Ala Lys Asn Ser Gly Tyr Glu Glu
                100                 105                 110

Pro Leu Gly Asp Leu Gln Thr Ile Thr Ser Leu Lys Phe Gly Asn Thr
                115                 120                 125

Lys Val Glu Thr Phe Tyr Pro Gly Lys Gly His Thr Glu Asp Asn Ile
130                 135                 140

Val Val Trp Leu Pro Gln Tyr Gln Ile Leu Ala Gly Gly Cys Leu Val
145                 150                 155                 160

Lys Ser Ala Glu Ala Lys Asp Leu Gly Asn Val Ala Asp Ala Tyr Val
                165                 170                 175

Asn Glu Trp Ser Thr Ser Ile Glu Asn Val Leu Lys Arg Tyr Gly Asn
                180                 185                 190

Ile Asn Ser Val Val Pro Gly His Gly Glu Val Gly Asp Lys Gly Leu
                195                 200                 205

Leu Leu His Thr Leu Asp Leu Leu Lys
                210                 215

<210> SEQ ID NO 20
<211> LENGTH: 239
<212> TYPE: PRT
<213> ORGANISM: Artificial Sequence
<220> FEATURE:
<223> OTHER INFORMATION: Synthetic sequence

<400> SEQUENCE: 20

Met Lys Lys Asn Ile Ala Phe Leu Leu Ala Ser Met Phe Val Phe Ser
 1               5                  10                  15

Ile Ala Thr Asn Ala Tyr Ala Glu Thr Gly Thr Ile Ser Ile Ser Gln
                20                  25                  30

Leu Asn Lys Asn Val Trp Val His Thr Glu Leu Gly Tyr Phe Asn Gly
            35                  40                  45

Glu Ala Val Pro Ser Asn Gly Leu Val Leu Asn Thr Ser Lys Gly Leu
 50                  55                  60

Val Leu Val Asp Ser Ser Trp Asp Asn Lys Leu Thr Lys Glu Leu Ile
 65                  70                  75                  80

Glu Met Val Glu Lys Lys Phe Gln Lys Arg Val Thr Asp Val Ile Ile
                    85                  90                  95

Thr His Ala His Ala Asp Arg Ile Gly Gly Ile Thr Ala Leu Lys Glu
                100                 105                 110

Arg Gly Ile Lys Ala His Ser Thr Ala Leu Thr Ala Glu Leu Ala Lys
                115                 120                 125

Asn Ser Gly Tyr Glu Glu Pro Leu Gly Asp Leu Gln Thr Ile Thr Ser
130                 135                 140

Leu Lys Phe Gly Asn Thr Lys Val Glu Thr Phe Tyr Pro Gly Lys Gly
145                 150                 155                 160

His Thr Glu Asp Asn Ile Val Val Trp Leu Pro Gln Tyr Gln Ile Leu
                165                 170                 175

```
Ala Gly Gly Cys Leu Val Lys Ser Ala Glu Ala Lys Asp Leu Gly Asn
            180                 185                 190

Val Ala Asp Ala Tyr Val Asn Glu Trp Ser Thr Ser Ile Glu Asn Val
        195                 200                 205

Leu Lys Arg Tyr Gly Asn Ile Asn Ser Val Val Pro Gly His Gly Glu
    210                 215                 220

Val Gly Asp Lys Gly Leu Leu His Thr Leu Asp Leu Lys
225                 230                 235
```

<210> SEQ ID NO 21
<211> LENGTH: 237
<212> TYPE: PRT
<213> ORGANISM: Artificial Sequence
<220> FEATURE:
<223> OTHER INFORMATION: Synthetic sequence

<400> SEQUENCE: 21

```
Met Lys Gln Ala Leu Arg Val Ala Phe Gly Phe Leu Ile Leu Trp Ala
1               5                   10                  15

Ser Val Leu His Ala Glu Thr Gly Thr Ile Ser Ile Ser Gln Leu Asn
            20                  25                  30

Lys Asn Val Trp Val His Thr Glu Leu Gly Tyr Phe Asn Gly Glu Ala
        35                  40                  45

Val Pro Ser Asn Gly Leu Val Leu Asn Thr Ser Lys Gly Leu Val Leu
    50                  55                  60

Val Asp Ser Ser Trp Asp Asn Lys Leu Thr Lys Glu Leu Ile Glu Met
65                  70                  75                  80

Val Glu Lys Lys Phe Gln Lys Arg Val Thr Asp Val Ile Ile Thr His
                85                  90                  95

Ala His Ala Asp Arg Ile Gly Gly Ile Thr Ala Leu Lys Glu Arg Gly
            100                 105                 110

Ile Lys Ala His Ser Thr Ala Leu Thr Ala Glu Leu Ala Lys Asn Ser
        115                 120                 125

Gly Tyr Glu Glu Pro Leu Gly Asp Leu Gln Thr Ile Thr Ser Leu Lys
    130                 135                 140

Phe Gly Asn Thr Lys Val Glu Thr Phe Tyr Pro Gly Lys Gly His Thr
145                 150                 155                 160

Glu Asp Asn Ile Val Val Trp Leu Pro Gln Tyr Gln Ile Leu Ala Gly
                165                 170                 175

Gly Cys Leu Val Lys Ser Ala Glu Ala Lys Asp Leu Gly Asn Val Ala
            180                 185                 190

Asp Ala Tyr Val Asn Glu Trp Ser Thr Ser Ile Glu Asn Val Leu Lys
        195                 200                 205

Arg Tyr Gly Asn Ile Asn Ser Val Val Pro Gly His Gly Glu Val Gly
    210                 215                 220

Asp Lys Gly Leu Leu His Thr Leu Asp Leu Leu Lys
225                 230                 235
```

<210> SEQ ID NO 22
<211> LENGTH: 232
<212> TYPE: PRT
<213> ORGANISM: Artificial Sequence
<220> FEATURE:
<223> OTHER INFORMATION: Synthetic sequence

<400> SEQUENCE: 22

```
Met Glu Thr Gly Asp Gln Arg Phe Gly Asp Leu Val Phe Arg Gln Leu
1               5                   10                  15
```

Ala Pro Asn Val Trp Gln His Thr Ser Tyr Leu Asp Met Pro Gly Phe
            20                  25                  30

Gly Ala Val Ala Ser Asn Gly Leu Ile Val Arg Asp Gly Gly Arg Val
        35                  40                  45

Leu Val Val Asp Thr Ala Trp Thr Asp Gln Thr Ala Gln Ile Leu
    50                  55                  60

Asn Trp Ile Lys Gln Glu Ile Asn Leu Pro Val Ala Leu Ala Val Val
65                  70                  75                  80

Thr His Ala His Gln Asp Lys Met Gly Gly Met Asp Ala Leu His Ala
                85                  90                  95

Ala Gly Ile Ala Thr Tyr Ala Asn Ala Leu Ser Asn Gln Leu Ala Pro
            100                 105                 110

Gln Glu Gly Met Val Ala Ala Gln His Ser Leu Thr Phe Ala Ala Asn
        115                 120                 125

Gly Trp Val Glu Pro Ala Thr Ala Pro Asn Phe Gly Pro Leu Lys Val
130                 135                 140

Phe Tyr Pro Gly Pro Gly His Thr Ser Asp Asn Ile Thr Val Gly Ile
145                 150                 155                 160

Asp Gly Thr Asp Ile Ala Phe Gly Gly Cys Leu Ile Lys Asp Ser Lys
                165                 170                 175

Ala Lys Ser Leu Gly Asn Leu Gly Asp Ala Asp Thr Glu His Tyr Ala
            180                 185                 190

Ala Ser Ala Arg Ala Phe Gly Ala Ala Phe Pro Lys Ala Ser Met Ile
        195                 200                 205

Val Met Ser His Ser Ala Pro Asp Ser Arg Ala Ala Ile Thr His Thr
210                 215                 220

Ala Arg Met Ala Asp Lys Leu Arg
225                 230

<210> SEQ ID NO 23
<211> LENGTH: 255
<212> TYPE: PRT
<213> ORGANISM: Artificial Sequence
<220> FEATURE:
<223> OTHER INFORMATION: Synthetic sequence

<400> SEQUENCE: 23

Met Lys Lys Asn Ile Ala Phe Leu Leu Ala Ser Met Phe Val Phe Ser
1               5                   10                  15

Ile Ala Thr Asn Ala Tyr Ala Met Glu Thr Gly Asp Gln Arg Phe Gly
            20                  25                  30

Asp Leu Val Phe Arg Gln Leu Ala Pro Asn Val Trp Gln His Thr Ser
        35                  40                  45

Tyr Leu Asp Met Pro Gly Phe Gly Ala Val Ala Ser Asn Gly Leu Ile
    50                  55                  60

Val Arg Asp Gly Gly Arg Val Leu Val Val Asp Thr Ala Trp Thr Asp
65                  70                  75                  80

Asp Gln Thr Ala Gln Ile Leu Asn Trp Ile Lys Gln Glu Ile Asn Leu
                85                  90                  95

Pro Val Ala Leu Ala Val Val Thr His Ala His Gln Asp Lys Met Gly
            100                 105                 110

Gly Met Asp Ala Leu His Ala Ala Gly Ile Ala Thr Tyr Ala Asn Ala
        115                 120                 125

Leu Ser Asn Gln Leu Ala Pro Gln Glu Gly Met Val Ala Ala Gln His
130                 135                 140

```
Ser Leu Thr Phe Ala Ala Asn Gly Trp Val Glu Pro Ala Thr Ala Pro
145                 150                 155                 160

Asn Phe Gly Pro Leu Lys Val Phe Tyr Pro Gly Pro Gly His Thr Ser
                165                 170                 175

Asp Asn Ile Thr Val Gly Ile Asp Gly Thr Asp Ile Ala Phe Gly Gly
            180                 185                 190

Cys Leu Ile Lys Asp Ser Lys Ala Lys Ser Leu Gly Asn Leu Gly Asp
                195                 200                 205

Ala Asp Thr Glu His Tyr Ala Ala Ser Ala Arg Ala Phe Gly Ala Ala
210                 215                 220

Phe Pro Lys Ala Ser Met Ile Val Met Ser His Ser Ala Pro Asp Ser
225                 230                 235                 240

Arg Ala Ala Ile Thr His Thr Ala Arg Met Ala Asp Lys Leu Arg
                245                 250                 255

<210> SEQ ID NO 24
<211> LENGTH: 254
<212> TYPE: PRT
<213> ORGANISM: Artificial Sequence
<220> FEATURE:
<223> OTHER INFORMATION: Synthetic sequence

<400> SEQUENCE: 24

Met Lys Tyr Leu Leu Pro Thr Ala Ala Gly Leu Leu Leu Leu Ala
1               5                   10                  15

Ala Gln Pro Ala Met Ala Met Glu Thr Gly Asp Gln Arg Phe Gly Asp
                20                  25                  30

Leu Val Phe Arg Gln Leu Ala Pro Asn Val Trp Gln His Thr Ser Tyr
            35                  40                  45

Leu Asp Met Pro Gly Phe Gly Ala Val Ala Ser Asn Gly Leu Ile Val
    50                  55                  60

Arg Asp Gly Gly Arg Val Leu Val Asp Thr Ala Trp Thr Asp Asp
65                  70                  75                  80

Gln Thr Ala Gln Ile Leu Asn Trp Ile Lys Gln Glu Ile Asn Leu Pro
                85                  90                  95

Val Ala Leu Ala Val Val Thr His Ala His Gln Asp Lys Met Gly Gly
            100                 105                 110

Met Asp Ala Leu His Ala Ala Gly Ile Ala Thr Tyr Ala Asn Ala Leu
        115                 120                 125

Ser Asn Gln Leu Ala Pro Gln Glu Gly Met Val Ala Ala Gln His Ser
130                 135                 140

Leu Thr Phe Ala Ala Asn Gly Trp Val Glu Pro Ala Thr Ala Pro Asn
145                 150                 155                 160

Phe Gly Pro Leu Lys Val Phe Tyr Pro Gly Pro Gly His Thr Ser Asp
                165                 170                 175

Asn Ile Thr Val Gly Ile Asp Gly Thr Asp Ile Ala Phe Gly Gly Cys
            180                 185                 190

Leu Ile Lys Asp Ser Lys Ala Lys Ser Leu Gly Asn Leu Gly Asp Ala
        195                 200                 205

Asp Thr Glu His Tyr Ala Ala Ser Ala Arg Ala Phe Gly Ala Ala Phe
210                 215                 220

Pro Lys Ala Ser Met Ile Val Met Ser His Ser Ala Pro Asp Ser Arg
225                 230                 235                 240

Ala Ala Ile Thr His Thr Ala Arg Met Ala Asp Lys Leu Arg
                245                 250
```

<210> SEQ ID NO 25
<211> LENGTH: 234
<212> TYPE: PRT
<213> ORGANISM: Artificial Sequence
<220> FEATURE:
<223> OTHER INFORMATION: Synthetic sequence

<400> SEQUENCE: 25

```
Met Gln Met Glu Thr Gly Asp Gln Arg Phe Gly Asp Leu Val Phe Arg
1               5                   10                  15

Gln Leu Ala Pro Asn Val Trp Gln His Thr Ser Tyr Leu Asp Met Pro
            20                  25                  30

Gly Phe Gly Ala Val Ala Ser Asn Gly Leu Ile Val Arg Asp Gly Gly
        35                  40                  45

Arg Val Leu Val Val Asp Thr Ala Trp Thr Asp Gln Thr Ala Gln
    50                  55                  60

Ile Leu Asn Trp Ile Lys Gln Glu Ile Asn Leu Pro Val Ala Leu Ala
65                  70                  75                  80

Val Val Thr His Ala His Gln Asp Lys Met Gly Gly Met Asp Ala Leu
                85                  90                  95

His Ala Ala Gly Ile Ala Thr Tyr Ala Asn Ala Leu Ser Asn Gln Leu
            100                 105                 110

Ala Pro Gln Glu Gly Met Val Ala Ala Gln His Ser Leu Thr Phe Ala
        115                 120                 125

Ala Asn Gly Trp Val Glu Pro Ala Thr Ala Pro Asn Phe Gly Pro Leu
    130                 135                 140

Lys Val Phe Tyr Pro Gly Pro Gly His Thr Ser Asp Asn Ile Thr Val
145                 150                 155                 160

Gly Ile Asp Gly Thr Asp Ile Ala Phe Gly Gly Cys Leu Ile Lys Asp
                165                 170                 175

Ser Lys Ala Lys Ser Leu Gly Asn Leu Gly Asp Ala Asp Thr Glu His
            180                 185                 190

Tyr Ala Ala Ser Ala Arg Ala Phe Gly Ala Ala Phe Pro Lys Ala Ser
        195                 200                 205

Met Ile Val Met Ser His Ser Ala Pro Asp Ser Arg Ala Ala Ile Thr
    210                 215                 220

His Thr Ala Arg Met Ala Asp Lys Leu Arg
225                 230
```

<210> SEQ ID NO 26
<211> LENGTH: 256
<212> TYPE: PRT
<213> ORGANISM: Artificial Sequence
<220> FEATURE:
<223> OTHER INFORMATION: Synthetic sequence

<400> SEQUENCE: 26

```
Met Lys Lys Asn Ile Ala Phe Leu Leu Ala Ser Met Phe Val Phe Ser
1               5                   10                  15

Ile Ala Thr Asn Ala Tyr Ala Gln Met Glu Thr Gly Asp Gln Arg Phe
            20                  25                  30

Gly Asp Leu Val Phe Arg Gln Leu Ala Pro Asn Val Trp Gln His Thr
        35                  40                  45

Ser Tyr Leu Asp Met Pro Gly Phe Gly Ala Val Ala Ser Asn Gly Leu
    50                  55                  60

Ile Val Arg Asp Gly Gly Arg Val Leu Val Val Asp Thr Ala Trp Thr
```

```
                 65                  70                  75                  80
Asp Asp Gln Thr Ala Gln Ile Leu Asn Trp Ile Lys Gln Glu Ile Asn
                            85                  90                  95

Leu Pro Val Ala Leu Ala Val Val Thr His Ala His Gln Asp Lys Met
                100                 105                 110

Gly Gly Met Asp Ala Leu His Ala Gly Ile Ala Thr Tyr Ala Asn
            115                 120                 125

Ala Leu Ser Asn Gln Leu Ala Pro Gln Glu Gly Met Val Ala Ala Gln
130                 135                 140

His Ser Leu Thr Phe Ala Ala Asn Gly Trp Val Glu Pro Ala Thr Ala
145                 150                 155                 160

Pro Asn Phe Gly Pro Leu Lys Val Phe Tyr Pro Gly Pro Gly His Thr
                165                 170                 175

Ser Asp Asn Ile Thr Val Gly Ile Asp Gly Thr Asp Ile Ala Phe Gly
            180                 185                 190

Gly Cys Leu Ile Lys Asp Ser Lys Ala Lys Ser Leu Gly Asn Leu Gly
            195                 200                 205

Asp Ala Asp Thr Glu His Tyr Ala Ala Ser Arg Ala Phe Gly Ala
        210                 215                 220

Ala Phe Pro Lys Ala Ser Met Ile Val Met Ser His Ser Ala Pro Asp
225                 230                 235                 240

Ser Arg Ala Ala Ile Thr His Thr Ala Arg Met Ala Asp Lys Leu Arg
                245                 250                 255

<210> SEQ ID NO 27
<211> LENGTH: 236
<212> TYPE: PRT
<213> ORGANISM: Artificial Sequence
<220> FEATURE:
<223> OTHER INFORMATION: Synthetic sequence

<400> SEQUENCE: 27

Met Gly Gln Gln Met Glu Thr Gly Asp Gln Arg Phe Gly Asp Leu Val
1               5                   10                  15

Phe Arg Gln Leu Ala Pro Asn Val Trp Gln His Thr Ser Tyr Leu Asp
                20                  25                  30

Met Pro Gly Phe Gly Ala Val Ala Ser Asn Gly Leu Ile Val Arg Asp
            35                  40                  45

Gly Gly Arg Val Leu Val Asp Thr Ala Trp Thr Asp Gln Thr
        50                  55                  60

Ala Gln Ile Leu Asn Trp Ile Lys Gln Glu Ile Asn Leu Pro Val Ala
65                  70                  75                  80

Leu Ala Val Val Thr His Ala His Gln Asp Lys Met Gly Gly Met Asp
                85                  90                  95

Ala Leu His Ala Ala Gly Ile Ala Thr Tyr Ala Asn Ala Leu Ser Asn
                100                 105                 110

Gln Leu Ala Pro Gln Glu Gly Met Val Ala Ala Gln His Ser Leu Thr
            115                 120                 125

Phe Ala Ala Asn Gly Trp Val Glu Pro Ala Thr Ala Pro Asn Phe Gly
130                 135                 140

Pro Leu Lys Val Phe Tyr Pro Gly Pro Gly His Thr Ser Asp Asn Ile
145                 150                 155                 160

Thr Val Gly Ile Asp Gly Thr Asp Ile Ala Phe Gly Gly Cys Leu Ile
                165                 170                 175

Lys Asp Ser Lys Ala Lys Ser Leu Gly Asn Leu Gly Asp Ala Asp Thr
```

```
                    180                 185                 190
Glu His Tyr Ala Ala Ser Ala Arg Ala Phe Gly Ala Ala Phe Pro Lys
                195                 200                 205

Ala Ser Met Ile Val Met Ser His Ser Ala Pro Asp Ser Arg Ala Ala
            210                 215                 220

Ile Thr His Thr Ala Arg Met Ala Asp Lys Leu Arg
225                 230                 235

<210> SEQ ID NO 28
<211> LENGTH: 258
<212> TYPE: PRT
<213> ORGANISM: Artificial Sequence
<220> FEATURE:
<223> OTHER INFORMATION: Synthetic sequence

<400> SEQUENCE: 28

Met Lys Lys Asn Ile Ala Phe Leu Leu Ala Ser Met Phe Val Phe Ser
1               5                   10                  15

Ile Ala Thr Asn Ala Tyr Ala Gly Gln Gln Met Glu Thr Gly Asp Gln
                20                  25                  30

Arg Phe Gly Asp Leu Val Phe Arg Gln Leu Ala Pro Asn Val Trp Gln
            35                  40                  45

His Thr Ser Tyr Leu Asp Met Pro Gly Phe Gly Ala Val Ala Ser Asn
        50                  55                  60

Gly Leu Ile Val Arg Asp Gly Gly Arg Val Leu Val Val Asp Thr Ala
65                  70                  75                  80

Trp Thr Asp Asp Gln Thr Ala Gln Ile Leu Asn Trp Ile Lys Gln Glu
                85                  90                  95

Ile Asn Leu Pro Val Ala Leu Ala Val Val Thr His Ala His Gln Asp
            100                 105                 110

Lys Met Gly Gly Met Asp Ala Leu His Ala Ala Gly Ile Ala Thr Tyr
        115                 120                 125

Ala Asn Ala Leu Ser Asn Gln Leu Ala Pro Gln Glu Gly Met Val Ala
    130                 135                 140

Ala Gln His Ser Leu Thr Phe Ala Ala Asn Gly Trp Val Glu Pro Ala
145                 150                 155                 160

Thr Ala Pro Asn Phe Gly Pro Leu Lys Val Phe Tyr Pro Gly Pro Gly
                165                 170                 175

His Thr Ser Asp Asn Ile Thr Val Gly Ile Asp Gly Thr Asp Ile Ala
            180                 185                 190

Phe Gly Gly Cys Leu Ile Lys Asp Ser Lys Ala Lys Ser Leu Gly Asn
        195                 200                 205

Leu Gly Asp Ala Asp Thr Glu His Tyr Ala Ala Ser Ala Arg Ala Phe
    210                 215                 220

Gly Ala Ala Phe Pro Lys Ala Ser Met Ile Val Met Ser His Ser Ala
225                 230                 235                 240

Pro Asp Ser Arg Ala Ala Ile Thr His Thr Ala Arg Met Ala Asp Lys
                245                 250                 255

Leu Arg

<210> SEQ ID NO 29
<211> LENGTH: 253
<212> TYPE: PRT
<213> ORGANISM: Artificial Sequence
<220> FEATURE:
<223> OTHER INFORMATION: Synthetic sequence
```

<400> SEQUENCE: 29

```
Met Lys Gln Ala Leu Arg Val Ala Phe Gly Phe Leu Ile Leu Trp Ala
1               5                   10                  15

Ser Val Leu His Ala Met Glu Thr Gly Asp Gln Arg Phe Gly Asp Leu
            20                  25                  30

Val Phe Arg Gln Leu Ala Pro Asn Val Trp Gln His Thr Ser Tyr Leu
        35                  40                  45

Asp Met Pro Gly Phe Gly Ala Val Ala Ser Asn Gly Leu Ile Val Arg
    50                  55                  60

Asp Gly Gly Arg Val Leu Val Val Asp Thr Ala Trp Thr Asp Asp Gln
65                  70                  75                  80

Thr Ala Gln Ile Leu Asn Trp Ile Lys Gln Glu Ile Asn Leu Pro Val
                85                  90                  95

Ala Leu Ala Val Val Thr His Ala His Gln Asp Lys Met Gly Gly Met
            100                 105                 110

Asp Ala Leu His Ala Ala Gly Ile Ala Thr Tyr Ala Asn Ala Leu Ser
        115                 120                 125

Asn Gln Leu Ala Pro Gln Glu Gly Met Val Ala Gln His Ser Leu
    130                 135                 140

Thr Phe Ala Ala Asn Gly Trp Val Glu Pro Ala Thr Ala Pro Asn Phe
145                 150                 155                 160

Gly Pro Leu Lys Val Phe Tyr Pro Gly Pro Gly His Thr Ser Asp Asn
                165                 170                 175

Ile Thr Val Gly Ile Asp Gly Thr Asp Ile Ala Phe Gly Gly Cys Leu
            180                 185                 190

Ile Lys Asp Ser Lys Ala Lys Ser Leu Gly Asn Leu Gly Asp Ala Asp
        195                 200                 205

Thr Glu His Tyr Ala Ala Ser Ala Arg Ala Phe Gly Ala Ala Phe Pro
    210                 215                 220

Lys Ala Ser Met Ile Val Met Ser His Ser Ala Pro Asp Ser Arg Ala
225                 230                 235                 240

Ala Ile Thr His Thr Ala Arg Met Ala Asp Lys Leu Arg
                245                 250
```

<210> SEQ ID NO 30
<211> LENGTH: 273
<212> TYPE: PRT
<213> ORGANISM: Artificial Sequence
<220> FEATURE:
<223> OTHER INFORMATION: Synthetic sequence

<400> SEQUENCE: 30

```
Met Ala Thr Ala Leu Thr Asn Leu Val Ala Glu Pro Phe Ala Lys Leu
1               5                   10                  15

Glu Gln Asp Phe Gly Gly Ser Ile Gly Val Tyr Ala Met Asp Thr Gly
            20                  25                  30

Ser Gly Ala Thr Val Ser Tyr Arg Ala Glu Glu Arg Phe Pro Leu Cys
        35                  40                  45

Ser Ser Phe Lys Gly Phe Leu Ala Ala Val Leu Ala Arg Ser Gln
    50                  55                  60

Gln Gln Ala Gly Leu Leu Asp Thr Pro Ile Arg Tyr Gly Lys Asn Ala
65                  70                  75                  80

Leu Val Pro Trp Ser Pro Ile Ser Glu Lys Tyr Leu Thr Thr Gly Met
                85                  90                  95

Thr Val Ala Glu Leu Ser Ala Ala Ala Val Gln Tyr Ser Asp Asn Ala
```

```
        100                 105                 110
Ala Ala Asn Leu Leu Lys Glu Leu Gly Gly Pro Ala Gly Leu Thr
        115                 120                 125

Ala Phe Met Arg Ser Ile Gly Asp Thr Thr Phe Arg Leu Asp Arg Trp
    130                 135                 140

Glu Leu Glu Leu Asn Ser Ala Ile Pro Ser Asp Ala Arg Asp Thr Ser
145                 150                 155                 160

Ser Pro Arg Ala Val Thr Glu Ser Leu Gln Lys Leu Thr Leu Gly Ser
                165                 170                 175

Ala Leu Ala Ala Pro Gln Arg Gln Phe Val Asp Trp Leu Lys Gly
            180                 185                 190

Asn Thr Thr Gly Asn His Arg Ile Arg Ala Ala Val Pro Ala Asp Trp
        195                 200                 205

Ala Val Gly Asp Lys Thr Gly Thr Cys Gly Val Tyr Gly Thr Ala Asn
        210                 215                 220

Asp Tyr Ala Val Val Trp Pro Thr Gly Arg Ala Pro Ile Val Leu Ala
225                 230                 235                 240

Val Tyr Thr Arg Ala Pro Asn Lys Asp Asp Lys His Ser Glu Ala Val
                245                 250                 255

Ile Ala Ala Ala Arg Leu Ala Leu Glu Gly Leu Gly Val Asn Gly
            260                 265                 270

Gln

<210> SEQ ID NO 31
<211> LENGTH: 295
<212> TYPE: PRT
<213> ORGANISM: Artificial Sequence
<220> FEATURE:
<223> OTHER INFORMATION: Synthetic sequence

<400> SEQUENCE: 31

Met Lys Lys Asn Ile Ala Phe Leu Leu Ala Ser Met Phe Val Phe Ser
1               5                   10                  15

Ile Ala Thr Asn Ala Tyr Ala Ala Thr Ala Leu Thr Asn Leu Val Ala
            20                  25                  30

Glu Pro Phe Ala Lys Leu Glu Gln Asp Phe Gly Gly Ser Ile Gly Val
        35                  40                  45

Tyr Ala Met Asp Thr Gly Ser Gly Ala Thr Val Ser Tyr Arg Ala Glu
    50                  55                  60

Glu Arg Phe Pro Leu Cys Ser Ser Phe Lys Gly Phe Leu Ala Ala Ala
65                  70                  75                  80

Val Leu Ala Arg Ser Gln Gln Gln Ala Gly Leu Leu Asp Thr Pro Ile
                85                  90                  95

Arg Tyr Gly Lys Asn Ala Leu Val Pro Trp Ser Pro Ile Ser Glu Lys
            100                 105                 110

Tyr Leu Thr Thr Gly Met Thr Val Ala Glu Leu Ser Ala Ala Ala Val
        115                 120                 125

Gln Tyr Ser Asp Asn Ala Ala Ala Asn Leu Leu Leu Lys Glu Leu Gly
    130                 135                 140

Gly Pro Ala Gly Leu Thr Ala Phe Met Arg Ser Ile Gly Asp Thr Thr
145                 150                 155                 160

Phe Arg Leu Asp Arg Trp Glu Leu Glu Leu Asn Ser Ala Ile Pro Ser
                165                 170                 175

Asp Ala Arg Asp Thr Ser Ser Pro Arg Ala Val Thr Glu Ser Leu Gln
            180                 185                 190
```

```
Lys Leu Thr Leu Gly Ser Ala Leu Ala Ala Pro Gln Arg Gln Gln Phe
        195                 200                 205

Val Asp Trp Leu Lys Gly Asn Thr Thr Gly Asn His Arg Ile Arg Ala
    210                 215                 220

Ala Val Pro Ala Asp Trp Ala Val Gly Asp Lys Thr Gly Thr Cys Gly
225                 230                 235                 240

Val Tyr Gly Thr Ala Asn Asp Tyr Ala Val Trp Pro Thr Gly Arg
                245                 250                 255

Ala Pro Ile Val Leu Ala Val Tyr Thr Arg Ala Pro Asn Lys Asp Asp
                260                 265                 270

Lys His Ser Glu Ala Val Ile Ala Ala Ala Arg Leu Ala Leu Glu
        275                 280                 285

Gly Leu Gly Val Asn Gly Gln
        290                 295

<210> SEQ ID NO 32
<211> LENGTH: 271
<212> TYPE: PRT
<213> ORGANISM: Artificial Sequence
<220> FEATURE:
<223> OTHER INFORMATION: Synthetic sequence

<400> SEQUENCE: 32

Met Ala Leu Thr Asn Leu Val Ala Glu Pro Phe Ala Lys Leu Glu Gln
1               5                   10                  15

Asp Phe Gly Gly Ser Ile Gly Val Tyr Ala Met Asp Thr Gly Ser Gly
                20                  25                  30

Ala Thr Val Ser Tyr Arg Ala Glu Glu Arg Phe Pro Leu Cys Ser Ser
            35                  40                  45

Phe Lys Gly Phe Leu Ala Ala Ala Val Leu Ala Arg Ser Gln Gln Gln
        50                  55                  60

Ala Gly Leu Leu Asp Thr Pro Ile Arg Tyr Gly Lys Asn Ala Leu Val
65                  70                  75                  80

Pro Trp Ser Pro Ile Ser Glu Lys Tyr Leu Thr Thr Gly Met Thr Val
                85                  90                  95

Ala Glu Leu Ser Ala Ala Ala Val Gln Tyr Ser Asp Asn Ala Ala Ala
            100                 105                 110

Asn Leu Leu Leu Lys Glu Leu Gly Gly Pro Ala Gly Leu Thr Ala Phe
        115                 120                 125

Met Arg Ser Ile Gly Asp Thr Thr Phe Arg Leu Asp Arg Trp Glu Leu
    130                 135                 140

Glu Leu Asn Ser Ala Ile Pro Ser Asp Ala Arg Asp Thr Ser Ser Pro
145                 150                 155                 160

Arg Ala Val Thr Glu Ser Leu Gln Lys Leu Thr Leu Gly Ser Ala Leu
                165                 170                 175

Ala Ala Pro Gln Arg Gln Gln Phe Val Asp Trp Leu Lys Gly Asn Thr
            180                 185                 190

Thr Gly Asn His Arg Ile Arg Ala Ala Val Pro Ala Asp Trp Ala Val
        195                 200                 205

Gly Asp Lys Thr Gly Thr Cys Gly Val Tyr Gly Thr Ala Asn Asp Tyr
    210                 215                 220

Ala Val Val Trp Pro Thr Gly Arg Ala Pro Ile Val Leu Ala Val Tyr
225                 230                 235                 240

Thr Arg Ala Pro Asn Lys Asp Asp Lys His Ser Glu Ala Val Ile Ala
                245                 250                 255
```

Ala Ala Ala Arg Leu Ala Leu Glu Gly Leu Gly Val Asn Gly Gln
            260                 265                 270

<210> SEQ ID NO 33
<211> LENGTH: 293
<212> TYPE: PRT
<213> ORGANISM: Artificial Sequence
<220> FEATURE:
<223> OTHER INFORMATION: Synthetic sequence

<400> SEQUENCE: 33

Met Lys Lys Asn Ile Ala Phe Leu Leu Ala Ser Met Phe Val Phe Ser
1               5                   10                  15

Ile Ala Thr Asn Ala Tyr Ala Ala Leu Thr Asn Leu Val Ala Glu Pro
            20                  25                  30

Phe Ala Lys Leu Glu Gln Asp Phe Gly Gly Ser Ile Gly Val Tyr Ala
        35                  40                  45

Met Asp Thr Gly Ser Gly Ala Thr Val Ser Tyr Arg Ala Glu Glu Arg
    50                  55                  60

Phe Pro Leu Cys Ser Ser Phe Lys Gly Phe Leu Ala Ala Ala Val Leu
65                  70                  75                  80

Ala Arg Ser Gln Gln Gln Ala Gly Leu Leu Asp Thr Pro Ile Arg Tyr
                85                  90                  95

Gly Lys Asn Ala Leu Val Pro Trp Ser Pro Ile Ser Glu Lys Tyr Leu
            100                 105                 110

Thr Thr Gly Met Thr Val Ala Glu Leu Ser Ala Ala Ala Val Gln Tyr
        115                 120                 125

Ser Asp Asn Ala Ala Ala Asn Leu Leu Leu Lys Glu Leu Gly Gly Pro
    130                 135                 140

Ala Gly Leu Thr Ala Phe Met Arg Ser Ile Gly Asp Thr Thr Phe Arg
145                 150                 155                 160

Leu Asp Arg Trp Glu Leu Glu Leu Asn Ser Ala Ile Pro Ser Asp Ala
                165                 170                 175

Arg Asp Thr Ser Ser Pro Arg Ala Val Thr Glu Ser Leu Gln Lys Leu
            180                 185                 190

Thr Leu Gly Ser Ala Leu Ala Ala Pro Gln Arg Gln Gln Phe Val Asp
        195                 200                 205

Trp Leu Lys Gly Asn Thr Thr Gly Asn His Arg Ile Arg Ala Ala Val
    210                 215                 220

Pro Ala Asp Trp Ala Val Gly Asp Lys Thr Gly Thr Cys Gly Val Tyr
225                 230                 235                 240

Gly Thr Ala Asn Asp Tyr Ala Val Val Trp Pro Thr Gly Arg Ala Pro
                245                 250                 255

Ile Val Leu Ala Val Tyr Thr Arg Ala Pro Asn Lys Asp Asp Lys His
            260                 265                 270

Ser Glu Ala Val Ile Ala Ala Ala Arg Leu Ala Leu Glu Gly Leu
        275                 280                 285

Gly Val Asn Gly Gln
    290

<210> SEQ ID NO 34
<211> LENGTH: 265
<212> TYPE: PRT
<213> ORGANISM: Artificial Sequence
<220> FEATURE:
<223> OTHER INFORMATION: Synthetic sequence

<400> SEQUENCE: 34

```
Met Ala Glu Pro Phe Ala Lys Leu Glu Gln Asp Phe Gly Gly Ser Ile
1               5                   10                  15

Gly Val Tyr Ala Met Asp Thr Gly Ser Gly Ala Thr Val Ser Tyr Arg
            20                  25                  30

Ala Glu Glu Arg Phe Pro Leu Cys Ser Ser Phe Lys Gly Phe Leu Ala
        35                  40                  45

Ala Ala Val Leu Ala Arg Ser Gln Gln Gln Ala Gly Leu Leu Asp Thr
    50                  55                  60

Pro Ile Arg Tyr Gly Lys Asn Ala Leu Val Pro Trp Ser Pro Ile Ser
65                  70                  75                  80

Glu Lys Tyr Leu Thr Thr Gly Met Thr Val Ala Glu Leu Ser Ala Ala
                85                  90                  95

Ala Val Gln Tyr Ser Asp Asn Ala Ala Asn Leu Leu Leu Lys Glu
            100                 105                 110

Leu Gly Gly Pro Ala Gly Leu Thr Ala Phe Met Arg Ser Ile Gly Asp
            115                 120                 125

Thr Thr Phe Arg Leu Asp Arg Trp Glu Leu Glu Leu Asn Ser Ala Ile
    130                 135                 140

Pro Ser Asp Ala Arg Asp Thr Ser Ser Pro Arg Ala Val Thr Glu Ser
145                 150                 155                 160

Leu Gln Lys Leu Thr Leu Gly Ser Ala Leu Ala Ala Pro Gln Arg Gln
                165                 170                 175

Gln Phe Val Asp Trp Leu Lys Gly Asn Thr Thr Gly Asn His Arg Ile
            180                 185                 190

Arg Ala Ala Val Pro Ala Asp Trp Ala Val Gly Asp Lys Thr Gly Thr
        195                 200                 205

Cys Gly Val Tyr Gly Thr Ala Asn Asp Tyr Ala Val Val Trp Pro Thr
    210                 215                 220

Gly Arg Ala Pro Ile Val Leu Ala Val Tyr Thr Arg Ala Pro Asn Lys
225                 230                 235                 240

Asp Asp Lys His Ser Glu Ala Val Ile Ala Ala Ala Arg Leu Ala
                245                 250                 255

Leu Glu Gly Leu Gly Val Asn Gly Gln
            260                 265
```

<210> SEQ ID NO 35
<211> LENGTH: 250
<212> TYPE: PRT
<213> ORGANISM: Artificial Sequence
<220> FEATURE:
<223> OTHER INFORMATION: Synthetic sequence

<400> SEQUENCE: 35

```
Met Lys Lys Asn Ile Ala Phe Leu Leu Ala Ser Met Phe Val Phe Ser
1               5                   10                  15

Ile Ala Thr Asn Ala Tyr Ala Ala Glu Pro Phe Ala Lys Leu Glu Gln
            20                  25                  30

Asp Phe Gly Gly Ser Ile Gly Val Tyr Ala Met Asp Thr Gly Ser Gly
        35                  40                  45

Ala Thr Val Ser Tyr Arg Ala Glu Glu Arg Phe Pro Leu Cys Ser Ser
    50                  55                  60

Phe Lys Gly Phe Leu Ala Ala Ala Val Leu Ala Arg Ser Gln Gln Gln
65                  70                  75                  80

Ala Gly Leu Leu Asp Thr Pro Ile Arg Tyr Gly Lys Asn Ala Leu Val
```

```
                    85                  90                  95
Pro Trp Ser Pro Ile Ser Glu Lys Tyr Leu Thr Thr Gly Met Thr Val
                100                 105                 110

Ala Glu Leu Ser Ala Ala Val Gln Tyr Ser Asp Asn Ala Ala Ala
            115                 120                 125

Asn Leu Leu Lys Glu Leu Gly Gly Pro Ala Gly Leu Thr Ala Phe
            130                 135                 140

Met Arg Ser Ile Gly Asp Thr Thr Phe Arg Leu Asp Arg Trp Glu Leu
145                 150                 155                 160

Glu Leu Asn Ser Ala Ile Pro Ser Asp Ala Arg Asp Thr Ser Ser Pro
                165                 170                 175

Arg Ala Val Thr Glu Ser Leu Gln Lys Leu Thr Leu Gly Ser Ala Leu
                180                 185                 190

Ala Ala Pro Gln Arg Gln Gln Phe Val Asp Trp Leu Lys Gly Asn Thr
            195                 200                 205

Thr Gly Asn His Arg Ile Arg Ala Ala Val Pro Ala Asp Trp Ala Val
        210                 215                 220

Gly Asp Lys Thr Gly Thr Cys Gly Val Tyr Gly Thr Ala Asn Asp Tyr
225                 230                 235                 240

Ala Val Val Trp Pro Thr Gly Arg Ala Pro
                245                 250

<210> SEQ ID NO 36
<211> LENGTH: 293
<212> TYPE: PRT
<213> ORGANISM: Artificial Sequence
<220> FEATURE:
<223> OTHER INFORMATION: Synthetic sequence

<400> SEQUENCE: 36

Met Lys Gln Ala Leu Arg Val Ala Phe Gly Phe Leu Ile Leu Trp Ala
1               5                   10                  15

Ser Val Leu His Ala Ala Thr Ala Leu Thr Asn Leu Val Ala Glu Pro
                20                  25                  30

Phe Ala Lys Leu Glu Gln Asp Phe Gly Gly Ser Ile Gly Val Tyr Ala
            35                  40                  45

Met Asp Thr Gly Ser Gly Ala Thr Val Ser Tyr Arg Ala Glu Glu Arg
        50                  55                  60

Phe Pro Leu Cys Ser Ser Phe Lys Gly Phe Leu Ala Ala Val Leu
65              70                  75                  80

Ala Arg Ser Gln Gln Gln Ala Gly Leu Leu Asp Thr Pro Ile Arg Tyr
                85                  90                  95

Gly Lys Asn Ala Leu Val Pro Trp Ser Pro Ile Ser Glu Lys Tyr Leu
                100                 105                 110

Thr Thr Gly Met Thr Val Ala Glu Leu Ser Ala Ala Val Gln Tyr
        115                 120                 125

Ser Asp Asn Ala Ala Ala Asn Leu Leu Lys Glu Leu Gly Gly Pro
        130                 135                 140

Ala Gly Leu Thr Ala Phe Met Arg Ser Ile Gly Asp Thr Thr Phe Arg
145                 150                 155                 160

Leu Asp Arg Trp Glu Leu Glu Leu Asn Ser Ala Ile Pro Ser Asp Ala
                165                 170                 175

Arg Asp Thr Ser Ser Pro Arg Ala Val Thr Glu Ser Leu Gln Lys Leu
                180                 185                 190

Thr Leu Gly Ser Ala Leu Ala Ala Pro Gln Arg Gln Gln Phe Val Asp
```

```
                195                 200                 205
Trp Leu Lys Gly Asn Thr Thr Gly Asn His Arg Ile Arg Ala Ala Val
210                 215                 220

Pro Ala Asp Trp Ala Val Gly Asp Lys Thr Gly Thr Cys Gly Val Tyr
225                 230                 235                 240

Gly Thr Ala Asn Asp Tyr Ala Val Val Trp Pro Thr Gly Arg Ala Pro
                245                 250                 255

Ile Val Leu Ala Val Tyr Thr Arg Ala Pro Asn Lys Asp Asp Lys His
                260                 265                 270

Ser Glu Ala Val Ile Ala Ala Ala Arg Leu Ala Leu Glu Gly Leu
                275                 280                 285

Gly Val Asn Gly Gln
                290
```

```
<210> SEQ ID NO 37
<211> LENGTH: 216
<212> TYPE: PRT
<213> ORGANISM: Artificial Sequence
<220> FEATURE:
<223> OTHER INFORMATION: Synthetic sequence

<400> SEQUENCE: 37

Glu Thr Gly Thr Ile Ser Ile Ser Gln Leu Asn Lys Asn Val Trp Val
1               5                   10                  15

His Thr Glu Leu Gly Tyr Phe Asn Gly Glu Ala Val Pro Ser Asn Gly
                20                  25                  30

Leu Val Leu Asn Thr Ser Lys Gly Leu Val Leu Val Asp Ser Ser Trp
            35                  40                  45

Asp Asn Lys Leu Thr Lys Glu Leu Ile Glu Met Val Glu Lys Lys Phe
        50                  55                  60

Gln Lys Arg Val Thr Asp Val Ile Ile Thr His Ala His Ala Asp Arg
65                  70                  75                  80

Ile Gly Gly Ile Thr Ala Leu Lys Glu Arg Gly Ile Lys Ala His Ser
                85                  90                  95

Thr Ala Leu Thr Ala Glu Leu Ala Lys Asn Ser Gly Tyr Glu Glu Pro
            100                 105                 110

Leu Gly Asp Leu Gln Thr Ile Thr Ser Leu Lys Phe Gly Asn Thr Lys
        115                 120                 125

Val Glu Thr Phe Tyr Pro Gly Lys Gly His Thr Glu Asp Asn Ile Val
130                 135                 140

Val Trp Leu Pro Gln Tyr Gln Ile Leu Ala Gly Gly Cys Leu Val Lys
145                 150                 155                 160

Ser Ala Glu Ala Lys Asp Leu Gly Asn Val Ala Asp Ala Tyr Val Asn
                165                 170                 175

Glu Trp Ser Thr Ser Ile Glu Asn Val Leu Lys Arg Tyr Gly Asn Ile
            180                 185                 190

Asn Ser Val Val Pro Gly His Gly Glu Val Gly Asp Lys Gly Leu Leu
        195                 200                 205

Leu His Thr Leu Asp Leu Leu Lys
    210                 215
```

```
<210> SEQ ID NO 38
<211> LENGTH: 293
<212> TYPE: PRT
<213> ORGANISM: Artificial Sequence
<220> FEATURE:
<223> OTHER INFORMATION: Synthetic sequence
```

<400> SEQUENCE: 38

Met Ser Leu Tyr Arg Arg Leu Val Leu Leu Ser Cys Leu Ser Trp Pro
1               5                   10                  15

Leu Ala Gly Phe Ser Ala Thr Ala Leu Thr Asn Leu Val Ala Glu Pro
            20                  25                  30

Phe Ala Lys Leu Glu Gln Asp Phe Gly Gly Ser Ile Gly Val Tyr Ala
        35                  40                  45

Met Asp Thr Gly Ser Gly Ala Thr Val Ser Tyr Arg Ala Glu Glu Arg
50                  55                  60

Phe Pro Leu Cys Ser Ser Phe Lys Gly Phe Leu Ala Ala Val Leu
65                  70                  75                  80

Ala Arg Ser Gln Gln Gln Ala Gly Leu Leu Asp Thr Pro Ile Arg Tyr
                85                  90                  95

Gly Lys Asn Ala Leu Val Pro Trp Ser Pro Ile Ser Glu Lys Tyr Leu
            100                 105                 110

Thr Thr Gly Met Thr Val Ala Glu Leu Ser Ala Ala Val Gln Tyr
        115                 120                 125

Ser Asp Asn Ala Ala Ala Asn Leu Leu Leu Lys Glu Leu Gly Gly Pro
130                 135                 140

Ala Gly Leu Thr Ala Phe Met Arg Ser Ile Gly Asp Thr Thr Phe Arg
145                 150                 155                 160

Leu Asp Arg Trp Glu Leu Glu Leu Asn Ser Ala Ile Pro Ser Asp Ala
                165                 170                 175

Arg Asp Thr Ser Ser Pro Arg Ala Val Thr Glu Ser Leu Gln Lys Leu
            180                 185                 190

Thr Leu Gly Ser Ala Leu Ala Ala Pro Gln Arg Gln Gln Phe Val Asp
        195                 200                 205

Trp Leu Lys Gly Asn Thr Thr Gly Asn His Arg Ile Arg Ala Ala Val
210                 215                 220

Pro Ala Asp Trp Ala Val Gly Asp Lys Thr Gly Thr Cys Gly Val Tyr
225                 230                 235                 240

Gly Thr Ala Asn Asp Tyr Ala Val Val Trp Pro Thr Gly Arg Ala Pro
                245                 250                 255

Ile Val Leu Ala Val Tyr Thr Arg Ala Pro Asn Lys Asp Asp Lys His
            260                 265                 270

Ser Glu Ala Val Ile Ala Ala Ala Arg Leu Ala Leu Glu Gly Leu
        275                 280                 285

Gly Val Asn Gly Gln
        290

<210> SEQ ID NO 39
<211> LENGTH: 293
<212> TYPE: PRT
<213> ORGANISM: Artificial Sequence
<220> FEATURE:
<223> OTHER INFORMATION: Synthetic sequence

<400> SEQUENCE: 39

Met Ser Leu Tyr Arg Arg Leu Val Leu Leu Ser Cys Leu Ser Trp Pro
1               5                   10                  15

Leu Ala Gly Phe Ser Ala Thr Ala Leu Thr Asn Leu Val Ala Glu Pro
            20                  25                  30

Phe Ala Lys Leu Glu Gln Asp Phe Gly Gly Ser Ile Gly Val Tyr Ala
        35                  40                  45

Met Asp Thr Gly Ser Gly Ala Thr Val Ser Tyr Arg Ala Glu Arg
 50                  55                  60

Phe Pro Leu Cys Ser Ser Phe Lys Gly Phe Leu Ala Ala Val Leu
 65                  70                  75                  80

Ala Arg Ser Gln Gln Gln Ala Gly Leu Leu Asp Thr Pro Ile Arg Tyr
                 85                  90                  95

Gly Lys Asn Ala Leu Val Pro Trp Ser Pro Ile Ser Glu Lys Tyr Leu
                100                 105                 110

Thr Thr Gly Met Thr Val Ala Glu Leu Ser Ala Ala Val Gln Tyr
                115                 120                 125

Ser Asp Asn Ala Ala Asn Leu Leu Leu Lys Glu Leu Gly Gly Pro
                130                 135                 140

Ala Gly Leu Thr Ala Phe Met Arg Ser Ile Gly Asp Thr Thr Phe Arg
145                 150                 155                 160

Leu Asp Arg Trp Glu Leu Glu Leu Asn Ser Ala Ile Pro Gly Asp Ala
                165                 170                 175

Arg Asp Thr Ser Ser Pro Arg Ala Val Thr Glu Ser Leu Gln Lys Leu
                180                 185                 190

Thr Leu Gly Ser Ala Leu Ala Ala Pro Gln Arg Gln Gln Phe Val Asp
                195                 200                 205

Trp Leu Lys Gly Asn Thr Thr Gly Asn His Arg Ile Arg Ala Ala Val
210                 215                 220

Pro Ala Asp Trp Ala Val Gly Asp Lys Thr Gly Thr Cys Gly Val Tyr
225                 230                 235                 240

Gly Thr Ala Asn Asp Tyr Ala Val Val Trp Pro Thr Gly Arg Ala Pro
                245                 250                 255

Ile Val Leu Ala Val Tyr Thr Arg Ala Pro Asn Lys Asp Asp Lys Tyr
                260                 265                 270

Ser Glu Ala Val Ile Ala Ala Ala Arg Leu Ala Leu Glu Gly Leu
                275                 280                 285

Gly Val Asn Gly Gln
                290

<210> SEQ ID NO 40
<211> LENGTH: 293
<212> TYPE: PRT
<213> ORGANISM: Artificial Sequence
<220> FEATURE:
<223> OTHER INFORMATION: Synthetic sequence

<400> SEQUENCE: 40

Met Ser Leu Tyr Arg Arg Leu Val Leu Leu Ser Cys Leu Ser Trp Pro
 1               5                  10                  15

Leu Ala Gly Phe Ser Ala Thr Ala Leu Thr Asn Leu Val Ala Glu Pro
                 20                  25                  30

Phe Ala Lys Leu Glu Gln Asp Phe Gly Gly Ser Ile Gly Val Tyr Ala
                 35                  40                  45

Met Asp Thr Gly Ser Gly Ala Thr Val Ser Tyr Arg Ala Glu Glu Arg
 50                  55                  60

Phe Pro Leu Cys Ser Ser Phe Lys Gly Phe Leu Ala Ala Val Leu
 65                  70                  75                  80

Ala Arg Ser Gln Gln Gln Ala Gly Leu Leu Asp Thr Pro Ile Arg Tyr
                 85                  90                  95

Gly Lys Asn Ala Leu Val Arg Trp Ser Pro Ile Ser Glu Lys Tyr Leu
                100                 105                 110

```
Thr Thr Gly Met Thr Val Ala Glu Leu Ser Ala Ala Ala Val Gln Tyr
            115                 120                 125

Ser Asp Asn Ala Ala Asn Leu Leu Lys Glu Leu Gly Gly Pro
130                 135                 140

Ala Gly Leu Thr Ala Phe Met Arg Ser Ile Gly Asp Thr Thr Phe Arg
145                 150                 155                 160

Leu Asp Arg Trp Glu Leu Glu Leu Asn Ser Ala Ile Pro Gly Asp Ala
                165                 170                 175

Arg Asp Thr Ser Ser Pro Arg Ala Val Thr Glu Ser Leu Gln Lys Leu
                180                 185                 190

Thr Leu Gly Ser Ala Leu Ala Ala Pro Gln Arg Gln Gln Phe Val Asp
            195                 200                 205

Trp Leu Lys Gly Asn Thr Thr Gly Asn His Arg Ile Arg Ala Ala Val
210                 215                 220

Pro Ala Asp Trp Ala Val Gly Asp Lys Thr Gly Thr Cys Gly Gly Tyr
225                 230                 235                 240

Gly Thr Ala Asn Asp Tyr Ala Val Val Trp Pro Thr Gly Arg Ala Pro
                245                 250                 255

Ile Val Leu Ala Val Tyr Thr Arg Ala Pro Asn Lys Asp Asp Lys His
                260                 265                 270

Ser Glu Ala Val Ile Ala Ala Ala Arg Leu Ala Leu Glu Gly Leu
            275                 280                 285

Gly Val Asn Gly Gln
            290

<210> SEQ ID NO 41
<211> LENGTH: 293
<212> TYPE: PRT
<213> ORGANISM: Artificial Sequence
<220> FEATURE:
<223> OTHER INFORMATION: Synthetic sequence

<400> SEQUENCE: 41

Met Ser Leu Tyr Arg Arg Leu Val Leu Leu Ser Cys Leu Ser Trp Pro
1               5                   10                  15

Leu Ala Gly Phe Ser Ala Thr Ala Leu Thr Asn Leu Val Ala Glu Pro
                20                  25                  30

Phe Ala Lys Leu Glu Gln Asp Phe Gly Gly Ser Ile Gly Val Tyr Ala
                35                  40                  45

Met Asp Thr Gly Ser Gly Ala Thr Val Ser Tyr Arg Ala Glu Glu Arg
            50                  55                  60

Phe Pro Leu Cys Ser Ser Phe Lys Gly Phe Leu Ala Ala Ala Val Leu
65                  70                  75                  80

Ala Arg Ser Gln Gln Gln Ala Gly Leu Leu Asp Thr Pro Ile Arg Tyr
                85                  90                  95

Gly Lys Asn Ala Leu Val Arg Trp Ser Pro Ile Ser Glu Lys Tyr Leu
            100                 105                 110

Thr Thr Gly Met Thr Val Ala Glu Leu Ser Ala Ala Ala Val Gln Tyr
            115                 120                 125

Ser Asp Asn Ala Ala Asn Leu Leu Lys Glu Leu Gly Gly Pro
130                 135                 140

Ala Gly Leu Thr Ala Phe Met Arg Ser Ile Gly Asp Thr Thr Phe Arg
145                 150                 155                 160

Leu Asp Arg Trp Glu Leu Glu Leu Asn Ser Ala Ile Pro Gly Asp Ala
                165                 170                 175
```

```
Arg Asp Thr Ser Ser Pro Arg Ala Val Thr Glu Ser Leu Gln Lys Leu
            180                 185                 190

Thr Leu Gly Ser Ala Leu Ala Ala Pro Gln Arg Gln Gln Phe Val Asp
        195                 200                 205

Trp Leu Lys Gly Asn Thr Thr Gly Asn His Arg Ile Arg Ala Ala Val
    210                 215                 220

Pro Ala Asp Trp Ala Val Gly Asp Lys Thr Gly Thr Cys Gly Val Tyr
225                 230                 235                 240

Gly Thr Ala Asn Asp Tyr Ala Val Val Trp Pro Thr Gly Arg Ala Pro
                245                 250                 255

Ile Val Leu Ala Val Tyr Thr Arg Ala Pro Asn Lys Asp Asp Lys His
            260                 265                 270

Ser Glu Ala Val Ile Ala Ala Ala Arg Leu Ala Leu Glu Gly Leu
        275                 280                 285

Gly Val Asn Gly Gln
    290
```

<210> SEQ ID NO 42
<211> LENGTH: 293
<212> TYPE: PRT
<213> ORGANISM: Artificial Sequence
<220> FEATURE:
<223> OTHER INFORMATION: Synthetic sequence

<400> SEQUENCE: 42

```
Met Ser Leu Tyr Arg Arg Leu Val Leu Leu Ser Cys Leu Ser Trp Pro
1               5                   10                  15

Leu Ala Gly Phe Ser Ala Thr Ala Leu Thr Asn Leu Val Ala Glu Pro
            20                  25                  30

Phe Ala Lys Leu Glu Gln Asp Phe Gly Gly Ser Ile Gly Val Tyr Ala
        35                  40                  45

Met Asp Thr Gly Ser Gly Ala Thr Val Ser Tyr Arg Ala Glu Glu Arg
    50                  55                  60

Phe Pro Leu Cys Ser Ser Phe Lys Gly Phe Leu Ala Ala Ala Val Leu
65                  70                  75                  80

Ala Arg Ser Gln Gln Gln Ala Gly Leu Leu Asp Thr Pro Ile Arg Tyr
                85                  90                  95

Gly Lys Asn Ala Leu Val Pro Trp Ser Pro Ile Ser Glu Lys Tyr Leu
            100                 105                 110

Thr Thr Gly Met Thr Val Ala Glu Leu Ser Ala Ala Ala Val Gln Tyr
        115                 120                 125

Ser Asp Asn Ala Ala Ala Asn Leu Leu Leu Lys Glu Leu Gly Gly Pro
    130                 135                 140

Ala Gly Leu Thr Ala Phe Met Arg Ser Ile Gly Asp Thr Thr Phe Arg
145                 150                 155                 160

Leu Asp Arg Trp Glu Leu Glu Leu Asn Ser Ala Ile Pro Gly Asp Ala
                165                 170                 175

Arg Asp Thr Ser Ser Pro Arg Ala Val Thr Glu Ser Leu Gln Lys Leu
            180                 185                 190

Thr Leu Gly Ser Ala Leu Ala Ala Pro Gln Arg Gln Gln Phe Val Asp
        195                 200                 205

Trp Leu Lys Gly Asn Thr Thr Gly Asn His Arg Ile Arg Ala Ala Val
    210                 215                 220

Pro Ala Asp Trp Ala Val Gly Asp Lys Thr Gly Thr Cys Gly Val Tyr
225                 230                 235                 240
```

```
Gly Thr Ala Asn Asp Tyr Ala Val Val Trp Pro Thr Gly Arg Ala Pro
                245                 250                 255

Ile Val Leu Ala Val Tyr Thr Arg Ala Pro Asn Lys Asp Asp Lys His
            260                 265                 270

Ser Glu Ala Val Ile Ala Ala Ala Arg Leu Ala Leu Glu Gly Leu
        275                 280                 285

Gly Val Asn Gly Gln
    290

<210> SEQ ID NO 43
<211> LENGTH: 293
<212> TYPE: PRT
<213> ORGANISM: Artificial Sequence
<220> FEATURE:
<223> OTHER INFORMATION: Synthetic sequence

<400> SEQUENCE: 43

Met Ser Leu Tyr Arg Arg Leu Val Leu Leu Ser Cys Leu Ser Trp Pro
1               5                   10                  15

Leu Ala Gly Phe Ser Ala Thr Ala Leu Thr Asn Leu Val Ala Glu Pro
            20                  25                  30

Phe Ala Lys Leu Glu Gln Asp Phe Gly Gly Ser Ile Gly Val Tyr Ala
        35                  40                  45

Ile Asp Thr Gly Ser Gly Ala Thr Val Ser Tyr Arg Ala Glu Glu Arg
50                  55                  60

Phe Pro Leu Cys Ser Ser Phe Lys Gly Phe Leu Ala Ala Ala Val Leu
65                  70                  75                  80

Ala Arg Ser Gln Gln Gln Ala Gly Leu Leu Asp Thr Pro Ile Arg Tyr
                85                  90                  95

Gly Lys Asn Ala Leu Val Pro Trp Ser Pro Ile Ser Glu Lys Tyr Leu
            100                 105                 110

Thr Thr Gly Met Thr Val Ala Glu Leu Ser Ala Ala Ala Val Gln Tyr
        115                 120                 125

Ser Asp Asn Ala Ala Ala Asn Leu Leu Leu Lys Glu Leu Gly Gly Pro
    130                 135                 140

Ala Gly Leu Thr Ala Phe Met Arg Ser Ile Gly Asp Thr Thr Phe Arg
145                 150                 155                 160

Leu Asp Arg Trp Glu Leu Glu Leu Asn Ser Ala Ile Pro Gly Asp Ala
                165                 170                 175

Arg Asp Thr Ser Ser Pro Arg Ala Val Thr Glu Ser Leu Gln Lys Leu
            180                 185                 190

Thr Leu Gly Ser Ala Leu Ala Ala Pro Gln Arg Gln Gln Phe Val Asp
        195                 200                 205

Trp Leu Lys Gly Asn Thr Thr Gly Asn His Arg Ile Arg Ala Ala Val
    210                 215                 220

Pro Ala Asp Trp Ala Val Gly Asp Lys Thr Gly Thr Cys Gly Val Tyr
225                 230                 235                 240

Gly Thr Ala Asn Asp Tyr Ala Val Val Trp Pro Thr Gly Arg Ala Pro
                245                 250                 255

Ile Val Leu Ala Val Tyr Thr Arg Ala Pro Asn Lys Asp Asp Lys Tyr
            260                 265                 270

Ser Glu Ala Val Ile Ala Ala Ala Arg Leu Ala Leu Glu Gly Leu
        275                 280                 285

Gly Val Asn Gly Gln
    290
```

<210> SEQ ID NO 44
<211> LENGTH: 293
<212> TYPE: PRT
<213> ORGANISM: Artificial Sequence
<220> FEATURE:
<223> OTHER INFORMATION: Synthetic sequence

<400> SEQUENCE: 44

```
Met Ser Leu Tyr Arg Arg Leu Val Leu Leu Ser Cys Leu Ser Trp Pro
1               5                   10                  15

Leu Ala Gly Phe Ser Ala Thr Ala Leu Thr Asn Leu Val Ala Glu Pro
            20                  25                  30

Phe Ala Lys Leu Glu Gln Asp Phe Gly Gly Ser Ile Gly Val Tyr Ala
        35                  40                  45

Met Asp Thr Gly Ser Gly Ala Thr Val Ser Tyr Arg Ala Glu Glu Arg
    50                  55                  60

Phe Pro Leu Cys Ser Ser Phe Lys Gly Phe Leu Ala Ala Ala Val Leu
65                  70                  75                  80

Ala Arg Ser Gln Gln Gln Ala Gly Leu Leu Asp Thr Pro Ile Arg Tyr
                85                  90                  95

Gly Lys Asn Ala Leu Val Pro Trp Ser Pro Ile Ser Glu Lys Tyr Leu
            100                 105                 110

Thr Thr Gly Met Thr Val Ala Glu Leu Ser Ala Ala Val Gln Tyr
        115                 120                 125

Ser Asp Asn Ala Ala Ala Asn Leu Leu Leu Lys Glu Leu Gly Gly Pro
    130                 135                 140

Ala Gly Leu Thr Ala Phe Met Arg Ser Ile Gly Asp Thr Thr Phe Arg
145                 150                 155                 160

Leu Asp Arg Trp Glu Leu Glu Leu Asn Ser Ala Ile Pro Gly Asp Ala
                165                 170                 175

Arg Asp Thr Ser Ser Pro Arg Ala Val Thr Glu Ser Leu Gln Lys Leu
            180                 185                 190

Thr Leu Gly Ser Ala Leu Ala Ala Pro Gln Arg Gln Gln Phe Val Asp
        195                 200                 205

Trp Leu Lys Gly Asn Thr Thr Gly Asn His Arg Ile Arg Ala Ala Val
    210                 215                 220

Pro Ala Asp Trp Ala Val Gly Asp Lys Thr Gly Thr Cys Gly Gly Tyr
225                 230                 235                 240

Gly Thr Ala Asn Asp Tyr Ala Val Val Trp Pro Thr Gly Arg Ala Pro
                245                 250                 255

Ile Val Leu Ala Val Tyr Thr Arg Ala Pro Asn Lys Asp Asp Lys Tyr
            260                 265                 270

Ser Glu Ala Val Ile Ala Ala Ala Arg Leu Ala Leu Glu Gly Leu
        275                 280                 285

Gly Val Asn Gly Gln
        290
```

<210> SEQ ID NO 45
<211> LENGTH: 293
<212> TYPE: PRT
<213> ORGANISM: Artificial Sequence
<220> FEATURE:
<223> OTHER INFORMATION: Synthetic sequence

<400> SEQUENCE: 45

```
Met Ser Lys Tyr Arg Arg Leu Val Leu Leu Ser Cys Leu Ser Trp Pro
1               5                   10                  15
```

```
Leu Ala Gly Phe Ser Ala Thr Ala Leu Thr Asn Leu Val Ala Glu Pro
            20                  25                  30

Phe Ala Lys Leu Glu Gln Asp Phe Gly Gly Ser Ile Gly Val Tyr Ala
        35                  40                  45

Met Asp Thr Gly Ser Gly Ala Thr Val Ser Tyr Arg Ala Glu Glu Arg
 50                  55                  60

Phe Pro Leu Cys Ser Ser Phe Lys Gly Phe Leu Ala Ala Ala Val Leu
65                  70                  75                  80

Ala Arg Ser Gln Gln Gln Ala Gly Leu Leu Asp Thr Pro Ile Arg Tyr
                85                  90                  95

Gly Lys Asn Ala Leu Val Pro Trp Ser Pro Ile Ser Glu Lys Tyr Leu
            100                 105                 110

Thr Thr Gly Met Thr Val Ala Glu Leu Ser Ala Ala Val Gln Tyr
        115                 120                 125

Ser Asp Asn Ala Ala Asn Leu Leu Leu Lys Glu Leu Gly Gly Pro
130                 135                 140

Ala Gly Leu Thr Ala Phe Met Arg Ser Ile Gly Asp Thr Thr Phe Arg
145                 150                 155                 160

Leu Asp Arg Trp Glu Leu Glu Leu Asn Ser Ala Ile Pro Gly Asp Ala
                165                 170                 175

Arg Asp Thr Ser Ser Pro Arg Ala Val Thr Glu Ser Leu Gln Lys Leu
            180                 185                 190

Thr Leu Gly Ser Ala Leu Ala Ala Pro Gln Arg Gln Gln Phe Val Asp
        195                 200                 205

Trp Leu Lys Gly Asn Thr Thr Gly Asn His Arg Ile Arg Ala Ala Val
210                 215                 220

Pro Ala Asp Trp Ala Val Gly Asp Lys Thr Gly Thr Cys Gly Ala Tyr
225                 230                 235                 240

Gly Thr Ala Asn Asp Tyr Ala Val Val Trp Pro Thr Gly Arg Ala Pro
                245                 250                 255

Ile Val Leu Ala Val Tyr Thr Arg Ala Pro Asn Lys Asp Asp Lys Tyr
            260                 265                 270

Ser Glu Ala Val Ile Ala Ala Ala Arg Leu Ala Leu Glu Gly Leu
        275                 280                 285

Gly Val Asn Gly Gln
        290

<210> SEQ ID NO 46
<211> LENGTH: 293
<212> TYPE: PRT
<213> ORGANISM: Artificial Sequence
<220> FEATURE:
<223> OTHER INFORMATION: Synthetic sequence

<400> SEQUENCE: 46

Met Ser Leu Tyr Arg Arg Leu Val Leu Leu Ser Cys Leu Ser Trp Pro
1               5                   10                  15

Leu Ala Gly Phe Ser Ala Thr Ala Leu Thr Asn Leu Val Ala Glu Pro
            20                  25                  30

Phe Ala Lys Leu Glu Gln Asp Phe Gly Gly Ser Ile Gly Val Tyr Ala
        35                  40                  45

Met Asp Thr Gly Ser Gly Ala Thr Val Ser Tyr Arg Ala Glu Glu Arg
 50                  55                  60

Phe Pro Leu Cys Ser Ser Phe Lys Gly Phe Leu Ala Ala Ala Val Leu
65                  70                  75                  80
```

Ala Arg Ser Gln Gln Gln Ala Gly Leu Leu Asp Thr Pro Ile Arg Tyr
                85                  90                  95

Gly Lys Asn Ala Leu Val Arg Trp Ser Pro Ile Ser Glu Lys Tyr Leu
            100                 105                 110

Thr Thr Gly Met Thr Val Ala Glu Leu Ser Ala Ala Val Gln Tyr
        115                 120                 125

Ser Asp Asn Ala Ala Ala Asn Leu Leu Leu Lys Glu Leu Gly Gly Pro
130                 135                 140

Ala Gly Leu Thr Ala Phe Met Arg Ser Ile Gly Asp Thr Thr Phe Arg
145                 150                 155                 160

Leu Asp Arg Trp Glu Leu Glu Leu Asn Ser Ala Ile Pro Gly Asp Ala
                165                 170                 175

Arg Asp Thr Ser Ser Pro Arg Ala Val Thr Glu Ser Leu Gln Lys Leu
            180                 185                 190

Thr Leu Gly Ser Ala Leu Ala Ala Pro Gln Arg Gln Gln Phe Val Asp
        195                 200                 205

Trp Leu Lys Gly Asn Thr Thr Gly Asn His Arg Ile Arg Ala Ala Val
210                 215                 220

Pro Ala Asp Trp Ala Val Gly Asp Lys Thr Gly Thr Cys Gly Val Tyr
225                 230                 235                 240

Gly Thr Ala Asn Asp Tyr Ala Val Val Trp Pro Thr Gly Arg Ala Pro
                245                 250                 255

Ile Val Leu Ala Val Tyr Thr Arg Ala Pro Asn Lys Asp Asp Lys Tyr
            260                 265                 270

Ser Glu Ala Val Ile Ala Ala Ala Arg Leu Ala Leu Glu Gly Leu
        275                 280                 285

Gly Val Asn Gly Gln
    290

<210> SEQ ID NO 47
<211> LENGTH: 293
<212> TYPE: PRT
<213> ORGANISM: Artificial Sequence
<220> FEATURE:
<223> OTHER INFORMATION: Synthetic sequence

<400> SEQUENCE: 47

Met Ser Leu Tyr Arg Arg Leu Val Leu Leu Ser Cys Leu Ser Trp Pro
1               5                   10                  15

Leu Ala Gly Phe Ser Ala Thr Ala Leu Thr Asn Leu Val Ala Glu Pro
            20                  25                  30

Phe Ala Lys Leu Glu Gln Asp Phe Gly Gly Ser Ile Gly Val Tyr Ala
        35                  40                  45

Met Asp Thr Gly Ser Gly Ala Thr Val Ser Tyr Arg Ala Glu Glu Arg
50                  55                  60

Phe Pro Leu Cys Ser Ser Phe Lys Gly Phe Leu Ala Ala Ala Val Leu
65                  70                  75                  80

Ala Arg Ser Gln Gln Gln Ala Gly Leu Leu Asp Thr Pro Ile Arg Tyr
                85                  90                  95

Gly Lys Asn Ala Leu Val Leu Trp Ser Pro Ile Ser Glu Lys Tyr Leu
            100                 105                 110

Thr Thr Gly Met Thr Val Ala Glu Leu Ser Ala Ala Val Gln Tyr
        115                 120                 125

Ser Asp Asn Ala Ala Ala Asn Leu Leu Leu Lys Glu Leu Gly Gly Pro
130                 135                 140

Ala Gly Leu Thr Ala Phe Met Arg Ser Ile Gly Asp Thr Thr Phe Arg
145                 150                 155                 160

Leu Asp Arg Trp Glu Leu Glu Leu Asn Ser Ala Ile Pro Gly Asp Ala
            165                 170                 175

Arg Asp Thr Ser Ser Pro Arg Ala Val Thr Glu Ser Leu Gln Lys Leu
        180                 185                 190

Thr Leu Gly Ser Ala Leu Ala Ala Pro Gln Arg Gln Gln Phe Val Asp
        195                 200                 205

Trp Leu Lys Gly Asn Thr Thr Gly Asn His Arg Ile Arg Ala Ala Val
        210                 215                 220

Pro Ala Asp Trp Ala Val Gly Asp Lys Thr Gly Thr Cys Gly Val Tyr
225                 230                 235                 240

Gly Thr Ala Asn Asp Tyr Ala Val Val Trp Pro Thr Gly Arg Ala Pro
            245                 250                 255

Ile Val Leu Ala Val Tyr Thr Arg Ala Pro Asn Lys Asp Asp Lys His
            260                 265                 270

Ser Glu Ala Val Ile Ala Ala Ala Arg Leu Ala Leu Glu Gly Leu
        275                 280                 285

Gly Val Asn Gly Gln
    290

<210> SEQ ID NO 48
<211> LENGTH: 293
<212> TYPE: PRT
<213> ORGANISM: Artificial Sequence
<220> FEATURE:
<223> OTHER INFORMATION: Synthetic sequence

<400> SEQUENCE: 48

Met Ser Leu Tyr Arg Arg Leu Val Leu Leu Ser Cys Leu Ser Trp Pro
1               5                   10                  15

Leu Ala Gly Phe Ser Ala Thr Ala Leu Thr Asn Leu Val Ala Glu Pro
            20                  25                  30

Phe Ala Lys Leu Glu Gln Asp Phe Gly Gly Ser Ile Gly Val Tyr Ala
        35                  40                  45

Met Asp Thr Gly Ser Gly Ala Thr Val Ser Tyr Arg Ala Glu Glu Arg
    50                  55                  60

Phe Pro Leu Cys Ser Ser Phe Lys Gly Phe Leu Ala Ala Ala Val Leu
65                  70                  75                  80

Ala Arg Ser Gln Gln Gln Ala Gly Leu Leu Asp Thr Pro Ile Arg Tyr
                85                  90                  95

Gly Lys Asn Ala Leu Val Pro Trp Ser Pro Ile Ser Glu Lys Tyr Leu
            100                 105                 110

Thr Thr Gly Met Thr Val Ala Glu Leu Ser Ala Ala Ala Val Gln Tyr
        115                 120                 125

Ser Asp Asn Ala Ala Ala Asn Leu Leu Leu Lys Glu Leu Gly Gly Pro
    130                 135                 140

Ala Gly Leu Thr Ala Phe Met Arg Ser Ile Gly Asp Thr Thr Phe Arg
145                 150                 155                 160

Leu Asp Arg Trp Glu Leu Glu Met Asn Ser Ala Ile Pro Gly Asp Ala
            165                 170                 175

Arg Asp Thr Ser Ser Pro Arg Ala Val Thr Glu Ser Leu Gln Lys Leu
        180                 185                 190

Thr Leu Gly Ser Ala Leu Ala Ala Pro Gln Arg Gln Gln Phe Val Asp
        195                 200                 205

Trp Leu Lys Gly Asn Thr Thr Gly Asn His Arg Ile Arg Ala Ala Val
            210                 215                 220

Pro Ala Asp Trp Ala Val Gly Asp Lys Thr Gly Thr Cys Gly Val Tyr
225                 230                 235                 240

Gly Thr Ala Asn Asp Tyr Ala Val Val Trp Pro Thr Gly Arg Ala Pro
                245                 250                 255

Ile Val Leu Ala Val Tyr Thr Arg Ala Pro Asn Lys Asp Asp Lys His
            260                 265                 270

Ser Glu Ala Val Ile Ala Ala Ala Arg Leu Ala Leu Glu Gly Leu
        275                 280                 285

Gly Val Asn Gly Gln
        290

<210> SEQ ID NO 49
<211> LENGTH: 293
<212> TYPE: PRT
<213> ORGANISM: Artificial Sequence
<220> FEATURE:
<223> OTHER INFORMATION: Synthetic sequence

<400> SEQUENCE: 49

Met Ser Leu Tyr Arg Arg Leu Val Leu Leu Ser Cys Leu Ser Trp Pro
1               5                   10                  15

Leu Ala Gly Phe Ser Ala Thr Ala Leu Thr Asn Leu Val Ala Glu Pro
            20                  25                  30

Phe Ala Lys Leu Glu Gln Asp Phe Gly Gly Ser Ile Gly Val Tyr Ala
        35                  40                  45

Met Asp Thr Gly Ser Gly Ala Thr Val Ser Tyr Arg Ala Glu Glu Arg
    50                  55                  60

Phe Pro Leu Cys Ser Ser Phe Lys Gly Phe Leu Ala Ala Ala Val Leu
65                  70                  75                  80

Ala Arg Ser Gln Gln Gln Ala Gly Leu Leu Gly Thr Pro Ile Arg Tyr
                85                  90                  95

Gly Lys Asn Ala Leu Val Pro Trp Ser Pro Ile Ser Glu Lys Tyr Leu
            100                 105                 110

Thr Thr Gly Met Thr Val Ala Glu Leu Ser Ala Ala Ala Val Gln Tyr
        115                 120                 125

Ser Asp Asn Ala Ala Ala Asn Leu Leu Leu Lys Glu Leu Gly Gly Pro
    130                 135                 140

Ala Gly Leu Thr Ala Phe Met Arg Ser Ile Gly Asp Thr Thr Phe Arg
145                 150                 155                 160

Leu Asp Arg Trp Glu Leu Glu Leu Asn Ser Ala Ile Pro Gly Asp Ala
                165                 170                 175

Arg Asp Thr Ser Ser Pro Arg Ala Val Thr Glu Ser Leu Gln Lys Leu
            180                 185                 190

Thr Leu Gly Ser Ala Leu Ala Ala Pro Gln Arg Gln Gln Phe Val Asp
        195                 200                 205

Trp Leu Lys Gly Asn Thr Thr Gly Asn His Arg Ile Arg Ala Ala Val
    210                 215                 220

Pro Ala Asp Trp Ala Val Gly Asp Lys Thr Gly Thr Cys Gly Val Tyr
225                 230                 235                 240

Gly Thr Ala Asn Asp Tyr Ala Val Val Trp Pro Thr Gly Arg Ala Pro
                245                 250                 255

Ile Val Leu Ala Val Tyr Thr Arg Ala Pro Asn Lys Asp Asp Lys Tyr
            260                 265                 270

Ser Glu Ala Val Ile Ala Ala Ala Arg Leu Ala Leu Glu Gly Leu
        275                 280                 285

Gly Val Asn Gly Gln
    290

<210> SEQ ID NO 50
<211> LENGTH: 291
<212> TYPE: PRT
<213> ORGANISM: Artificial Sequence
<220> FEATURE:
<223> OTHER INFORMATION: Synthetic sequence

<400> SEQUENCE: 50

Met Ser Leu Tyr Arg Arg Leu Val Leu Ser Cys Leu Ser Trp Pro
1               5                   10                  15

Leu Ala Gly Phe Ser Ala Thr Ala Leu Thr Asn Leu Val Ala Glu Pro
            20                  25                  30

Phe Ala Lys Leu Glu Gln Asp Phe Gly Gly Ser Ile Gly Val Tyr Ala
        35                  40                  45

Met Asp Thr Gly Ser Gly Ala Thr Val Ser Tyr Arg Ala Glu Glu Arg
    50                  55                  60

Phe Pro Leu Cys Ser Ser Phe Lys Gly Phe Leu Ala Ala Val Leu
65                  70                  75                  80

Ala Arg Ser Gln Gln Gln Ala Gly Leu Leu Asp Thr Pro Ile Arg Tyr
                85                  90                  95

Gly Lys Asn Ala Leu Val Pro Trp Ser Pro Ile Ser Glu Lys Tyr Leu
            100                 105                 110

Thr Thr Gly Met Thr Val Ala Glu Leu Ser Ala Ala Ala Val Gln Tyr
        115                 120                 125

Ser Asp Asn Ala Ala Ala Asn Leu Leu Leu Lys Glu Leu Gly Gly Pro
    130                 135                 140

Ala Gly Leu Thr Ala Phe Met Arg Ser Ile Gly Asp Thr Thr Phe Arg
145                 150                 155                 160

Leu Asp Arg Trp Glu Leu Glu Leu Asn Ser Ala Ile Pro Gly Asp Ala
                165                 170                 175

Arg Asp Thr Ser Ser Pro Arg Ala Val Thr Glu Ser Leu Gln Lys Leu
            180                 185                 190

Thr Leu Gly Ser Ala Leu Ala Ala Pro Gln Arg Gln Gln Phe Val Asp
        195                 200                 205

Trp Leu Lys Gly Asn Thr Thr Gly Asn His Arg Ile Arg Ala Ala Val
    210                 215                 220

Pro Ala Asp Trp Ala Val Gly Asp Lys Thr Gly Thr Cys Gly Val Tyr
225                 230                 235                 240

Ala Asn Asp Tyr Ala Val Val Trp Pro Thr Gly Arg Ala Pro Ile Val
                245                 250                 255

Leu Ala Val Tyr Thr Arg Ala Pro Asn Lys Asp Asp Lys His Ser Glu
            260                 265                 270

Ala Val Ile Ala Ala Ala Arg Leu Ala Leu Glu Gly Leu Gly Val
        275                 280                 285

Asn Gly Gln
    290

<210> SEQ ID NO 51
<211> LENGTH: 293
<212> TYPE: PRT
<213> ORGANISM: Artificial Sequence
<220> FEATURE:
<223> OTHER INFORMATION: Synthetic sequence

<400> SEQUENCE: 51

```
Met Ser Leu Tyr Arg Arg Leu Val Leu Leu Ser Cys Leu Ser Trp Pro
1               5                   10                  15

Leu Ala Gly Phe Ser Ala Thr Ala Leu Thr Asn Leu Val Ala Glu Pro
            20                  25                  30

Phe Ala Lys Leu Glu Gln Asp Phe Gly Gly Ser Ile Gly Val Tyr Ala
        35                  40                  45

Met Asp Thr Gly Ser Gly Ala Thr Val Ser Tyr Arg Ala Glu Glu Arg
    50                  55                  60

Phe Pro Leu Cys Ser Ser Phe Lys Gly Phe Leu Ala Ala Val Leu
65              70                  75                  80

Ala Arg Ser Gln Gln Gln Ala Gly Leu Leu Asp Thr Pro Ile Arg Tyr
                85                  90                  95

Gly Lys Asn Ala Leu Val Arg Trp Ser Pro Ile Ser Glu Lys Tyr Leu
            100                 105                 110

Thr Thr Gly Met Thr Val Leu Glu Leu Ser Ala Ala Val Gln Tyr
        115                 120                 125

Ser Asp Asn Ala Ala Ala Asn Leu Leu Leu Lys Glu Leu Gly Gly Pro
    130                 135                 140

Ala Lys Leu Thr Ala Phe Met Arg Ser Ile Gly Asp Thr Thr Phe Arg
145                 150                 155                 160

Leu Asp Arg Trp Glu Leu Glu Leu Asn Ser Ala Ile Pro Gly Asp Ala
                165                 170                 175

Arg Asp Thr Ser Ser Pro Arg Ala Val Thr Glu Ser Leu Gln Lys Leu
            180                 185                 190

Thr Leu Gly Ser Ala Leu Ala Ala Pro Gln Arg Gln Phe Val Asp
        195                 200                 205

Trp Leu Lys Gly Asn Thr Thr Gly Asn His Arg Ile Arg Ala Ala Val
    210                 215                 220

Pro Ala Asp Trp Ala Val Gly Asp Lys Thr Gly Thr Cys Gly Gly Tyr
225                 230                 235                 240

Gly Thr Ala Asn Asp Tyr Ala Val Val Trp Pro Thr Gly Arg Ala Pro
                245                 250                 255

Ile Val Leu Ala Val Tyr Thr Arg Ala Pro Asn Lys Asp Asp Lys Tyr
            260                 265                 270

Ser Glu Ala Val Ile Ala Ala Ala Arg Leu Ala Leu Glu Gly Leu
        275                 280                 285

Gly Val Asn Gly Gln
    290
```

<210> SEQ ID NO 52
<211> LENGTH: 293
<212> TYPE: PRT
<213> ORGANISM: Artificial Sequence
<220> FEATURE:
<223> OTHER INFORMATION: Synthetic sequence

<400> SEQUENCE: 52

```
Met Ser Leu Tyr Arg Arg Leu Val Leu Leu Ser Cys Leu Ser Trp Pro
1               5                   10                  15

Leu Ala Gly Phe Ser Ala Thr Ala Leu Thr Asn Leu Val Ala Glu Pro
            20                  25                  30

Phe Ala Lys Leu Glu Gln Asp Phe Gly Gly Ser Ile Gly Val Tyr Ala
```

```
                35                  40                  45
Met Asp Thr Gly Ser Gly Ala Thr Val Ser Tyr Arg Ala Glu Glu Arg
 50                  55                  60

Phe Pro Leu Cys Ser Ser Phe Lys Gly Phe Leu Ala Ala Val Leu
65                  70                  75                  80

Ala Arg Ser Gln Gln Ala Gly Leu Leu Asp Thr Pro Ile Arg Tyr
                85                  90                  95

Gly Lys Asn Ala Leu Val Pro Trp Ser Pro Ile Ser Glu Lys Tyr Leu
                100                 105                 110

Thr Thr Gly Met Thr Val Ala Glu Leu Ser Ala Ala Val Gln Tyr
                115                 120                 125

Ser Asp Asn Ala Ala Ala Asn Leu Leu Leu Lys Glu Leu Gly Gly Pro
130                 135                 140

Ala Gly Leu Thr Ala Phe Met Arg Ser Ile Gly Asp Thr Thr Phe Arg
145                 150                 155                 160

Leu Asp Arg Trp Glu Leu Glu Leu Asn Ser Ala Ile Pro Gly Asp Ala
                165                 170                 175

Arg Asp Thr Ser Ser Pro Arg Ala Val Thr Glu Ser Leu Gln Lys Leu
                180                 185                 190

Thr Leu Gly Ser Ala Leu Ala Ala Pro Gln Arg Gln Gln Leu Val Asp
                195                 200                 205

Trp Leu Lys Gly Asn Thr Thr Gly Asn His Arg Ile Arg Ala Ala Val
210                 215                 220

Pro Ala Asp Trp Ala Val Gly Asp Lys Thr Gly Thr Cys Gly Val Tyr
225                 230                 235                 240

Gly Thr Ala Asn Asp Tyr Ala Val Val Trp Pro Thr Gly Arg Ala Pro
                245                 250                 255

Ile Val Leu Ala Val Tyr Thr Arg Ala Pro Asn Lys Asp Asp Lys His
                260                 265                 270

Ser Glu Ala Val Ile Ala Ala Ala Arg Leu Ala Leu Glu Gly Leu
                275                 280                 285

Gly Val Asn Gly Gln
    290

<210> SEQ ID NO 53
<211> LENGTH: 270
<212> TYPE: PRT
<213> ORGANISM: Artificial Sequence
<220> FEATURE:
<223> OTHER INFORMATION: Synthetic sequence

<400> SEQUENCE: 53

Met Glu Leu Pro Asn Ile Met His Pro Val Ala Lys Leu Ser Thr Ala
1               5                   10                  15

Leu Ala Ala Ala Leu Met Leu Ser Gly Cys Met Pro Gly Glu Ile Arg
                20                  25                  30

Pro Thr Ile Gly Gln Gln Met Glu Thr Gly Asp Gln Arg Phe Gly Asp
                35                  40                  45

Leu Val Phe Arg Gln Leu Ala Pro Asn Val Trp Gln His Thr Ser Tyr
 50                  55                  60

Leu Asp Met Pro Gly Phe Gly Ala Val Ala Ser Asn Gly Leu Ile Val
65                  70                  75                  80

Arg Asp Gly Gly Arg Val Leu Val Val Asp Thr Ala Trp Thr Asp Asp
                85                  90                  95

Gln Thr Ala Gln Ile Leu Asn Trp Ile Lys Gln Glu Ile Asn Leu Pro
```

```
                    100                 105                 110
Val Ala Leu Ala Val Val Thr His Ala His Gln Asp Lys Met Gly Gly
            115                 120                 125

Met Asp Ala Leu His Ala Ala Gly Ile Ala Thr Tyr Ala Asn Ala Leu
130                 135                 140

Ser Asn Gln Leu Ala Pro Gln Glu Gly Met Val Ala Ala Gln His Ser
145                 150                 155                 160

Leu Thr Phe Ala Ala Asn Gly Trp Val Glu Pro Ala Thr Ala Pro Asn
                165                 170                 175

Phe Gly Pro Leu Lys Val Phe Tyr Pro Gly Pro Gly His Thr Ser Asp
                180                 185                 190

Asn Ile Thr Val Gly Ile Asp Gly Thr Asp Ile Ala Phe Gly Gly Cys
                195                 200                 205

Leu Ile Lys Asp Ser Lys Ala Lys Ser Leu Gly Asn Leu Gly Asp Ala
                210                 215                 220

Asp Thr Glu His Tyr Ala Ala Ser Ala Arg Ala Phe Gly Ala Ala Phe
225                 230                 235                 240

Pro Lys Ala Ser Met Ile Val Met Ser His Ser Ala Pro Asp Ser Arg
                245                 250                 255

Ala Ala Ile Thr His Thr Ala Arg Met Ala Asp Lys Leu Arg
                260                 265                 270

<210> SEQ ID NO 54
<211> LENGTH: 270
<212> TYPE: PRT
<213> ORGANISM: Artificial Sequence
<220> FEATURE:
<223> OTHER INFORMATION: Synthetic sequence

<400> SEQUENCE: 54

Met Glu Leu Pro Asn Ile Met His Pro Val Ala Lys Leu Ser Thr Ala
1               5                   10                  15

Leu Ala Ala Ala Leu Met Leu Ser Gly Cys Met Ala Gly Glu Ile Arg
                20                  25                  30

Pro Thr Ile Gly Gln Gln Met Glu Thr Gly Asp Gln Arg Phe Gly Asp
            35                  40                  45

Leu Val Phe Arg Gln Leu Ala Pro Asn Val Trp Gln His Thr Ser Tyr
        50                  55                  60

Leu Asp Met Pro Gly Phe Gly Ala Val Ala Ser Asn Gly Leu Ile Val
65                  70                  75                  80

Arg Asp Gly Gly Arg Val Leu Val Val Asp Thr Ala Trp Thr Asp Asp
                85                  90                  95

Gln Thr Ala Gln Ile Leu Asn Trp Ile Lys Gln Glu Ile Asn Leu Pro
            100                 105                 110

Val Ala Leu Ala Val Val Thr His Ala His Gln Asp Lys Met Gly Gly
        115                 120                 125

Met Asp Ala Leu His Ala Ala Gly Ile Ala Thr Tyr Ala Asn Ala Leu
130                 135                 140

Ser Asn Gln Leu Ala Pro Gln Glu Gly Met Val Ala Ala Gln His Ser
145                 150                 155                 160

Leu Thr Phe Ala Ala Asn Gly Trp Val Glu Pro Ala Thr Ala Pro Asn
                165                 170                 175

Phe Gly Pro Leu Lys Val Phe Tyr Pro Gly Pro Gly His Thr Ser Asp
                180                 185                 190

Asn Ile Thr Val Gly Ile Asp Gly Thr Asp Ile Ala Phe Gly Gly Cys
```

```
                195                 200                 205
Leu Ile Lys Asp Ser Lys Ala Lys Ser Leu Gly Asn Leu Gly Asp Ala
            210                 215                 220
Asp Thr Glu His Tyr Ala Ala Ser Ala Arg Ala Phe Gly Ala Ala Phe
225                 230                 235                 240
Pro Lys Ala Ser Met Ile Val Met Ser His Ser Ala Pro Asp Ser Arg
                245                 250                 255
Ala Ala Ile Thr His Thr Ala Arg Met Ala Asp Lys Leu Arg
            260                 265                 270
```

<210> SEQ ID NO 55
<211> LENGTH: 270
<212> TYPE: PRT
<213> ORGANISM: Artificial Sequence
<220> FEATURE:
<223> OTHER INFORMATION: Synthetic sequence

<400> SEQUENCE: 55

```
Met Glu Leu Pro Asn Ile Met His Pro Val Ala Lys Leu Ser Thr Ala
1               5                   10                  15
Leu Ala Ala Ala Leu Met Leu Ser Gly Cys Met Pro Gly Glu Ile Arg
            20                  25                  30
Pro Thr Ile Gly Gln Gln Met Glu Thr Gly Asp Gln Arg Phe Gly Asp
        35                  40                  45
Leu Val Phe Arg Gln Leu Ala Pro Asn Val Trp Gln His Thr Ser Tyr
    50                  55                  60
Leu Asp Met Pro Gly Phe Gly Ala Val Ala Ser Asn Gly Leu Ile Val
65                  70                  75                  80
Arg Asp Gly Gly Arg Val Leu Val Asp Thr Ala Trp Thr Asn Asp
                85                  90                  95
Gln Thr Ala Gln Ile Leu Asn Trp Ile Lys Gln Glu Ile Asn Leu Pro
            100                 105                 110
Val Ala Leu Ala Val Val Thr His Ala His Gln Asp Lys Met Gly Gly
        115                 120                 125
Met Asp Ala Leu His Ala Ala Gly Ile Ala Thr Tyr Ala Asn Ala Leu
130                 135                 140
Ser Asn Gln Leu Ala Pro Gln Glu Gly Met Val Ala Ala Gln His Ser
145                 150                 155                 160
Leu Thr Phe Ala Ala Asn Gly Trp Val Glu Pro Ala Thr Ala Pro Asn
                165                 170                 175
Phe Gly Pro Leu Lys Val Phe Tyr Pro Gly Pro Gly His Thr Ser Asp
            180                 185                 190
Asn Ile Thr Val Gly Ile Asp Gly Thr Asp Ile Ala Phe Gly Gly Cys
        195                 200                 205
Leu Ile Lys Asp Ser Lys Ala Lys Ser Leu Gly Asn Leu Gly Asp Ala
    210                 215                 220
Asp Thr Glu His Tyr Ala Ala Ser Ala Arg Ala Phe Gly Ala Ala Phe
225                 230                 235                 240
Pro Lys Ala Ser Met Ile Val Met Ser His Ser Ala Pro Asp Ser Arg
                245                 250                 255
Ala Ala Ile Thr His Thr Ala Arg Met Ala Asp Lys Leu Arg
            260                 265                 270
```

<210> SEQ ID NO 56
<211> LENGTH: 270
<212> TYPE: PRT

<213> ORGANISM: Artificial Sequence
<220> FEATURE:
<223> OTHER INFORMATION: Synthetic sequence

<400> SEQUENCE: 56

```
Met Glu Leu Pro Asn Ile Met His Pro Val Ala Lys Leu Ser Thr Ala
1               5                   10                  15

Leu Ala Ala Ala Leu Met Leu Ser Gly Cys Met Pro Gly Glu Ile Arg
            20                  25                  30

Pro Thr Ile Gly Gln Gln Met Glu Thr Gly Asp Gln Arg Phe Gly Asp
        35                  40                  45

Leu Val Phe Arg Gln Leu Ala Pro Asn Val Trp Gln His Thr Ser Tyr
50                  55                  60

Leu Asp Met Pro Gly Phe Gly Ala Val Ala Ser Asn Gly Leu Ile Val
65                  70                  75                  80

Arg Asp Gly Gly Arg Val Leu Val Asp Thr Ala Trp Thr Asp Asp
                85                  90                  95

Gln Thr Ala Gln Ile Leu Asn Trp Ile Lys Gln Glu Ile Asn Leu Pro
            100                 105                 110

Val Ala Leu Ala Val Val Thr His Ala His Gln Asp Lys Met Gly Gly
        115                 120                 125

Met Asp Ala Leu His Ala Ala Gly Ile Ala Thr Tyr Ala Asn Ala Leu
130                 135                 140

Ser Asn Gln Leu Ala Pro Gln Glu Gly Leu Val Ala Ala Gln His Ser
145                 150                 155                 160

Leu Thr Phe Ala Ala Asn Gly Trp Val Glu Pro Ala Thr Ala Pro Asn
                165                 170                 175

Phe Gly Pro Leu Lys Val Phe Tyr Pro Gly Pro Gly His Thr Ser Asp
            180                 185                 190

Asn Ile Thr Val Gly Ile Asp Gly Thr Asp Ile Ala Phe Gly Gly Cys
        195                 200                 205

Leu Ile Lys Asp Ser Lys Ala Lys Ser Leu Gly Asn Leu Gly Asp Ala
210                 215                 220

Asp Thr Glu His Tyr Ala Ala Ser Ala Arg Ala Phe Gly Ala Ala Phe
225                 230                 235                 240

Pro Lys Ala Ser Met Ile Val Met Ser His Ser Ala Pro Asp Ser Arg
                245                 250                 255

Ala Ala Ile Thr His Thr Ala Arg Met Ala Asp Lys Leu Arg
            260                 265                 270
```

<210> SEQ ID NO 57
<211> LENGTH: 270
<212> TYPE: PRT
<213> ORGANISM: Artificial Sequence
<220> FEATURE:
<223> OTHER INFORMATION: Synthetic sequence

<400> SEQUENCE: 57

```
Met Glu Leu Pro Asn Ile Met His Pro Val Ala Lys Leu Ser Thr Ala
1               5                   10                  15

Leu Ala Ala Ala Leu Met Leu Ser Gly Cys Met Pro Gly Glu Ile Arg
            20                  25                  30

Pro Thr Ile Gly Gln Gln Met Glu Thr Gly Asp Gln Arg Phe Gly Asp
        35                  40                  45

Leu Val Phe Arg Gln Leu Ala Pro Asn Val Trp Gln His Thr Ser Tyr
50                  55                  60
```

```
Leu Asp Met Pro Gly Phe Gly Ala Val Ala Ser Asn Gly Leu Ile Val
 65                  70                  75                  80

Arg Asp Gly Gly Arg Val Leu Val Asp Thr Ala Trp Thr Asp Asp
                 85                  90                  95

Gln Thr Ala Gln Ile Leu Asn Trp Ile Lys Gln Glu Ile Asn Leu Pro
                100                 105                 110

Val Ala Leu Ala Val Val Thr His Ala His Gln Asp Lys Met Gly Gly
            115                 120                 125

Met Asp Ala Leu His Ala Ala Gly Ile Ala Thr Tyr Ala Asn Ala Leu
        130                 135                 140

Ser Asn Gln Leu Ala Pro Gln Glu Gly Leu Val Ala Ala Gln His Ser
145                 150                 155                 160

Leu Thr Phe Ala Ala Asn Gly Trp Val Glu Pro Ala Thr Ala Pro Asn
                165                 170                 175

Phe Gly Pro Leu Lys Val Phe Tyr Pro Gly Pro Gly His Thr Ser Asp
                180                 185                 190

Asn Ile Thr Val Gly Ile Asp Gly Thr Asp Ile Ala Phe Gly Gly Cys
            195                 200                 205

Leu Ile Lys Asp Ser Lys Ala Lys Ser Leu Gly Asn Leu Gly Asp Ala
        210                 215                 220

Asp Thr Glu His Tyr Ala Ala Ser Ala Arg Ala Phe Gly Ala Ala Phe
225                 230                 235                 240

Pro Lys Ala Ser Met Ile Val Met Ser His Ser Ala Pro Asp Ser Arg
                245                 250                 255

Ala Ala Ile Thr His Thr Ala Arg Met Ala Asp Lys Leu Arg
                260                 265                 270

<210> SEQ ID NO 58
<211> LENGTH: 270
<212> TYPE: PRT
<213> ORGANISM: Artificial Sequence
<220> FEATURE:
<223> OTHER INFORMATION: Synthetic sequence

<400> SEQUENCE: 58

Met Glu Leu Pro Asn Ile Met His Pro Val Ala Lys Leu Ser Thr Ala
 1               5                  10                  15

Leu Ala Ala Ala Leu Met Leu Ser Gly Cys Met Pro Gly Glu Ile Arg
                20                  25                  30

Pro Thr Ile Gly Gln Gln Met Glu Thr Gly Asp Gln Arg Phe Gly Asp
            35                  40                  45

Leu Val Phe Arg Gln Leu Ala Pro Asn Val Trp Gln His Thr Ser Tyr
 50                  55                  60

Leu Asp Met Pro Gly Phe Gly Ala Val Ala Ser Asn Gly Leu Ile Val
 65                  70                  75                  80

Arg Asp Gly Gly Arg Val Leu Val Asp Thr Ala Trp Thr Asp Asp
                 85                  90                  95

Gln Thr Ala Gln Ile Leu Asn Trp Ile Lys Gln Glu Ile Asn Leu Pro
                100                 105                 110

Val Ala Leu Ala Val Val Thr His Ala His Gln Asp Lys Met Gly Gly
            115                 120                 125

Met Asp Ala Leu His Ala Ala Gly Ile Ala Thr Tyr Ala Asn Ala Leu
        130                 135                 140

Ser Asn Gln Leu Ala Pro Gln Glu Gly Met Val Ala Ala Gln His Ser
145                 150                 155                 160
```

Leu Thr Phe Ala Ala Asn Gly Trp Val Glu Pro Ala Thr Ala Pro Asn
            165                 170                 175

Phe Gly Pro Leu Lys Val Phe Tyr Pro Gly Pro Gly His Thr Ser Asp
            180                 185                 190

Asn Ile Thr Val Gly Ile Asp Gly Thr Asp Ile Ala Phe Gly Gly Cys
            195                 200                 205

Leu Ile Lys Asp Ser Lys Ala Lys Ser Leu Gly Asn Leu Gly Asp Ala
            210                 215                 220

Asp Thr Glu His Tyr Ala Ala Ser Val Arg Ala Phe Gly Ala Ala Phe
225                 230                 235                 240

Pro Lys Ala Ser Met Ile Val Met Ser His Ser Ala Pro Asp Ser Arg
            245                 250                 255

Ala Ala Ile Thr His Thr Ala Arg Met Ala Asp Lys Leu Arg
            260                 265                 270

<210> SEQ ID NO 59
<211> LENGTH: 270
<212> TYPE: PRT
<213> ORGANISM: Artificial Sequence
<220> FEATURE:
<223> OTHER INFORMATION: Synthetic sequence

<400> SEQUENCE: 59

Met Glu Leu Pro Asn Ile Met His Pro Val Ala Lys Leu Ser Thr Ala
1               5                   10                  15

Leu Ala Ala Ala Leu Met Leu Ser Gly Cys Met Pro Gly Glu Ile Arg
            20                  25                  30

Pro Thr Ile Gly Gln Gln Met Glu Thr Gly Asp Gln Arg Phe Gly Asp
            35                  40                  45

Leu Val Phe Arg Gln Leu Ala Pro Asn Val Trp Gln His Thr Ser Tyr
        50                  55                  60

Leu Asp Met Pro Gly Phe Gly Ala Val Ala Ser Asn Gly Leu Ile Val
65                  70                  75                  80

Arg Asp Gly Gly Arg Val Leu Val Val Asp Thr Ala Trp Thr Asp Asp
            85                  90                  95

Gln Thr Ala Gln Ile Leu Asn Trp Ile Lys Gln Glu Ile Asn Leu Pro
            100                 105                 110

Val Ala Leu Ala Val Val Thr His Ala His Gln Asp Lys Met Gly Gly
            115                 120                 125

Met Asn Ala Leu His Ala Ala Gly Ile Ala Thr Tyr Ala Asn Ala Leu
130                 135                 140

Ser Asn Gln Leu Ala Pro Gln Glu Gly Leu Val Ala Ala Gln His Ser
145                 150                 155                 160

Leu Thr Phe Ala Ala Asn Gly Trp Val Glu Pro Ala Thr Ala Pro Asn
            165                 170                 175

Phe Gly Pro Leu Lys Val Phe Tyr Pro Gly Pro Gly His Thr Ser Asp
            180                 185                 190

Asn Ile Thr Val Gly Ile Asp Gly Thr Asp Ile Ala Phe Gly Gly Cys
            195                 200                 205

Leu Ile Lys Asp Ser Lys Ala Lys Ser Leu Gly Asn Leu Gly Asp Ala
            210                 215                 220

Asp Thr Glu His Tyr Ala Ala Ser Ala Arg Ala Phe Gly Ala Ala Phe
225                 230                 235                 240

Pro Lys Ala Ser Met Ile Val Met Ser His Ser Ala Pro Asp Ser Arg
            245                 250                 255

```
Ala Ala Ile Thr His Thr Ala Arg Met Ala Asp Lys Leu Arg
        260                 265                 270
```

<210> SEQ ID NO 60
<211> LENGTH: 270
<212> TYPE: PRT
<213> ORGANISM: Artificial Sequence
<220> FEATURE:
<223> OTHER INFORMATION: Synthetic sequence

<400> SEQUENCE: 60

```
Met Glu Leu Pro Asn Ile Met His Pro Val Ala Lys Leu Ser Thr Ala
1               5                   10                  15

Leu Ala Ala Ala Leu Met Leu Ser Gly Cys Met Pro Gly Glu Ile Arg
            20                  25                  30

Pro Thr Ile Gly Gln Gln Met Glu Thr Gly Asp Gln Arg Phe Gly Asp
        35                  40                  45

Leu Val Phe Arg Gln Leu Ala Pro Asn Val Trp Gln His Thr Ser Tyr
    50                  55                  60

Leu Asp Met Pro Gly Phe Gly Ala Val Ala Ser Asn Gly Leu Ile Val
65                  70                  75                  80

Arg Asp Gly Gly Arg Val Leu Val Asp Thr Ala Trp Thr Asp Asp
                85                  90                  95

Gln Thr Ala Gln Ile Leu Asn Trp Ile Lys Gln Glu Ile Asn Leu Pro
            100                 105                 110

Val Ala Leu Ala Val Val Thr His Ala His Gln Asp Lys Met Gly Gly
        115                 120                 125

Met Gly Ala Leu His Ala Gly Ile Ala Thr Tyr Ala Asn Ala Leu
    130                 135                 140

Ser Asn Gln Leu Ala Pro Gln Glu Gly Leu Val Ala Ala Gln His Ser
145                 150                 155                 160

Leu Thr Phe Ala Ala Asn Gly Trp Val Glu Pro Ala Thr Ala Pro Asn
                165                 170                 175

Phe Gly Pro Leu Lys Val Phe Tyr Pro Gly Pro Gly His Thr Ser Asp
            180                 185                 190

Asn Ile Thr Val Gly Ile Asp Gly Thr Asp Ile Ala Phe Gly Gly Cys
        195                 200                 205

Leu Ile Lys Asp Ser Lys Ala Lys Ser Leu Gly Asn Leu Gly Asp Ala
    210                 215                 220

Asp Thr Glu His Tyr Ala Ala Ser Ala Arg Ala Phe Gly Ala Ala Phe
225                 230                 235                 240

Pro Lys Ala Ser Met Ile Val Met Ser His Ser Ala Pro Asp Ser Arg
                245                 250                 255

Ala Ala Ile Thr His Thr Ala Arg Met Ala Asp Lys Leu Arg
            260                 265                 270
```

<210> SEQ ID NO 61
<211> LENGTH: 270
<212> TYPE: PRT
<213> ORGANISM: Artificial Sequence
<220> FEATURE:
<223> OTHER INFORMATION: Synthetic sequence

<400> SEQUENCE: 61

```
Met Glu Leu Pro Asn Ile Met His Pro Val Ala Lys Leu Ser Thr Ala
1               5                   10                  15

Leu Ala Ala Ala Leu Met Leu Ser Gly Cys Met Pro Gly Glu Ile Arg
            20                  25                  30
```

Pro Thr Ile Gly Gln Gln Met Glu Thr Gly Asp Gln Arg Phe Gly Asp
            35                  40                  45

Leu Val Phe Arg Gln Leu Ala Pro Asn Val Trp Gln His Thr Ser Tyr
 50                      55                  60

Leu Asp Met Pro Gly Phe Gly Ala Val Ala Ser Asn Gly Leu Ile Val
 65                  70                  75                      80

Arg Asp Gly Gly Arg Val Leu Val Asp Thr Ala Trp Thr Asp Asp
                    85                  90                  95

Gln Thr Ala Gln Ile Leu Asn Trp Ile Lys Gln Glu Ile Asn Leu Pro
                100                 105                 110

Val Ala Leu Ala Val Val Thr His Ala His Gln Asp Lys Met Gly Gly
                115                 120                 125

Met Asp Ala Leu His Ala Ala Gly Ile Ala Thr Tyr Ala Asn Ala Leu
            130                 135                 140

Ser Asn Gln Leu Ala Pro Gln Lys Gly Met Val Ala Ala Gln His Ser
145                 150                 155                 160

Leu Thr Phe Ala Ala Asn Gly Trp Val Glu Pro Ala Thr Ala Pro Asn
                165                 170                 175

Phe Gly Pro Leu Lys Val Phe Tyr Pro Gly Pro Gly His Thr Ser Asp
            180                 185                 190

Asn Ile Thr Val Gly Ile Asp Gly Thr Asp Ile Ala Phe Gly Gly Cys
            195                 200                 205

Leu Ile Lys Asp Ser Lys Ala Lys Ser Leu Gly Asn Leu Gly Asp Ala
            210                 215                 220

Asp Thr Glu His Tyr Ala Ala Ser Ala Arg Ala Phe Gly Ala Ala Phe
225                 230                 235                 240

Pro Lys Ala Ser Met Ile Val Met Ser His Ser Ala Pro Asp Ser Arg
                245                 250                 255

Ala Ala Ile Thr His Thr Ala Arg Met Ala Asp Lys Leu Arg
                260                 265                 270

<210> SEQ ID NO 62
<211> LENGTH: 270
<212> TYPE: PRT
<213> ORGANISM: Artificial Sequence
<220> FEATURE:
<223> OTHER INFORMATION: Synthetic sequence

<400> SEQUENCE: 62

Met Glu Leu Pro Asn Ile Met His Pro Val Ala Lys Leu Ser Thr Ala
 1                   5                  10                  15

Leu Ala Ala Ala Leu Met Leu Ser Gly Cys Met Pro Gly Glu Ile Ser
                 20                  25                  30

Pro Thr Ile Asp Gln Gln Met Glu Thr Gly Asp Gln Arg Phe Gly Asp
            35                  40                  45

Leu Val Phe Arg Gln Leu Ala Pro Asn Val Trp Gln His Thr Ser Tyr
 50                      55                  60

Leu Asp Met Pro Ser Phe Gly Ala Val Thr Ser Asn Gly Leu Ile Val
 65                  70                  75                      80

Arg Asp Gly Gly Arg Val Leu Val Asp Thr Ala Trp Thr Asp Asp
                    85                  90                  95

Gln Thr Ala Gln Ile Leu Asn Trp Ile Lys Gln Glu Ile Asn Leu Pro
                100                 105                 110

Val Ala Leu Ala Val Val Thr His Ala His Gln Asp Lys Met Gly Gly
                115                 120                 125

```
Met Asp Ala Leu His Ala Ala Gly Ile Ala Thr Tyr Ala Asn Ala Leu
    130                 135                 140

Ser Asn Gln Leu Ala Pro Gln Glu Gly Met Val Ala Ala Gln His Ser
145                 150                 155                 160

Leu Thr Phe Ala Ala Asn Gly Trp Val Glu Pro Ala Thr Ala Pro Asn
                165                 170                 175

Phe Gly Pro Leu Lys Val Phe Tyr Pro Gly Pro Gly His Thr Ser Asp
                180                 185                 190

Asn Ile Thr Val Gly Ile Asp Arg Thr Asp Ile Ala Phe Gly Gly Cys
            195                 200                 205

Leu Ile Lys Asp Ser Lys Ala Lys Ser Leu Gly Asn Leu Gly Asp Ala
    210                 215                 220

Asp Thr Glu His Tyr Ala Ala Ser Ala Arg Ala Phe Gly Ala Ala Phe
225                 230                 235                 240

Pro Lys Ala Ser Met Ile Val Met Ser His Ser Ala Pro Asp Ser Arg
                245                 250                 255

Ala Ala Ile Thr His Thr Ala Arg Met Ala Asp Lys Leu Arg
            260                 265                 270

<210> SEQ ID NO 63
<211> LENGTH: 270
<212> TYPE: PRT
<213> ORGANISM: Artificial Sequence
<220> FEATURE:
<223> OTHER INFORMATION: Synthetic sequence

<400> SEQUENCE: 63

Met Glu Leu Pro Asn Ile Met His Pro Val Ala Lys Leu Ser Thr Ala
1               5                   10                  15

Leu Ala Ala Ala Leu Met Leu Ser Gly Cys Met Pro Gly Glu Ile Arg
                20                  25                  30

Pro Thr Ile Gly Gln Gln Met Glu Thr Gly Asp Gln Arg Phe Gly Asp
            35                  40                  45

Leu Val Phe Arg Gln Leu Ala Pro Asn Val Trp Gln His Thr Ser Tyr
50                  55                  60

Leu Asp Met Pro Gly Phe Gly Ala Val Ala Ser Asn Gly Leu Ile Val
65                  70                  75                  80

Arg Asp Gly Gly Arg Val Leu Val Val Asp Thr Ala Trp Thr Asp Asp
                85                  90                  95

Gln Thr Ala Gln Ile Leu Asn Trp Ile Lys Gln Glu Ile Asn Leu Pro
            100                 105                 110

Val Ala Leu Ala Val Val Thr His Ala His Gln Asp Lys Met Gly Gly
        115                 120                 125

Met Asp Ala Leu His Ala Ala Gly Ile Ala Thr Tyr Ala Asn Ala Leu
    130                 135                 140

Ser Asn Gln Leu Ala Pro Gln Glu Gly Leu Val Ala Ala Gln His Ser
145                 150                 155                 160

Leu Thr Phe Ala Ala Asn Gly Trp Val Glu Pro Ala Thr Ala Pro Asn
                165                 170                 175

Phe Gly Pro Leu Lys Val Phe Tyr Pro Gly Pro Gly His Thr Ser Asp
                180                 185                 190

Asn Ile Thr Val Gly Ile Asp Gly Thr Asp Ile Ala Phe Gly Gly Cys
            195                 200                 205

Leu Ile Lys Asp Ser Lys Ala Lys Ser Leu Gly Asn Leu Asp Asp Ala
    210                 215                 220
```

```
Asp Thr Glu His Tyr Ala Ala Ser Ala Arg Ala Phe Gly Ala Ala Phe
225                 230                 235                 240

Pro Lys Ala Ser Met Ile Val Met Ser His Ser Ala Pro Asp Ser Arg
                245                 250                 255

Ala Ala Ile Thr His Thr Ala Arg Met Ala Asp Lys Leu Arg
            260                 265                 270
```

<210> SEQ ID NO 64
<211> LENGTH: 270
<212> TYPE: PRT
<213> ORGANISM: Artificial Sequence
<220> FEATURE:
<223> OTHER INFORMATION: Synthetic sequence

<400> SEQUENCE: 64

```
Met Glu Leu Pro Asn Ile Met His Pro Val Ala Lys Leu Ser Thr Ala
1               5                   10                  15

Leu Ala Ala Leu Met Leu Ser Gly Cys Met Pro Gly Glu Ile Arg
                20                  25                  30

Pro Thr Ile Gly Gln Gln Met Glu Thr Gly Asp Gln Arg Phe Gly Asp
            35                  40                  45

Leu Val Phe Arg Gln Leu Ala Pro Asn Val Trp Gln His Thr Ser Tyr
50                  55                  60

Leu Asp Met Pro Gly Phe Gly Ala Val Ala Ser Asn Gly Leu Ile Val
65                  70                  75                  80

Arg Asp Gly Gly Arg Val Leu Val Val Asp Thr Ala Trp Thr Asp Asp
                85                  90                  95

Gln Thr Ala Gln Ile Leu Asn Trp Ile Lys Gln Glu Ile Asn Leu Pro
            100                 105                 110

Val Ala Leu Ala Val Val Thr His Ala His Gln Asp Lys Met Gly Gly
                115                 120                 125

Met Asp Ala Leu His Ala Ala Gly Ile Ala Thr Tyr Ala Asn Ala Leu
130                 135                 140

Ser Asn Gln Leu Ala Pro Gln Glu Gly Leu Val Ala Ala Gln His Ser
145                 150                 155                 160

Leu Thr Phe Ala Ala Asn Gly Trp Val Glu Pro Ala Thr Ala Pro Asn
                165                 170                 175

Phe Gly Pro Leu Lys Val Phe Tyr Pro Gly Pro Gly His Thr Ser Asp
            180                 185                 190

Asn Ile Thr Val Gly Ile Asp Gly Thr Asp Ile Ala Phe Gly Gly Cys
                195                 200                 205

Leu Ile Lys Asp Ser Lys Ala Lys Ser Leu Gly Asn Leu Asp Asp Ala
210                 215                 220

Asp Thr Glu His Tyr Ala Ala Ser Ala Arg Ala Phe Gly Ala Ala Phe
225                 230                 235                 240

Pro Lys Ala Ser Met Ile Val Met Ser His Ser Ala Pro Asp Ser Arg
                245                 250                 255

Ala Ala Ile Thr His Thr Ala Arg Met Ala Asp Lys Leu Arg
            260                 265                 270
```

<210> SEQ ID NO 65
<211> LENGTH: 270
<212> TYPE: PRT
<213> ORGANISM: Artificial Sequence
<220> FEATURE:
<223> OTHER INFORMATION: Synthetic sequence

<400> SEQUENCE: 65

Met Glu Leu Pro Asn Ile Met His Pro Val Ala Lys Leu Ser Thr Ala
1               5                   10                  15

Leu Ala Ala Ala Leu Met Leu Ser Gly Cys Met Pro Gly Glu Ile Arg
            20                  25                  30

Pro Thr Ile Gly Gln Gln Met Glu Thr Gly Asp Gln Arg Phe Gly Asp
        35                  40                  45

Leu Val Phe Arg Gln Leu Ala Pro Asn Val Trp Gln His Thr Ser Tyr
    50                  55                  60

Leu Asp Met Pro Gly Phe Gly Ala Val Ala Ser Asn Gly Leu Ile Val
65                  70                  75                  80

Arg Asp Gly Gly Arg Val Leu Val Asp Thr Ala Trp Thr Asn Asp
                85                  90                  95

Gln Thr Ala Gln Ile Leu Asn Trp Ile Lys Gln Glu Ile Asn Leu Pro
            100                 105                 110

Val Ala Leu Ala Val Val Thr His Ala His Gln Asp Lys Met Gly Gly
        115                 120                 125

Met Asp Ala Leu His Ala Ala Gly Ile Ala Thr Tyr Ala Asn Ala Leu
130                 135                 140

Ser Asn Gln Leu Ala Pro Gln Glu Gly Leu Val Ala Ala Gln His Ser
145                 150                 155                 160

Leu Thr Phe Ala Ala Asn Gly Trp Val Glu Pro Ala Thr Ala Pro Asn
                165                 170                 175

Phe Gly Pro Leu Lys Val Phe Tyr Pro Gly Pro Gly His Thr Ser Asp
            180                 185                 190

Asn Ile Thr Val Gly Ile Asp Gly Thr Asp Ile Ala Phe Gly Gly Cys
        195                 200                 205

Leu Ile Lys Asp Ser Lys Ala Lys Ser Leu Gly Asn Leu Gly Asp Ala
    210                 215                 220

Asp Thr Glu His Tyr Ala Ala Ser Ala Arg Ala Phe Gly Ala Ala Phe
225                 230                 235                 240

Pro Lys Ala Ser Met Ile Val Met Ser His Ser Ala Pro Asp Ser Arg
                245                 250                 255

Ala Ala Ile Thr His Thr Ala Arg Met Ala Asp Lys Leu Arg
                260                 265                 270

<210> SEQ ID NO 66
<211> LENGTH: 239
<212> TYPE: PRT
<213> ORGANISM: Artificial Sequence
<220> FEATURE:
<223> OTHER INFORMATION: Synthetic sequence

<400> SEQUENCE: 66

Met Lys Lys Asn Ile Ala Phe Leu Leu Ala Ser Met Phe Val Phe Ser
1               5                   10                  15

Ile Ala Thr Asn Ala Tyr Ala Glu Thr Gly Thr Ile Ser Ile Ser Gln
            20                  25                  30

Leu Asn Lys Asn Val Trp Val His Thr Glu Leu Gly Tyr Phe Asn Gly
        35                  40                  45

Glu Ala Val Pro Ser Asn Gly Leu Val Leu Asn Thr Ser Lys Gly Leu
    50                  55                  60

Val Leu Val Asp Ser Ser Trp Asp Asn Lys Leu Thr Lys Glu Leu Ile
65                  70                  75                  80

Glu Met Val Glu Lys Lys Phe Gln Lys Arg Val Thr Asp Val Ile Ile

```
                  85                  90                  95

Thr His Ala His Ala Asp Arg Ile Gly Gly Ile Thr Ala Leu Lys Glu
                100                 105                 110

Arg Gly Ile Lys Ala His Ser Thr Ala Leu Thr Ala Glu Leu Ala Lys
            115                 120                 125

Asn Ser Gly Tyr Glu Glu Pro Leu Gly Asp Leu Gln Thr Ile Thr Ser
        130                 135                 140

Leu Lys Phe Gly Asn Thr Lys Val Glu Thr Phe Tyr Pro Gly Lys Gly
145                 150                 155                 160

His Thr Glu Asp Asn Ile Val Val Trp Leu Pro Gln Tyr Gln Ile Leu
                165                 170                 175

Ala Gly Gly Cys Leu Val Lys Ser Ala Glu Ala Lys Asp Leu Gly Asn
            180                 185                 190

Val Ala Asp Ala Tyr Val Asn Glu Trp Ser Thr Ser Ile Glu Asn Val
        195                 200                 205

Leu Lys Arg Tyr Gly Asn Ile Asn Ser Val Val Pro Gly His Gly Glu
    210                 215                 220

Val Gly Asp Lys Gly Leu Leu Leu His Thr Leu Asp Leu Leu Lys
225                 230                 235

<210> SEQ ID NO 67
<211> LENGTH: 731
<212> TYPE: DNA
<213> ORGANISM: Artificial Sequence
<220> FEATURE:
<223> OTHER INFORMATION: Synthetic sequence

<400> SEQUENCE: 67
catatgaaaa aaaacattgc atttctgctg gcgagcatgt ttgtttttag cattgcaacc    60
aatgcatacg ccgaaacggg caccattagc attagccaac tcaacaaaaa cgtttgggtc   120
cacaccgagt taggctattt caacggtgaa gccgtgccga gcaatggttt ggttctgaat   180
acgtccaagg gtctggtgtg gtagactcca gctgggacaa taagctgacc aaagaactga   240
tcgaaatggt tgagaaaaag ttccagaagc gtgtgactga tgtcattatc acccatgcgc   300
acgcggaccg catcggtggc attaccgcgc tgaaagagcg tggcattaaa gcacatagca   360
cggcactgac ggctgagctg gcgaagaaca gcggctacga agaaccgctg ggtgatctgc   420
agaccatcac gtcgctgaag tttggcaaca ccaaagtcga acttttttac ccaggtaagg   480
gtcataccga agataacatc gtggtttggc tgccgcagta ccaaatcctg gccggtggct   540
gcctggttaa gagcgcagag gcgaaagatc tgggtaatgt cgcggacgct tatgtgaacg   600
agtggagcac ctctattgaa aatgttttga acgttatgg taatatcaat agcgttgtgc   660
cgggtcacgg tgaggtcggc gacaaaggtc tgctgttgca cacgctggat ctgctgaagt   720
gataactcga g                                                         731

<210> SEQ ID NO 68
<211> LENGTH: 217
<212> TYPE: PRT
<213> ORGANISM: Artificial Sequence
<220> FEATURE:
<223> OTHER INFORMATION: Synthetic sequence

<400> SEQUENCE: 68

Met Glu Thr Gly Thr Ile Ser Ile Ser Gln Leu Asn Lys Asn Val Trp
1               5                   10                  15

Val His Thr Glu Leu Gly Tyr Phe Asn Gly Glu Ala Val Pro Ser Asn
```

```
                20                  25                  30
Gly Leu Val Leu Asn Thr Ser Lys Gly Leu Val Leu Asp Ser Ser
            35                  40                  45

Trp Asp Asn Lys Leu Thr Lys Glu Leu Ile Glu Met Val Glu Lys Lys
 50                  55                  60

Phe Gln Lys Arg Val Thr Asp Val Ile Ile Thr His Ala His Ala Asp
 65                  70                  75                  80

Arg Ile Gly Gly Ile Thr Ala Leu Lys Glu Arg Gly Ile Lys Ala His
                 85                  90                  95

Ser Thr Ala Leu Thr Ala Glu Leu Ala Lys Asn Ser Gly Tyr Glu Glu
            100                 105                 110

Pro Leu Gly Asp Leu Gln Thr Ile Thr Ser Leu Lys Phe Gly Asn Thr
            115                 120                 125

Lys Val Glu Thr Phe Tyr Pro Gly Lys Gly His Thr Glu Asp Asn Ile
            130                 135                 140

Val Val Trp Leu Pro Gln Tyr Gln Ile Leu Ala Gly Gly Cys Leu Val
145                 150                 155                 160

Lys Ser Ala Glu Ala Lys Asp Leu Gly Asn Val Ala Asp Ala Tyr Val
                165                 170                 175

Asn Glu Trp Ser Thr Ser Ile Glu Asn Val Leu Lys Arg Tyr Gly Asn
            180                 185                 190

Ile Asn Ser Val Val Pro Gly His Gly Glu Val Gly Asp Lys Gly Leu
            195                 200                 205

Leu Leu His Thr Leu Asp Leu Leu Lys
            210                 215

<210> SEQ ID NO 69
<211> LENGTH: 666
<212> TYPE: DNA
<213> ORGANISM: Artificial Sequence
<220> FEATURE:
<223> OTHER INFORMATION: Synthetic sequence

<400> SEQUENCE: 69
catatggaaa cgggcaccat tagcattagc caactcaaca aaaacgtttg ggtccacacc      60
gagttaggct atttcaacgg tgaagccgtg ccgagcaatg gtttggttct gaatacgtcc     120
aagggtctgg tgttggtaga ctccagctgg acaataagc tgaccaaaga actgatcgaa     180
atggttgaga aaaagttcca gaagcgtgtg actgatgtca ttatcaccca tgcgcacgcg     240
gaccgcatcg gtggcattac cgcgctgaaa gagcgtggca ttaaagcaca tagcacggca     300
ctgacggctg agctggcgaa gaacagcggc tacgaagaac cgctgggtga tctgcagacc     360
atcacgtcgc tgaagtttgg caacaccaaa gtcgagactt tttacccagg taagggtcat     420
accgaagata catcgtggt ttggctgccg cagtaccaaa tcctggccgg tggctgcctg     480
gttaagagcg cagaggcgaa agatctgggt aatgtcgcgg acgcttatgt gaacgagtgg     540
agcacctcta ttgaaaatgt tttgaaacgt tatggtaata tcaatagcgt tgtgccgggt     600
cacggtgagg tcggcgacaa aggtctgctg ttgcacacgc tggatctgct gaagtgataa     660
ctcgag                                                                666

<210> SEQ ID NO 70
<211> LENGTH: 5
<212> TYPE: PRT
<213> ORGANISM: Artificial Sequence
<220> FEATURE:
<223> OTHER INFORMATION: Synthetic sequence
```

<400> SEQUENCE: 70

Gly Gln Gln Met Glu
1               5

<210> SEQ ID NO 71
<211> LENGTH: 235
<212> TYPE: PRT
<213> ORGANISM: Artificial Sequence
<220> FEATURE:
<223> OTHER INFORMATION: Synthetic sequence

<400> SEQUENCE: 71

Gly Gln Gln Met Glu Thr Gly Asp Gln Arg Phe Gly Asp Leu Val Phe
1               5                   10                  15

Arg Gln Leu Ala Pro Asn Val Trp Gln His Thr Ser Tyr Leu Asp Met
            20                  25                  30

Pro Gly Phe Gly Ala Val Ala Ser Asn Gly Leu Ile Val Arg Asp Gly
        35                  40                  45

Gly Arg Val Leu Val Val Asp Thr Ala Trp Thr Asp Asp Gln Thr Ala
    50                  55                  60

Gln Ile Leu Asn Trp Ile Lys Gln Glu Ile Asn Leu Pro Val Ala Leu
65                  70                  75                  80

Ala Val Val Thr His Ala His Gln Asp Lys Met Gly Gly Met Asp Ala
                85                  90                  95

Leu His Ala Ala Gly Ile Ala Thr Tyr Ala Asn Ala Leu Ser Asn Gln
            100                 105                 110

Leu Ala Pro Gln Glu Gly Met Val Ala Ala Gln His Ser Leu Thr Phe
        115                 120                 125

Ala Ala Asn Gly Trp Val Glu Pro Ala Thr Ala Pro Asn Phe Gly Pro
    130                 135                 140

Leu Lys Val Phe Tyr Pro Gly Pro Gly His Thr Ser Asp Asn Ile Thr
145                 150                 155                 160

Val Gly Ile Asp Gly Thr Asp Ile Ala Phe Gly Gly Cys Leu Ile Lys
                165                 170                 175

Asp Ser Lys Ala Lys Ser Leu Gly Asn Leu Gly Asp Ala Asp Thr Glu
            180                 185                 190

His Tyr Ala Ala Ser Ala Arg Ala Phe Gly Ala Ala Phe Pro Lys Ala
        195                 200                 205

Ser Met Ile Val Met Ser His Ser Ala Pro Asp Ser Arg Ala Ala Ile
    210                 215                 220

Thr His Thr Ala Arg Met Ala Asp Lys Leu Arg
225                 230                 235

<210> SEQ ID NO 72
<211> LENGTH: 184
<212> TYPE: PRT
<213> ORGANISM: Artificial Sequence
<220> FEATURE:
<223> OTHER INFORMATION: Synthetic sequence

<400> SEQUENCE: 72

Gly Gln Gln Met Glu Thr Gly Asp Gln Arg Phe Gly Asp Leu Val Phe
1               5                   10                  15

Arg Gln Leu Ala Pro Asn Val Trp Gln His Thr Ser Tyr Leu Asp Met
            20                  25                  30

Pro Gly Phe Gly Ala Val Ala Ser Asn Gly Leu Ile Val Arg Asp Gly
        35                  40                  45

```
Gly Arg Val Leu Val Val Asp Thr Ala Trp Thr Asp Asp Gln Thr Ala
        50                  55                  60

Gln Ile Leu Asn Trp Ile Lys Gln Glu Ile Asn Leu Pro Val Ala Leu
 65                  70                  75                  80

Ala Val Val Thr His Ala His Gln Asp Lys Met Gly Gly Met Asp Ala
                    85                  90                  95

Leu His Ala Ala Gly Ile Ala Thr Tyr Ala Asn Ala Leu Ser Asn Gln
                    100                 105                 110

Leu Ala Pro Gln Glu Gly Met Val Ala Ala Gln His Ser Leu Thr Phe
                115                 120                 125

Ala Ala Asn Gly Trp Val Glu Pro Ala Thr Ala Pro Asn Phe Gly Pro
            130                 135                 140

Leu Lys Val Phe Tyr Pro Gly Pro Gly His Thr Ser Asp Asn Ile Thr
145                 150                 155                 160

Val Gly Ile Asp Gly Thr Asp Ile Ala Phe Gly Gly Cys Leu Ile Lys
                    165                 170                 175

Asp Ser Lys Ala Lys Ser Leu Gly
                    180
```

<210> SEQ ID NO 73
<211> LENGTH: 124
<212> TYPE: PRT
<213> ORGANISM: Artificial Sequence
<220> FEATURE:
<223> OTHER INFORMATION: Synthetic sequence

<400> SEQUENCE: 73

```
Gly Gln Gln Met Glu Thr Gly Asp Gln Arg Phe Gly Asp Leu Val Phe
 1                   5                  10                  15

Arg Gln Leu Ala Pro Asn Val Trp Gln His Thr Ser Tyr Leu Asp Met
                20                  25                  30

Pro Gly Phe Gly Ala Val Ala Ser Asn Gly Leu Ile Val Arg Asp Gly
            35                  40                  45

Gly Arg Val Leu Val Val Asp Thr Ala Trp Thr Asp Asp Gln Thr Ala
        50                  55                  60

Gln Ile Leu Asn Trp Ile Lys Gln Glu Ile Asn Leu Pro Val Ala Leu
 65                  70                  75                  80

Ala Val Val Thr His Ala His Gln Asp Lys Met Gly Gly Met Asp Ala
                    85                  90                  95

Leu His Ala Ala Gly Ile Ala Thr Tyr Ala Asn Ala Leu Ser Asn Gln
                    100                 105                 110

Leu Ala Pro Gln Glu Gly Met Val Ala Ala Gln His
                115                 120
```

<210> SEQ ID NO 74
<211> LENGTH: 77
<212> TYPE: PRT
<213> ORGANISM: Artificial Sequence
<220> FEATURE:
<223> OTHER INFORMATION: Synthetic sequence

<400> SEQUENCE: 74

```
Ser Leu Thr Phe Ala Ala Asn Gly Trp Val Glu Pro Ala Thr Ala Pro
 1                   5                  10                  15

Asn Phe Gly Pro Leu Lys Val Phe Tyr Pro Gly Pro Gly His Thr Ser
                20                  25                  30

Asp Asn Ile Thr Val Gly Ile Asp Gly Thr Asp Ile Ala Phe Gly Gly
```

```
                35                  40                  45
Cys Leu Ile Lys Asp Ser Lys Ala Lys Ser Leu Gly Asn Leu Gly Asp
    50                  55                  60
Ala Asp Thr Glu His Tyr Ala Ala Ser Ala Arg Ala Phe
65                  70                  75

<210> SEQ ID NO 75
<211> LENGTH: 60
<212> TYPE: PRT
<213> ORGANISM: Artificial Sequence
<220> FEATURE:
<223> OTHER INFORMATION: Synthetic sequence

<400> SEQUENCE: 75

Ser Leu Thr Phe Ala Ala Asn Gly Trp Val Glu Pro Ala Thr Ala Pro
1               5                   10                  15
Asn Phe Gly Pro Leu Lys Val Phe Tyr Pro Gly Pro His Thr Ser
                20                  25                  30
Asp Asn Ile Thr Val Gly Ile Asp Gly Thr Asp Ile Ala Phe Gly Gly
            35                  40                  45
Cys Leu Ile Lys Asp Ser Lys Ala Lys Ser Leu Gly
    50                  55                  60

<210> SEQ ID NO 76
<211> LENGTH: 51
<212> TYPE: PRT
<213> ORGANISM: Artificial Sequence
<220> FEATURE:
<223> OTHER INFORMATION: Synthetic sequence

<400> SEQUENCE: 76

Asn Leu Gly Asp Ala Asp Thr Glu His Tyr Ala Ala Ser Ala Arg Ala
1               5                   10                  15
Phe Gly Ala Ala Phe Pro Lys Ala Ser Met Ile Val Met Ser His Ser
                20                  25                  30
Ala Pro Asp Ser Arg Ala Ala Ile Thr His Thr Ala Arg Met Ala Asp
            35                  40                  45
Lys Leu Arg
    50

<210> SEQ ID NO 77
<211> LENGTH: 5
<212> TYPE: PRT
<213> ORGANISM: Artificial Sequence
<220> FEATURE:
<223> OTHER INFORMATION: Synthetic sequence

<400> SEQUENCE: 77

Ser Leu Thr Phe Ala
1               5

<210> SEQ ID NO 78
<211> LENGTH: 5
<212> TYPE: PRT
<213> ORGANISM: Artificial Sequence
<220> FEATURE:
<223> OTHER INFORMATION: Synthetic sequence

<400> SEQUENCE: 78

Asn Leu Gly Asp Ala
1               5
```